US009023843B2

(12) United States Patent
Duffy et al.

(10) Patent No.: US 9,023,843 B2
(45) Date of Patent: May 5, 2015

(54) ANTIMICROBIAL COMPOUNDS AND METHODS OF MAKING AND USING THE SAME

(75) Inventors: Erin M. Duffy, Deep River, CT (US); Ashoke Bhattacharjee, Cheshire, CT (US); Hardwin O'Dowd, Cambridge, MA (US); Shili Chen, Cheshire, CT (US); Marco DeVivo, Rimini (IT); Rongliang Lou, Cheshire, CT (US); Brian T. Wimberly, Denver, CO (US)

(73) Assignee: Melinta Therapeutics, Inc., New Haven, CT (US)

( * ) Notice: Subject to any disclaimer, the term of this patent is extended or adjusted under 35 U.S.C. 154(b) by 157 days.

(21) Appl. No.: 13/501,836

(22) PCT Filed: Oct. 15, 2010

(86) PCT No.: PCT/US2010/052924
§ 371 (c)(1),
(2), (4) Date: Apr. 13, 2012

(87) PCT Pub. No.: WO2011/047320
PCT Pub. Date: Apr. 21, 2011

(65) Prior Publication Data
US 2012/0202792 A1 Aug. 9, 2012

Related U.S. Application Data

(60) Provisional application No. 61/252,478, filed on Oct. 16, 2009, provisional application No. 61/314,287, filed on Mar. 16, 2010, provisional application No. 61/358,201, filed on Jun. 24, 2010.

(51) Int. Cl.
| | | |
|---|---|---|
| *C07D 487/04* | (2006.01) | |
| *C07D 491/048* | (2006.01) | |
| *C07D 519/00* | (2006.01) | |
| *C07D 498/04* | (2006.01) | |
| *A61K 31/5383* | (2006.01) | |
| *A61K 31/519* | (2006.01) | |

(52) U.S. Cl.
CPC .......... *C07D 487/04* (2013.01); *C07D 491/048* (2013.01); *C07D 519/00* (2013.01)

(58) Field of Classification Search
CPC .............. C07D 487/04; C07D 498/04; A61K 31/5383; A61K 31/519
USPC ........................ 544/101, 65; 514/230.2, 229.8
See application file for complete search history.

(56) References Cited

U.S. PATENT DOCUMENTS

| | | |
|---|---|---|
| 4,522,811 A | 6/1985 | Eppstein et al. |
| 5,434,257 A * | 7/1995 | Matteucci et al. ........... 536/24.3 |
| 5,763,263 A | 6/1998 | Dehlinger |
| 5,763,588 A | 6/1998 | Matteucci et al. |
| 6,028,183 A | 2/2000 | Lin et al. |
| 2003/0158403 A1 | 8/2003 | Manoharan et al. |

FOREIGN PATENT DOCUMENTS

| | | |
|---|---|---|
| JP | 4-077488 A | 3/1992 |
| JP | 9-506859 A | 7/1997 |
| JP | 2001-522860 A | 11/2001 |
| JP | 2004-537503 A | 12/2004 |
| JP | 2005-504020 A | 2/2005 |
| WO | WO-9529894 A1 | 11/1995 |
| WO | WO 99/24452 A2 | 5/1999 |
| WO | WO-0248138 A1 | 6/2002 |
| WO | WO 02/061110 A2 | 8/2002 |
| WO | WO-02097134 A2 | 12/2002 |
| WO | WO 03/004602 A2 | 1/2003 |
| WO | WO-2005019228 A1 | 3/2005 |
| WO | WO-2007014308 A1 | 2/2007 |

OTHER PUBLICATIONS

Journal of the American Chemical Society, (1995), 117(13), 3873-4.*
Ausin et al. "Synthesis of Amino- and Guanidino-G-Clamp PNA Monomers." *Org. Lett.* 4.23(2002):4073-4075.
Cahn et al. "Specification of Configuration About Quadricovalent Asymmetric Atoms." *J. Chem. Soc.* (1951):612-622.
Cahn et al. "Specification of Molecular Chirality." *Angew. Chem. Int. Ed.* 5.4(1966):385-415.
Cahn et al. "Errata: Specification of Molecular Chirality." *Angew. Chem. Int. Ed.* 5.5(1966):511.
Cahn et al. "The Specification of Asymmetric Configuration in Organic Chemistry." *Experientia.* 12(1956):81-94.
Cahn. "An Introduction to the Sequence Rule: A System for the Specification of Absolute Configuration." *J. Chem. Educ.* 41.3(1964):116-125.
Debaene et al. "Expanding the Scope of PNA-Encoded Libraries: Divergent Synthesis of Libraries Targeting Cysteine, Serine and Metallo-Proteases as Well as Tyrosine Phosphatases." *Tetrahedron.* 63.28(2007):6577-6586.
Fattori et al. "Drug-Eluting Stents in Vascular Intervention." *Lancet.* 361(2003):247-249.
Franceschi et al. "Structure-Based Drug Design Meets the Ribosome." *Biochem. Pharmacol.* 71(2006):1016-1025.
Gold et al. "Antimicrobial Drug Resistance." *N. Engl. J. Med.* 335. 19(1996):1445-1453.
Lowry. "Antimicrobial Resistance: The Example of *Staphylococcus aureus*." *J. Clin. Invest.* 111.9(2003):1265-1273.
Morice. "A New Era in the Treatment of Coronary Disease?" *Eur. Heart J.* 24(2003):209-211.
Ortega et al. "Binding Affinities of Oligonucleotides and PNAs Containing Phenoxazine and G-Clamp Cytosine Analogues are Unusually Sequence-Dependent." *Org. Lett.* 9.22(2007):4503-4506.
Rajeev et al. "High-Affinity Peptide Nucleic Acid Oligomers Containing Tricyclic Cytosine Analogues." *Org. Lett.* 4.25(2002):4395-4398.

(Continued)

*Primary Examiner* — Kahsay Habte
(74) *Attorney, Agent, or Firm* — Cooley LLP; Heidi A. Erlacher; Lian Ouyang

(57) ABSTRACT

The present invention relates generally to the field of antimicrobial compounds and to methods of making and using them. These compounds are useful for treating, preventing, and/or reducing the risk of microbial infections in humans and animals.

13 Claims, No Drawings

(56) References Cited

OTHER PUBLICATIONS

Ravin et al. "Preformulation." *Remington's Pharmaceutical Sciences.* Easton, PA: Mack Publishing Company. 18th ed. (1990):1435-1450.
Sanders et al. "Disease-Related Misassembly of Membrane Proteins." *Annu. Rev. Biophys. Biomol. Struct.* 33(2004):25-51.
Stoss et al. "Novel Pyrimidine and Pyrimido[1,2-*a*]pyrimidine Derivatives." *J. Heterocyclic Chem.* 28.2(1991):231-236.
Toutouzas et al. "Sirolimus-Eluting Stents: A Review of Experimental and Clinical Findings." *Z. Kardiol.* 91.3(2002):49-57.
PubChem Database No. 1112068, Jul. 10, 2005.
PubChem Database No. 23522053, Dec. 6, 2007.

* cited by examiner

ANTIMICROBIAL COMPOUNDS AND METHODS OF MAKING AND USING THE SAME

RELATED APPLICATIONS

This application is a national stage application, filed under 35 U.S.C. §371 of International Application No. PCT/US2010/052924 filed Oct. 15, 2010, which claims priority to U.S. Provisional Application No. 61/252,478 filed on Oct. 16, 2009; U.S. Provisional Application No. 61/314,287 filed on Mar. 16, 2010; and U.S. Provisional Application No. 61/358,201 filed on Jun. 24, 2010, the contents of which are hereby incorporated by reference in their entireties.

FIELD OF THE INVENTION

The present invention relates generally to the field of antimicrobial compounds and to methods of making and using them. These compounds are useful for treating, preventing, and reducing the risk of microbial infections in humans and animals.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. Resistant bacteria can cause serious and even fatal results for infected patients. See, e.g., Lowry, F. D. "Antimicrobial Resistance: The Example of *Staphylococcus aureus*," *J. Clin. Invest.*, vol. 111, no. 9, pp. 1265-1273 (2003); and Gold, H. S, and Moellering, R. C., Jr., "Antimicrobial-Drug Resistance," *N. Engl. J. Med.*, vol. 335, pp. 1445-53 (1996).

The discovery and development of new antibacterial agents has been for decades a major focus in many pharmaceutical companies. Nonetheless, in more recent years there has been an exodus of pharmaceutical companies from this area of research and drug development. As a consequence of this exodus, there have been very few new antibiotics entering the market. This lack of new antibiotics is particularly disturbing, especially at a time when bacterial resistance to current therapies is increasing both in the hospital and community settings.

In the search for new antibiotic agents, researchers have tried combining or linking various portions of antibiotic molecules to create multifunctional or hybrid compounds Other researchers have tried making derivatives of known classes of antibiotics, e.g., telithromycin, which is sold under the trade name Ketek®, is a derivative of erythromycin. However, these approaches have met with limited success.

An approach to developing new antimicrobial compounds is to design modulators, for example, inhibitors, of bacterial ribosome function. By modulating or inhibiting bacterial ribosome function such antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

The present invention utilizes a structure based drug design approach for discovering and developing new antimicrobial agents. This approach starts with the high resolution X-ray crystal of the ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present invention describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present invention can provide better activity, especially against resistant strains of bacteria, than current antibiotic compounds.

The present invention utilizes a structure based drug design approach for discovering and developing new antimicrobial agents. This approach starts with the high resolution X-ray crystal of the ribosome to design new classes of antimicrobial compounds having specific chemical structures, ribosome binding characteristics, and desired antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

The present invention therefore fills an important ongoing need for providing new antimicrobial agents, particularly for antimicrobial agents, having activity against resistant pathogenic bacterial organisms.

SUMMARY OF THE INVENTION

The present invention relates generally to the field of antimicrobial compounds and to methods of making and using them. These compounds are useful for treating, preventing, and reducing the risk of microbial infections in humans and animals. The present invention also provides pharmaceutically acceptable salts, esters, N-oxides, and prodrugs of these compounds.

The present invention provides compounds having the structure

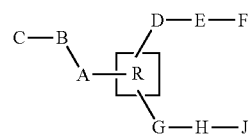

wherein

is a chemical moiety selected from:

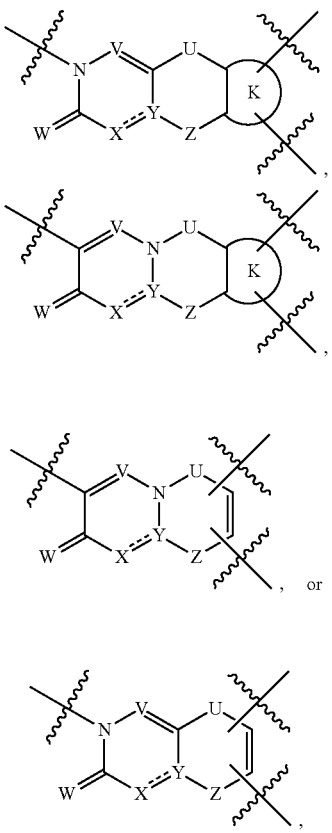

wherein U is selected from the group consisting of CR³R³, O, NR⁴, or S(O)$_n$, C=O, C=NOR³, alternatively, two R³s are taken together to form a carbonyl, V is independently selected from —CR$^{4a}$— or —N—; wherein

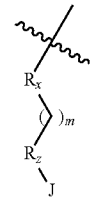

represents a fused 5 to 7 member saturated, unsaturated, or aromatic carbocyclic or heterocyclic ring system;

W is O, NR¹, NOR¹, or S, alternatively W= is selected from the combination of HO— and H— both attached to the same carbon atom or the combination of (C$_{1-8}$ alkyl)O— and H— both attached to the same carbon atom;

X= = =Y represents a single bond or a double bond such that when X= = =Y is a single bond, X is selected from O, NR², and S(O)$_n$ and Y is C—R³, and when X= = =Y is a double bond, X is N and Y is a carbon atom, Z is selected from the group consisting of O, NR⁴, or S(O)$_n$, R¹ is selected from H and C$_{1-8}$ alkyl, R² is selected from H and C$_{1-8}$ alkyl, R³ is selected from H and C$_{1-8}$ alkyl, R⁴ is selected from H and C$_{1-8}$ alkyl, R$^{4a}$ is selected from H and C$_{1-8}$ alkyl, n is 0, 1, or 2, alternatively, -G-H-J is selected from:

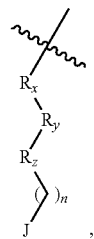

wherein R$_x$ is selected from CH₂, NH, N(C$_{1-8}$ alkyl), S, or O; R$_y$ and R$_z$ are C or CH each independently substituted with one or more F, CH₃, CF₃, OH, and OCH₃; or R$_x$, R$_y$, and R$_z$ are each independently selected from CH₂ or CR$^a$R$^b$, wherein R$^a$ and R$^b$ are taken together to form a C$_{1-5}$ carbocycle;

J is selected from NH₂, NH(C$_{1-8}$ alkyl), N(C$_{1-8}$ alkyl)₂, NHC(=O)CH₃, NHC(=O)NH₂, NHC(=NH)NH₂, NHC(=NH)H;

wherein n is 0, 1, or 2;

alternatively, -G-H-J is selected from wherein R$_x$ is selected from CH₂, NH, N(C$_{1-8}$ alkyl), S, or O; R$_z$ is a C or CH, substituted with one or more CH₃ or R$_z$ is CR$^a$R$^b$ wherein R$^a$ and R$^b$ are taken together to form a C$_{1-5}$ carbocycle, wherein m is 1, 2, or 3;

J is selected from NH₂, NH(C$_{1-8}$ alkyl), N(C$_{1-8}$ alkyl)₂, NHC(=O)CH₃, NHC(=O)NH₂, NHC(=NH)NH₂, NHC(=NH)H;

C-B-A, -D-E-F, and -G-H-J are chemical moieties, wherein A, D and G are independently selected from the group consisting of:

(a) a single bond, (b) —(C$_{1-8}$ alkyl)-, (c) —(C$_{2-8}$ alkenyl)-, (d) —(C$_{2-8}$ alkynyl)-, wherein
  i) 0-4 carbon atoms in any of (b)-(d) immediately above optionally is replaced by a moiety selected from the group consisting of —O—, —S(O)$_p$—, —NR⁶—, —(C=O)—, —S(O)$_p$NR⁶—, —NR⁶S(O)$_p$—, and —NR⁶S(O)$_p$NR⁶—,
  ii) any of (b)-(d) immediately above optionally is substituted with one or more R⁵ groups, and
  iii) any of (b)-(d) immediately above optionally is substituted with —(C$_{1-8}$ alkyl)-R⁵ groups;

(e) —O—, (f) —NR⁶—, (g) —S(O)$_p$—, (h) —C(O)—, (i) —C(O)O—, (j) —OC(O)—, k) —OC(O)O—, (l) —C(O)NR⁶—, (m) —NR⁶CO—, (n) —NR⁶C(O)NR⁶—, (o) —C(=NR⁶)—, (p) —C(=NR⁶)O—, (q) —OC(=NR⁶)—, (r) —C(=NR⁶)NR⁶—, (s) —NR⁶C(=NR⁶)—, (t) —C(=S)—, (u) —C(=S)NR⁶—, (v) —NR⁶C(=S)—, (w) —C(O)S—, (x) —SC(O)—, (y) —OC(=S)—, (z) —C(=S)O—, (aa) —NR⁶(CNR⁶)NR⁶—, (bb) —CR⁶R⁶C(O)—, (cc) —C(O)NR⁶(CR⁶R⁶)$_t$—, (dd) a 3-14 member saturated, unsaturated, or aromatic heterocycle containing one or more heteroatoms selected from the group consisting of nitrogen, oxygen, and sulfur,
  (ee) a 3-14 member saturated, unsaturated, or aromatic carbocycle, and
  (ff) —$(CR^6R^6)_t$—
wherein (dd) or (ee) is optionally substituted with one or more $R^5$ groups;
B, E, and H are independently selected from the group consisting of:
  (a) a single bond,
  (b) a 3-14 member saturated, unsaturated, or aromatic heterocycle containing one or more heteroatoms selected from the group consisting of nitrogen, oxygen, and sulfur,
  (c) a 3-14 member saturated, unsaturated, or aromatic carbocycle,
wherein (b) or (c) is optionally substituted with one or more $R^5$ groups;
  (d) —($C_{1-8}$ alkyl)-, (e) —($C_{2-8}$ alkenyl)-, (f) —($C_{2-8}$ alkynyl)-, wherein
    i) 0-4 carbon atoms in any of (d)-(f) immediately above optionally is replaced by a moiety selected from the group consisting of —O—, —S(O)$_p$—, —$NR^6$—, —(C=O)—, —C(=$NR^6$)—, —S(O)$_p NR^6$—, —$NR^6$S(O)$_p$—, and —$NR^6$S(O)$_p NR^6$—,
    ii) any of (d)-(f) immediately above optionally is substituted with one or more $R^5$ groups, and
    iii) any of (d)-(f) immediately above optionally is substituted with —($C_{1-8}$ alkyl)-$R^5$ groups;
and (g) —$(CR^6R^6)_t$—,
C, F, and J are independently selected from the group consisting of:
  (a) hydrogen, (c) F, (d) Cl, (e) Br, (f) I, (g) —$CF_3$, (h) —CN, (i) —$N_3$ (j) —$NO_2$, (k) —$NR^6(CR^6R^6)_t R^8$, (l) —$OR^8$, (m) —S(O)$_p(CR^6R^6)_t R^8$, (n) —C(O)($CR^6R^6$)$_t R^8$, (o) —OC(O)($CR^6R^6$)$_t R^8$, (p) —SC(O)($CR^6R^6$)$_t R^8$, (q) —C(O)O($CR^6R^6$)$_t R^8$, (r) —$NR^6$C(O)($CR^6R^6$)$_t R^8$, (s) —C(O)$NR^6$($CR^6R^6$)$_t R^8$, (t) —C(=$NR^6$)($CR^6R^6$)$_t R^8$, (u) —C(=$NNR^6R^6$)($CR^6R^6$)$_t R^8$, (v) —C(=$NNR^6$C(O)$R^6$)($CR^6R^6$)$_t R^8$, (w) —C(=$NOR^8$)($CR^6R^6$)$_t R^8$, (x) —$NR^6$C(O)O($CR^6R^6$)$_t R^8$, (y) —OC(O)$NR^6$($CR^6R^6$)$_t R^8$, (z) —$NR^6$C(O)$NR^6$($CR^6R^6$)$_t R^8$, (aa) —$NR^6$S(O)$_p$($CR^6R^6$)$_t R^8$, (bb) —S(O)$_p NR^6$($CR^6R^6$)$_t R^8$, (cc) —$NR^6$S(O)$_p NR^6$($CR^6R^6$)$_t R^8$, (dd) —$NR^6 R^8$, (ee) —$NR^6$($CR^6R^6$)$R^8$, (ff) —OH, (gg) —$NR^8 R^8$, (hh) —$OCH_3$, (ii) —S(O)$_p R^8$, (jj) —NC(O)$R^8$, (kk) —$NR^6$C($NR^6$)$NR^6 R^8$, (ll) a $C_{1-8}$ alkyl group, (mm) a $C_{2-8}$ alkenyl group, (nn) a $C_{2-8}$ alkynyl group, (oo) a 3-14 member saturated, unsaturated, or aromatic heterocycle containing one or more heteroatoms selected from the group consisting of nitrogen, oxygen, and sulfur, (pp) a 3-14 member saturated, unsaturated, or aromatic carbocycle, (qq) —($CR^6R^6$)$_t NR^6$($CR^6R^6$)$_t R^8$, (rr) —N[($CR^6R^6$)$_t R^8$][C=O($CR^6R^6$)$_t R^8$], (ss) —($CR^6R^6$)$_t$N[($CR^6R^6$)$_t R^8$][($CR^6R^6$)$_t R^8$], (tt) —($CR^6R^6$)$_t NR^6$(C=O)($CR^6R^6$)$_t R^8$, (uu) -haloalkyl, (vv) —C(O)($CR^6$)[($CR^6R^6$)$_t R^8$]$R^8$, (ww) —($CR^6R^6$)$_t$C(O)$NR^8 R^8$, (xx) —($CR^6R^6$)$_t$C(O)O($CR^6R^6$)$_t R^8$, (yy) —$NR^6$C(O)$CR^8 R^8$, (zz) —N[($CR^6R^6$)$_t R^8$]C(O)$R^8$, and (aaa) —S(O)$_p NR^8 R^8$,
wherein (ll) through (pp) is optionally substituted with one or more $R^7$ groups;
$R^5$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^8$, (l) —$NR^6$(C$NR^6$)$NR^6R^6$, (m) —$C_{1-8}$ alkyl, (n) —$C_{1-8}$ alkenyl, (o) —$C_{1-8}$ alkynyl, (p) —($C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -haloalkyl, (s) —$SR^6$, (t) -3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle; alternatively, two $R^5$ groups are taken together to form a carbocycle;
wherein (m) through (r) and (t) through (u) is optionally substituted with one or more $R^8$;
$R^6$ is selected from (a) hydrogen, (b) —$C_{1-8}$ alkyl or alternatively two $R^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle;
wherein (b) through (e) is optionally substituted with one or more $R^8$;
$R^7$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^6$, (l) —$NR^6$(C$NR^6$)$NR^6R^6$, (m) —$C_{1-8}$ alkyl, (n) —$C_{1-8}$ alkenyl, (o) —$C_{1-8}$ alkynyl, (p) —($C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -haloalkyl, (s) —$NR^6R^8$, (t) —$OR^8$, (u) —($CR^6R^6$)$_t NR^6R^8$ (v) —$CR^6R^8R^8$, (w) —$SR^6$, (x) -3-14 member saturated, unsaturated, or aromatic heterocycle containing one or more heteroatoms selected from the group consisting of nitrogen, oxygen, and sulfur, (y) -3-14 member saturated, unsaturated, or aromatic carbocycle, (z) —($CR^6R^6$)$_t$C(O)$NR^8R^8$, (aa) —S(O)$_p R^8$, (bb) —$NR^6$C(O)$NR^6R^6$, (cc) —$NR^6$C(O)$R^6$, and (dd) —C(=$NR^6$)$NR^6R^6$;
wherein (m) through (q) and (x) through (y) are optionally substituted with one or more $R^9$;
$R^8$ is selected from (a) hydrogen, (b) F, (c) Cl, (d) Br, (e) I, (f) —$CF_3$, (g) —CN, (h) —$N_3$ (i) —$NO_2$, (j) —$NR^6R^9$, (k) —$OR^9$, (l) —$NR^6$(C$NR^6$)$NR^6R^6$, (m) —$C_{1-8}$ alkyl, (n) —$C_{1-8}$ alkenyl, (o) —$C_{1-8}$ alkynyl, (p) —($C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -3-14 member saturated, unsaturated, or aromatic heterocycle containing one or more heteroatoms selected from the group consisting of nitrogen, oxygen, and sulfur, (s) -3-14 member saturated, unsaturated, or aromatic carbocycle, (t) -haloalkyl, (u) —C(O)($CR^6R^6$)$_t R^9$, (v) —$SR^6$, (w) —OC(O)($CR^6R^6$)$_t R^9$, (x) —$NR^6$C(O)$NR^6R^9$, (y) —$NR^6$C(O)$R_9$, (z) —$NR^6$(C$NR^9$)($NR^6R^6$), (aa) —$ONR^6$(C$NR^6$)$NR^6R^6$, (bb) —C(=$NR^9$)$NR^6R^6$, (cc) —S(O)$_p R^9$, (dd) —($CR^6R^6$)$_t$C(O)$NR^6R^9$, (ee) —($CR^6R^6$)$_t OR^9$, and (ff) —($CR^6R^6$)$_t NR^6R^9$;
wherein (m) through (s) is optionally substituted with one or more $R^9$;
$R^9$ is selected from (a) hydrogen, (b) F, (c) Cl, (d) Br, (e) I, (f) —$CF_3$, (g) —CN, (h) —$N_3$ (i) —$NO_2$, (j) —$NR^6R^{10}$, (k) —$OR^6$, (l) —$NR^6$(C$NR^6$)$NR^6R^6$, (m) —C(O)($CR^6R^6$)$_t NR^6R^6$, (n) —$C_{1-8}$ alkyl, (o) —$C_{1-8}$ alkenyl, (p) —$C_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —$(CR^6R^6)_tOR^6$, (u) —$O(CR^6R^6)_tNR^6R^{10}$, (v) —$C(O)R^6$, (w) —$SR^6$, (x) —$C(O)OR^{10}$, (y) —$S(O)_pR^6$, (z) —$(C_{1-8}$ alkyl)-(3-14 member saturated, unsaturated, or aromatic heterocycle containing one or more heteroatoms selected from the group consisting of nitrogen, oxygen, and sulfur), (aa) —$(C_{1-8}$ alkyl)-(3-14 member saturated, unsaturated, or aromatic carbocycle), (bb) —$O(CR^6R^6)_tOR^6$, (cc) —$C(=NR^6)NR^6R^6$, (dd) —$ONR^6R^6$, (ee) —$NR^6C(O)NR^6R^6$, (ff) —$O(CR^6R^6)_tOR^6$, (gg) —$NR^6C(O)R^6$, and (hh) —$(CR^6R^6)_tNR^6R^{10}$;

wherein (n) through (r) and (z) through (aa) is optionally substituted with one or more $R^{10}$;

$R^{10}$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^6$, (l) —$NR^6(CNR^6)NR^6R^6$, (m) —$C(O)(CR^6R^6)_tNR^6R^6$, (n) —$C_{1-8}$ alkyl, (o) —$C_{1-8}$ alkenyl, (p) —$C_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —$(CR^6R^6)_tOR^6$, (u) —$O(CR^6R^6)_tNR^6R^6$, (v) —$C(O)R^6$, (w) —$SR^6$, (x) —$C(O)OR^6$, (y) —$S(O)_pR^6$, (z) —$(C_{1-8}$ alkyl)-(3-14 member saturated, unsaturated, or aromatic heterocycle containing one or more heteroatoms selected from the group consisting of nitrogen, oxygen, and sulfur), (aa) —$(C_{1-8}$ alkyl)-(3-14 member saturated, unsaturated, or aromatic carbocycle), (bb) —$O(CR^6R^6)_tOR^6$, (cc) —$C(=NR^6)NR^6R^6$, (dd) —$ONR^6R^6$, (ee) —$NR^6C(O)NR^6R^6$, (ff) —$O(CR^6R^6)_tOR^6$, (gg) —$NR^6C(O)R^6$, and (hh) —$(CR^6R^6)_tNR^6R^6$;

optionally, wherein either the group -D-E-F or the group -G-H-J is absent (e.g., the group D-E-F or the group -G-H-J represents hydrogen), but both -D-E-F and -G-H-J are not simultaneously absent;

p is 0, 1, or 2, and t is 0, 1, 2, or 3, or a pharmaceutically acceptable salt, ester, tautomer, or prodrug thereof.

In addition, the invention provides methods of synthesizing the foregoing compounds. Following synthesis, a therapeutically effective amount of one or more of the compounds can be formulated with a pharmaceutically acceptable carrier for administration to a human or animal for use as antimicrobial agents, particularly as antibacterial agents. In certain embodiments, the compounds of the present invention are useful for treating, preventing, or reducing the risk of microbial infections or for the manufacture of a medicament for treating, preventing, or reducing the risk of microbial infections. Accordingly, the compounds or the formulations can be administered, for example, via oral, parenteral, otic, ophthalmic, nasal, or topical routes, to provide an effective amount of the compound to the human or animal.

The foregoing and other aspects and embodiments of the invention can be more fully understood by reference to the following detailed description and claims.

DETAILED DESCRIPTION OF THE INVENTION

The present invention provides a family of compounds that can be used as antimicrobial agents, more particularly as antibacterial agents.

The present invention includes pharmaceutically acceptable salts, esters, tautomers, N-oxides, and prodrugs thereof.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with one or more $R^6$ moieties, then $R^6$ at each occurrence is selected independently from the definition of $R^6$. Also, combinations of substituents and/or variables are permissible, but only if such combinations result in stable compounds within a designated atom's normal valency.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein there are nitrogen atoms in the compounds of the present invention, these, where appropriate, can be converted to N-oxides by treatment with an oxidizing agent (e.g., MCPBA and/or hydrogen peroxides). Thus, shown and claimed nitrogen atoms are considered to cover both the shown nitrogen and its N-oxide (N→O) derivative, as appropriate.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al.

(2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e. the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. Definitions

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomers" refers to compounds whose structures differ markedly in arrangement of atoms, but which exist in easy and rapid equilibrium. It is to be understood that compounds of the present invention may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. An example below is included for illustrative purposes, and the present invention is not limited to this example:

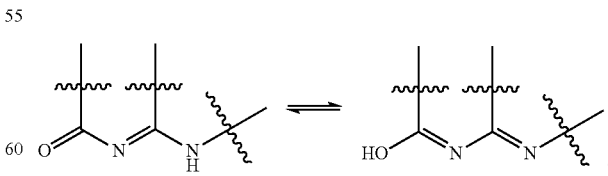

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, N=N, etc.).

As used herein, the term "anomeric carbon" means the acetal carbon of a glycoside.

As used herein, the term "glycoside" is a cyclic acetal.

As used herein, "alkyl" is intended to include both branched and straight-chain saturated aliphatic hydrocarbon groups having the specified number of carbon atoms. For example $C_{1-6}$ alkyl is intended to include $C_1$, $C_2$, $C_3$, $C_4$, $C_5$, and $C_6$ alkyl groups. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example $C_{2-6}$ alkenyl is intended to include $C_2$, $C_3$, $C_4$, $C_5$, and $C_6$ alkenyl groups.

As used herein, "alkynyl" is intended to include hydrocarbon chains of either straight or branched configuration and one or more triple carbon-carbon bonds that can occur in any stable point along the chain, such as ethynyl and propynyl. For example, $C_{2-6}$ alkynyl is intended to include $C_2$, $C_3$, $C_4$, $C_5$, and $C_6$ alkynyl groups.

Furthermore, "alkyl", "alkenyl", and "alkynyl" are intended to include moieties which are diradicals, i.e., having two points of attachment, an example of which in the present invention is when D is selected from these chemical groups. A nonlimiting example of such an alkyl moiety that is a diradical is —CH$_2$CH$_2$—, i.e., a $C_2$ alkyl group that is covalently bonded via each terminal carbon atom to the remainder of the molecule. The alkyl diradicals are also known as "alkylenyl" radicals. The alkenyl diradicals are also known as "alkenylenyl" radicals. The alkynyl diradicals are also known as "alkynylenyl" radicals.

As used herein, "cycloalkyl" is intended to include saturated ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups.

As used herein "counterion" is used to mean a positively or negatively charged species present in conjunction with an ion of opposite charge. A nonlimiting example of a counterion is an ion or ions present to counterbalance the charge or charges on an organic compound. Nonlimiting examples of counterions include chloride, bromide, hydroxide, acetate, sulfate, and ammonium.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with 1 or more halogen (for example —C$_v$F$_w$ wherein v=1 to 3 and w=1 to (2v+1)). Examples of haloalkyl include, but are not limited to, trifluoromethyl, trichloromethyl, pentafluoroethyl, and pentachloroethyl.

As used herein, "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-6}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through a sulfur bridge. $C_{1-6}$ alkylthio, is intended to include $C_1$, $C_2$, $C_3$, $C_4$, $C_5$, and $C_6$ alkylthio groups. $C_{1-6}$ alkylthio, is intended to include $C_1$, $C_2$, $C_3$, $C_4$, $C_5$, $C_6$, $C_7$, and $C_8$ alkylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

As used herein, the term "heterocycle" means, unless otherwise stated, a stable 3, 4, 5, 6, 7, 8, 9, 10, 11, or 12-membered monocyclic, bicyclic or tricyclic ring which is saturated, unsaturated (including partially and fully unsaturated), or aromatic, and consists of carbon atoms and one or more ring heteroatoms, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused or attached to a second ring (e.g., a benzene ring). The nitrogen and sulfur heteroatoms can optionally be oxidized (i.e., N→O and S(O)$_p$, wherein p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocyclic ring can be attached to its pendant group at any heteroatom or carbon atom that results in a stable structure. The heterocyclic rings described herein can be substituted on carbon or on a nitrogen atom if the resulting compound is stable. A nitrogen in the heterocycle can optionally be quaternized. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. When a ring is bridged, the substituents recited for the ring can also be present on the bridge. Spiro and fused rings are also included.

As used herein, the term "aromatic heterocycle" or "heteroaryl" is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S $(O)_p$, wherein p=1 or 2). In certain compounds, the total number of S and O atoms in the aromatic heterocycle is not more than 1.

Examples of heterocycles include, but are not limited to, acridinyl, azabicyclooctanonyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzodioxoly, benzooxadiazoly, carbazolyl, 4aH-carbazolyl, carbolinyl, chromanyl, chromenyl, cinnolinyl, cycloheptyl, decahydroquinolinyl, dihydrobenzodioxinyl, 2H,6H-1,5,2-dithiazinyl, dihydrofuro[2,3-b]tetrahydrofuran, furanyl, furazanyl, imidazolidinyl, imidazolidinylimine, imidazolinyl, imidazolyl, imidazolonyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, methylbenztriazoly, methylfuranyl, methylimidazolyl, methylthiazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinonyl, oxazolyl, oxindolyl, phenanthridinyl, phenanthrolinyl, phenazinyl, phenothiazinyl, phenoxathinyl, phenoxazinyl, phthalazinyl, piperazinyl, piperazinonyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazolyl, pyridothiazolyl, pyridinyl, pyridinonyl, pyridyl, pyrimidinyl, pyrroldionyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, thiomorpholinyldioxidyl, triazinyl, triazolopyrimidinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

As used herein, "stable compound" and "stable structure" are meant to indicate a compound that is sufficiently robust to survive isolation to a useful degree of purity from a reaction mixture, and formulation into an efficacious therapeutic agent.

As used herein, the term "patient", as used herein, means the human or animal (in the case of an animal, more typically a mammal) subject that would be subjected to a surgical or invasive medical procedure. Such patient or subject could be considered to be in need of the methods of reducing the risk of or preventing the infection due to a surgical procedure or an invasive medical procedure. Such patient or subject can also be considered to be in need of peri-operative prophylaxis.

As used herein, the term "treating" means to provide a therapeutic intervention to cure or ameliorate an infection.

As used herein, the term "preventing", as used herein means, to completely or almost completely stop an infection from occurring, for example when the patient or subject is predisposed to an infection or at risk of contracting an infection. Preventing can also include inhibiting, i.e. arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound, or a combination of compounds, of the present invention effective when administered alone or in combination as an antimicrobial agent. For example, an effective amount refers to an amount of the compound present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an effective amount of a compound or compounds, of the present invention that is administered to prevent or reduce the risk of an infection due to a surgical procedure or an invasive medical procedure.

It is to be further understood that the representations for "Hydrogen Bond Acceptor—Hydrogen Bond Acceptor—Hydrogen Bond Donor" and "Hydrogen Bond Acceptor—Hydrogen Bond Acceptor—Hydrogen Bond Acceptor" are meant to indicate the relative orientation of the hydrogen bond acceptors and donor and not meant to limit that such groups are directly connected together as it is contemplated that additional atoms or groups of atoms can be included between such groups.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control. As used herein, "mammal" refers to human and non-human patients.

As used herein, the term "therapeutically effective amount" refers to a compound, or a combination of compounds, of the present invention present in or on a recipient in an amount sufficient to elicit biological activity, for example, anti-microbial activity, anti-fungal activity, anti-viral activity, anti-parasitic activity, anti-diarrheal activity, and/or anti-proliferative activity. The combination of compounds is preferably a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

As used herein, the term "RNA microhelix binding site" refers to the ribofunctional locus of the large ribosomal subunit occupied by the RNA microhelix of Formula III. The RNA microhelix binding site defines at least a portion of or overlaps with the E-site.

As used herein, the term "A-site" refers to the ribofunctional locus occupied by an aminoacyl-tRNA molecule immediately prior to its participation in the peptide-bond forming reaction.

As used herein, the term "E-site" refers to the ribofunctional locus occupied by a deacylated tRNA molecule following its participation in the peptide-bond forming reaction.

As used herein, the term "P-site" refers to the ribofunctional locus occupied by a peptidyl-tRNA at the time it participates in the peptide-bond forming reaction.

As used herein, the term "A-space" refers to the portion of the A-site within the peptidyl transferase center in which the amino acid portion of the aminoacylated t-RNA binds, or alternatively the portion of the A-site in which the oxazolidinone ring of linezolid binds.

As used herein and in reference to a ribosome or ribosomal subunit, the terms "a portion of" or "a portion of the three-dimensional structure of" are understood to mean a portion of the three-dimensional structure of a ribosome or ribosomal subunit, including charge distribution and hydrophilicity/hydrophobicity characteristics, formed by at least three, more preferably at least three to ten, and most preferably at least ten amino acid residues and/or nucleotide residues of the ribosome or ribosomal subunit. The residues forming such a portion can be, for example, (i) contiguous residues based upon, for example, a primary sequence of a ribosomal RNA or ribosomal protein, (ii) residues which form a contiguous portion of the three-dimensional structure of the ribosome or ribosomal subunit, or (c) a combination thereof. As used herein and in reference to the RNA microhelix, the terms "a portion of" or "a portion of the three-dimensional structure of" are understood to mean a portion of the three-dimensional structure of RNA microhelix, including charge distribution and hydrophilicity/hydrophobicity characteristics, formed by at least three, more preferably at least three to ten atoms of one or more core residues of Formula III. The atoms forming such a portion can be, for example, (i) solvent inaccessible atoms buried within the core of the RNA microhelix, (ii) solvent accessible atoms of the RNA microhelix, or (iii) a combination thereof.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

2. Compounds of the Invention

In one aspect, the invention relates to a compound having the structure:

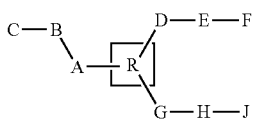

wherein

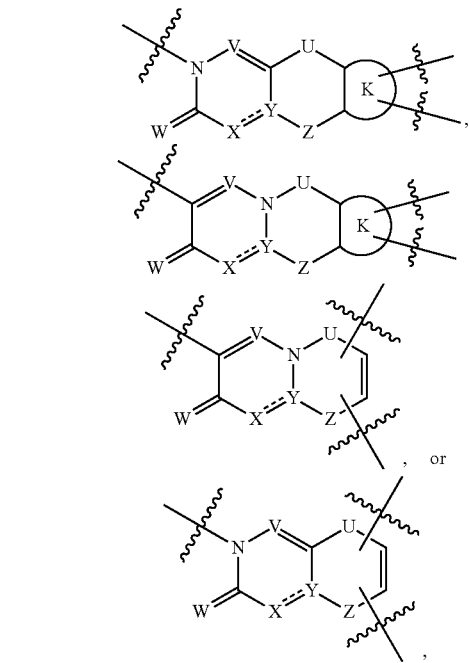

is a chemical moiety selected from:

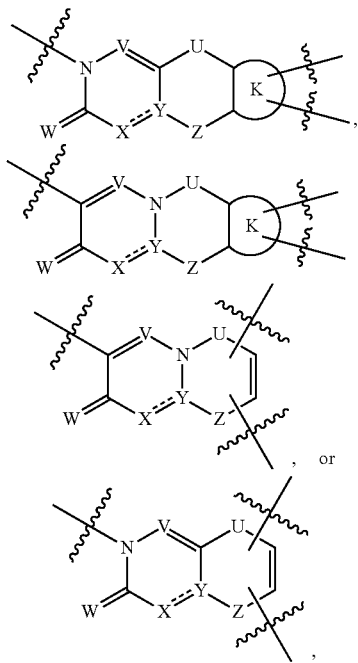, or

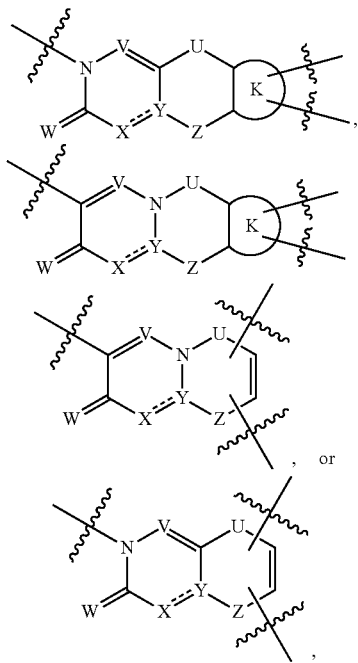, wherein U is selected from the group consisting of $CR^3R^3$, O, $NR^4$, or $S(O)_n$, C=O, C=$NOR^3$, alternatively, two $R^3$s are taken together to form a carbonyl, V is independently selected from —$CR^{4a}$— or —N—;
wherein

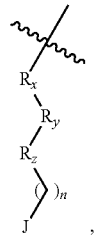

represents a fused 5 to 7 member saturated, unsaturated, or aromatic carbocyclic or heterocyclic ring system;

W is O, $NR^1$, $NOR^1$, or S, alternatively W= is selected from the combination of HO— and H— both attached to the same carbon atom or the combination of ($C_{1-8}$ alkyl)O— and H— both attached to the same carbon atom;

X═══Y represents a single bond or a double bond such that when X═══Y is a single bond, X is selected from O, $NR^2$, and $S(O)_n$ and Y is C—$R^3$, and when X═══Y is a double bond, X is N and Y is a carbon atom, Z is selected from the group consisting of O, $NR^4$, or $S(O)_n$, $R^1$ is selected from H and $C_{1-8}$ alkyl,
$R^2$ is selected from H and $C_{1-8}$ alkyl,
$R^3$ is selected from H and $C_{1-8}$ alkyl,
$R^4$ is selected from H and $C_{1-8}$ alkyl,
$R^{4a}$ is selected from H and $C_{1-8}$ alkyl,
n is 0, 1, or 2,
alternatively, -G-H-J is selected from:

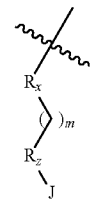, wherein $R_x$ is selected from $CH_2$, NH, N($C_{1-8}$ alkyl), S, or O; $R_y$ and $R_z$ are C or CH each independently substituted with one or more F, $CH_3$, $CF_3$, OH, and $OCH_3$; or $R_x$, $R_y$, and $R_z$ are each independently selected from $CH_2$ or $CR^aR^b$ wherein $R^a$ and $R^b$ are taken together to form a $C_{1-5}$ carbocycle;

J is selected from $NH_2$, NH($C_{1-8}$ alkyl), N($C_{1-8}$ alkyl)$_2$, NHC(=O)$CH_3$, NHC(=O)$NH_2$, NHC(=NH)$NH_2$, NHC(=NH)H;

wherein n is 0, 1, or 2;
alternatively, -G-H-J is selected from

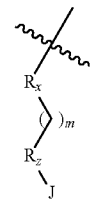

wherein $R_x$ is selected from $CH_2$, NH, N($C_{1-8}$ alkyl), S, or O; $R_z$ is a C or CH, substituted with one or more $CH_3$ or $R_z$ is $CR^aR^b$ wherein $R^a$ and $R^b$ are taken together to form a $C_{1-5}$ carbocycle, wherein m is 1, 2, or 3;

J is selected from $NH_2$, NH($C_{1-8}$ alkyl), N($C_{1-8}$ alkyl)$_2$, NHC(=O)$CH_3$, NHC(=O)$NH_2$, NHC(=NH)$NH_2$, NHC(=NH)H;

C-B-A, D-E-F, and -G-H-J are chemical moieties, wherein
A, D and G are independently selected from the group consisting of:

(a) a single bond, (b) —($C_{1-8}$ alkyl)-, (c) —($C_{2-8}$ alkenyl)-, (d) —($C_{2-8}$ alkynyl)-, wherein
  i) 0-4 carbon atoms in any of (b)-(d) immediately above optionally is replaced by a moiety selected from the group consisting of —O—, —$S(O)_p$—, —$NR^6$—, —(C=O)—, —$S(O)_pNR^6$—, —$NR^6S(O)_p$—, and —$NR^6S(O)_pNR^6$—,
  ii) any of (b)-(d) immediately above optionally is substituted with one or more $R^5$ groups, and
  iii) any of (b)-(d) immediately above optionally is substituted with —($C_{1-8}$ alkyl)-$R^5$ groups;

(e) —O—, (f) —$NR^6$—, (g) —$S(O)_p$—, (h) —C(O)—, (i) —C(O)O—, (j) —OC(O)—, k) —OC(O)O—, (l) —C(O)$NR^6$—, (m) —$NR^6$CO—, (n) —$NR^6$C(O)$NR^6$—, (o) —C(=$NR^6$)—, (p) —C(=$NR^6$)O—, (q) —OC(=$NR^6$)—, (r) —C(=$NR^6$)$NR^6$—, (s) —$NR^6$C(=$NR^6$)—, (t) —C(=S)—, (u) —C(=S)$NR^6$—, (v) —$NR^6$C(=S)—, (w) —C(O)S—, (x) —SC(O)—, (y)

—OC(=S)—, (z) —C(=S)O—, (aa) —NR$^6$(CNR$^6$)NR$^6$—, (bb) —CR$^6$R$^6$C(O)—, (cc) —C(O)NR$^6$(CR$^6$R$^6$)$_t$—, (dd) a 3-14 member saturated, unsaturated, or aromatic heterocycle containing one or more heteroatoms selected from the group consisting of nitrogen, oxygen, and sulfur, (ee) a 3-14 member saturated, unsaturated, or aromatic carbocycle, and (ff) —(CR$^6$R$^6$)$_t$— wherein (dd) or (ee) is optionally substituted with one or more R$^5$ groups;

B, E, and H are independently selected from the group consisting of:
(a) a single bond,
(b) a 3-14 member saturated, unsaturated, or aromatic heterocycle containing one or more heteroatoms selected from the group consisting of nitrogen, oxygen, and sulfur,
(c) a 3-14 member saturated, unsaturated, or aromatic carbocycle,
wherein (b) or (c) is optionally substituted with one or more R$^5$ groups;
(d) —(C$_{1-8}$ alkyl)-, (e) —(C$_{2-8}$ alkenyl)-, (f) —(C$_{2-8}$ alkynyl)-, wherein
  i) 0-4 carbon atoms in any of (d)-(f) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—,
  ii) any of (d)-(f) immediately above optionally is substituted with one or more R$^5$ groups, and
  iii) any of (d)-(f) immediately above optionally is substituted with —(C$_{1-8}$ alkyl)-R$^5$ groups;
and (g) —(CR$^6$R$^6$)$_t$—

C, F, and J are independently selected from the group consisting of:
(a) hydrogen, (c) F, (d) Cl, (e) Br, (f) I, (g) —CF$_3$, (h) —CN, (i) —N$_3$ (j) —NO$_2$, (k) —NR$^6$(CR$^6$R$^6$)$_t$R$^8$, (l) —OR$^8$, (m) —S(O)$_p$(CR$^6$R$^6$)$_t$R$^8$, (n) —C(O)(CR$^6$R$^6$)$_t$R$^8$, (o) —OC(O)(CR$^6$R$^6$)$_t$R$^8$, (p) —SC(O)(CR$^6$R$^6$)$_t$R$^8$, (q) —C(O)O(CR$^6$R$^6$)$_t$R$^8$, (r) —NR$^6$C(O)(CR$^6$R$^6$)$_t$R$^8$, (s) —C(O)NR$^6$(CR$^6$R$^6$)$_t$R$^8$, (t) —C(=NR$^6$)(CR$^6$R$^6$)$_t$R$^8$, (u) —C(=NNR$^6$R$^6$)(CR$^6$R$^6$)$_t$R$^8$, (v) —C(=NNR$^6$C(O)R$^6$)(CR$^6$R$^6$)$_t$R$^8$, (w) —C(=NOR$^8$)(CR$^6$R$^6$)$_t$R$^8$, (x) —NR$^6$C(O)O(CR$^6$R$^6$)$_t$R$^8$, (y) —OC(O)NR$^6$(CR$^6$R$^6$)$_t$R$^8$, (z) —NR$^6$C(O)NR$^6$(CR$^6$R$^6$)$_t$R$^8$, (aa) —NR$^6$S(O)$_p$(CR$^6$R$^6$)$_t$R$^8$, (bb) —S(O)$_p$NR$^6$(CR$^6$R$^6$)$_t$R$^8$, (cc) —NR$^6$S(O)$_p$NR$^6$(CR$^6$R$^6$)$_t$R$^8$, (dd) —NR$^6$R$^8$, (ee) —NR$^6$(CR$^6$R$^6$)$_t$R$^8$, (ff) —OH, (gg) —NR$^8$R$^8$, (hh) —OCH$_3$, (ii) —S(O)$_p$R$^8$, (jj) —NC(O)R$^8$, (kk) —NR$^6$C(NR$^6$)NR$^6$R$^8$, (ll) a C$_{1-8}$ alkyl group, (mm) a C$_{2-8}$ alkenyl group, (nn) a C$_{2-8}$alkynyl group, (oo) a 3-14 member saturated, unsaturated, or aromatic heterocycle containing one or more heteroatoms selected from the group consisting of nitrogen, oxygen, and sulfur, (pp) a 3-14 member saturated, unsaturated, or aromatic carbocycle, (qq) —(CR$^6$R$^6$)$_t$NR$^6$(CR$^6$R$^6$)$_t$R$^8$, (rr) —N[(CR$^6$R$^6$)$_t$R$^8$][C=O(CR$^6$R$^6$)$_t$R$^8$], (ss) —(CR$^6$R$^6$)$_t$N[(CR$^6$R$^6$)$_t$R$^8$][(CR$^6$R$^6$)$_t$R$^8$], (tt) —(CR$^6$R$^6$)$_t$NR$^6$(C=O)(CR$^6$R$^6$)$_t$R$^8$, (uu) —haloalkyl, (vv) —C(O)(CR$^6$)[(CR$^6$R$^6$)$_t$R$^8$]R$^8$, (ww) —(CR$^6$R$^6$)$_t$C(O)NR$^8$R$^8$, (xx) —(CR$^6$R$^6$)$_t$C(O)O(CR$^6$R$^6$)$_t$R$^8$, (yy) —NR$^6$C(O)CR$^8$R$^8$R$^8$, (zz) —N[(CR$^6$R$^6$)$_t$R$^8$]C(O)R$^8$, and (aaa) —S(O)$_p$NR$^8$R$^8$;

wherein (ll) through (pp) is optionally substituted with one or more R$^7$ groups;

R$^5$ is selected from (a) hydrogen, (b) F, (c) Cl, (d) Br, (e) I, (f) —CF$_3$, (g) —CN, (h) —N$_3$ (i) —NO$_2$, (j) —NR$^6$R$^6$, (k) —OR$^8$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) —(C$_{1-8}$ alkyl)-(3-14 member saturated, unsaturated, or aromatic heterocycle containing one or more heteroatoms selected from the group consisting of nitrogen, oxygen, and sulfur), (q) —(C$_{1-8}$ alkyl)-(3-14 member saturated, unsaturated, or aromatic carbocycle), (r) -haloalkyl, (s) —SR$^6$, (t) —3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle; alternatively, two R$^5$ groups are taken together to form a carbocycle;

wherein (m) through (r) and (t) through (u) is optionally substituted with one or more R$^8$;

R$^6$ is selected from (a) hydrogen, (b) —C$_{1-8}$ alkyl or alternatively two R$^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle;

wherein (b) through (e) is optionally substituted with one or more R$^8$;

R$^7$ is selected from (a) hydrogen, (b) F, (c) Cl, (d) Br, (e) I, (f) —CF$_3$, (g) —CN, (h) —N$_3$ (i) —NO$_2$, (j) —NR$^6$R$^6$, (k) —OR$^6$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) —(C$_{1-8}$ alkyl)-(3-14 member saturated, unsaturated, or aromatic heterocycle containing one or more heteroatoms selected from the group consisting of nitrogen, oxygen, and sulfur), (q) —(C$_{1-8}$ alkyl)-(3-14 member saturated, unsaturated, or aromatic carbocycle), (r) -haloalkyl, (s) —NR$^6$R$^8$, (t) —OR$^8$, (u) —(CR$^6$R$^6$)$_t$NR$^6$R$^8$, (v) —CR$^6$R$^8$R$^8$, (w) —SR$^6$, (x) -3-14 member saturated, unsaturated, or aromatic heterocycle containing one or more heteroatoms selected from the group consisting of nitrogen, oxygen, and sulfur, (y) -3-14 member saturated, unsaturated, or aromatic carbocycle, (z) —(CR$^6$R$^6$)$_t$C(O)NR$^8$R$^8$, (aa) —S(O)$_p$R$^8$, (bb) —NR$^6$C(O)NR$^6$R$^6$, (cc) —NR$^6$C(O)R$^6$, and (dd) —C(=NR$^6$)NR$^6$R$^6$;

wherein (m) through (q) and (x) through (y) are optionally substituted with one or more R$^9$;

R$^8$ is selected from (a) hydrogen, (b) F, (c) Cl, (d) Br, (e) I, (f) —CF$_3$, (g) —CN, (h) —N$_3$ (i) —NO$_2$, (j) —NR$^6$R$^9$, (k) —OR$^9$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) —(C$_{1-8}$ alkyl)-(3-14 member saturated, unsaturated, or aromatic heterocycle containing one or more heteroatoms selected from the group consisting of nitrogen, oxygen, and sulfur), (q) —(C$_{1-8}$ alkyl)-(3-14 member saturated, unsaturated, or aromatic carbocycle), (r) -3-14 member saturated, unsaturated, or aromatic heterocycle containing one or more heteroatoms selected from the group consisting of nitrogen, oxygen, and sulfur, (s) -3-14 member saturated, unsaturated, or aromatic carbocycle, (t) -haloalkyl, (u) —C(O)(CR$^6$R$^6$)$_t$R$^9$, (v) —SR$^6$, (w) —OC(O)(CR$^6$R$^6$)$_t$R$^9$, (x) —NR$^6$C(O)NR$^6$R$^9$, (y) —NR$^6$C(O)R$^9$, (z) —NR$^6$(CNR$^9$)(NR$^6$R$^6$), (aa) —ONR$^6$(CNR$^6$)NR$^6$R$^6$, (bb) —C(=NR$^9$)NR$^6$R$^6$, (cc) —S(O)$_p$R$^9$, (dd) —(CR$^6$R$^6$)$_t$C(O)NR$^6$R$^9$, (ee) —(CR$^6$R$^6$)$_t$OR$^9$, and (ff) —(CR$^6$R$^6$)$_t$NR$^6$R$^9$;

wherein (m) through (s) is optionally substituted with one or more R$^9$;

R$^9$ is selected from (a) hydrogen, (b) F, (c) Cl, (d) Br, (e) I, (f) —CF$_3$, (g) —CN, (h) —N$_3$ (i) —NO$_2$, (j) —NR$^6$R$^{10}$, (k)

—OR⁶, (l) —NR⁶(CNR⁶)NR⁶R⁶, (m) —C(O)(CR⁶R⁶)$_t$ NR⁶R⁶, (n) —C$_{1-8}$ alkyl, (o) —C$_{1-8}$ alkenyl, (p) —C$_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —(CR⁶R⁶)$_t$OR⁶, (u) —O(CR⁶R⁶)$_t$NR⁶R¹⁰, (v) —C(O)R⁶, (w) —SR⁶, (x) —C(O)OR¹⁰, (y) —S(O)$_p$R⁶, (z) —(C$_{1-8}$ alkyl)-(3-14 member saturated, unsaturated, or aromatic heterocycle containing one or more heteroatoms selected from the group consisting of nitrogen, oxygen, and sulfur), (aa) —(C$_{1-8}$ alkyl)-(3-14 member saturated, unsaturated, or aromatic carbocycle), (bb) —O(CR⁶R⁶)$_t$OR⁶, (cc) —C(=NR⁶)NR⁶R⁶, (dd) —ONR⁶R⁶, (ee) —NR⁶C(O) NR⁶R⁶, (ff) —O(CR⁶R⁶)$_t$OR⁶, (gg) —NR⁶C(O)R⁶, and (hh) —(CR⁶R⁶)$_t$NR⁶R¹⁰;

wherein (n) through (r) and (z) through (aa) is optionally substituted with one or more R¹⁰;

R¹⁰ is selected from (a) hydrogen, (b) F, (c) Cl, (d) Br, (e) I, (f) —CF₃, (g) —CN, (h) —N₃ (i) —NO₂, (j) —NR⁶R⁶, (k) —OR⁶, (l) —NR⁶(CNR⁶)NR⁶R⁶, (m) —C(O)(CR⁶R⁶)$_t$ NR⁶R⁶ (n) —C$_{1-8}$ alkyl, (o) —C$_{1-8}$ alkenyl, (p) —C$_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t)—(CR⁶R⁶)$_t$OR⁶, (u) —O(CR⁶R⁶)$_t$NR⁶R⁶, (v) —C(O)R⁶, (w) —SR⁶, (x) —C(O)OR⁶, (y) —S(O)$_p$R⁶, (z) —(C$_{1-8}$ alkyl)-(3-14 member saturated, unsaturated, or aromatic heterocycle containing one or more heteroatoms selected from the group consisting of nitrogen, oxygen, and sulfur), (aa) —(C$_{1-8}$ alkyl)-(3-14 member saturated, unsaturated, or aromatic carbocycle), (bb) —O(CR⁶R⁶)$_t$OR⁶, (cc) —C(=NR⁶)NR⁶R⁶, (dd) —ONR⁶R⁶, (ee) —NR⁶C(O) NR⁶R⁶, (ff) —O(CR⁶R⁶)$_t$OR⁶, (gg) NR⁶C(O)R⁶, and (hh) —(CR⁶R⁶)$_t$NR⁶R⁶;

optionally, wherein either the group -D-E-F or the group -G-H-J is absent, but both -D-E-F and -G-H-J are not simultaneously absent;

p is 0, 1, or 2, and t is 0, 1, 2, or 3, or a pharmaceutically acceptable salt, ester, tautomer, or pro-drug thereof.

In some embodiments, the present invention relates to a compound or a pharmaceutically acceptable salt, ester, tautomer, or pro-drug thereof, wherein $$\boxed{R}$$

further comprises a hydrogen bond donor moiety or an additional hydrogen bond acceptor moiety.

In some embodiments, the present invention relates to a compound or a pharmaceutically acceptable salt, ester, tautomer, or pro-drug thereof, wherein $$\boxed{R}$$

is a chemical moiety comprising at least two hydrogen bond acceptor moieties and at least one hydrogen bond donor moiety.

In some embodiments, the present invention relates to a compound or a pharmaceutically acceptable salt, ester, tautomer, or pro-drug thereof, wherein the hydrogen bond acceptor moieties and hydrogen bond donor moieties are in the orientation of Hydrogen Bond Acceptor—Hydrogen Bond Acceptor—Hydrogen Bond Donor. As used above the term "in the orientation of" does not mean that the hydrogen bond donor or acceptor moieties are necessarily directly connected together as there can be other intervening atoms or groups of atoms in between the hydrogen bond donor or acceptor moieties.

In some embodiments, the present invention relates to a compound or a pharmaceutically acceptable salt, ester, tautomer, or pro-drug thereof, wherein the hydrogen bond acceptor moieties are within 5 Å of each other and the hydrogen bond donor moiety is within 5 Å of a hydrogen bond acceptor moiety.

In some embodiments, the present invention relates to a compound or a pharmaceutically acceptable salt, ester, tautomer, or pro-drug thereof, wherein the hydrogen bond acceptor moieties are within 3 Å of each other and the hydrogen bond donor moiety is within 3 Å of a hydrogen bond acceptor moiety.

In some embodiments, the present invention relates to a compound or a pharmaceutically acceptable salt, ester, tautomer, or pro-drug thereof, wherein the hydrogen bond acceptor moieties are comprised within a ring structure, wherein said ring structure is a single ring structure or a fused multiple ring structure.

In some embodiments, the present invention relates to a compound or a pharmaceutically acceptable salt, ester, tautomer, or pro-drug thereof, wherein $$\boxed{R}$$

is a chemical moiety comprising at least three hydrogen bond acceptor moieties.

In some embodiments, the present invention relates to a compound or a pharmaceutically acceptable salt, ester, tautomer, or pro-drug thereof, wherein the hydrogen bond acceptor moieties are in the orientation of Hydrogen Bond Acceptor—Hydrogen Bond Acceptor—Hydrogen Bond Acceptor. As used above the term "in the orientation of" does not mean that the hydrogen bond donor or acceptor moieties are necessarily directly connected together as there can be other intervening atoms or groups of atoms in between the hydrogen bond acceptor moieties.

In some embodiments, the present invention relates to a compound or a pharmaceutically acceptable salt, ester, tautomer, or pro-drug thereof, wherein each hydrogen bond acceptor moiety is within about 5 Å of at least one other hydrogen bond acceptor moiety.

In some embodiments, the present invention relates to a compound or a pharmaceutically acceptable salt, ester, tautomer, or pro-drug thereof, wherein each hydrogen bond acceptor moiety is within about 3 Å of at least one other hydrogen bond acceptor moiety.

In some embodiments, the present invention relates to a compound or a pharmaceutically acceptable salt, ester, tautomer, or pro-drug thereof, wherein at least two of the hydrogen bond acceptor moieties are comprised within a ring structure, wherein said ring structure is a single ring structure or a fused multiple ring structure.

In some embodiments, the present invention relates to a compound or a pharmaceutically acceptable salt, ester, tautomer, or pro-drug thereof, wherein said hydrogen bond acceptor moieties are independently selected from the group consisting of a carbonyl group, a thiocarbonyl group, an imine group, an alkyl substituted imine group, a sulfoxide group, a sulfone group, an oxime group, an alkyl substituted oxime group, a hydrazone group, a monoalkyl or dialkyl substituted hydrazone group, an oxygen ether (—O—) group, a sulfide, also known as a thioether group (—S—), a hydroxy group, an alkoxy group, an amino group, a monoalkyl or dialkyl substituted amino group, and a nitro group.

In some embodiments, the present invention relates to a compound of a pharmaceutically acceptable salt, ester, tautomer, or pro-drug thereof, wherein said hydrogen bond donor moiety is selected from the group consisting of a hydroxy group, a thiol group, an amino group, and a monosubstituted amino group.

In some embodiments, the present invention relates to a compound or a pharmaceutically acceptable salt, ester, tautomer, or pro-drug thereof, wherein

R comprises the structural moiety

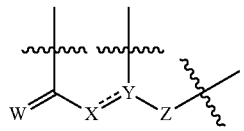

W is O, $NR^1$, $NOR^1$, or S, alternatively W= is selected from the combination of HO— and H— both attached to the same carbon atom or the combination of ($C_{1-8}$ alkyl)O— and H— both attached to the same carbon atom;

X═══Y represents a single bond or a double bond such that when X═══Y is a single bond, X is selected from O, $NR^2$, and $S(O)_n$ and Y is C—$R^3$, and when X═══Y is a double bond, X is N and Y is a carbon atom, Z is selected from the group consisting of O, $NR^4$, or $S(O)_n$, $R^1$ is selected from H and $C_{1-8}$ alkyl, $R^2$ is selected from H and $C_{1-8}$ alkyl, $R^3$ is selected from H and $C_{1-8}$ alkyl, $R^4$ is selected from H and $C_{1-8}$ alkyl, n is 0, 1, or 2.

In some embodiments, the present invention relates to a compound or a pharmaceutically acceptable salt, ester, tautomer, or pro-drug thereof, wherein W is O, $NR^1$, $NOR^1$, or S; wherein $R^1$ is selected from H and $C_{1-6}$ alkyl.

In some embodiments, the present invention relates to a compound or a pharmaceutically acceptable salt, ester, tautomer, or pro-drug thereof, wherein

R comprises the structural moiety

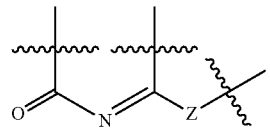

wherein Z is selected from the group consisting of O, $NR^4$, or $S(O)_n$;

$R^4$ is selected from H and $C_{1-6}$ alkyl, and n is 0, 1, and 2.

In some embodiments, the present invention relates to a compound or a pharmaceutically acceptable salt, ester, tautomer, or pro-drug thereof, wherein

R comprises the structural moiety

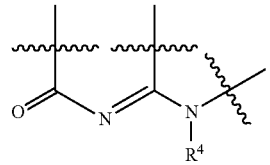

wherein $R^4$ is selected from H and $C_{1-6}$ alkyl.

In some embodiments, the present invention relates to a compound or a pharmaceutically acceptable salt, ester, tautomer, or pro-drug thereof, wherein $R^4$ is H.

In some embodiments, the present invention relates to a compound or a pharmaceutically acceptable salt, ester, tautomer, or pro-drug thereof, wherein

R comprises a cytosine or isocytosine moiety or a derivative thereof.

In some embodiments, the present invention relates to a compound or a pharmaceutically acceptable salt, ester, tautomer, or pro-drug thereof, wherein

R comprises the structural moiety

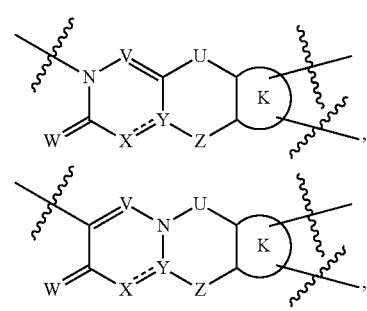

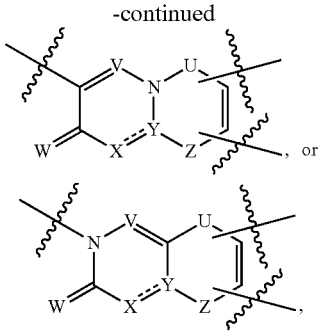, or

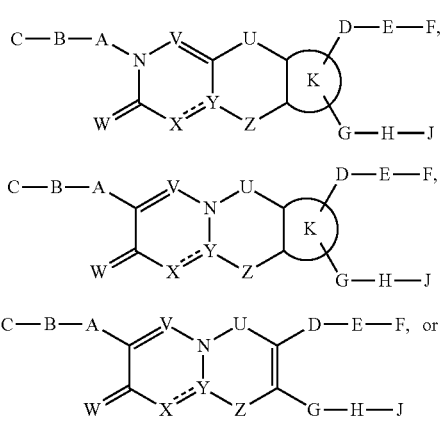

wherein U is selected from the group consisting of $CR^3R^3$, O, $NR^4$, or $S(O)_n$, C=O, C=$NOR^3$, alternatively, two $R^3$s are taken together to form a carbonyl, V is independently selected from —$CR^{4a}$— or —N—;

wherein

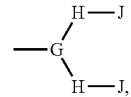

represents a fused 5 to 7 member saturated, unsaturated, or aromatic carbocyclic or heterocyclic ring system;

W is O, $NR^1$, $NOR^1$, or S, alternatively W= is selected from the combination of HO— and H— both attached to the same carbon atom or the combination of $(C_{1-8}$ alkyl)O— and H— both attached to the same carbon atom;

X⁼⁼⁼Y represents a single bond or a double bond such that when X⁼⁼⁼Y is a single bond, X is selected from O, $NR^2$, and $S(O)_n$ and Y is C—$R^3$, and when X⁼⁼⁼Y is a double bond, X is N and Y is a carbon atom, Z is selected from the group consisting of O, $NR^4$, or $S(O)_n$, $R^1$ is selected from H and $C_{1-8}$ alkyl, $R^2$ is selected from H and $C_{1-8}$ alkyl, $R^3$ is selected from H and $C_{1-8}$ alkyl, $R^4$ is selected from H and $C_{1-8}$ alkyl, $R^{4a}$ is selected from H and $C_{1-8}$ alkyl, n is 0, 1, or 2.

In some embodiments, the present invention relates to a compound having the formula:

(I)

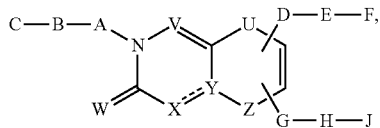

(II)

(III)

(IV)

wherein U is selected from the group consisting of $CR^3R^3$, O, $NR^4$, or $S(O)_n$, C=O, C=$NOR^3$, alternatively, two $R^3$s are taken together to form a carbonyl, V is independently selected from —$CR^{4a}$— or —N—;

wherein represents a fused 5 to 7 member saturated, unsaturated, or aromatic carbocyclic or heterocyclic ring system;

W is O, $NR^1$, $NOR^1$, or S, alternatively W= is selected from the combination of HO— and H— both attached to the same carbon atom or the combination of $(C_{1-8}$ alkyl)O— and H— both attached to the same carbon atom;

X⁼⁼⁼Y represents a single bond or a double bond such that when X⁼⁼⁼Y is a single bond, X is selected from O, $NR^2$, and $S(O)_n$ and Y is C—$R^3$, and when X⁼⁼⁼Y is a double bond, X is N and Y is a carbon atom, Z is selected from the group consisting of O, $NR^4$, or $S(O)_n$, $R^1$ is selected from H and $C_{1-8}$ alkyl, $R^2$ is selected from H and $C_{1-8}$ alkyl, $R^3$ is selected from H and $C_{1-8}$ alkyl, $R^4$ is selected from H and $C_{1-8}$ alkyl, $R^{4a}$ is selected from H and $C_{1-8}$ alkyl, n is 0, 1, or 2, alternatively, -G-H-J is selected from $$-G\begin{matrix}H-J\\H-J,\end{matrix}$$

wherein each H and J are independently selected, alternatively, -G-H-J is selected from:

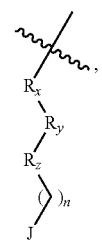

wherein $R_x$ is selected from $CH_2$, NH, N($C_{1-8}$ alkyl), S, or O;

$R_y$ and $R_z$ are C or CH each independently substituted with one or more F, $CH_3$, $CF_3$, OH, and $OCH_3$; or $R_x$, $R_y$, and $R_z$, are each independently selected from $CH_2$ or $CR^aR^b$ wherein $R^a$ and $R^b$ are taken together to form a $C_{1-5}$ carbocycle;

J is selected from $NH_2$, NH($C_{1-8}$ alkyl), N($C_{1-8}$ alkyl)$_2$, NHC(=O)$CH_3$, NHC(=O)$NH_2$, NHC(=NH)$NH_2$, NHC(=NH)H;

wherein n is 0, 1, or 2;
alternatively, -G-H-J is selected from

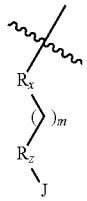

wherein $R_x$ is selected from $CH_2$, NH, $N(C_{1-8}$ alkyl), S, or O; $R_z$ is C or CH, substituted with one or more $CH_3$ or $R_z$ is $CR^aR^b$ wherein $R^a$ and $R^b$ are taken together to form a $C_{1-5}$ carbocycle,
wherein m is 1, 2, or 3;
J is selected from $NH_2$, $NH(C_{1-8}$ alkyl), $N(C_{1-8}$ alkyl)$_2$, $NHC(=O)CH_3$, $NHC(=O)NH_2$, $NHC(=NH)NH_2$, $NHC(=NH)H$;
C-B-A-, -D-E-F, and -G-H-J are chemical moieties, wherein A, D and G are independently selected from the group consisting of:
(a) a single bond, (b) —$(C_{1-8}$ alkyl)-, (c) —$(C_{2-8}$ alkenyl)-, (d) —$(C_{2-8}$ alkynyl)-, wherein
  i) 0-4 carbon atoms in any of (b)-(d) immediately above optionally is replaced by a moiety selected from the group consisting of —O—, —$S(O)_p$—, —$NR^6$—, —(C=O)—, —$S(O)_pNR^6$—, —$NR^6S(O)_p$—, and —$NR^6S(O)_pNR^6$—,
  ii) any of (b)-(d) immediately above optionally is substituted with one or more $R^5$ groups, and
  iii) any of (b)-(d) immediately above optionally is substituted with —$(C_{1-8}$ alkyl)-$R^5$ groups;
(e) —O—, (f) —$NR^6$—, (g) —$S(O)_p$—, (h) —C(O)—, (i) —C(O)O—, (j) —OC(O)—, (k) —OC(O)O—, (l) —$C(O)NR^6$—, (m) —$NR^6CO$—, (n) —$NR^6C(O)NR^6$—, (o) —$C(=NR^6)$—, (p) —$C(=NR^6)O$—, (q) —$OC(=NR^6)$—, (r) —$C(=NR^6)NR^6$—, (s) —$NR^6C(=NR^6)$—, (t) —C(=S)—, (u) —$C(=S)NR^6$—, (v) —$NR^6C(=S)$—, (w) —C(O)S—, (x) —SC(O)—, (y) —OC(=S)—, (z) —C(=S)O—, (aa) —$NR^6(CNR^6)NR^6$—, (bb) —$CR^6R^6C(O)$—, (cc) —$C(O)NR^6(CR^6R^6)_t$—, (dd) a 3-14 member saturated, unsaturated, or aromatic heterocycle containing one or more heteroatoms selected from the group consisting of nitrogen, oxygen, and sulfur, (ee) a 3-14 member saturated, unsaturated, or aromatic carbocycle, and (ff) —$(CR^6R^6)_t$—,
wherein (dd) or (ee) is optionally substituted with one or more $R^5$ groups;
B, E, and H are independently selected from the group consisting of:
(a) a single bond,
(b) a 3-14 member saturated, unsaturated, or aromatic heterocycle containing one or more heteroatoms selected from the group consisting of nitrogen, oxygen, and sulfur,
(c) a 3-14 member saturated, unsaturated, or aromatic carbocycle,
wherein (b) or (c) is optionally substituted with one or more $R^5$ groups;
(d) —$(C_{1-8}$ alkyl)-, (e) —$(C_{2-8}$ alkenyl)-, (f) —$(C_{2-8}$ alkynyl)-, wherein
  i) 0-4 carbon atoms in any of (d)-(f) immediately above optionally is replaced by a moiety selected from the group consisting of —O—, —$S(O)_p$—, —$NR^6$—, —(C=O)—, —$C(=NR^6)$—, —$S(O)_pNR^6$—, —$NR^6S(O)_p$—, and —$NR^6S(O)_pNR^6$—,
  ii) any of (d)-(f) immediately above optionally is substituted with one or more $R^5$ groups, and
  iii) any of (d)-(f) immediately above optionally is substituted with —$(C_{1-8}$ alkyl)-$R^5$ groups;
and (g) —$(CR^6R^6)_t$—,
C, F, and J are independently selected from the group consisting of:
(a) hydrogen, (c) F, (d) Cl, (e) Br, (f) I, (g) —$CF_3$, (h) —CN, (i) —$N_3$ (j) —$NO_2$, (k) —$NR^6(CR^6R^6)_tR^8$, (l) —$OR^8$, (m) —$S(O)_p(CR^6R^6)_tR^8$, (n) —$C(O)(CR^6R^6)_tR^8$, (o) —$OC(O)(CR^6R^6)_tR^8$, (p) —$SC(O)(CR^6R^6)_tR^8$, (q) —$C(O)O(CR^6R^6)_tR^8$, (r) —$NR^6C(O)(CR^6R^6)_tR^8$, (s) —$C(O)NR^6(CR^6R^6)_tR^8$, (t) —$C(=NR^6)(CR^6R^6)_tR^8$, (u) —$C(=NNR^6R^6)(CR^6R^6)_tR^8$, (v) —$C(=NNR^6C(O)R^6)(CR^6R^6)_tR^8$, (w) —$C(=NOR^8)(CR^6R^6)_tR^8$, (x) —$NR^6C(O)O(CR^6R^6)_tR^8$, (y) —$OC(O)NR^6(CR^6R^6)_tR^8$, (z) —$NR^6C(O)NR^6(CR^6R^6)_tR^8$, (aa) —$NR^6S(O)_p(CR^6R^6)_tR^8$, (bb) —$S(O)_pNR^6(CR^6R^6)_tR^8$, (cc) —$NR^6S(O)_pNR^6(CR^6R^6)_tR^8$, (dd) —$NR^6R^8$, (ee) —$NR^6(CR^6R^6)R^8$, (ff) —OH, (gg) —$NR^8R^8$, (hh) —$OCH_3$, (ii) —$S(O)_pR^8$, (jj) —$NC(O)R^8$, (kk) —$NR^6C(NR^6)NR^6R^8$, (ll) a $C_{1-8}$ alkyl group, (mm) a $C_{2-8}$ alkenyl group, (nn) a $C_{2-8}$ alkynyl group, (oo) a 3-14 member saturated, unsaturated, or aromatic heterocycle containing one or more heteroatoms selected from the group consisting of nitrogen, oxygen, and sulfur, (pp) a 3-14 member saturated, unsaturated, or aromatic carbocycle, (qq) —$(CR^6R^6)_tNR^6(CR^6R^6)_tR^8$, (rr) —$N[(CR^6R^6)_tR^8][C=O(CR^6R^6)_tR^8]$, (ss) —$(CR^6R^6)_tN[(CR^6R^6)_tR^8][(CR^6R^6)_tR^8]$, (tt) —$(CR^6R^6)_tNR^6(C=O)(CR^6R^6)_tR^8$, (uu) —haloalkyl, (vv) —$C(O)(CR^6)[(CR^6R^6)_tR^8]R^8$, (ww) —$(CR^6R^6)_tC(O)NR^8R^8$, (xx) —$(CR^6R^6)_tC(O)O(CR^6R^6)_tR^8$, (yy) —$NR^6C(O)CR^8R^8R^8$, (zz) —$N[(CR^6R^6)_tR^8]C(O)R^8$, and (aaa) —$S(O)_pNR^8R^8$;
wherein (ll) through (pp) is optionally substituted with one or more $R^7$ groups;
$R^5$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^8$, (l) —$NR^6(CNR^6)NR^6R^6$, (m) —$C_{1-8}$ alkyl, (n) —$C_{1-8}$ alkenyl, (o) —$C_{1-8}$ alkynyl, (p) —$(C_{1-8}$ alkyl)-(3-14 member saturated, unsaturated, or aromatic heterocycle containing one or more heteroatoms selected from the group consisting of nitrogen, oxygen, and sulfur), (q) —$(C_{1-8}$ alkyl)-(3-14 member saturated, unsaturated, or aromatic carbocycle), (r) -haloalkyl, (s) —$SR^6$, (t) -3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle;
wherein (m) through (r) and (t) through (u) is optionally substituted with one or more $R^8$;
$R^6$ is selected from (a) hydrogen, (b) —$C_{1-8}$ alkyl or alternatively two $R^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle;
wherein (b) through (e) is optionally substituted with one or more $R^8$;
$R^7$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^6$, (l) —$NR^6(CNR^6)NR^6R^6$, (m) —$C_{1-8}$ alkyl, (n) —$C_{1-8}$ alkenyl, (o) —$C_{1-8}$ alkynyl, (p) —$(C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -haloalkyl, (s) —$NR^6R^8$, (t) —$OR^8$, (u) —$(CR^6R^6)_tNR^6R^8$, (v) —$CR^6R^8R^8$, (w) —$SR^6$, (x) -3-14 member saturated, unsaturated, or aromatic heterocycle containing one or more heteroatoms selected from the group consisting of nitrogen, oxygen, and sulfur, (y) -3-14 member saturated, unsaturated, or aromatic carbocycle, (z) —$(CR^6R^6)_tC(O)NR^8R^8$, (aa) —$S(O)_pR^8$, (bb) —$NR^6C(O)NR^6R^6$, (cc) —$NR^6C(O)R^6$, and (dd) —$C(=NR^6)NR^6R^6$;

wherein (m) through (q) and (x) through (y) are optionally substituted with one or more $R^9$;

$R^8$ is selected from (a) hydrogen, (b) F, (c) Cl, (d) Br, (e) I, (f) —$CF_3$, (g) —CN, (h) —$N_3$ (i) —$NO_2$, (j) —$NR^6R^9$, (k) —$OR^9$, (l) —$NR^6(CNR^6)NR^6R^6$, (m) —$C_{1-8}$ alkyl, (n) —$C_{1-8}$ alkenyl, (o) —$C_{1-8}$ alkynyl, (p) —($C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -3-14 member saturated, unsaturated, or aromatic heterocycle containing one or more heteroatoms selected from the group consisting of nitrogen, oxygen, and sulfur, (s) -3-14 member saturated, unsaturated, or aromatic carbocycle, (t) -haloalkyl, (u) —$C(O)(CR^6R^6)_tR^9$, (v) —$SR^6$, (w) —$OC(O)(CR^6R^6)_tR^9$, (x) —$NR^6C(O)NR^6R^9$, (y) —$NR^6C(O)R^9$, (z) —$NR^6(CNR^9)(NR^6R^6)$, (aa) —$ONR^6(CNR^6)NR^6R^6$, (bb) —$C(=NR^9)NR^6R^6$, (cc) —$S(O)_pR^9$, (dd) —$(CR^6R^6)_tC(O)NR^6R^9$, (ee) —$(CR^6R^6)_tOR^9$, and (ff) —$(CR^6R^6)_tNR^6R^9$;

wherein (m) through (s) is optionally substituted with one or more $R^9$;

$R^9$ is selected from (a) hydrogen, (b) F, (c) Cl, (d) Br, (e) I, (f) —$CF_3$, (g) —CN, (h) —$N_3$ (i) —$NO_2$, (j) —$NR^6R^{10}$, (k) $OR^6$, (l) —$NR^6(CNR^6)NR^6R^6$, (m) —$C(O)(CR^6R^6)_tNR^6R^6$, (n) —$C_{1-8}$ alkyl, (o) —$C_{1-8}$ alkenyl, (p) —$C_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —$(CR^6R^6)_tOR^6$, (u) —$O(CR^6R^6)_tNR^6R^{10}$, (v) —$C(O)R^6$, (w) —$SR^6$, (x) —$C(O)OR^{10}$, (y) —$S(O)_pR^6$, (z) —($C_{1-8}$ alkyl)-(3-14 member saturated, unsaturated, or aromatic heterocycle containing one or more heteroatoms selected from the group consisting of nitrogen, oxygen, and sulfur), (aa) —($C_{1-8}$ alkyl)-(3-14 member saturated, unsaturated, or aromatic carbocycle), (bb) —$O(CR^6R^6)_tOR^6$, (cc) —$C(=NR^6)NR^6R^6$, (dd) —$ONR^6R^6$, (ee) —$NR^6C(O)NR^6R^6$, (ff) —$O(CR^6R^6)_tOR^6$, (gg) —$NR^6C(O)R^6$, and (hh) —$(CR^6R^6)_tNR^6R^{10}$;

wherein (n) through (r) and (z) through (aa) is optionally substituted with one or more $R^{10}$;

$R^{10}$ is selected from (a) hydrogen, (b) F, (c) Cl, (d) Br, (e) I, (f) —$CF_3$, (g) —CN, (h) —$N_3$ (i) —$NO_2$, (j) —$NR^6R^6$, (k) —$OR^6$, (l) —$NR^6(CNR^6)NR^6R^6$, (m) —$C(O)(CR^6R^6)_tNR^6R^6$, (n) —$C_{1-8}$ alkyl, (o) —$C_{1-8}$ alkenyl, (p) —$C_{1-8}$ alkynyl, (q) -3-14 member saturated, unsaturated, or aromatic heterocycle containing one or more heteroatoms selected from the group consisting of nitrogen, oxygen, and sulfur), (aa) —($C_{1-8}$ alkyl)-(3-14 member saturated, unsaturated, or aromatic carbocycle), (bb) —$O(CR^6R^6)_tOR^6$, (cc) —$C(=NR^6)NR^6R^6$, (dd) —$ONR^6R^6$, (ee) —$NR^6C(O)NR^6R^6$, (ff) —$O(CR^6R^6)_tOR^6$, (gg) —$NR^6C(O)R^6$, and (hh) —$(CR^6R^6)_tNR^6R^6$;

optionally, wherein either the group -D-E-F or the group -G-H-J is absent, but both -D-E-F and -G-H-J are not simultaneously absent;

p is 0, 1, or 2, and t is 0, 1, 2, or 3, or a pharmaceutically acceptable salt, ester, tautomer, or prodrug thereof.

In some embodiments, the present invention relates to a compound according to formula I, II, III, IV, V, VI, VII, or VIII, wherein A is selected from (a) a 3-14 member saturated, unsaturated, or aromatic heterocycle containing one or more heteroatoms selected from the group consisting of nitrogen, oxygen, and sulfur, and (b) a 3-14 member saturated, unsaturated, or aromatic carbocycle, (c) a single bond, wherein (a) or (b) is optionally substituted with one or more $R^5$ groups;

B is selected from (a) —($C_{1-8}$ alkyl)-, (b) —($C_{2-8}$ alkenyl)-, (c) —($C_{2-8}$ alkynyl)-, (d) a single bond, wherein i) 0-4 carbon atoms in any of (a)-(c) immediately above optionally is replaced by a moiety selected from the group consisting of —O—, —$S(O)_p$—, —$NR^6$—, —$(C=O)$—, —$C(=NR^6)$—, —$S(O)_pNR^6$—, and —$NR^6S(O)_pNR^6$—, ii) any of (a)-(c) immediately above optionally is substituted with one or more $R^5$ groups, and iii) any of (a)-(c) immediately above optionally is substituted with —($C_{1-8}$ alkyl)-$R^5$ groups, and C is selected from (a) $NH_2$, (b) —$NHC(=NH)NH_2$ and (c) hydrogen, or a pharmaceutically acceptable salt, ester, tautomer, or prodrug thereof.

In some embodiments, the present invention relates to a compound according to formula I, II, III, IV, V, VI, VII, or VIII, wherein A is selected from (a) a 4-7 member saturated, unsaturated, or aromatic heterocycle containing one or more heteroatoms selected from the group consisting of nitrogen, oxygen, and sulfur, and (b) a 4-7 member saturated, unsaturated, or aromatic carbocycle, (c) a single bond, wherein (a) or (b) is optionally substituted with one or more $R^5$ groups;

or a pharmaceutically acceptable salt, ester, tautomer, or prodrug thereof.

In some embodiments, the present invention relates to a compound according to formula I, II, III, IV, V, VI, VII, or VIII, wherein A is selected from azepanyl, cyclobutyl, cyclopentyl, cyclohexyl, cycloheptyl, phenyl, pyridinyl, cyclohexenyl, cyclohexadienyl, dihydropyridyl, furanyl, tetrahydrofuranyl, tetrahydropyridyl, azetidinyl, pyrrolidinyl, piperidinyl and piperidenyl;

wherein any of A immediately above optionally is substituted with one or more $R^5$ groups;

alternatively, A is a single bond;

B is selected from (a) —($C_{1-8}$ alkyl)-, wherein i) 0-4 carbon atoms in (a) immediately above optionally is replaced by a moiety selected from the group consisting of —O—, —S(O)$_p$—, —NR$^6$—, —(C=O)—, —S(O)$_p$NR$^6$—, and —NR$^6$S(O)$_p$NR$^6$—, ii) (a) immediately above optionally is substituted with one or more R$^5$ groups, and iii) (a) immediately above optionally is substituted with —(C$_{1-8}$ alkyl)-R$^5$ groups; and alternatively, B is a single bond;

C is selected from (a) NH$_2$, (b) —NHC(=NH)NH$_2$ and (c) hydrogen;

or a pharmaceutically acceptable salt, ester, tautomer, or prodrug thereof.

In some embodiments, the present invention relates to a compound according to formula I, II, III, IV, V, VI, VII, or VIII, G is selected from (a) a single bond, (b) —(C$_{1-8}$ alkyl)-, (c) —(C$_{2-8}$ alkenyl)-, (d) —(C$_{2-8}$ alkynyl)-, wherein
  i) 0-4 carbon atoms in any of (b)-(d) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—,
  ii) any of (b)-(d) immediately above optionally is substituted with one or more R$^5$ groups, and
  iii) any of (b)-(d) immediately above optionally is substituted with —(C$_{1-8}$ alkyl)-R$^5$ groups;

(e) a 3-14 member saturated, unsaturated, or aromatic heterocycle containing one or more heteroatoms selected from the group consisting of nitrogen, oxygen, and sulfur, and (f) a 3-14 member saturated, unsaturated, or aromatic carbocycle, wherein (e) or (f) is optionally substituted with one or more R$^5$ groups;

or a pharmaceutically acceptable salt, ester, tautomer, or prodrug thereof.

In some embodiments, the present invention relates to a compound according to formula I, II, III, IV, V, VI, VII, or VIII, G selected from (a) a single bond, (b) —(C$_{1-8}$ (c) —(C$_{2-8}$ alkenyl)-, (d) —(C$_{2-8}$ alkynyl)-, wherein
  i) 0-4 carbon atoms in any of (b)-(d) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—,
  ii) any of (b)-(d) immediately above optionally is substituted with one or more R$^5$ groups, and
  iii) any of (b)-(d) immediately above optionally is substituted with —(C$_{1-8}$ alkyl)-R$^5$ groups;

wherein p is 0, 1, or 2, or a pharmaceutically acceptable salt, ester, tautomer, or prodrug thereof.

In some embodiments, the present invention relates to a compound according to formula I, II, III, IV, V, VI, VII, or VIII, wherein

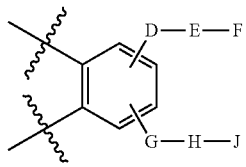

is selected from:

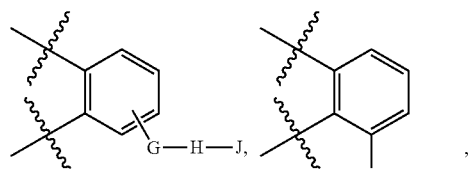

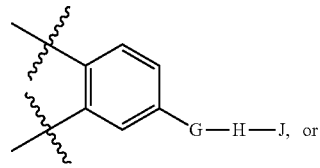

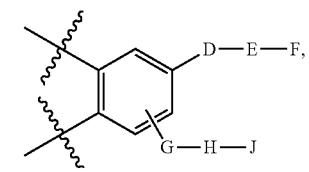

or a pharmaceutically acceptable salt, ester, tautomer, or prodrug thereof.

In some embodiments, the present invention relates to a compound according to formula I, II, III, IV, V, VI, VII, or VIII, wherein

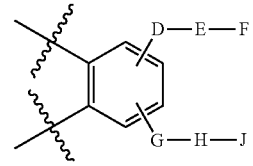

is selected from

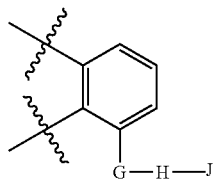

or a pharmaceutically acceptable salt, ester, tautomer, or prodrug thereof.

In some embodiments, the present invention relates to a compound according to formula I, II, III, IV, V, VI, VII, or VIII, wherein -G-H-J is selected from:

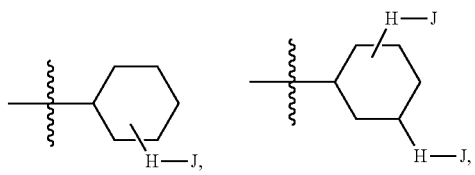

-continued

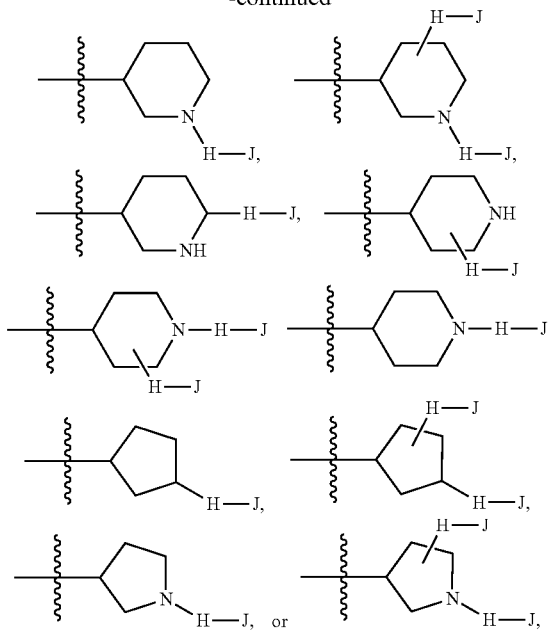

or a pharmaceutically acceptable salt, ester, tautomer, or prodrug thereof.

In some embodiments, the present invention relates to a compound having the formula:

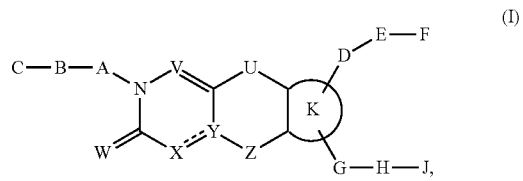

(I)

wherein C-B-A-, -D-E-F, -G-H-J, K, U, V, W, X, Y, and Z are as defined in formula (I) immediately above, or a pharmaceutically acceptable salt, ester, tautomer, or prodrug thereof.

In some embodiments, the present invention relates to a compound or a pharmaceutically acceptable salt, ester, tautomer, or pro-drug thereof, wherein

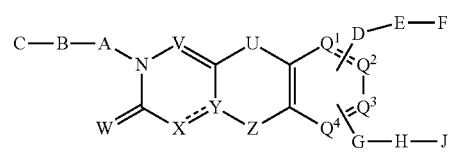

represents a fused six member saturated, unsaturated or aromatic carbocyclic or heterocyclic ring system.

In some embodiments, the present invention relates to a compound having the formula:

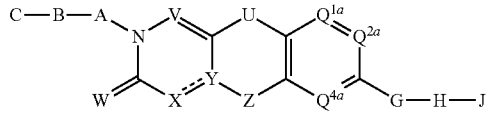

wherein C-B-A-, -D-E-F, -G-H-J, U, V, W, X, Y, and Z are as defined in formula (I),
wherein $Q^1$, $Q^2$, $Q^3$, and $Q^4$ are independently selected from a nitrogen atom, a carbon atom, or CH, wherein -D-E-F or -G-H-J, when it is present, is attached to a carbon, or a pharmaceutically acceptable salt, ester, tautomer, or pro-drug thereof.

In some embodiments, the present invention relates to a compound having the formula:

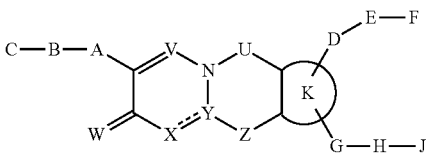

wherein C-B-A-, -G-H-J, U, V, W, X, Y, and Z are as defined in formula (I),
wherein $Q^{1a}$; $Q^{2a}$, and $Q^{4a}$ are independently selected from a nitrogen atom, a carbon atom, or CH, or a pharmaceutically acceptable salt, ester, tautomer, or prodrug thereof.

In some embodiments, the present invention relates to a compound having the formula:

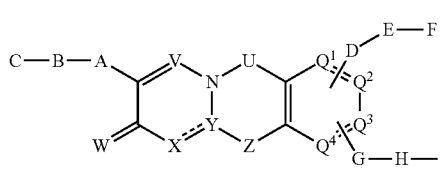

wherein C-B-A-, -D-E-F, -G-H-J, U, V, W, X, Y, and Z are as defined in formula (II), or a pharmaceutically acceptable salt, ester, tautomer, or pro-drug thereof.

In some embodiments, the present invention relates to a compound or a pharmaceutically acceptable salt, ester, tautomer, or pro-drug thereof, wherein (K)

represents a fused six membered saturated, unsaturated or aromatic carbocyclic or heterocyclic ring system.

In some embodiments, the present invention relates to a compound having the formula:

wherein C-B-A-, -D-E-F, -G-H-J, U, V, W, X, Y, and Z are as defined in formula (II),
wherein $Q^1$, $Q^2$, $Q^3$, and $Q^4$ are independently selected from a nitrogen atom, a carbon atom, or CH, wherein -D-E-F or -G-H-J, when it is present, is attached to a carbon, or a pharmaceutically acceptable salt, ester, tautomer, or prodrug thereof.

In some embodiments, the present invention relates to a compound having the formula:

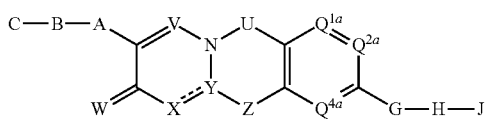

wherein C-B-A-, -G-H-J, U, V, W, X, Y, and Z are as defined in formula (II), wherein $Q^1$, $Q^2$, and $Q^4$ are independently selected from a nitrogen atom, a carbon atom, or a pharmaceutically acceptable salt, ester, tautomer, or prodrug thereof.

In some embodiments, the present invention relates to a compound having the formula:

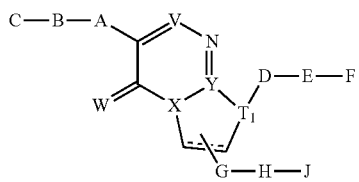

wherein C-B-A-, -G-H-J, V, W, X, and Y are as defined in formula (I), wherein $T^1$ is CH or NH, with the proviso that when $T^1$ is NH, -D-E-F is absent; or a pharmaceutically acceptable salt, ester, tautomer, or prodrug thereof.

In some embodiments, the present invention relates to a compound having the formula:

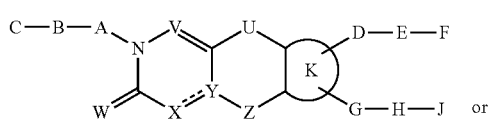

wherein C-B-A-, -D-E-F, -G-H-J, U, V, W, X, Y, and Z are as defined in formula (I) or formula (II), or a pharmaceutically acceptable salt, ester, tautomer, or prodrug thereof.

In some embodiments, the present invention relates to a compound having the formula (I) or (II), wherein

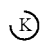

represents a fused 6 member aromatic carbocyclic or heterocyclic ring system; or a pharmaceutically acceptable salt, ester, tautomer, or prodrug thereof.

In some embodiments, the present invention relates to a compound having the formula:

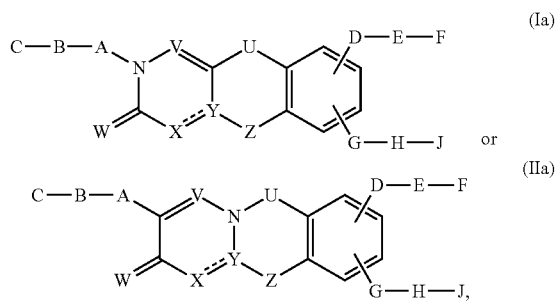

wherein C-B-A-, -D-E-F, -G-H-J, U, V, W, X, Y, and Z are as defined in formula (I) or formula (II), or a pharmaceutically acceptable salt, ester, tautomer, or prodrug thereof.

In some embodiments, the present invention relates to a compound having the

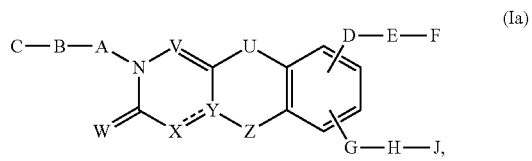

wherein C-B-A-, -D-E-F, -G-H-J, U, V, W, X, Y, and Z are as defined in formula (I), or a pharmaceutically acceptable salt, ester, tautomer, or prodrug thereof.

In some embodiments, the present invention relates to a compound having the formula V, VI, VII, or VIII:

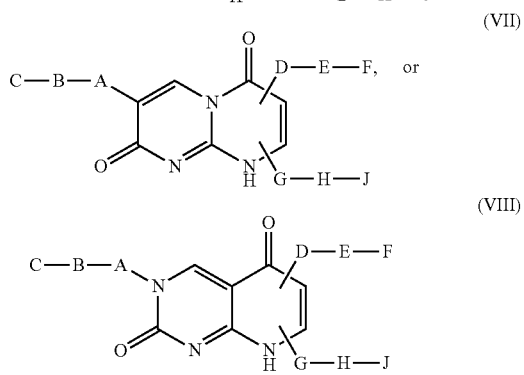

wherein C-B-A-, -D-E-F, and -G-H-J are as defined in formula (I), or a pharmaceutically acceptable salt, ester, tautomer, or prodrug thereof.

In some embodiments, the present invention relates to a compound having the formula:

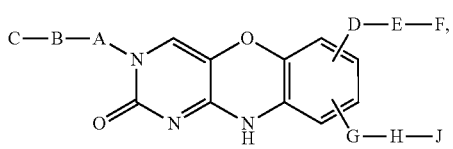
(V)

wherein C-B-A-, -D-E-F, and -G-H-J are as defined in formula (I), or a pharmaceutically acceptable salt, ester, tautomer, or prodrug thereof.

In some embodiments, the present invention relates to a compound having the

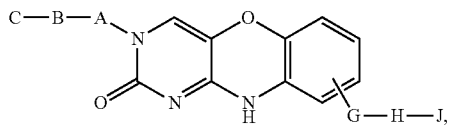

wherein D and E are single bonds, and F is hydrogen; wherein C-B-A- and -G-H-J are as defined in formula (I), or a pharmaceutically acceptable salt, ester, tautomer, or prodrug thereof.

In some embodiments, the present invention relates to a compound having the formula:

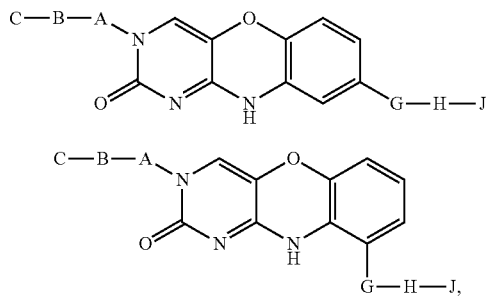
(Ib)

(Ic)

wherein C-B-A- and -G-H-J are as defined in formula (I), or a pharmaceutically acceptable salt, ester, tautomer, or prodrug thereof.

In some embodiments, the present invention relates to a compound having the formula:

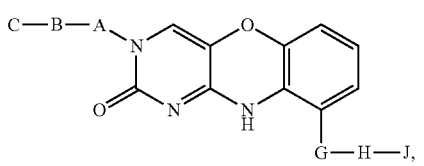
(Ic)

wherein C-B-A- and -G-H-J are as defined in formula (I), or a pharmaceutically acceptable salt, ester, tautomer, or prodrug thereof.

In some embodiments, the present invention relates to a compound having the formula:

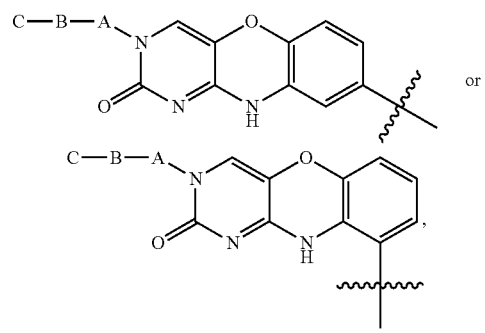

wherein A is selected from
(a) a 3-14 member saturated, unsaturated, or aromatic heterocycle containing one or more heteroatoms selected from the group consisting of nitrogen, oxygen, and sulfur, and
(b) a 3-14 member saturated, unsaturated, or aromatic carbocycle,
(c) a single bond,
wherein (a) or (b) is optionally substituted with one or more $R^5$ groups;
B is selected from (a) —($C_{1-8}$ alkyl)-, (b) —($C_{2-8}$ alkenyl)-, (c) —($C_{2-8}$ alkynyl)-, (d) a single bond, wherein
  i) 0-4 carbon atoms in any of (a)-(c) immediately above optionally is replaced by a moiety selected from the group consisting of —O—, —S(O)$_p$—, —NR$^6$—, —(C=O)—, —C(=NR$^6$)—, —S(O)$_p$NR$^6$—, and —NR$^6$S(O)$_p$NR$^6$—,
  ii) any of (a)-(c) immediately above optionally is substituted with one or more $R^5$ groups, and
  iii) any of (a)-(c) immediately above optionally is substituted with —($C_{1-8}$ alkyl)-$R^5$ groups, and
C is selected from (a) NH$_2$, (b) —NHC(=NH)NH$_2$ and (c) hydrogen,
or a pharmaceutically acceptable salt, ester, tautomer, or prodrug thereof.

In some embodiments, the present invention relates to a compound having the formula:

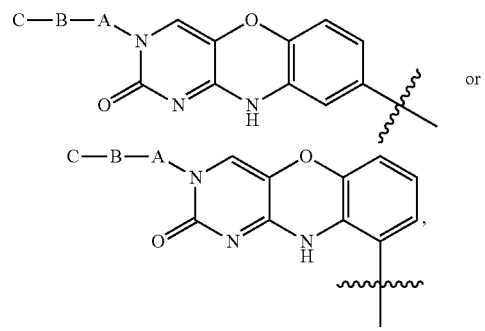

wherein A is selected from azepanyl, cyclobutyl, cyclopentyl, cyclohexyl, cycloheptyl, phenyl, pyridinyl, cyclohexenyl, cyclohexadienyl, dihydropyridyl, furanyl, tetrahydrofuranyl, tetrahydropyridyl, azetidinyl, pyrrolidinyl, piperidinyl and piperidenyl;
wherein any of A immediately above optionally is substituted with one or more $R^5$ groups;
alternatively, A is a single bond;

B is selected from (a) —(C$_{1-8}$ alkyl)-, wherein
  i) 0-4 carbon atoms in (a) immediately above optionally is replaced by a moiety selected from the group consisting of —O—, —S(O)$_p$—, —NR$^6$—, —(C=O)—, —S(O)$_p$NR$^6$—, and —NR$^6$S(O)$_p$NR$^6$—,
  ii) (a) immediately above optionally is substituted with one or more R$^5$ groups, and
  iii) (a) immediately above optionally is substituted with —(C$_{1-8}$ alkyl)-R$^5$ groups; and
alternatively, B is a single bond;
C is selected from (a) NH$_2$, (b) —NHC(=NH)NH$_2$ and (c) hydrogen;
or a pharmaceutically acceptable salt, ester, tautomer, or prodrug thereof.

In some embodiments, the present invention relates to a compound having the formula:

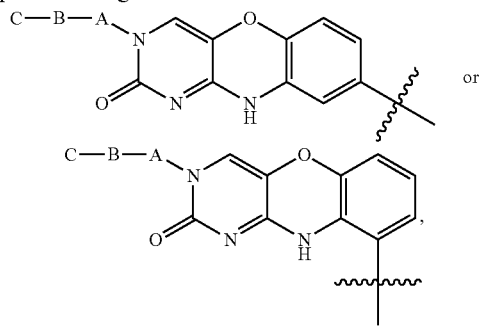

or

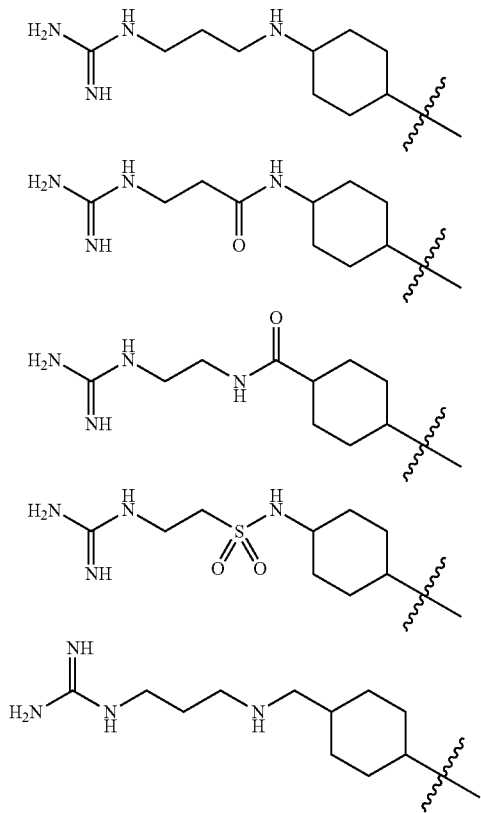

wherein C-B-A- is selected from the group consisting of:
hydrogen,

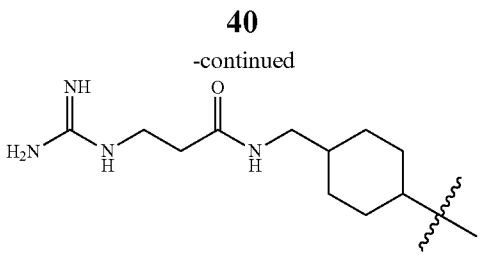

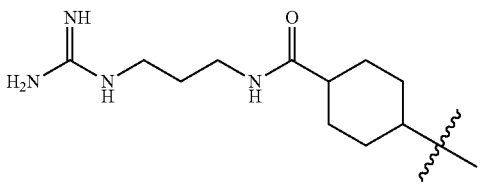

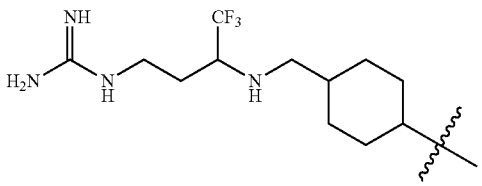

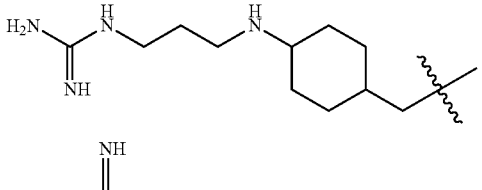

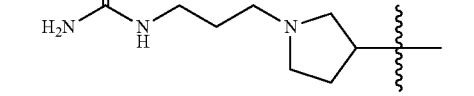

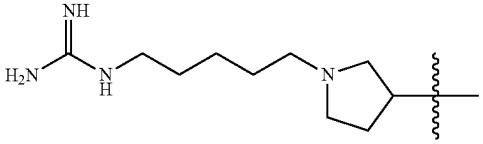

-continued

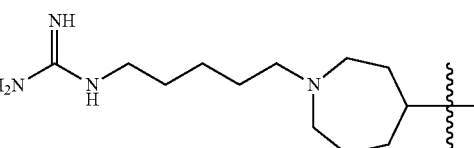

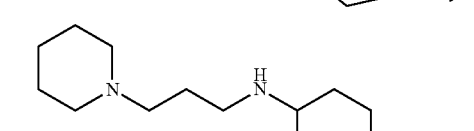

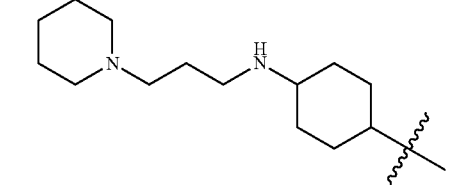

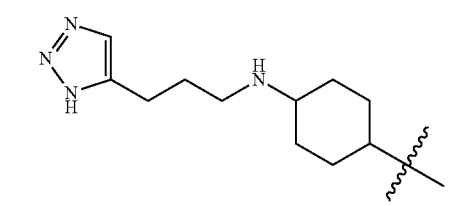

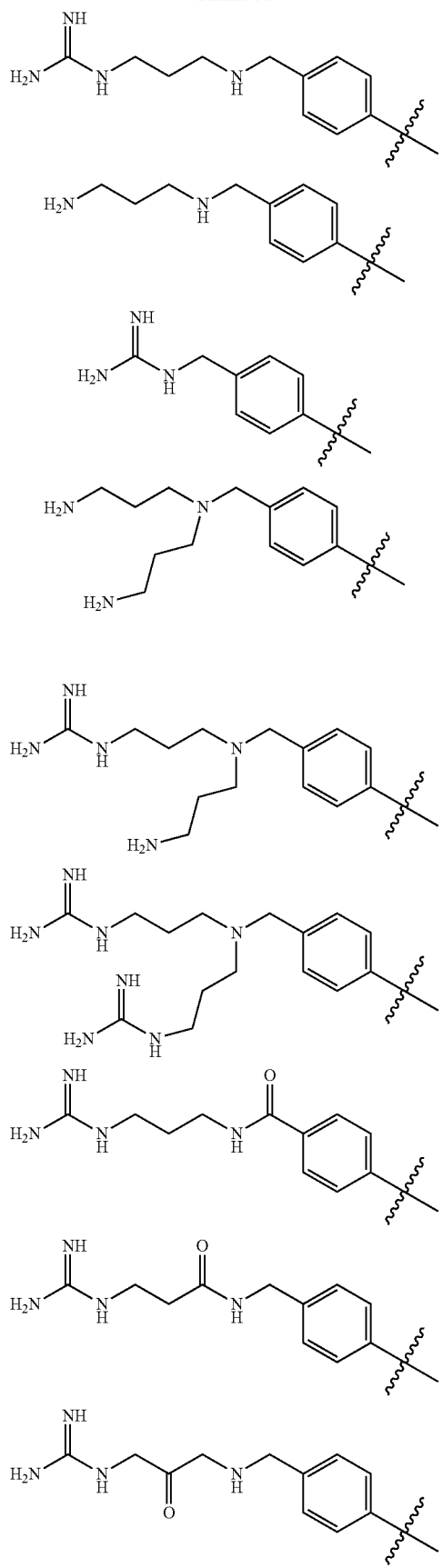
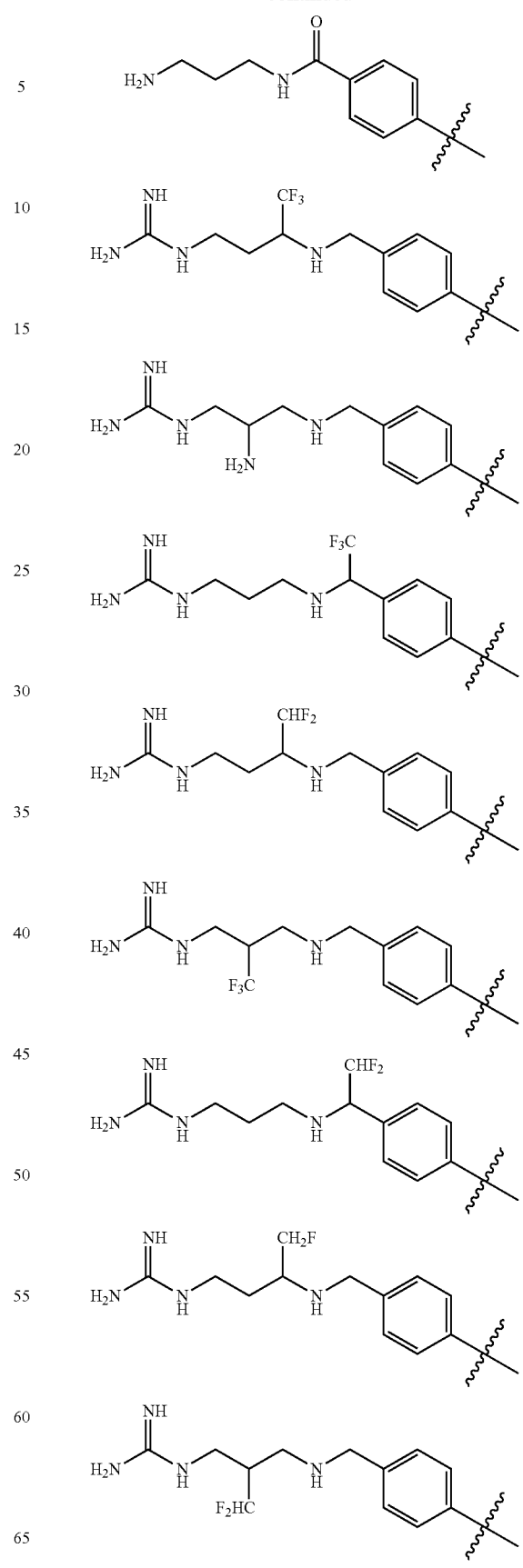

-continued
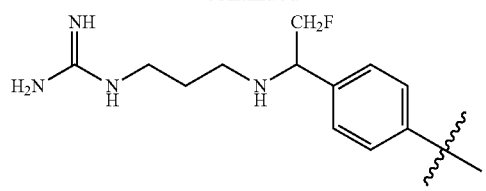
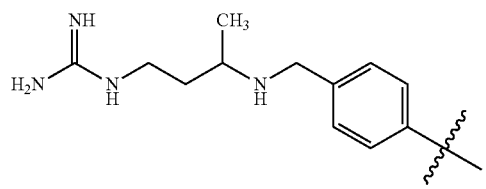
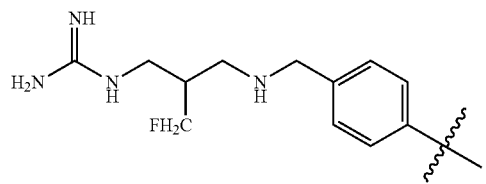
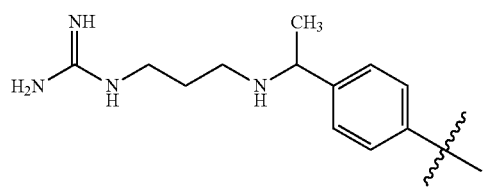
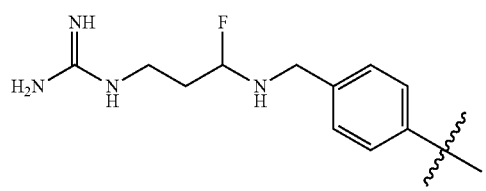
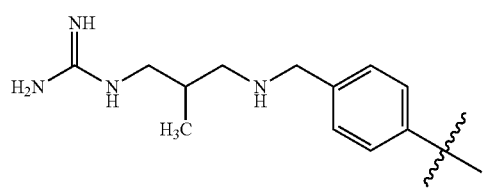
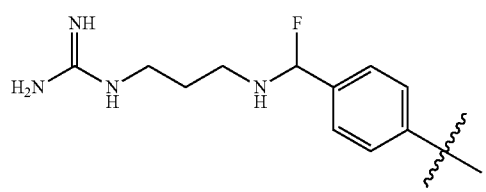
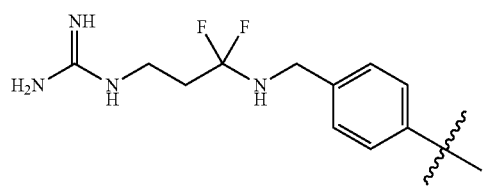
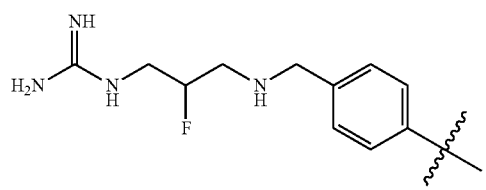
-continued
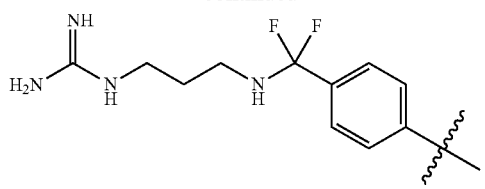
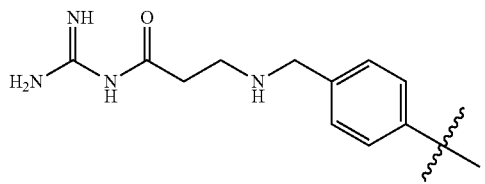
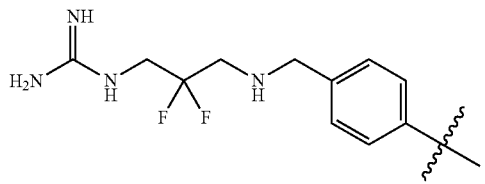
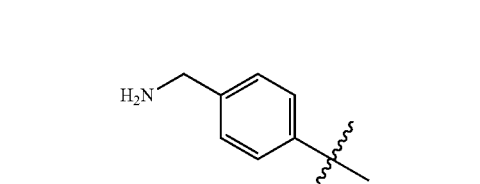
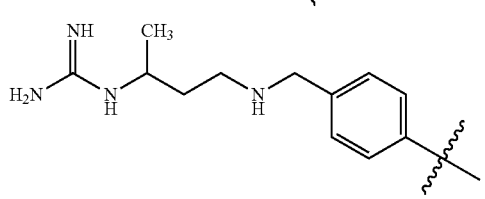
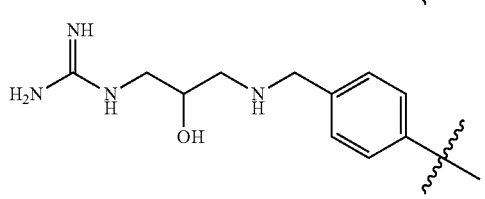
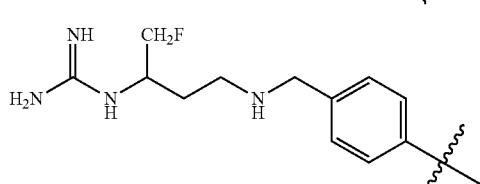
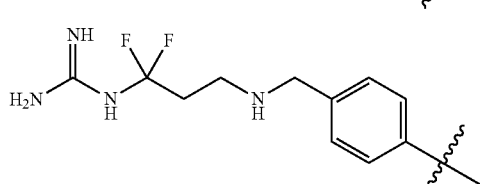
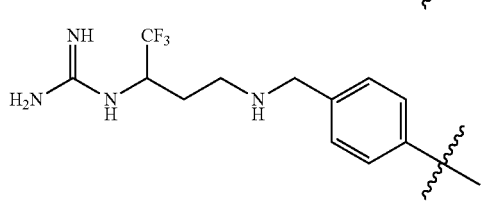

-continued

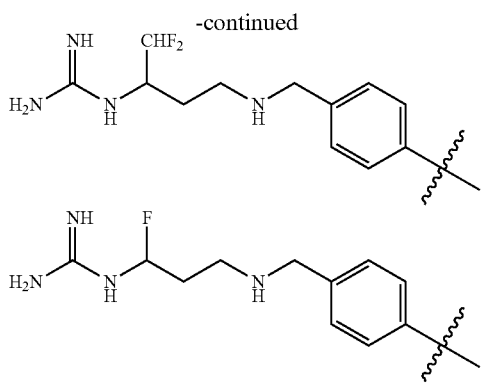

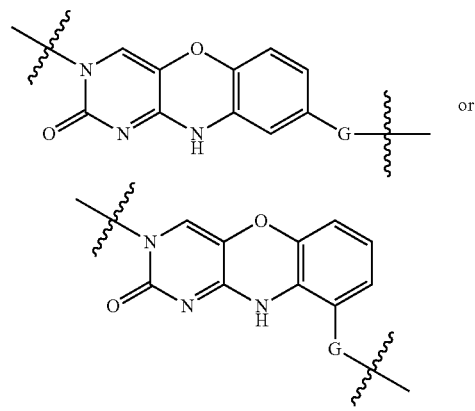

or a pharmaceutically acceptable salt, ester, tautomer, or prodrug thereof.

In some embodiments, the present invention relates to a compound having the formula:

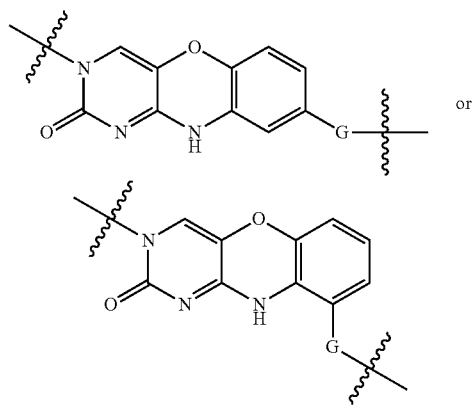

wherein G is selected from (a) a single bond, (b) —($C_{1-8}$ alkyl)-, (c) —($C_{2-8}$ alkenyl)-, (d) —($C_{2-8}$ alkynyl)-, wherein i) 0-4 carbon atoms in any of (b)-(d) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—, ii) any of (b)-(d) immediately above optionally is substituted with one or more R$^5$ groups, and iii) any of (b)-(d) immediately above optionally is substituted with —($C_{1-8}$ alkyl)-R$^5$ groups;

(e) a 3-14 member saturated, unsaturated, or aromatic heterocycle containing one or more heteroatoms selected from the group consisting of nitrogen, oxygen, and sulfur, and (f) a 3-14 member saturated, unsaturated, or aromatic carbocycle, wherein (e) or (f) is optionally substituted with one or more R$^5$ groups;

or a pharmaceutically acceptable salt, ester, tautomer, or prodrug thereof.

In some embodiments, the present invention relates to a compound having the formula:

wherein G is selected from (a) a single bond, (b) —($C_{1-8}$ alkyl)-, (c) —($C_{2-8}$ alkenyl)-, (d) —($C_{2-8}$ alkynyl)-, wherein i) 0-4 carbon atoms in any of (b)-(d) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—, ii) any of (b)-(d) immediately above optionally is substituted with one or more R$^5$ groups, and iii) any of (b)-(d) immediately above optionally is substituted with —($C_{1-8}$ alkyl)-R$^5$ groups;

wherein p is 0, 1, or 2, or a pharmaceutically acceptable salt, ester, tautomer, or prodrug thereof.

In some embodiments, the present invention relates to a compound having the formula

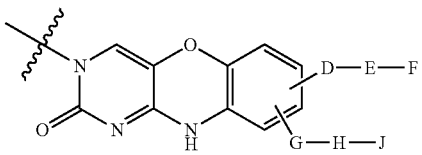

wherein

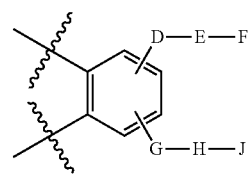

is selected from:

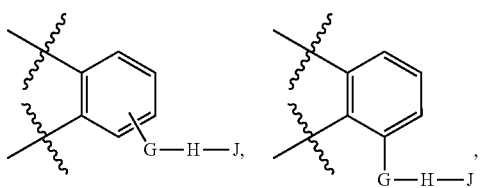

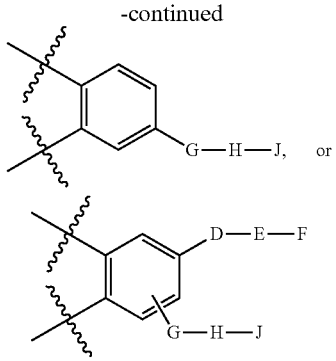

or a pharmaceutically acceptable salt, ester, tautomer, or prodrug thereof.

In some embodiments, the present invention relates to a compound having the formula

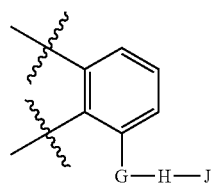

wherein -G-H-J is selected from:

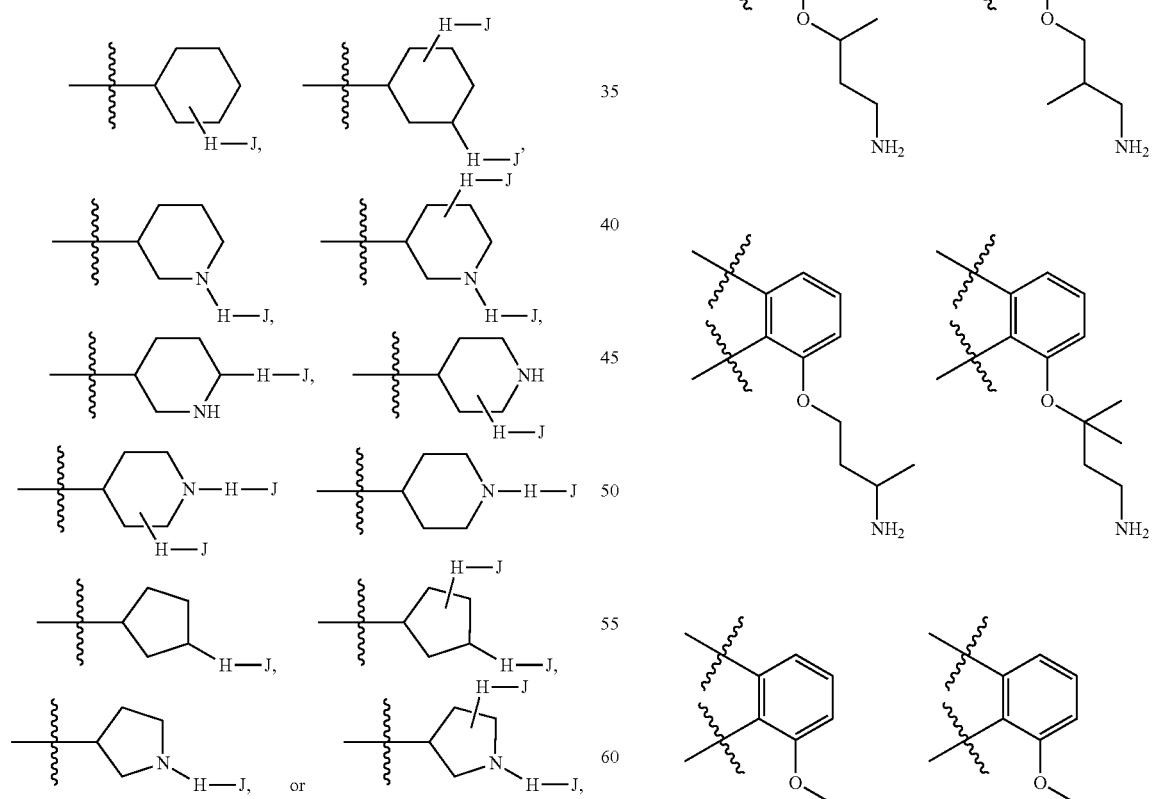

or a pharmaceutically acceptable salt, ester, tautomer, or prodrug thereof.

In some embodiments, the present invention relates to a compound having the formula

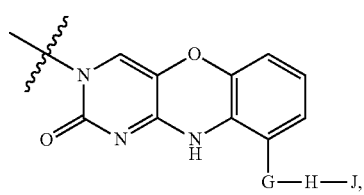

wherein is selected from:

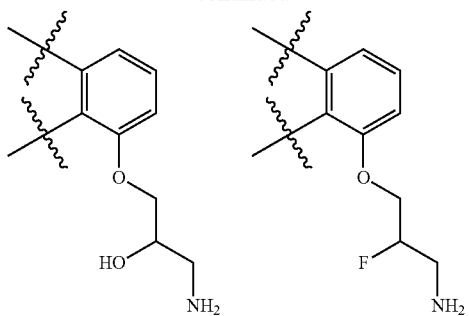
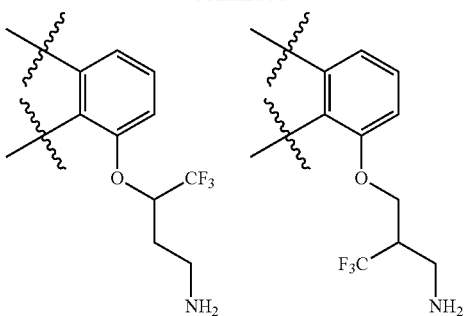
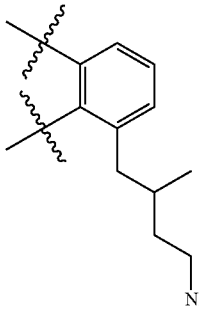
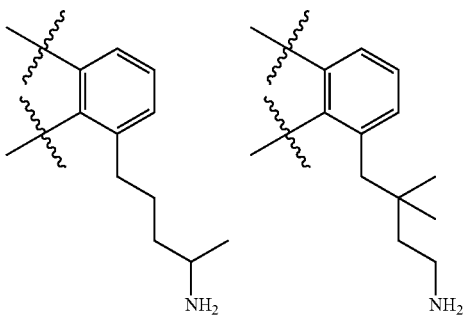
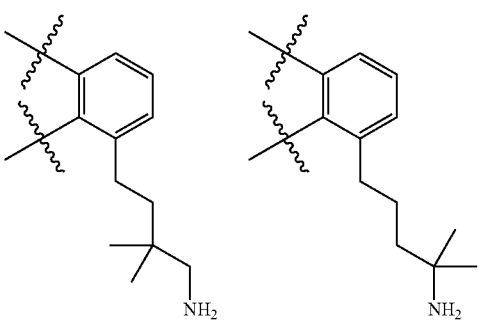
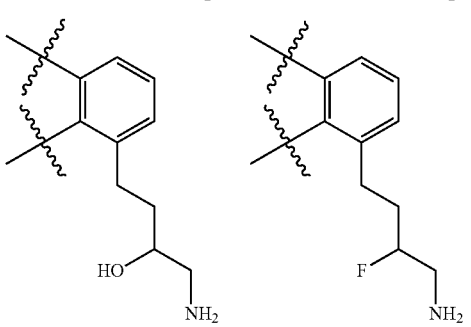

-continued

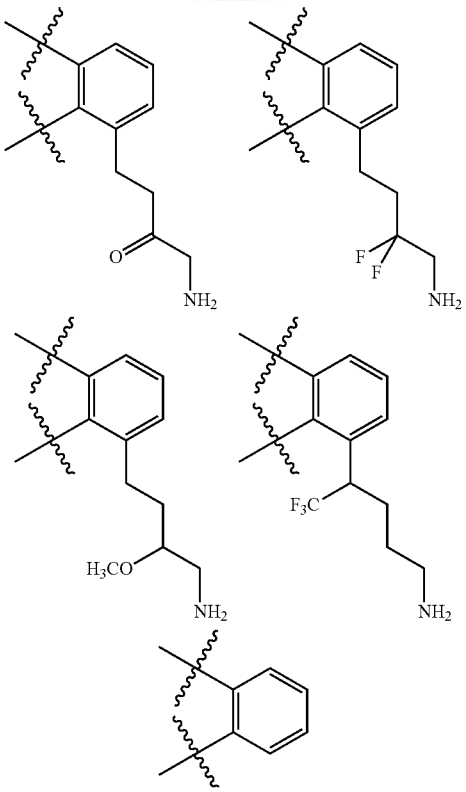

or -G-H-J is selected from:

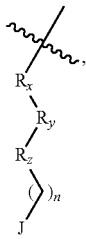

wherein $R_x$ is selected from $CH_2$, NH, $N(C_{1-8}$ alkyl), S, or O; $R_y$ and $R_z$ are C or CH each independently substituted with one or more F, $CH_3$, $CF_3$, OH, and $OCH_3$; or $R_x$, $R_y$, and $R_z$ are each independently selected from $CH_2$ or $CR^aR^b$ wherein $R^a$ and $R^b$ are taken together to form a $C_{1-5}$ carbocycle;
J is selected from $NH_2$, $NH(C_{1-8}$ alkyl), $N(C_{1-8}$ alkyl)$_2$, $NHC(\!\!=\!\!O)CH_3$, $NHC(\!\!=\!\!O)NH_2$, $NHC(\!\!=\!\!NH)NH_2$, $NHC(\!\!=\!\!NH)H$;
wherein n is 0, 1, or 2;
alternatively, -G-H-J is selected from

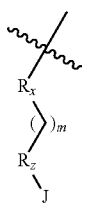

wherein $R_x$ is selected from $CH_2$, NH, $N(C_{1-8}$ alkyl), S, or O; $R_z$ is a C or CH, substituted with one or more $CH_3$ or $R_z$ is $CR^aR^b$ wherein $R^a$ and $R^b$ are taken together to form a $C_{1-5}$ carbocycle,
wherein m is 1, 2, or 3;
J is selected from $NH_2$, $NH(C_{1-8}$ alkyl), $N(C_{1-8}$ alkyl)$_2$, $NHC(\!\!=\!\!O)CH_3$, $NHC(\!\!=\!\!O)NH_2$, $NHC(\!\!=\!\!NH)NH_2$, $NHC(\!\!=\!\!NH)H$;
or a pharmaceutically acceptable salt, ester, tautomer, or prodrug thereof.

In some embodiments, the present invention relates to a compound containing $R^5$, wherein $R^5$ is selected from (a) hydrogen, (b) F, (c) Cl, (d) Br, (e) I, (f) —$CF_3$, (g) —CN, (h) —$N_3$ (i) —$NO_2$, (j) —$NH_2$, (k) —$OR^6$, (l) —NHC(=NH)$NH_2$, (m) —$C_{1-8}$ alkyl, (n) —$C_{1-8}$ alkenyl, (o) —$C_{1-8}$ alkynyl, (p) —($C_{1-8}$ alkyl)-(3-14 member saturated, unsaturated, or aromatic heterocycle containing one or more heteroatoms selected from the group consisting of nitrogen, oxygen, and sulfur), (q) —($C_{1-8}$ alkyl)-(3-14 member saturated, unsaturated, or aromatic carbocycle), (r) -haloalkyl, (s) —$SR^6$, (t) -3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle; alternatively, two $R^5$ groups are taken together to form a carbocycle; or a pharmaceutically acceptable salt, ester, tautomer, or prodrug thereof.

In some embodiments, the present invention relates to a compound containing $R^6$, wherein $R^6$ is selected from (a) hydrogen, (b) —$C_{1-8}$ alkyl or alternatively two $R^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle; or a pharmaceutically acceptable salt, ester, tautomer, or prodrug thereof.

In some embodiments, the present invention relates to a compound according to formula I, II, III, IV, V, VI, VII, or VIII, or a pharmaceutically acceptable salt, ester, tautomer, or pro-drug thereof, wherein -D-E-F represents hydrogen.

In some embodiments, the present invention relates to a compound according to formula I, II, III, IV, V, VI, VII, or VIII, or a pharmaceutically acceptable salt, ester, tautomer, or pro-drug thereof, wherein W, when it is present, is O, $NR^1$, $NOR^1$, or S.

In some embodiments, the present invention relates to a compound according to formula I, II, III, IV, V, VI, VII, or VIII, or a pharmaceutically acceptable salt, ester, tautomer, or pro-drug thereof, wherein X$=\!=\!=$Y, when it is present, is a double bond and X is N and Y is a carbon atom.

In some embodiments, the present invention relates to a compound according to formula I, II, III, IV, V, VI, VII, or VIII, or a pharmaceutically acceptable salt, ester, tautomer, or pro-drug thereof, wherein $R^{4a}$, when it is present, is H.

In some embodiments, the present invention relates to a compound according to formula I, II, III, IV, V, VI, VII, or VIII, or a pharmaceutically acceptable salt, ester, tautomer, or pro-drug thereof, wherein Z, when it is present, is $NR^4$.

In some embodiments, the present invention relates to a compound according to formula I, II, III, IV, V, VI, VII, or VIII, or a pharmaceutically acceptable salt, ester, tautomer, or pro-drug thereof, wherein $R^4$ is H.

In some embodiments, the present invention relates to a compound according to formula I, II, III, IV, V, VI, VII, or VIII, or a pharmaceutically acceptable salt, ester, tautomer, or pro-drug thereof, that binds to a ribosome.

In some embodiments, the present invention relates to a compound according to formula I, II, III, IV, V, VI, VII, or VIII, or a pharmaceutically acceptable salt, ester, tautomer, or pro-drug thereof, that binds to the ribosome wherein the ribosome is a bacterial ribosome.

In some embodiments, the present invention relates to a compound according to any of the compounds in Table 1 or a pharmaceutically acceptable salt, ester, tautomer, or prodrug thereof.

In some embodiments, the present invention relates to a pharmaceutical composition comprising a compound of the invention, or a pharmaceutically acceptable salt, ester, tautomer, or prodrug thereof, and a pharmaceutically acceptable carrier.

In some embodiments, the present invention relates to a method for treating, preventing or reducing the risk of a disease state in a human or animal comprising administering to a human or animal in need thereof an effective amount of a compound of the invention or a pharmaceutically acceptable salt, ester, tautomer, or prodrug thereof.

In some embodiments, the present invention relates to a method of treating a microbial infection in a human or animal comprising administering to the human or animal an effective amount of a compound of the invention, or a pharmaceutically acceptable salt, ester, tautomer, or prodrug thereof.

In some embodiments, the present invention relates to the use of a compound of the invention, or a pharmaceutically acceptable salt, ester, tautomer, or prodrug thereof, in the manufacture of a medicament for treating a microbial infection in a human or animal.

In some embodiments, the present invention relates to a method of treating, preventing or reducing the risk of a microbial infection in a human or animal comprising administering to the human or animal an effective amount of a compound of the invention, or a pharmaceutically acceptable salt, ester, tautomer, or prodrug thereof, or to the use of a compound of the invention, or a pharmaceutically acceptable salt, ester, tautomer, or prodrug thereof, in the manufacture of a medicament for treating, preventing, or reducing the risk of a microbial infection, wherein the microbial infection is selected from the group consisting of:

a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as CRTI, acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, a *Bacillus anthracis* infection, a *Francisella tularensis* infection, a *Yersinia pestis* infection, and tuberculosis.

In some embodiments, the present invention relates to a method or use wherein the compound of the invention, or a pharmaceutically acceptable salt, ester, tautomer, or prodrug thereof, is administered otically, ophthalmically, nasally, orally, parenterally, topically, or intravenously.

In some embodiments, the present invention relates to a method of treating, preventing or reducing the risk of a complicated intra-abdominal infection in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a complicated intra-abdominal infection, wherein the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis,* or *Clostridium perfringens.*

In some embodiments, the present invention relates to a method of treating, preventing or reducing the risk of a complicated skin and skin structure infection in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a complicated skin and skin structure infection wherein the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus species, Porphyromonas asaccharolytica,* or *Prevotella bivia.*

In some embodiments, the present invention relates to a method of treating, preventing or reducing the risk of a community acquired pneumonia in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a community acquired pneumonia, wherein the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis,* or atypical bacteria like *Mycoplasma* spp.

In some embodiments, the present invention relates to a method of treating, preventing or reducing the risk of a complicated urinary tract infection in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a complicated urinary tract infection wherein the complicated urinary tract infection is selected from pyelonephritis due to *Escherichia coli*, concurrent bacteremia, or *Klebsiella pneumoniae*.

In some embodiments, the present invention relates to a method of treating, preventing or reducing the risk of an acute pelvic infection in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of an acute pelvic infection wherein the acute pelvic infection including postpartum endomyometritis, septic abortion and post surgical gynecologic infections is due to *Streptococcus agalactiae*, *Escherichia coli*, *Bacteroides fragilis*, *Porphyromonas asaccharolytica*, *Peptostreptococcus* spp., or *Prevotella bivia*.

In some embodiments, the present invention relates to a method of treating, preventing or reducing the risk of a hospital acquired pneumonia/ventilator associated pneumonia in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a hospital acquired pneumonia/ventilator associated pneumonia, wherein the hospital acquired pneumonia/ventilator associated pneumonia is due to *Streptococcus pneumoniae* (penicillin susceptible and resistant isolates), *Staphylococcus aureus* (methicillin susceptible and resistant isolates), *Klebsiella pneumoniae*, *Pseudomonas aeruginosa*, *Acinetobacter* spp., *Stenotrophomonas maltophilia*, *Haemophilus influenzae* (including beta-lactamase positive isolates), or *Legionella pneumophilia*.

In some embodiments, the present invention relates to a method of treating, preventing or reducing the risk of a microbial infection associated with an aerobic and facultative gram-positive microorganism in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a microbial infection associated with an aerobic and facultative gram-positive microorganism, wherein the aerobic and facultative gram-positive microorganism is selected from: *Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae*, *Streptococcus pyogenes*, or *Staphylococcus epidermidis* (methicillin susceptible and resistant isolates).

In some embodiments, the present invention relates to a method of treating, preventing or reducing the risk of a microbial infection associated with an aerobic and facultative gram-negative microorganism in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a microbial infection associated with an aerobic and facultative gram-negative microorganism, wherein the aerobic and facultative gram-negative microorganism is selected from: *Escherichia coli* (including ESBL and KPC producing isolates), *Haemophilus influenzae* (including Beta-lactamase positive isolates), *Klebsiella pneumoniae* (including ESBL and KPC producing isolates), *Citrobacter freundii*, *Enterobacter aerogenes*, *Enterobacter cloacae*, *Morganella morganii*, *Serratia marcescens*, *Pseudomonas aeruginosa*, *Acinetobacter baumanni*, *Moraxella catarrhalis*, *Proteus mirabilis*, *Citrobacter koseri*, *Haemophilus parainfluenzae*, *Klebsiella oxytoca* (Including ESBL and KPC producing isolates), *Proteus vulgaris*, *Providencia rettgeri*, or *Providencia stuartii*.

In some embodiments, the present invention relates to a method of treating, preventing or reducing the risk of a microbial infection associated with an anaerobic microorganism in a human or animal comprising administering to the human or animal an effective amount of a compound according to formula I, II, III, IV, V, VI, VII, or VIII, or a pharmaceutically acceptable salt, ester, tautomer, or prodrug thereof, or to the use of a compound according to formula I, II, III, IV, V, VI, VII, or VIII, or a pharmaceutically acceptable salt, ester, tautomer, or prodrug thereof, in the manufacture of a medicament for treating, preventing, or reducing the risk of a microbial infection associated with an anaerobic microorganism, wherein the anaerobic microorganism is selected from: *Bacteroides fragilis*, *Bacteroides distasonis*, *Bacteroides ovatus*, *Bacteroides thetaiotaomicron*, *Bacteroides uniformis*, *Clostridium clostridioforme*, *Eubacterium lentum*, *Peptostreptococcus* species, *Porphyromonas asaccharolytica*, *Prevotella bivia*, *Bacteroides vulgates*, *Clostridium perfringens*, or *Fusobacterium* spp.

In some embodiments, the present invention relates to a method or use wherein the compound of the invention, or a pharmaceutically acceptable salt, ester, tautomer, or prodrug thereof, is administered otically, ophthalmically, nasally, orally, parenterally, topically, or intravenously.

In some embodiments, the present invention relates to a method of synthesizing a compound of the invention, or a pharmaceutically acceptable salt, ester, tautomer, or prodrug thereof.

In some embodiments, the present invention relates to a medical device containing a compound of the invention, or a pharmaceutically acceptable salt, ester, tautomer, or prodrug thereof.

In some embodiments, the present invention relates to a medical device containing a compound of the invention, wherein the device is a stent.

3. SYNTHESIS OF THE COMPOUNDS OF THE INVENTION

The invention provides methods for making the compounds of the invention. The following Schemes 1c-2c depict exemplary routes in general terms for synthesizing the compounds of the present invention. More specific chemical details are provided in the Examples.

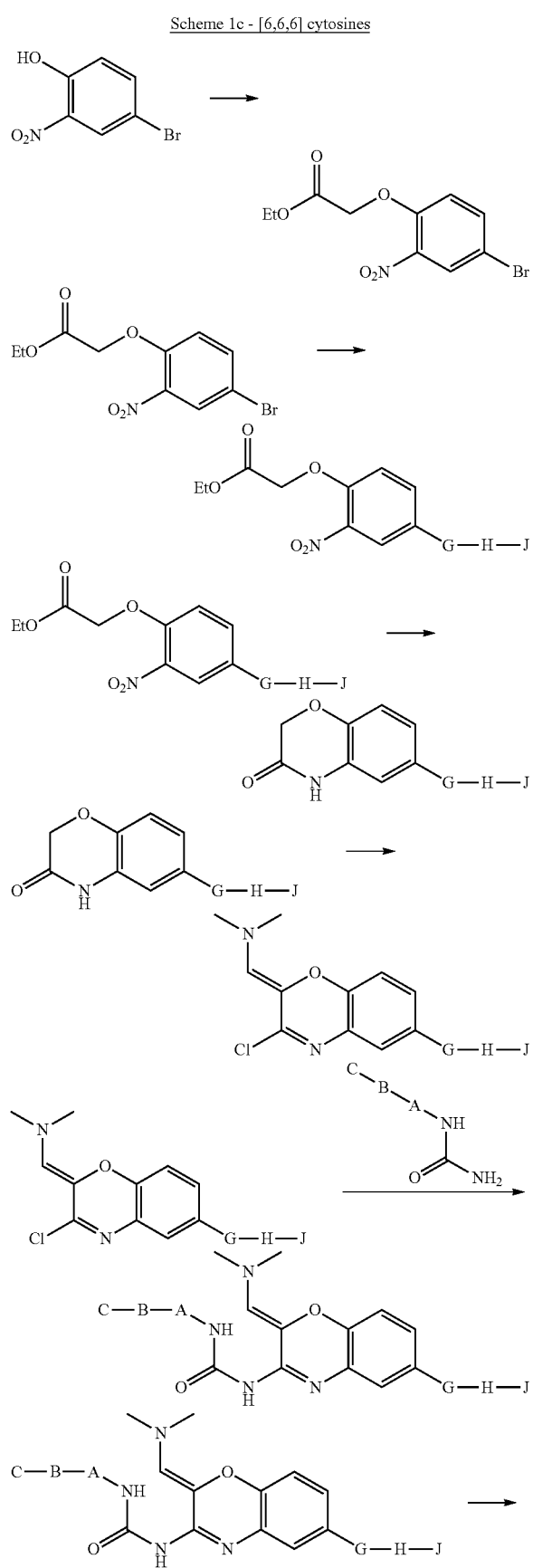

Scheme 1c - [6,6,6] cytosines

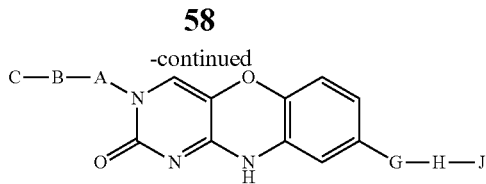

Scheme 2c - [6,6,6] isocytosines

4. CHARACTERIZATION OF COMPOUNDS OF THE INVENTION

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor™ from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

(4) Antimicrobial assays and other evaluations Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

Minimum inhibitory concentrations (MICs) are determined by the microdilution method, typically in a final volume of 100 microliters, according to protocols outlined by The Clinical and Laboratory Standards Institute [CLSI; formerly the National Committee for Clinical Laboratory Standards (NCCLS)]. See CLSI: Methods for dilution antimicrobial susceptibility tests for bacteria that grow aerobically; approved standard-fifth edition. Wayne, Pa.: NCCLS; 2000. The assays can be also be performed in microtiter trays according to conventional methodologies as published by the CLSI. See CLSI. Methods for Dilution Antimicrobial Susceptibility Tests for Bacteria That Grow Aerobically; Approved Standard-Seventh Edition. CLSI Document M7-A7 [ISBN 1-56238-587-9] CLSI, 940 West Valley Road, Suite 1400, Wayne Pa. 19087-1898 USA, 2006).

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

5. FORMULATION AND ADMINISTRATION

The compounds of the invention can be useful in the prevention or treatment of a variety of human or other animal, including mammalian and non mammalian, disorders, including for example, bacterial infection, fungal infections, viral infections, diarrhea, parasitic diseases, and cancer. It is contemplated that, once identified, the active molecules of the invention can be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral, otic, ophthalmic, nasal, or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or moulding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Moulded tablets can be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for otic, ophthalmic, nasal, parenteral or oral administration to humans or other mammals, for example, in therapeutically effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, e.g., by otic, ophthalmic, nasal, oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The compounds of the present invention can be administered directly to a tissue locus by applying the compound to a medical device that is placed in contact with the tissue. An example of a medical device is a stent, which contains or is coated with one or more of the compounds of the present invention.

For example, an active compound can be applied to a stent at the site of vascular injury. Stents can be prepared by any of the methods well known in the pharmaceutical art. See, e.g., Fattori, R. and Piva, T., "Drug Eluting Stents in Vascular Intervention," Lancet, 2003, 361, 247-249; Morice, M. C., "A New Era in the Treatment of Coronary Disease?" European Heart Journal, 2003, 24, 209-211; and Toutouzas, K. et al., "Sirolimus-Eluting Stents: A Review of Experimental and Clinical Findings," Z. Kardiol., 2002, 91(3), 49-57. The stent can be fabricated from stainless steel or another bio-compatible metal, or it can be made of a bio-compatible polymer. The active compound can be linked to the stent surface, embedded and released from polymer materials coated on the stent, or surrounded by and released through a carrier which coats or spans the stent. The stent can be used to administer single or multiple active compounds to tissues adjacent to the stent.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered otically, ophthalmically, nasally, orally, parenterally and/or topically at a dosage to obtain and maintain a concentration, that is, an amount, or blood-level or tissue level of active component in the animal undergoing treatment which will be anti-microbially effective. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day.

Various disease states or conditions in humans and other mammals are found to be caused by or mediated by nonsense or missense mutations. These mutations cause or mediate the disease state or condition by adversely affecting, for example, protein synthesis, folding, trafficking and/or function. Examples of disease states or conditions in which an appreciable percentage of the disease or condition is believed to result from nonsense or missense mutations include hemophilia (factor VIII gene), neurofibromatosis (NF1 and NF2 genes), retinitis pigmentosa (human USH2A gene), bullous skin diseases like Epidermolysis bullosa pruriginosa (COL7A1 gene), cystic fibrosis (cystic fibrosis transmembrane regulator gene), breast and ovarian cancer (BRCA1 and BRCA2 genes), Duchenne muscular dystrophy (dystrophin gene), colon cancer (mismatch repair genes, predominantly in MLH1 and MSH2), and lysosomal storage disorders such as Neimann-Pick disease (acid sphingomyelinase gene). See Sanders C R, Myers J K. Disease-related misassembly of membrane proteins. Annu Rev Biophys Biomol Struct. 2004; 33:25-51; National Center for Biotechnology Information (U.S.) *Genes and disease* Bethesda, Md.: NCBI, NLM ID: 101138560; and Raskó, István; Downes, C S *Genes in medicine: molecular biology and human genetic disorders* 1st ed. London; New York: Chapman & Hall, 1995. NLM ID: 9502404. The compounds of the present invention can be used to treat or prevent a disease state in a mammal caused or mediated by such nonsense or missense mutations by administering to a mammal in need thereof an effective amount of the present invention to suppress the nonsense or missense mutation involved in the disease state.

6. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds of the present invention can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; µM=micromolar; g=gram(s); µg=microgram(s); rt=room temperature; L=liter(s); mL=milliliter(s); Et$_2$O=diethyl ether; THF=tetrahydrofuran; DMSO=dimethyl sulfoxide; EtOAc=ethyl acetate; Et$_3$N=triethylamine; i-Pr$_2$NEt or DIPEA=diisopropylethylamine; CH$_2$Cl$_2$=methylene chloride; CHCl$_3$=chloroform; CDCl$_3$=deuterated chloroform; CCl$_4$=carbon tetrachloride; MeOH=methanol; CD$_3$OD=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; NaN$_3$=sodium azide; Na$_2$SO$_4$=sodium sulfate; NaHCO$_3$=sodium bicarbonate; NaOH=sodium hydroxide; MgSO$_4$=magnesium sulfate; K$_2$CO$_3$=potassium carbonate; KOH=potassium hydroxide; NH$_4$OH=ammonium hydroxide; NH$_4$Cl=ammonium chloride; SiO$_2$=silica; Pd—C=palladium on carbon; Pd(dppf)Cl$_2$=dichloro[1,1'-bis(diphenylphosphino)ferrocene] palladium (II).

Exemplary compounds synthesized in accordance with the invention are listed in Table 1. A bolded or dashed bond is shown to indicate a particular stereochemistry at a chiral center, whereas a wavy bond indicates that the substituent can be in either orientation or that the compound is a mixture thereof. It should also be known that in the interest of conserving space, the chemical structures of some compounds have been split into two parts with the two points of connection each being indicated by a bond crossed by a wavy line. See, e.g. compound 956, which was drawn in two parts as:

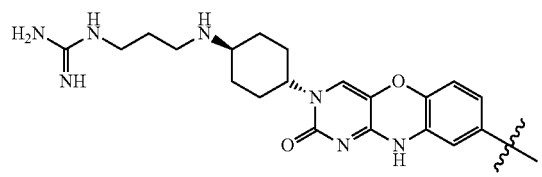

-continued

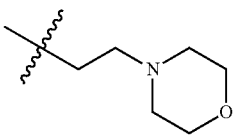

but corresponds to the complete chemical structure:

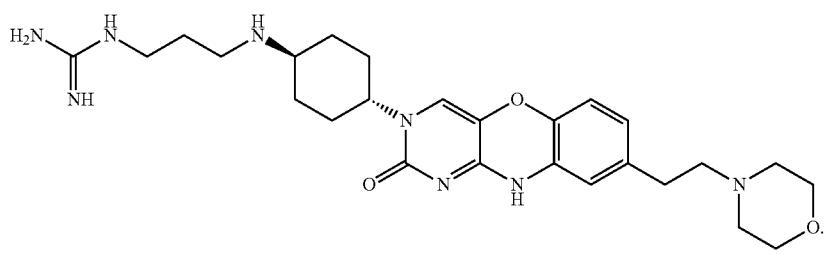 [SMILES: N=C(N)NCCCN[C@H]1CC[C@H](n2cc3c(nc2=O)Nc2cc(CCN4CCOCC4)ccc2O3)CC1]

The compounds of the present invention can be prepared, formulated, and delivered as salts, esters, and prodrugs. For convenience, the compounds are generally shown without indicating a particular salt, ester, or prodrug form.

Compounds of the present invention are shown in Table 1. LCMS (liquid chromatography mass spectral) data are provided, where available. When data is not available this is indicated by "NA". The LCMS data are provided using the convention for m/z in the format, $[M+H]^+$, except otherwise indicated.

TABLE 1

| Comp. No. | Structure | LCMS |
|---|---|---|
| 392 | 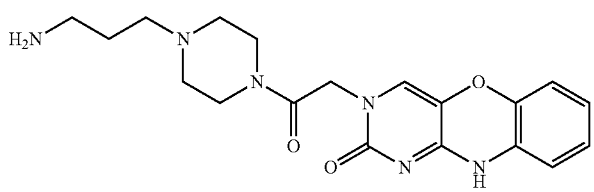 [SMILES: NCCCN1CCN(C(=O)Cn2cc3c(nc2=O)Nc2ccccc2O3)CC1] | 385.10 |
| 393 | 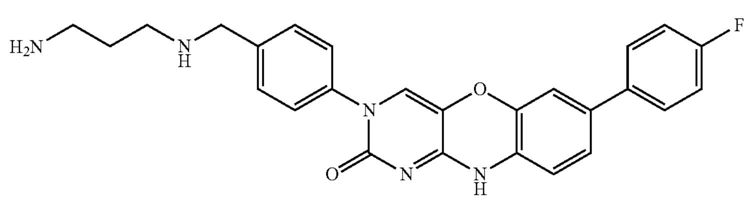 [SMILES: NCCCNCc1ccc(-n2cc3c(nc2=O)Nc2ccc(-c4ccc(F)cc4)cc2O3)cc1] | 458.00 |
| 396 | 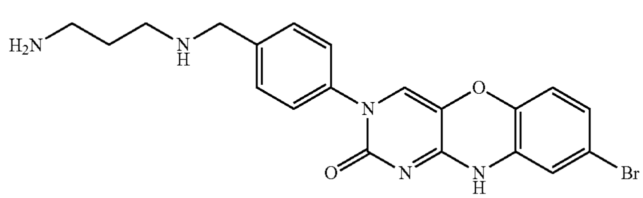 [SMILES: NCCCNCc1ccc(-n2cc3c(nc2=O)Nc2cc(Br)ccc2O3)cc1] | 442.00 |

TABLE 1-continued
| Comp. No. | Structure | LCMS |
|---|---|---|
| 400 | 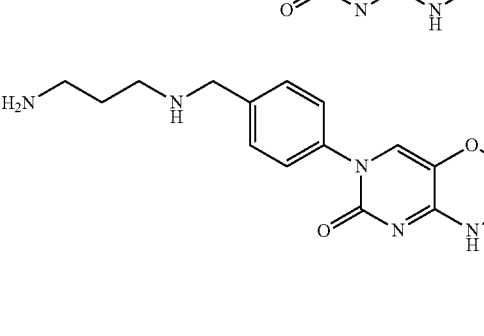 | 527.00 |
| 402 | 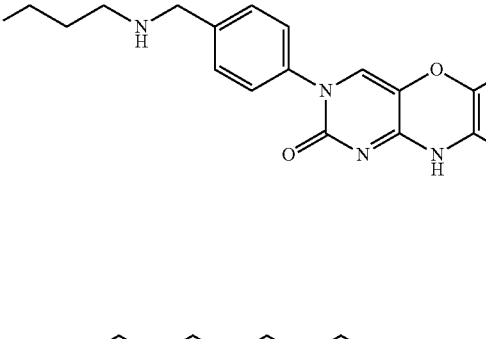 | 458.00 |
| 440 | 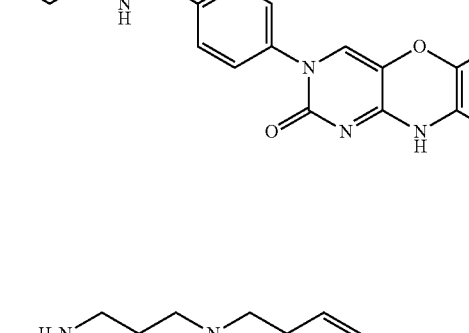 | 527.00 |
| 442 | 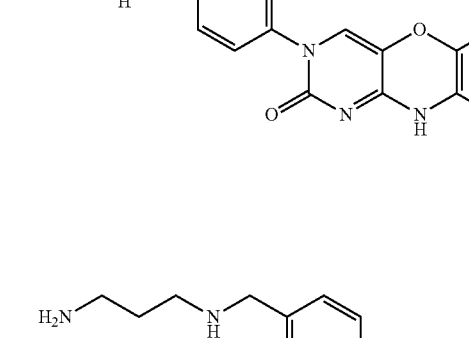 | 442.00 |
| 460 | 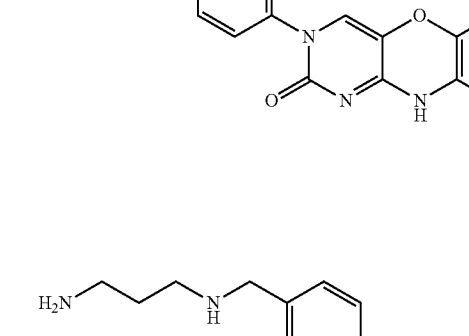 | 482.00 |
| 528 | 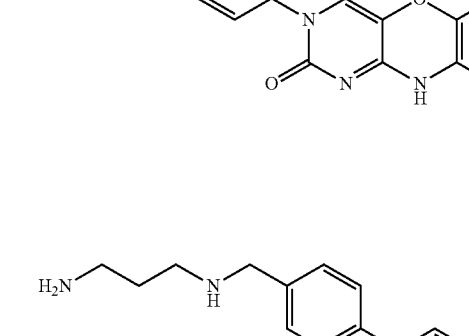 | 341.90 |

TABLE 1-continued

| Comp. No. | Structure | LCMS |
|---|---|---|
| 529 | 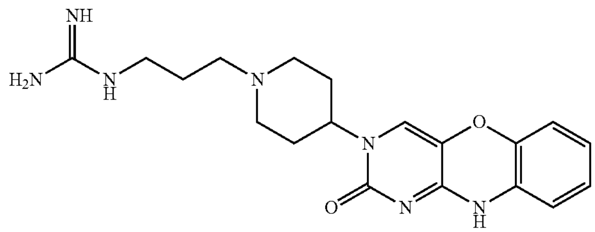 [SMILES: N=C(N)NCCCN1CCC(n2cc3c(nc2=O)Nc2ccccc2O3)CC1] | 383.90 |
| 543 | 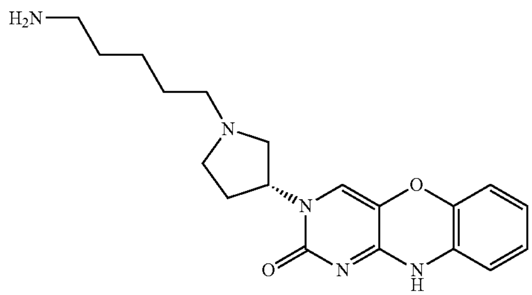 [SMILES: NCCCCCN1CC[C@@H](n2cc3c(nc2=O)Nc2ccccc2O3)C1] | 356.10 |
| 544 | 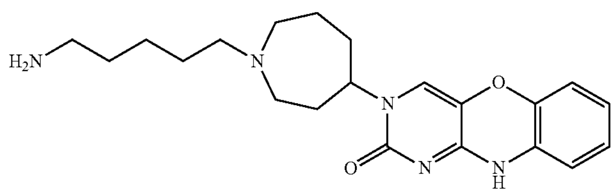 [SMILES: NCCCCCN1CCCC(n2cc3c(nc2=O)Nc2ccccc2O3)CC1] | 384.10 |
| 557 | 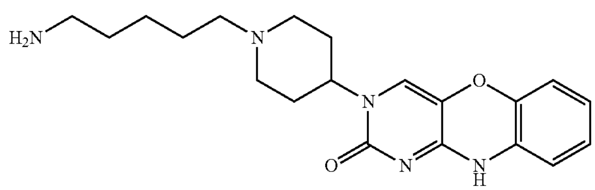 [SMILES: NCCCCCN1CCC(n2cc3c(nc2=O)Nc2ccccc2O3)CC1] | 370.20 |
| 558 | 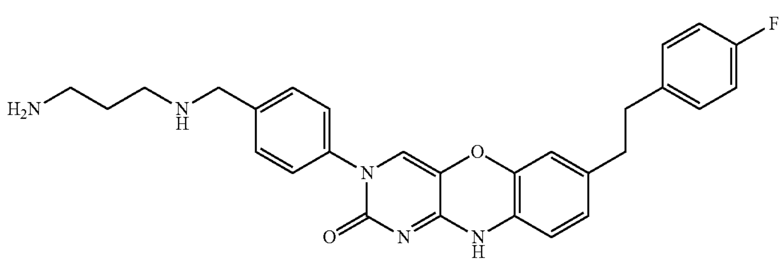 [SMILES: NCCCNCc1ccc(-n2cc3c(nc2=O)Nc2ccc(CCc4ccc(F)cc4)cc2O3)cc1] | 486.10 |
| 575 | 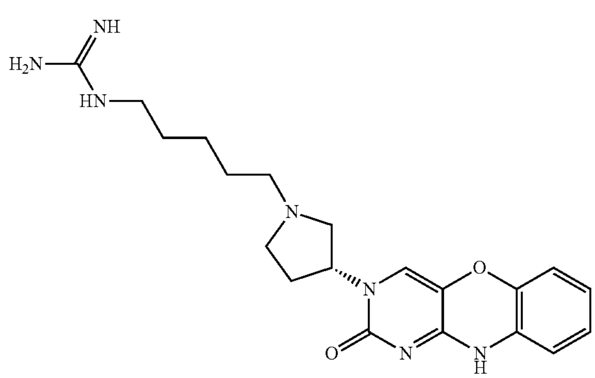 [SMILES: N=C(N)NCCCCCN1CC[C@@H](n2cc3c(nc2=O)Nc2ccccc2O3)C1] | 398.20 |

TABLE 1-continued

| Comp. No. | Structure | LCMS |
|---|---|---|
| 576 | 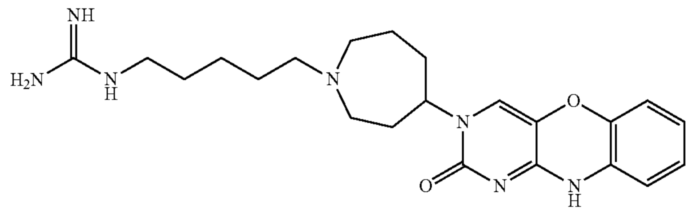 [SMILES: N=C(N)NCCCCCN1CCCC(n2cc3c(nc2=O)Nc2ccccc2O3)CC1] | 426.10 |
| 578 | 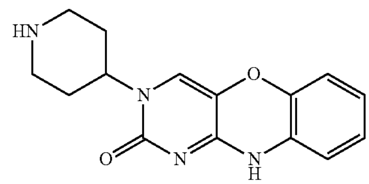 [SMILES: O=c1nc2c(cn1C1CCNCC1)Oc1ccccc1N2] | 285.00 |
| 579 | 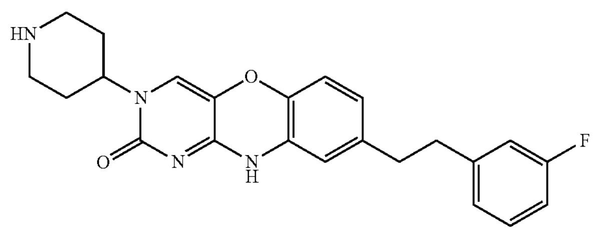 [SMILES: O=c1nc2c(cn1C1CCNCC1)Oc1ccc(CCc3cccc(F)c3)cc1N2] | 407.00 |
| 592 | 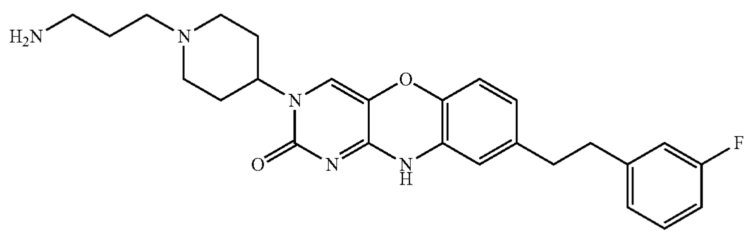 [SMILES: NCCCN1CCC(n2cc3c(nc2=O)Nc2cc(CCc4cccc(F)c4)ccc2O3)CC1] | 464.10 |
| 595 | 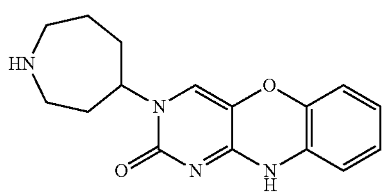 [SMILES: O=c1nc2c(cn1C1CCCNCC1)Oc1ccccc1N2] | 298.90 |
| 598 | 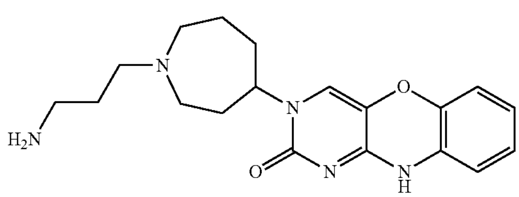 [SMILES: NCCCN1CCCC(n2cc3c(nc2=O)Nc2ccccc2O3)CC1] | 355.90 |
| 603 | 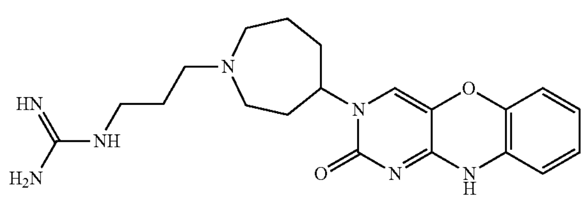 [SMILES: N=C(N)NCCCN1CCCC(n2cc3c(nc2=O)Nc2ccccc2O3)CC1] | 398.10 |

TABLE 1-continued

| Comp. No. | Structure | LCMS |
|---|---|---|
| 604 | 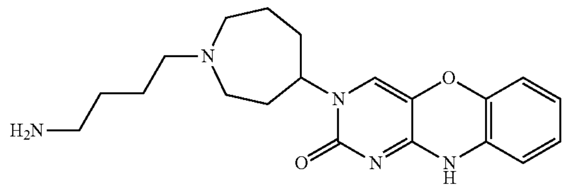 [SMILES: NCCCCN1CCCC(n2cc3c(nc2=O)Nc2ccccc2O3)CC1] | 370.30 |
| 606 | 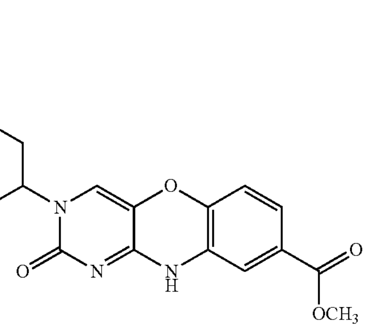 | 400.10 |
| 614 | 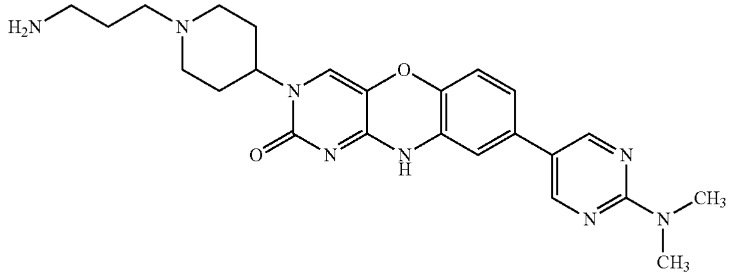 [SMILES: CN(C)c1ncc(-c2ccc3c(c2)Nc2nc(=O)n(C4CCN(CCCN)CC4)cc2O3)cn1] | 463.00 |
| 615 | 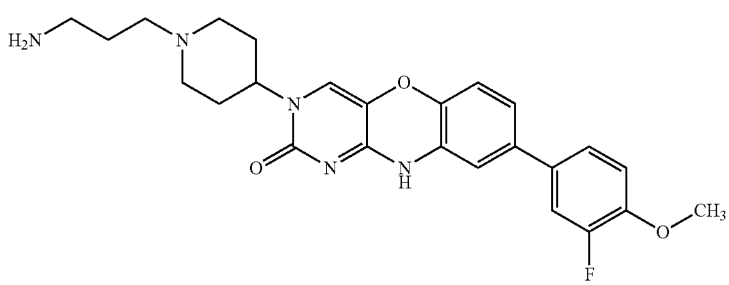 [SMILES: COc1ccc(-c2ccc3c(c2)Nc2nc(=O)n(C4CCN(CCCN)CC4)cc2O3)cc1F] | 466.10 |
| 627 | 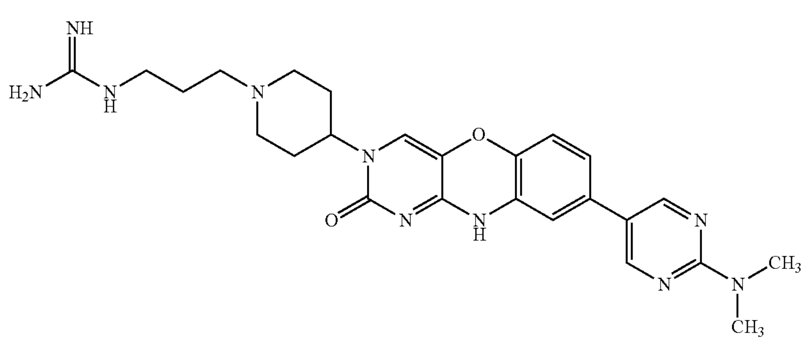 [SMILES: CN(C)c1ncc(-c2ccc3c(c2)Nc2nc(=O)n(C4CCN(CCCNC(=N)N)CC4)cc2O3)cn1] | 505.20 |

TABLE 1-continued
| Comp. No. | Structure | LCMS |
|---|---|---|
| 638 | 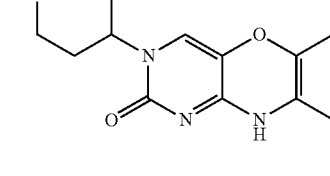 | 596.90 |
| 639 | 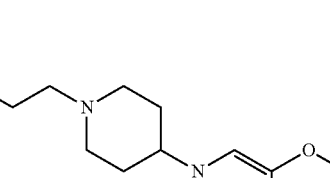 | 509.20 |
| 641 | 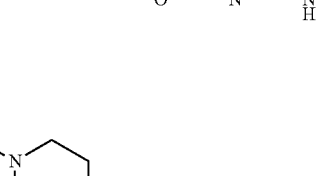 | 571.10 |
| 642 | 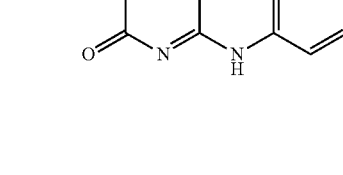 | 554.30 |
| 643 | 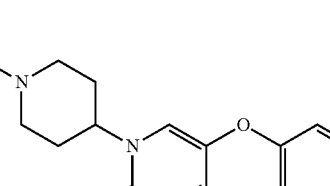 | 559.10 |

TABLE 1-continued

| Comp. No. | Structure | LCMS |
|---|---|---|
| 651 | 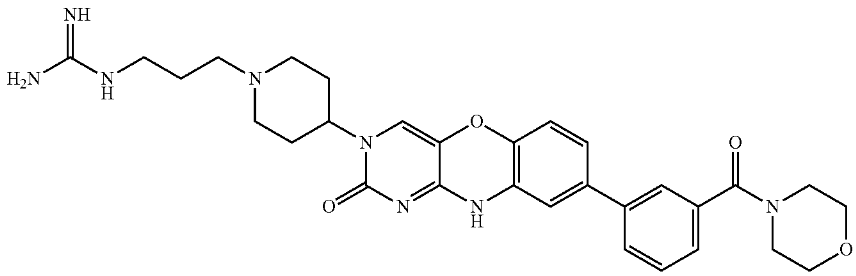 [SMILES: N=C(N)NCCCN1CCC(n2cc3c(nc2=O)Nc2cc(-c4cccc(C(=O)N5CCOCC5)c4)ccc2O3)CC1] | 573.10 |
| 656 | 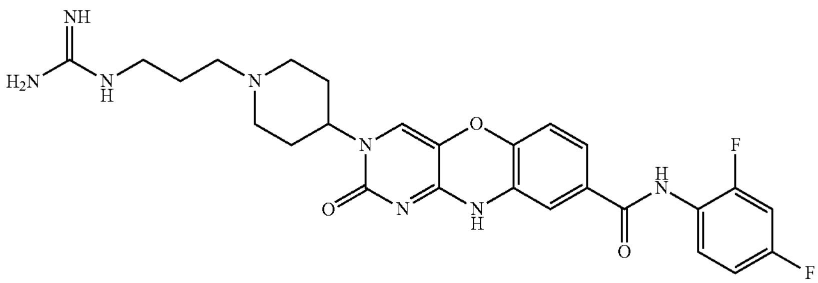 [SMILES: N=C(N)NCCCN1CCC(n2cc3c(nc2=O)Nc2cc(C(=O)Nc4ccc(F)cc4F)ccc2O3)CC1] | 539.20 |
| 657 | 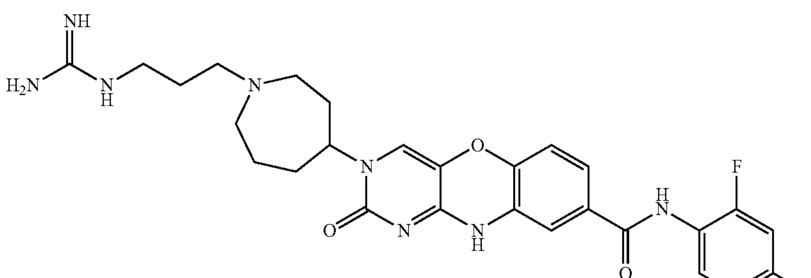 | 553.10 |
| 658 | 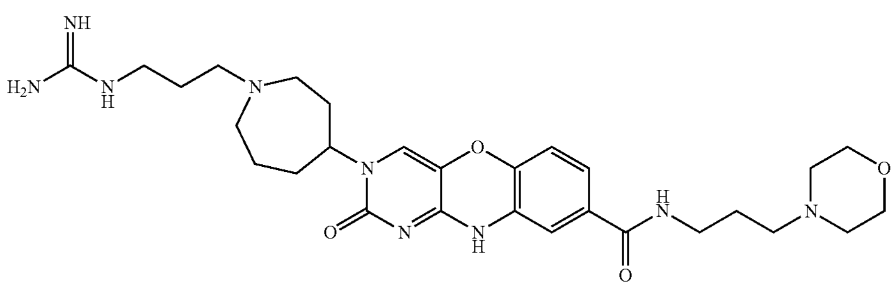 [SMILES: N=C(N)NCCCN1CCCC(n2cc3c(nc2=O)Nc2cc(C(=O)NCCCN4CCOCC4)ccc2O3)CC1] | 568.10 |
| 659 | 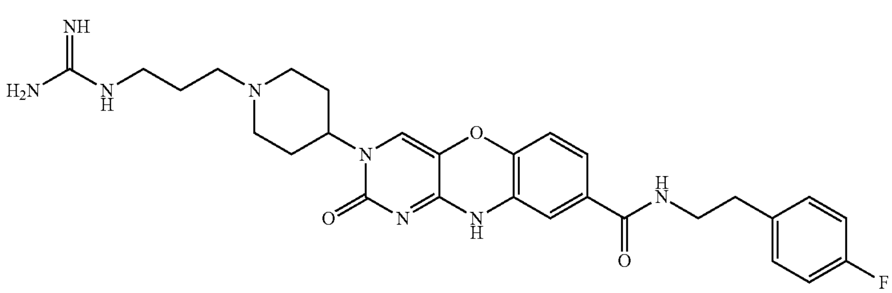 [SMILES: N=C(N)NCCCN1CCC(n2cc3c(nc2=O)Nc2cc(C(=O)NCCc4ccc(F)cc4)ccc2O3)CC1] | 549.10 |

TABLE 1-continued

| Comp. No. | Structure | LCMS |
|---|---|---|
| 660 | 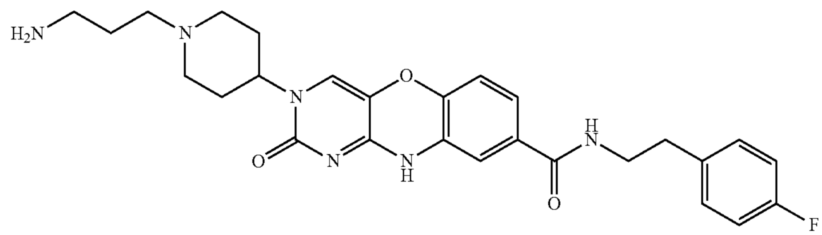 [SMILES: NCCCN1CCC(n2cc3c(nc2=O)Nc2cc(C(=O)NCCc4ccc(F)cc4)ccc2O3)CC1] | 507.20 |
| 664 | 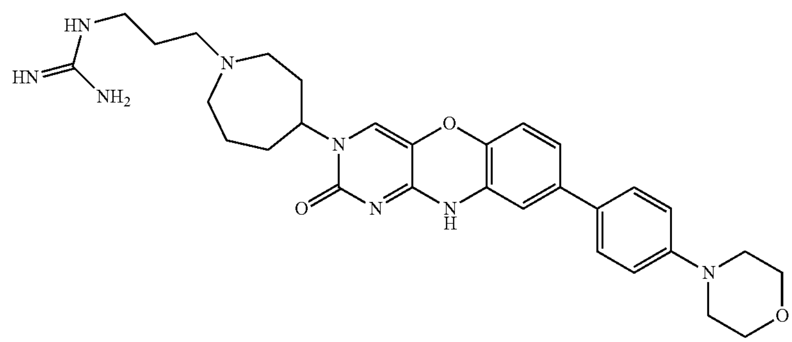 [SMILES: N=C(N)NCCCN1CCCC(n2cc3c(nc2=O)Nc2cc(-c4ccc(N5CCOCC5)cc4)ccc2O3)CC1] | 559.30 |
| 667 | 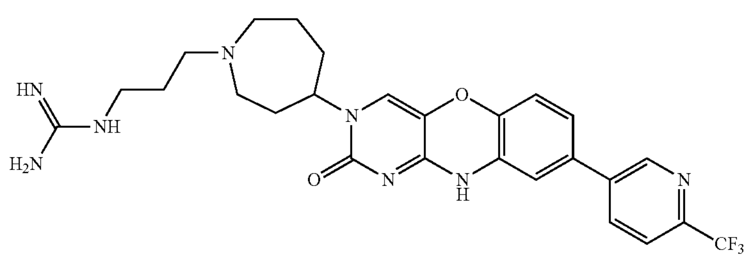 [SMILES: N=C(N)NCCCN1CCCC(n2cc3c(nc2=O)Nc2cc(-c4ccc(C(F)(F)F)nc4)ccc2O3)CC1] | 543.10 |
| 669 | 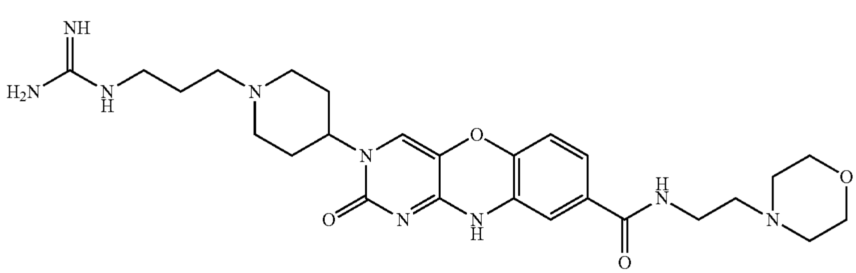 [SMILES: N=C(N)NCCCN1CCC(n2cc3c(nc2=O)Nc2cc(C(=O)NCCN4CCOCC4)ccc2O3)CC1] | 540.20 |
| 671 | 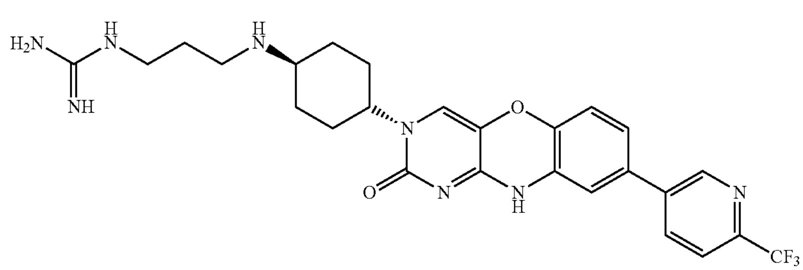 | 543.10 |

TABLE 1-continued
| Comp. No. | Structure | LCMS |
|---|---|---|
| 672 | 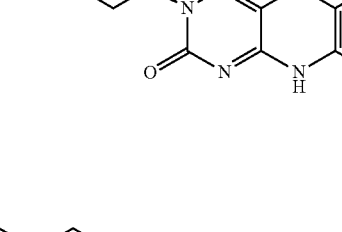 | 501.10 |
| 674 | 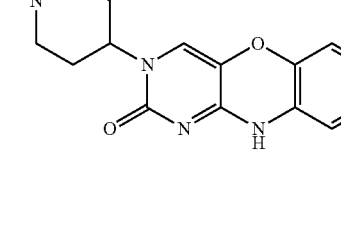 | 552.10 |
| 675 | 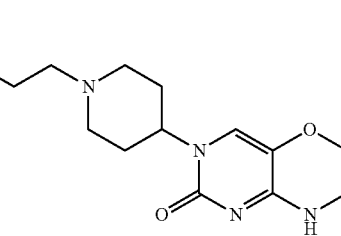 | 5871.10 |
| 676 | 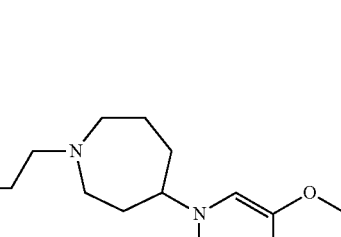 | 499.10 |
| 681 | 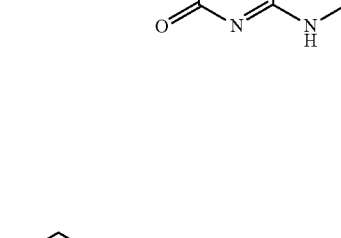 | 611.20 |

TABLE 1-continued

| Comp. No. | Structure | LCMS |
|---|---|---|
| 685 | 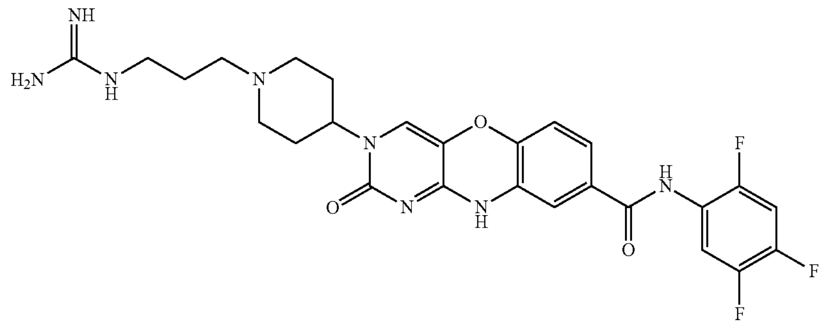 [SMILES: N=C(N)NCCCN1CCC(n2cc3c(nc2=O)Nc2cc(C(=O)Nc4cc(F)c(F)cc4F)ccc2O3)CC1] | 557.10 |
| 686 | 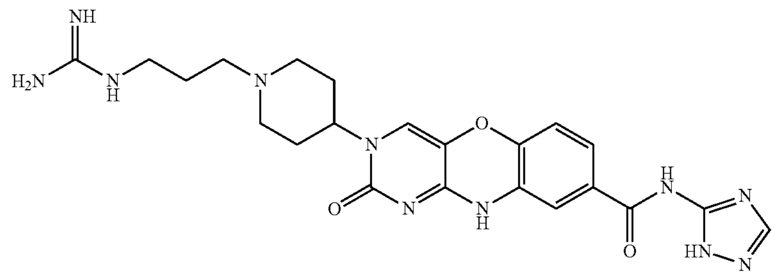 [SMILES: N=C(N)NCCCN1CCC(n2cc3c(nc2=O)Nc2cc(C(=O)Nc4ncn[nH]4)ccc2O3)CC1] | 494.10 |
| 689 | 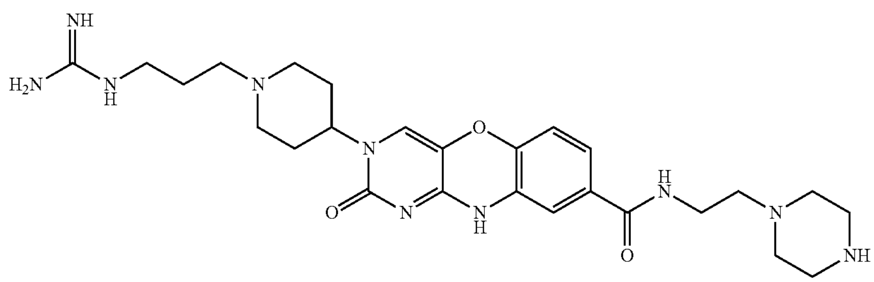 [SMILES: N=C(N)NCCCN1CCC(n2cc3c(nc2=O)Nc2cc(C(=O)NCCN4CCNCC4)ccc2O3)CC1] | 553.10 |
| 690 | 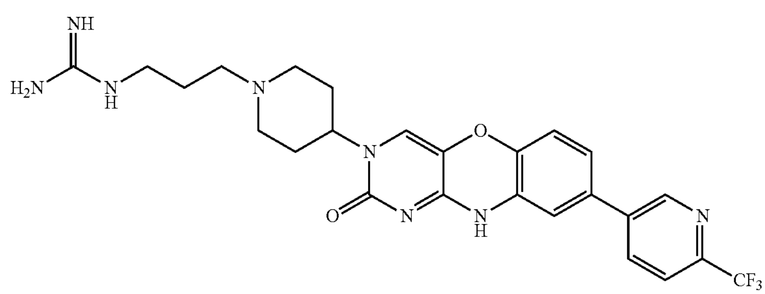 [SMILES: N=C(N)NCCCN1CCC(n2cc3c(nc2=O)Nc2cc(-c4ccc(C(F)(F)F)nc4)ccc2O3)CC1] | 529.20 |
| 691 | 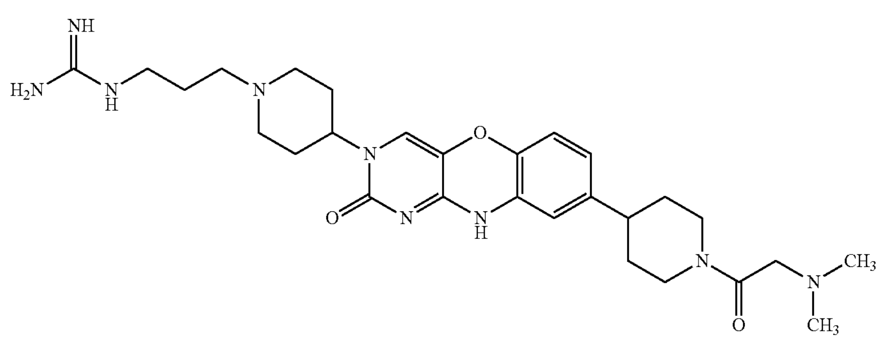 [SMILES: CN(C)CC(=O)N1CCC(c2ccc3c(c2)Nc2nc(=O)n(C4CCN(CCCNC(=N)N)CC4)cc2O3)CC1] | 552.40 |

| Comp. No. | Structure | LCMS |
|---|---|---|
| 694 | 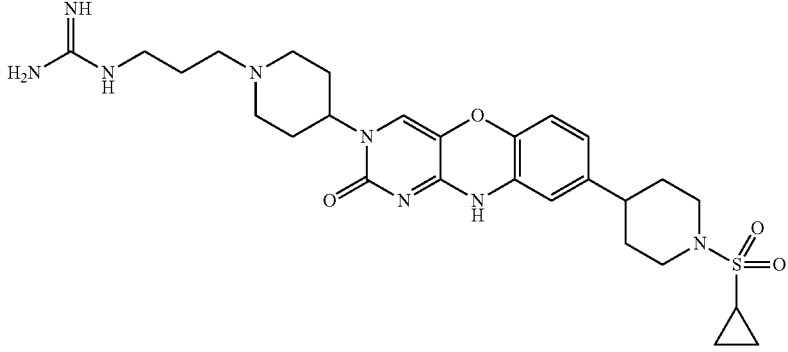 [SMILES: N=C(N)NCCCN1CCC(n2cc3c(nc2=O)Nc2cc(C4CCN(S(=O)(=O)C5CC5)CC4)ccc2O3)CC1] | 571.10 |
| 695 | 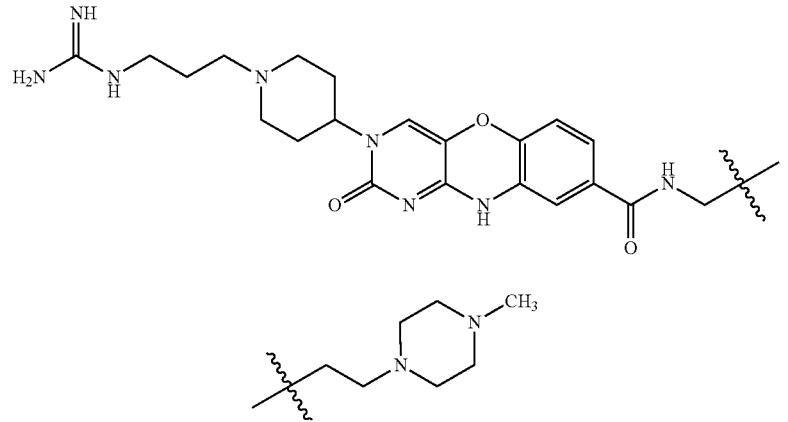 | 580.20 |
| 696 | 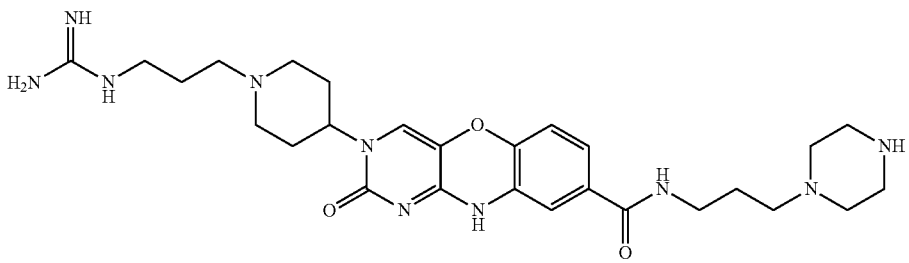 [SMILES: N=C(N)NCCCN1CCC(n2cc3c(nc2=O)Nc2cc(C(=O)NCCCN4CCNCC4)ccc2O3)CC1] | 567.10 |
| 707 | 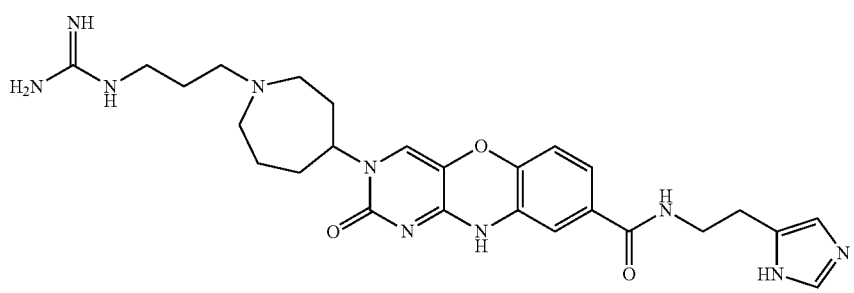 [SMILES: N=C(N)NCCCN1CCCC(n2cc3c(nc2=O)Nc2cc(C(=O)NCCc4cnc[nH]4)ccc2O3)CC1] | 535.20 |

TABLE 1-continued

| Comp. No. | Structure | LCMS |
|---|---|---|
| 708 | 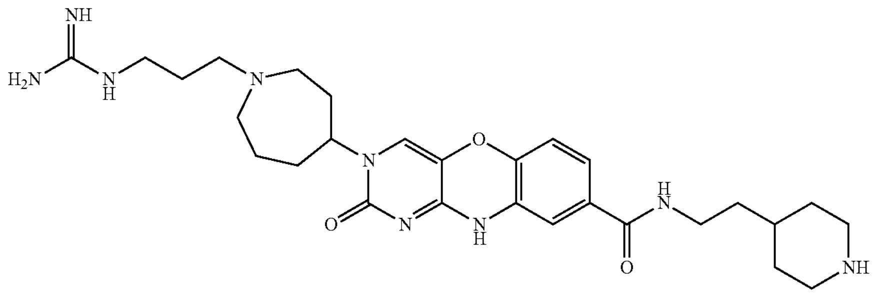 [SMILES: N=C(N)NCCCN1CCCC(n2cc3c(nc2=O)Nc2cc(C(=O)NCCC4CCNCC4)ccc2O3)CC1] | 552.30 |
| 714 | 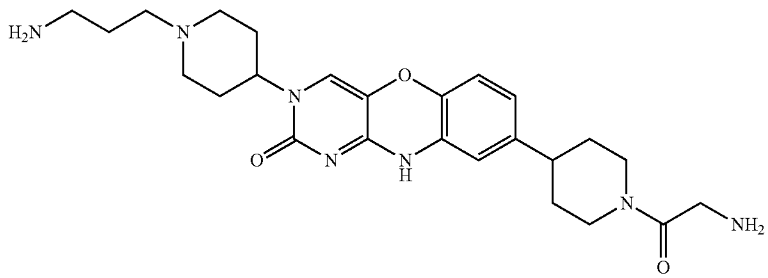 [SMILES: NCCCN1CCC(n2cc3c(nc2=O)Nc2cc(C4CCN(C(=O)CN)CC4)ccc2O3)CC1] | 482.20 |
| 715 | 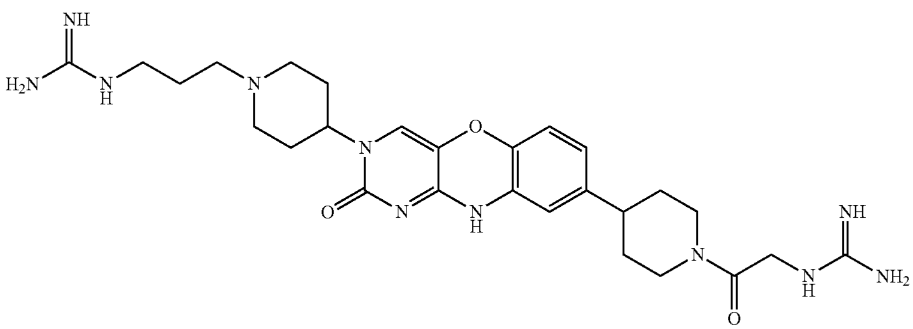 [SMILES: N=C(N)NCCCN1CCC(n2cc3c(nc2=O)Nc2cc(C4CCN(C(=O)CNC(=N)N)CC4)ccc2O3)CC1] | 566.30 |
| 718 | 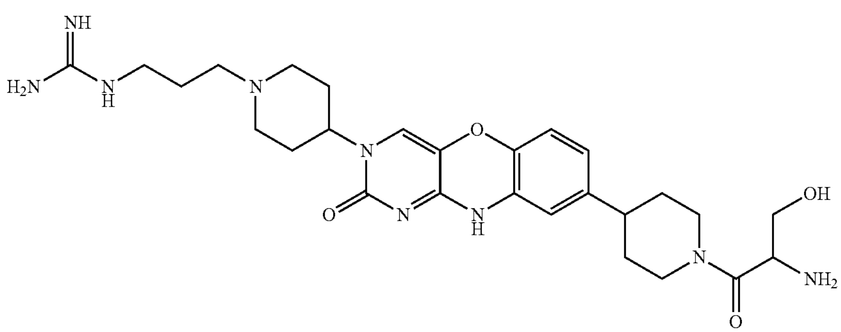 [SMILES: N=C(N)NCCCN1CCC(n2cc3c(nc2=O)Nc2cc(C4CCN(C(=O)C(N)CO)CC4)ccc2O3)CC1] | 554.30 |
| 729 | 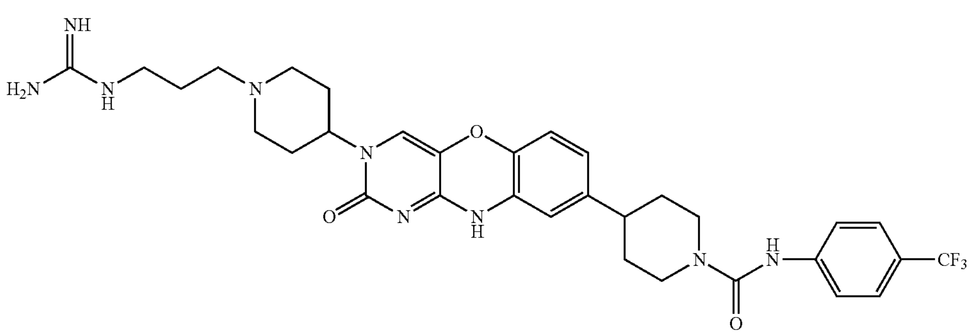 [SMILES: N=C(N)NCCCN1CCC(n2cc3c(nc2=O)Nc2cc(C4CCN(C(=O)Nc5ccc(C(F)(F)F)cc5)CC4)ccc2O3)CC1] | 654.40 |

TABLE 1-continued

| Comp. No. | Structure | LCMS |
|---|---|---|
| 730 | 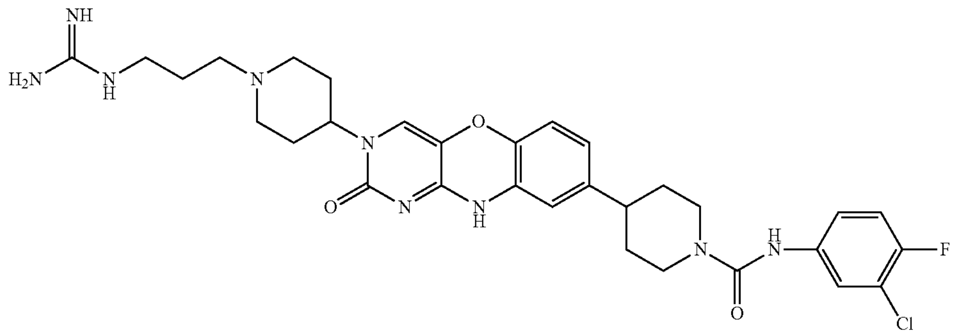 [SMILES: N=C(N)NCCCN1CCC(n2cc3c(nc2=O)Nc2cc(C4CCN(C(=O)Nc5ccc(F)c(Cl)c5)CC4)ccc2O3)CC1] | 638.30 |
| 731 | 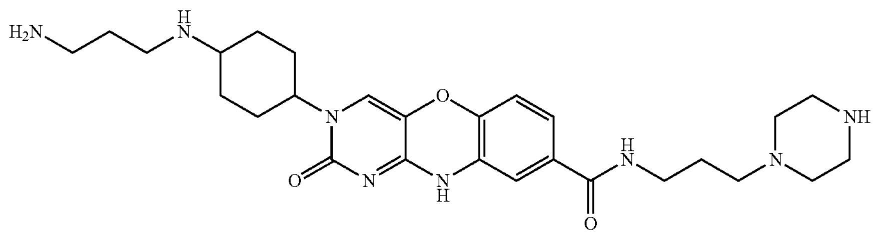 [SMILES: NCCCNC1CCC(n2cc3c(nc2=O)Nc2cc(C(=O)NCCCN4CCNCC4)ccc2O3)CC1] | 525.10 |
| 732 | 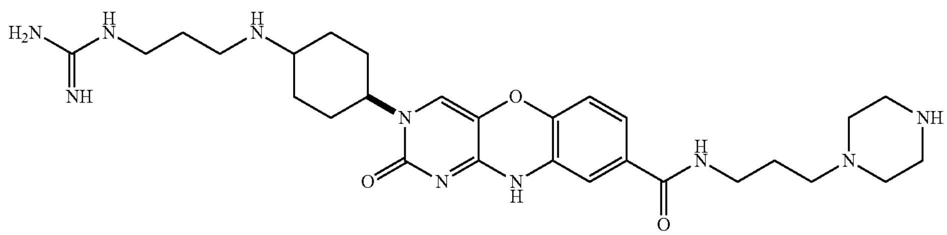 | 567.30 |
| 733 | 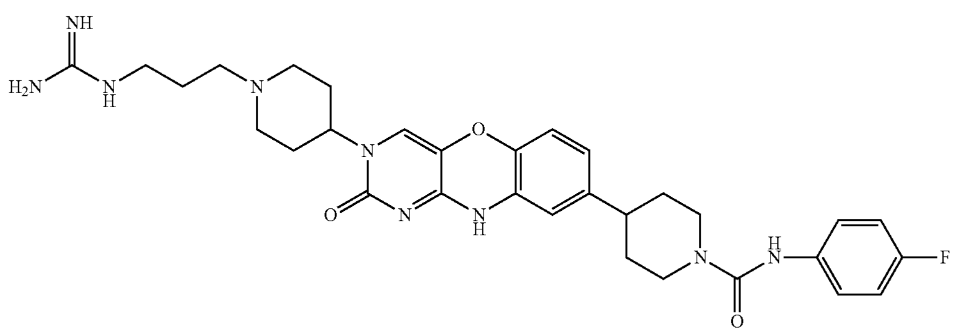 [SMILES: N=C(N)NCCCN1CCC(n2cc3c(nc2=O)Nc2cc(C4CCN(C(=O)Nc5ccc(F)cc5)CC4)ccc2O3)CC1] | 604.20 |
| 738 | 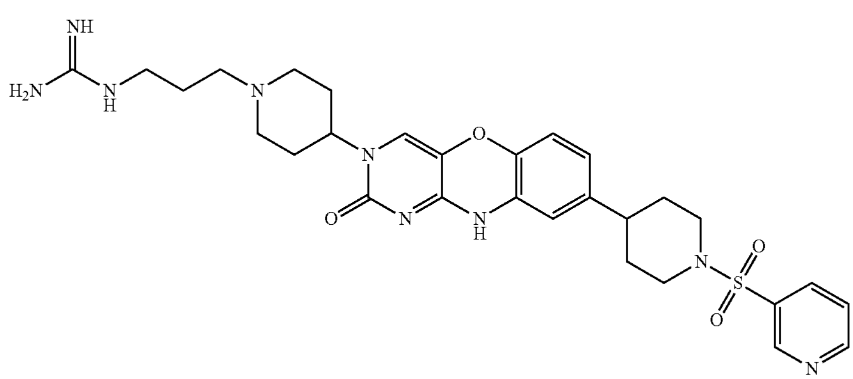 [SMILES: N=C(N)NCCCN1CCC(n2cc3c(nc2=O)Nc2cc(C4CCN(S(=O)(=O)c5cccnc5)CC4)ccc2O3)CC1] | 608.30 |

TABLE 1-continued

| Comp. No. | Structure | LCMS |
|---|---|---|
| 740 | 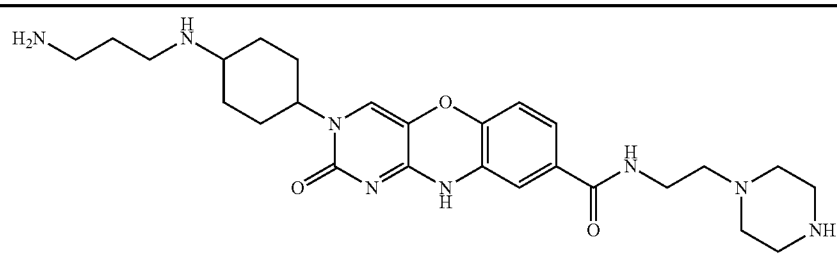 | 509.10 |
| 741 | 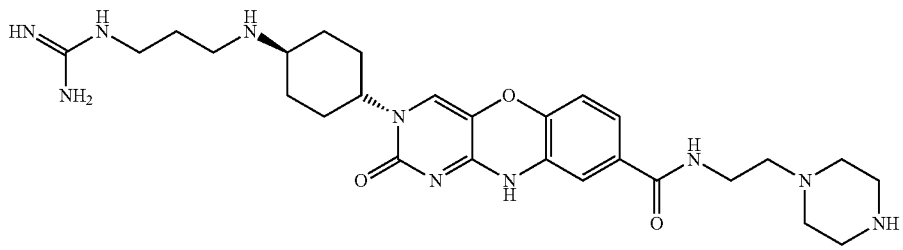 | 553.10 |
| 748 | 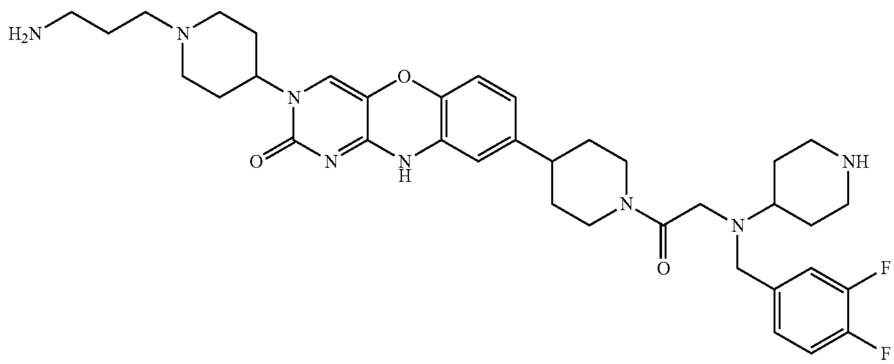 [SMILES: NCCCN1CCC(n2cc3c(nc2=O)Nc2cc(C4CCN(C(=O)CN(Cc5ccc(F)c(F)c5)C5CCNCC5)CC4)ccc2O3)CC1] | 691.30 |
| 749 | 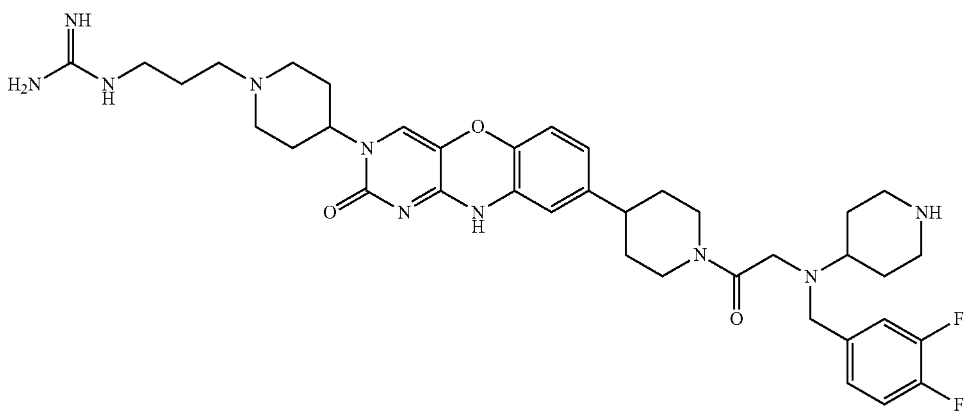 [SMILES: N=C(N)NCCCN1CCC(n2cc3c(nc2=O)Nc2cc(C4CCN(C(=O)CN(Cc5ccc(F)c(F)c5)C5CCNCC5)CC4)ccc2O3)CC1] | 733.40 |
| 750 | 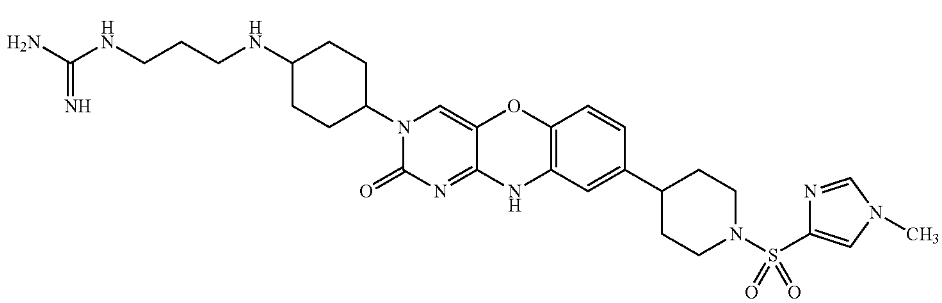 [SMILES: Cn1cnc(S(=O)(=O)N2CCC(c3ccc4c(c3)Nc3nc(=O)n(C5CCC(NCCCNC(=N)N)CC5)cc3O4)CC2)c1] | 625.30 |

TABLE 1-continued

| Comp. No. | Structure | LCMS |
|---|---|---|
| 751 | 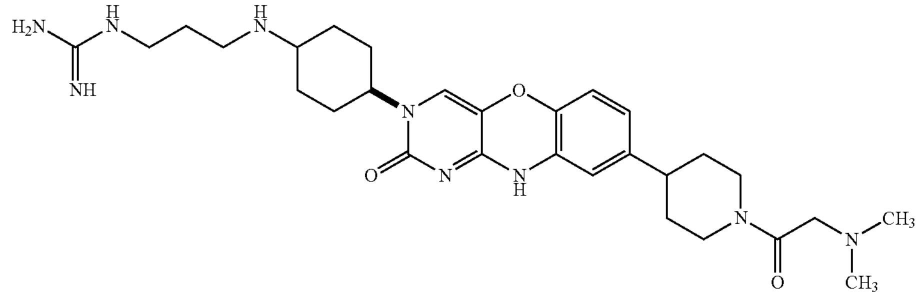 | 566.30 |
| 752 | 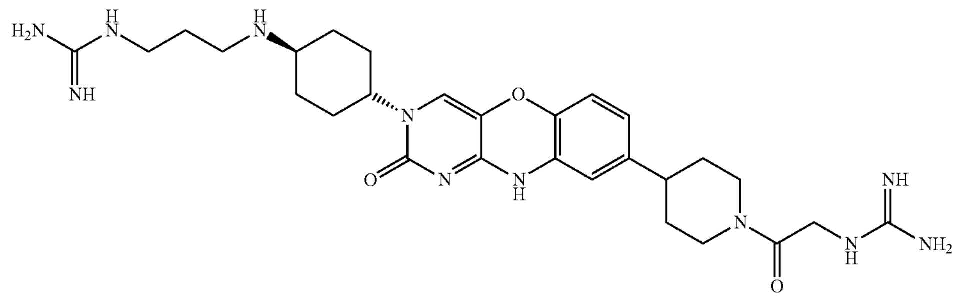 | 580.30 |
| 753 | 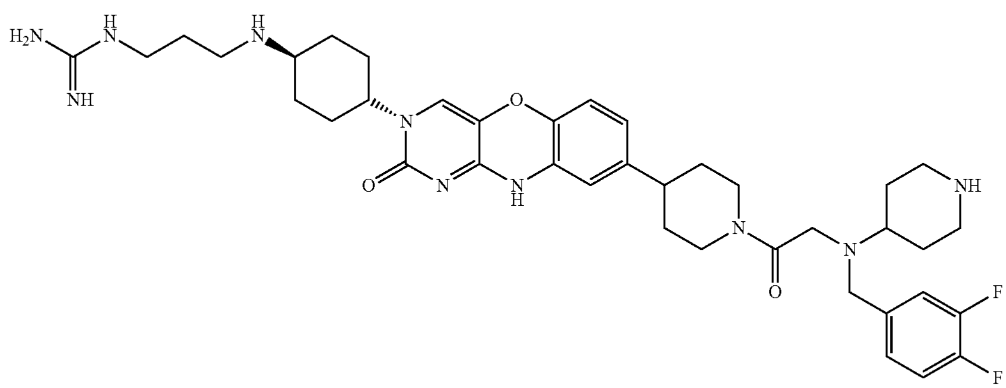 | 747.40 |
| 754 | 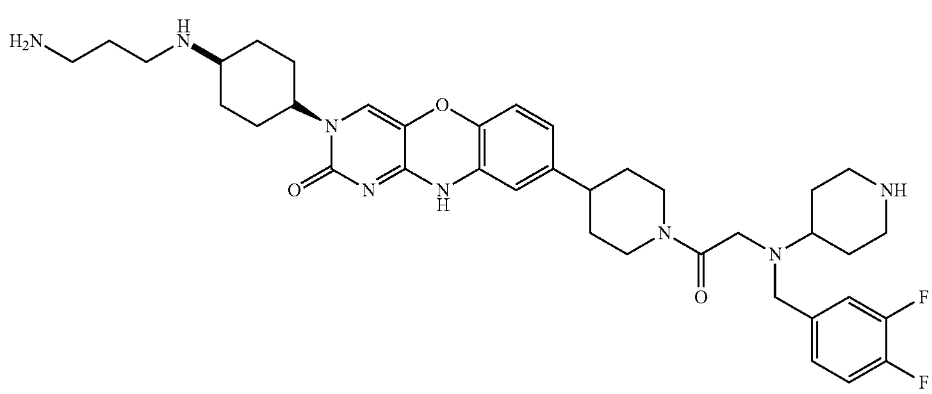 | 705.40 |

TABLE 1-continued

| Comp. No. | Structure | LCMS |
|---|---|---|
| 763 | 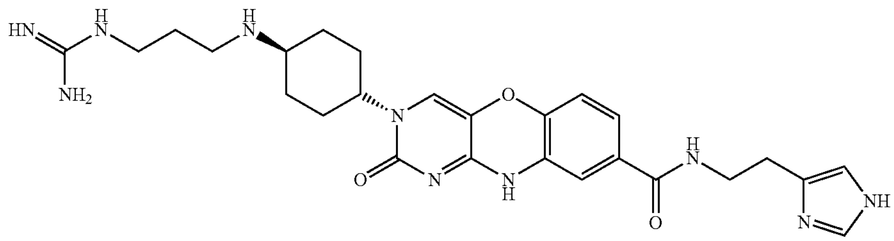 | 535.10 |
| 765 | 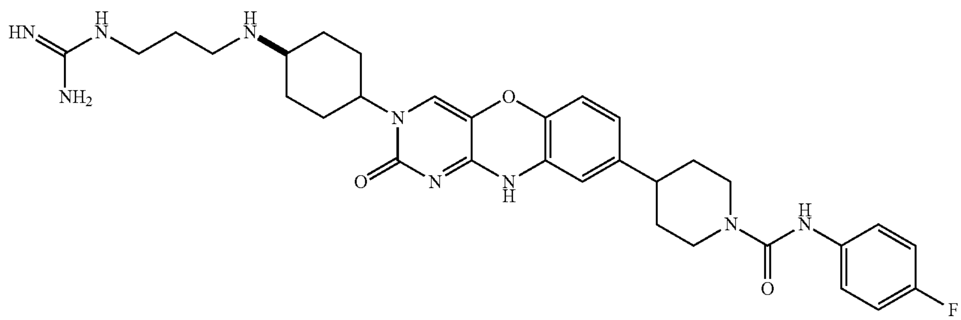 | 618.20 |
| 774 | 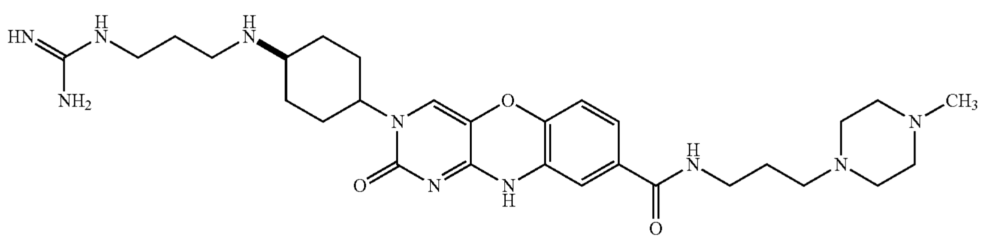 | 581.00 |
| 776 | 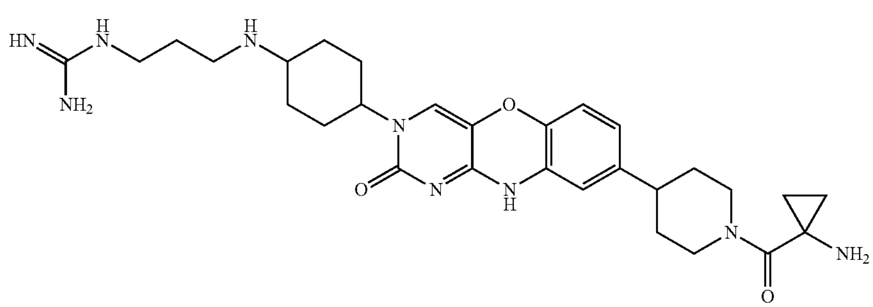 [SMILES: N=C(N)NCCCNC1CCC(n2cc3c(nc2=O)Nc2cc(C4CCN(C(=O)C5(N)CC5)CC4)ccc2O3)CC1] | 564.30 |
| 777 | 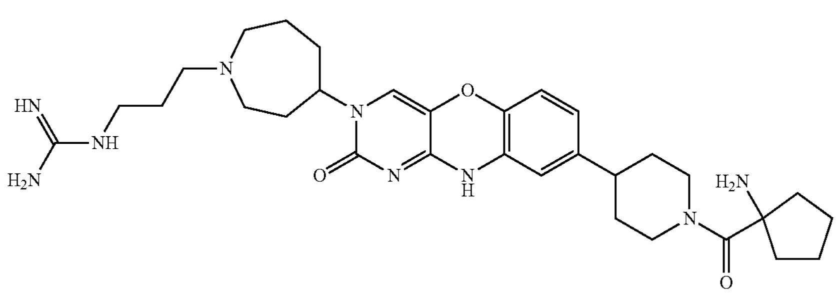 [SMILES: N=C(N)NCCCN1CCCC(n2cc3c(nc2=O)Nc2cc(C4CCN(C(=O)C5(N)CCCC5)CC4)ccc2O3)CC1] | 592.30 |

TABLE 1-continued
| Comp. No. | Structure | LCMS |
|---|---|---|
| 781 | 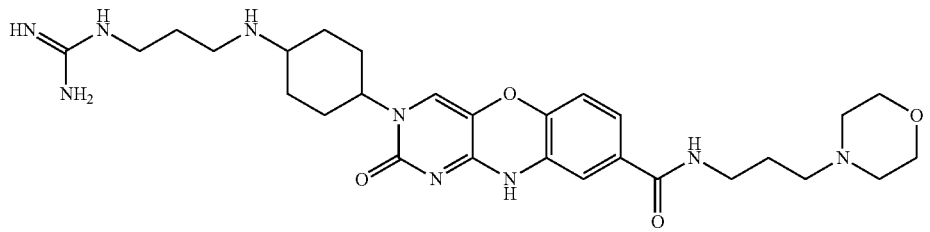 [SMILES: N=C(N)NCCCNC1CCC(n2cc3c(nc2=O)Nc2cc(C(=O)NCCCN4CCOCC4)ccc2O3)CC1] | 568.30 |
| 782 | 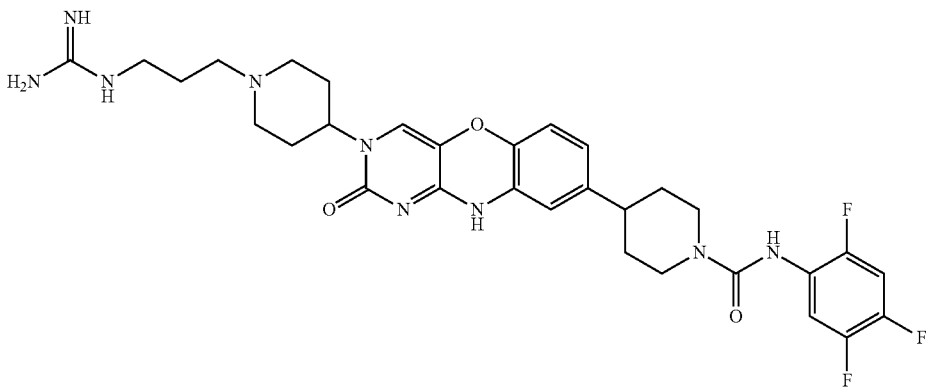 [SMILES: N=C(N)NCCCN1CCC(n2cc3c(nc2=O)Nc2cc(C4CCN(C(=O)Nc5cc(F)c(F)cc5F)CC4)ccc2O3)CC1] | 640.20 |
| 783 | 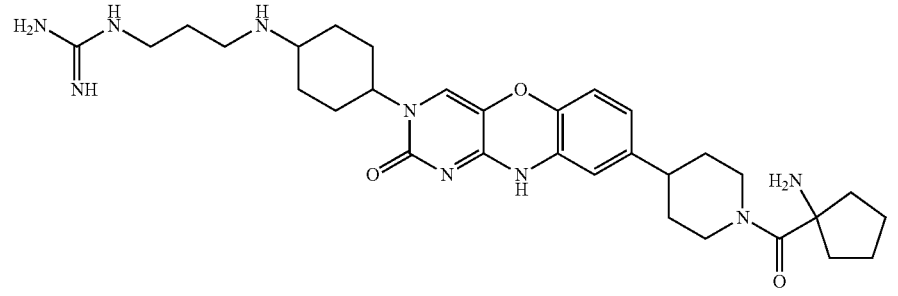 [SMILES: N=C(N)NCCCNC1CCC(n2cc3c(nc2=O)Nc2cc(C4CCN(C(=O)C5(N)CCCC5)CC4)ccc2O3)CC1] | 592.30 |
| 792 | 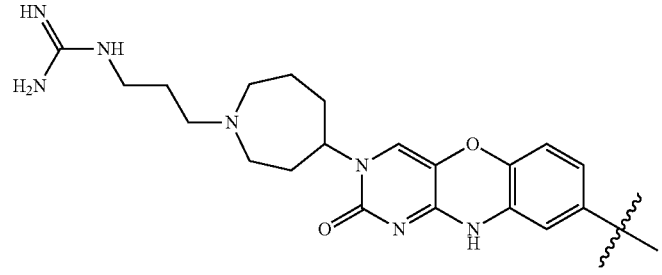 [SMILES: *c1ccc2c(c1)Nc1nc(=O)n(C3CCCN(CCCNC(=N)N)CC3)cc1O2] | 580.30 |

TABLE 1-continued
| Comp. No. | Structure | LCMS |
|---|---|---|
| 793 | 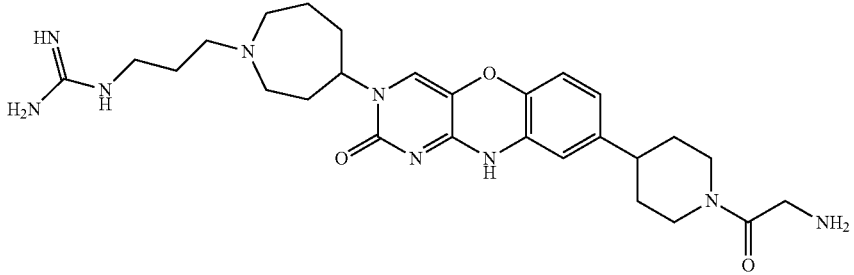 [SMILES: N=C(N)NCCCN1CCCC(n2cc3c(nc2=O)Nc2cc(C4CCN(C(=O)CN)CC4)ccc2O3)CC1] | 538.40 |
| 794 | 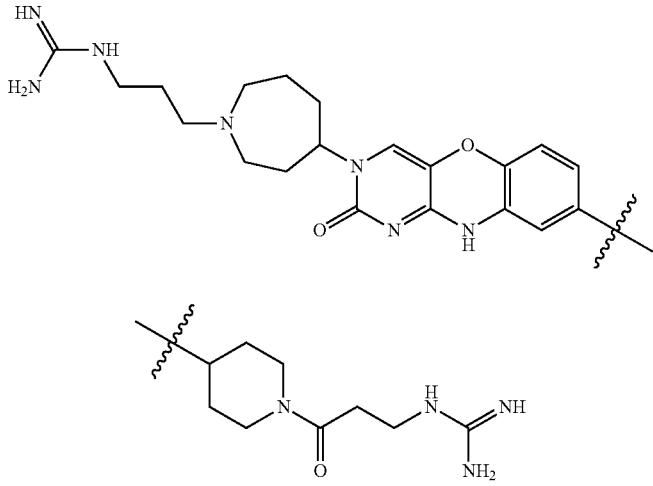 | 594.30 |
| 795 | 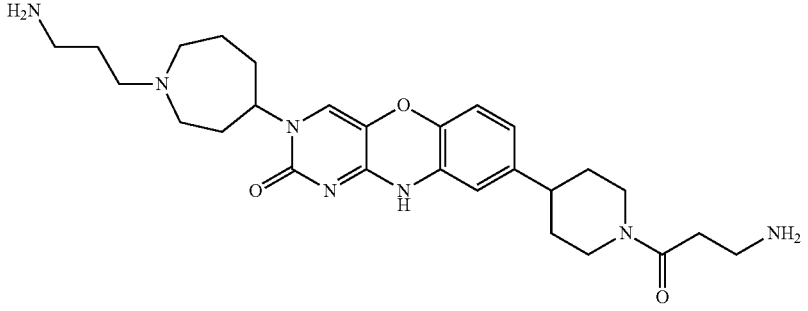 [SMILES: NCCCN1CCCC(n2cc3c(nc2=O)Nc2cc(C4CCN(C(=O)CCN)CC4)ccc2O3)CC1] | 510.30 |
| 798 | 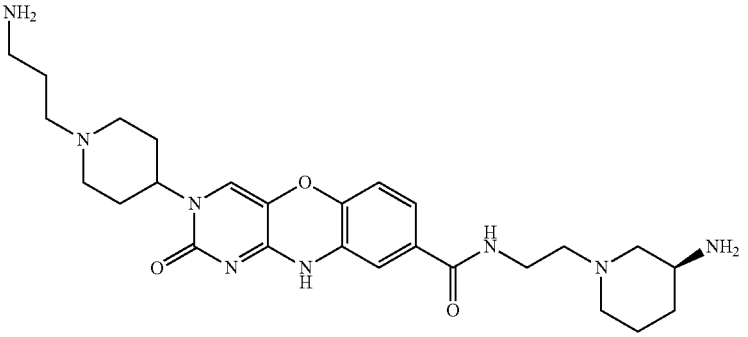 [SMILES: NCCCN1CCC(n2cc3c(nc2=O)Nc2cc(C(=O)NCCN4CCC[C@H](N)C4)ccc2O3)CC1] | 511.30 |

TABLE 1-continued
| Comp. No. | Structure | LCMS |
|---|---|---|
| 811 | 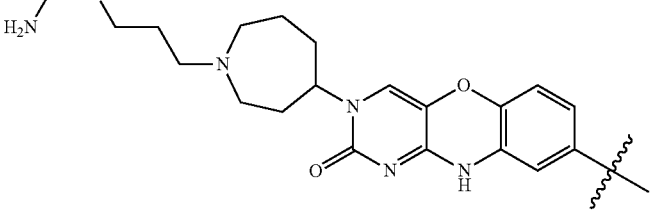 | 552.30 |
| 812 | 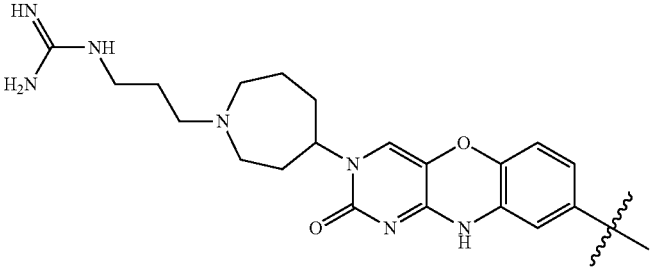 [SMILES: *c1ccc2c(c1)Nc1nc(=O)n(C3CCCN(CCCNC(=N)N)CC3)cc1O2] | 618.30 |
| 818 | 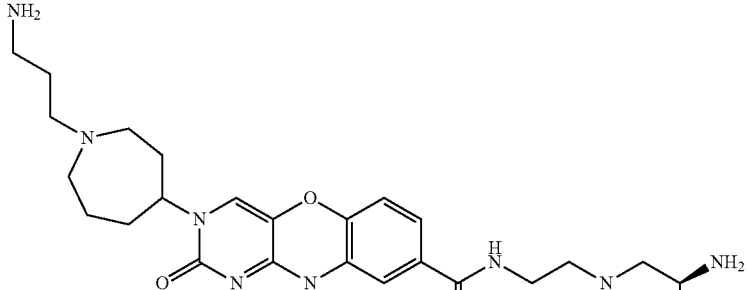 | 575.10 |

TABLE 1-continued
| Comp. No. | Structure | LCMS |
|---|---|---|
| 832 | 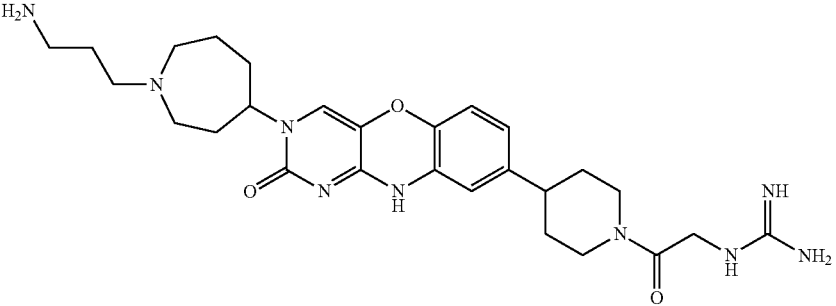 [SMILES: N=C(N)NCC(=O)N1CCC(c2ccc3c(c2)Nc2nc(=O)n(C4CCCN(CCCN)CC4)cc2O3)CC1] | 538.60 |
| 833 | 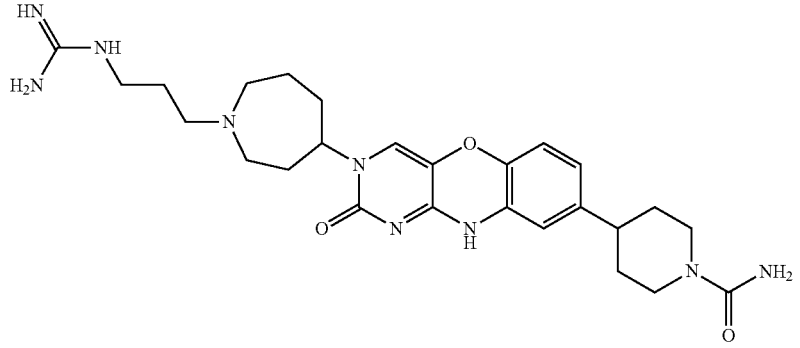 [SMILES: N=C(N)NCCCN1CCCC(n2cc3c(nc2=O)Nc2cc(C4CCN(C(N)=O)CC4)ccc2O3)CC1] | 523.40 |
| 858 | 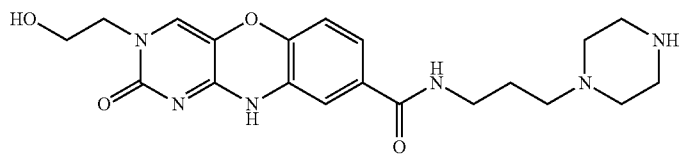 [SMILES: O=C(NCCCN1CCNCC1)c1ccc2c(c1)Nc1nc(=O)n(CCO)cc1O2] | 415.20 |
| 859 | 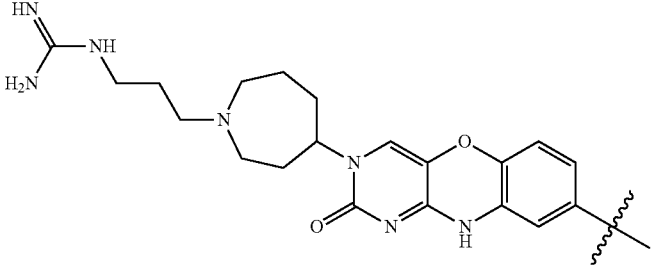 [SMILES: *c1ccc2c(c1)Nc1nc(=O)n(C3CCCN(CCCNC(=N)N)CC3)cc1O2]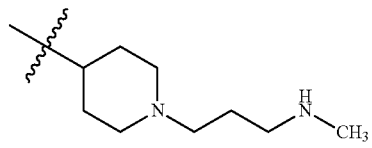 | 552.30 |
| 868 | 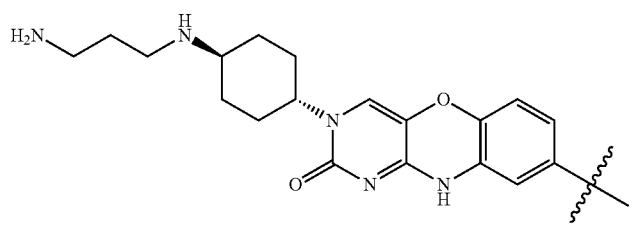 | 706.30 |

TABLE 1-continued
| Comp. No. | Structure | LCMS |
|---|---|---|
| | 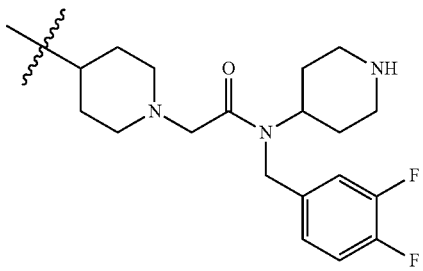 [SMILES: *C1CCN(CC(=O)N(Cc2ccc(F)c(F)c2)C2CCNCC2)CC1] | |
| 869 | 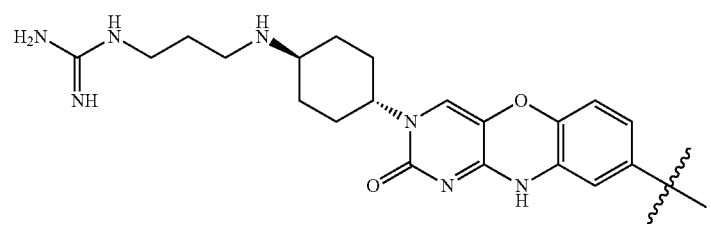 [SMILES: *c1ccc2c(c1)Nc1nc(=O)n([C@H]3CC[C@H](NCCCNC(=N)N)CC3)cc1O2] | 747.50 |
| | 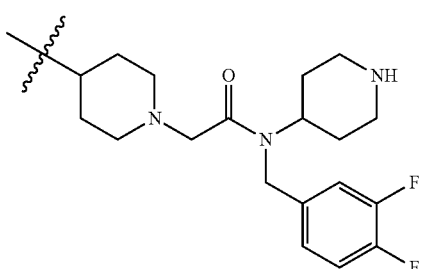 | |
| 870 | 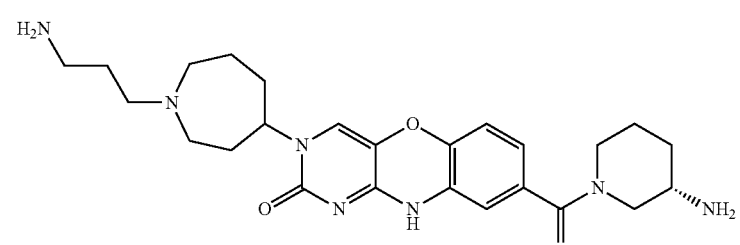 | 482.40 |
| 888 | 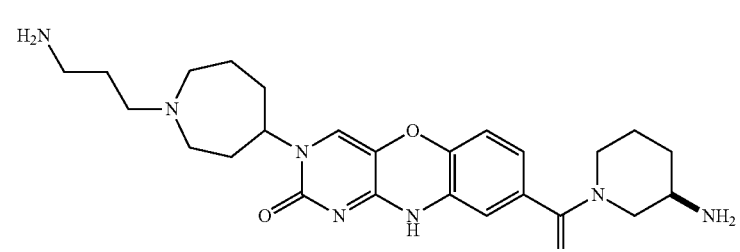 | 482.40 |
| 889 | 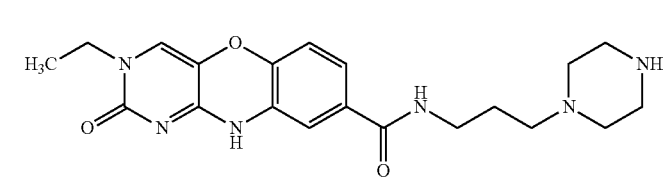 [SMILES: CCn1cc2c(nc1=O)Nc1cc(C(=O)NCCCN3CCNCC3)ccc1O2] | 499.20 |

| Comp. No. | Structure | LCMS |
|---|---|---|
| 890 | 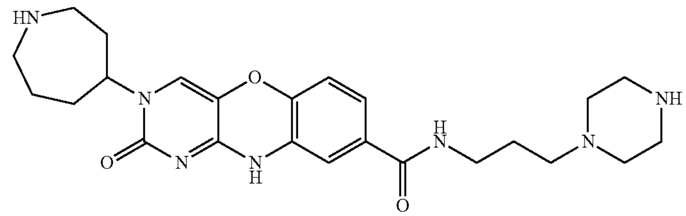 [SMILES: O=C(NCCCN1CCNCC1)c1ccc2c(c1)Nc1nc(=O)n(C3CCCNCC3)cc1O2] | 468.10 |
| 891 | 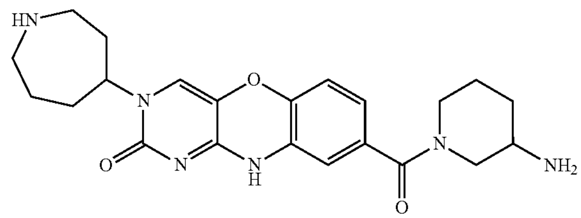 [SMILES: NC1CCCN(C(=O)c2ccc3c(c2)Nc2nc(=O)n(C4CCCNCC4)cc2O3)C1] | 425.10 |
| 903 | 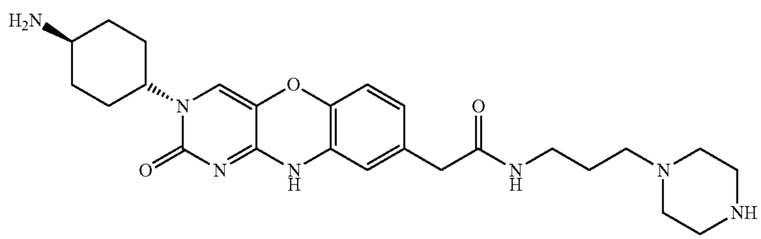 | 482.30 |
| 904 | 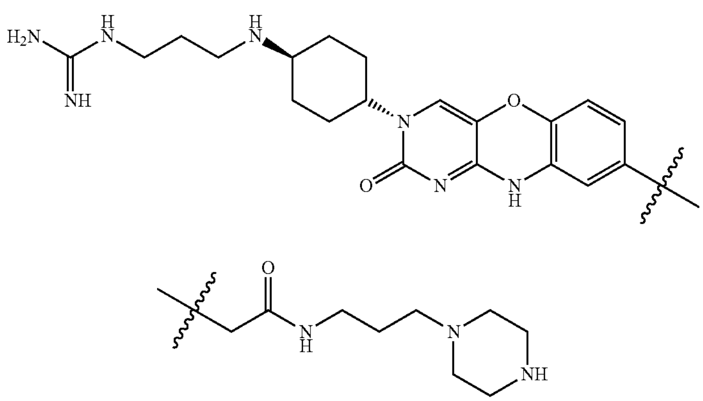 | 581.10 |
| 908 | 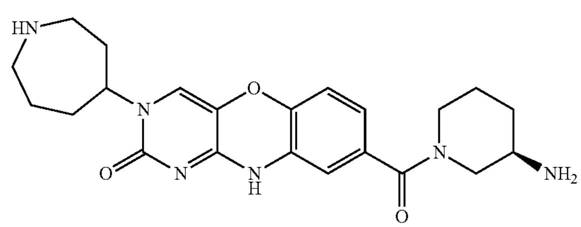 [SMILES: N[C@@H]1CCCN(C(=O)c2ccc3c(c2)Nc2nc(=O)n(C4CCCNCC4)cc2O3)C1] | 425.10 |
| 909 | 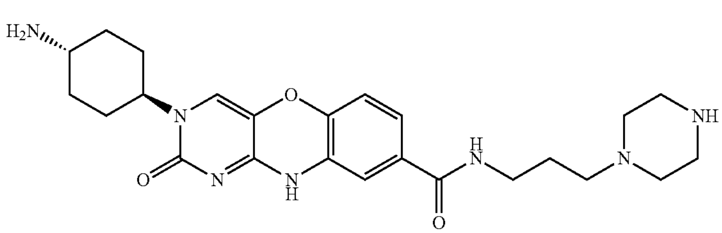 [SMILES: N[C@H]1CC[C@H](n2cc3c(nc2=O)Nc2cc(C(=O)NCCCN4CCNCC4)ccc2O3)CC1] | 425.20 |

TABLE 1-continued

| Comp. No. | Structure | LCMS |
|---|---|---|
| 916 | 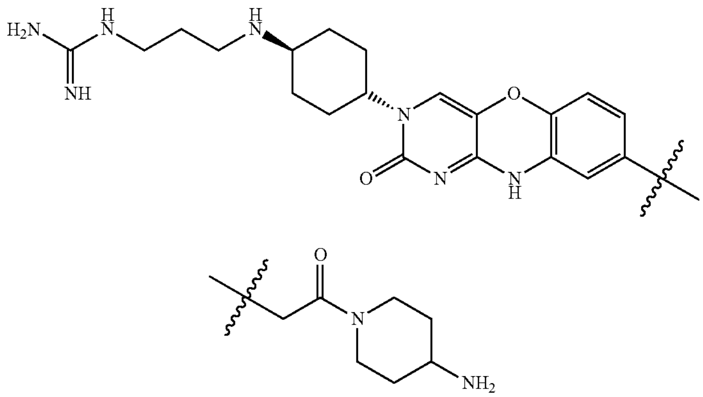 | 538.30 |
| 917 | 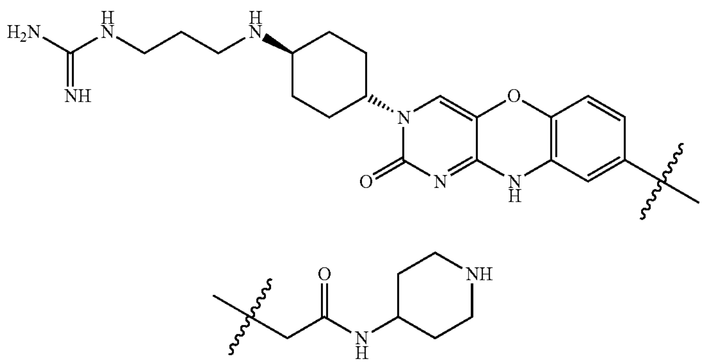 | 538.30 |
| 919 | 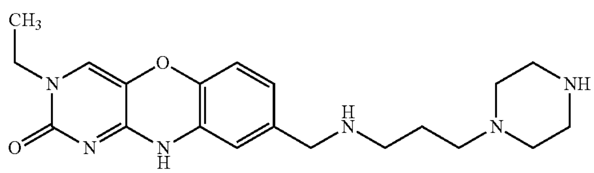 [SMILES: CCn1cc2c(nc1=O)Nc1cc(CNCCCN3CCNCC3)ccc1O2] | 386.20 |
| 920 | 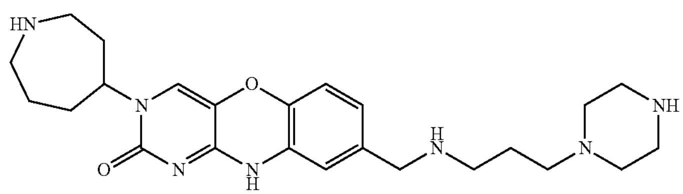 [SMILES: O=c1nc2c(cn1C1CCCNCC1)Oc1ccc(CNCCCN3CCNCC3)cc1N2] | 455.10 |
| 921 | 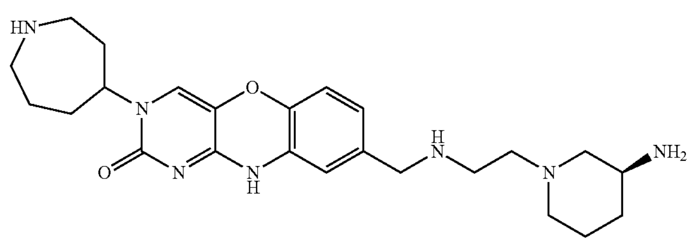 [SMILES: N[C@H]1CCCN(CCNCc2ccc3c(c2)Nc2nc(=O)n(C4CCCNCC4)cc2O3)C1] | 455.20 |
| 929 | 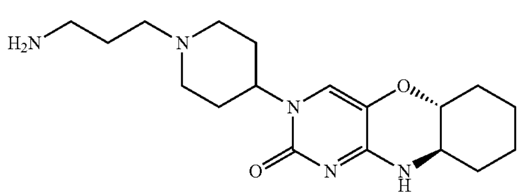 [SMILES: NCCCN1CCC(n2cc3c(nc2=O)N[C@@H]2CCCC[C@H]2O3)CC1] | 347.90 |

TABLE 1-continued

| Comp. No. | Structure | LCMS |
|---|---|---|
| 938 | 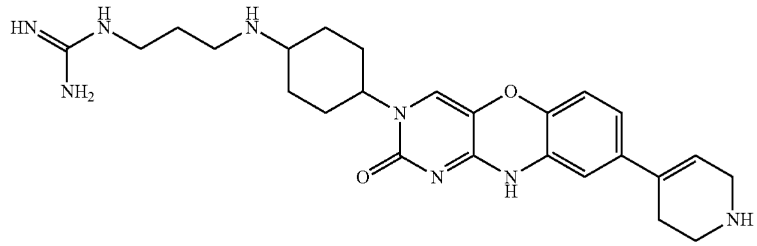 [SMILES: N=C(N)NCCCNC1CCC(n2cc3c(nc2=O)Nc2cc(C4=CCNCC4)ccc2O3)CC1] | 479.30 |
| 941 | 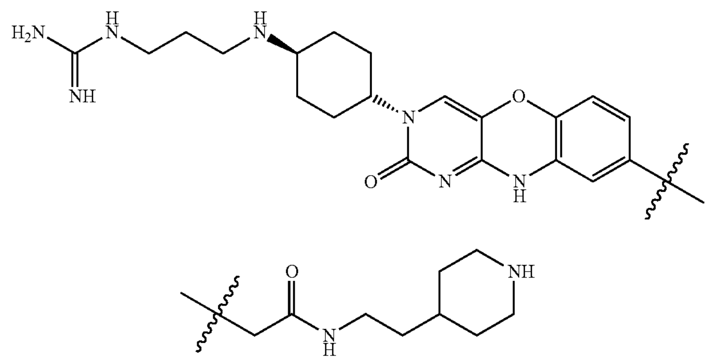 | 566.30 |
| 942 | 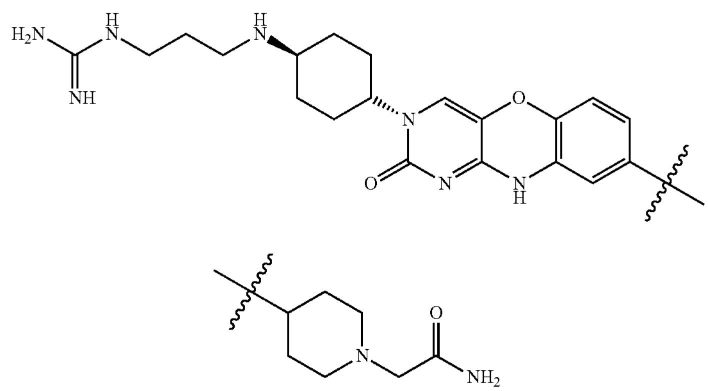 | 538.30 |
| 950 | 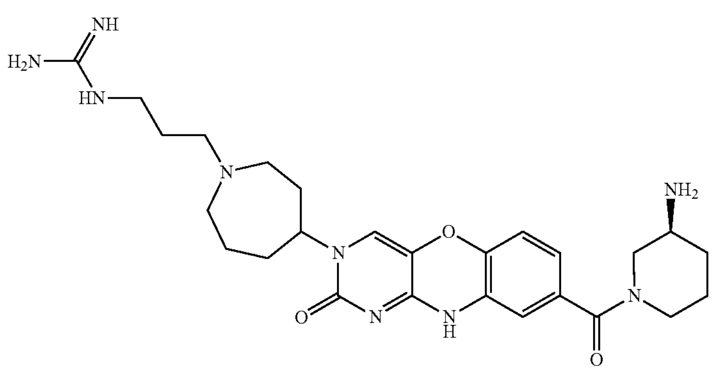 [SMILES: N=C(N)NCCCN1CCCC(n2cc3c(nc2=O)Nc2cc(C(=O)N4CCC[C@H](N)C4)ccc2O3)CC1] | 524.00 |
| 953 | 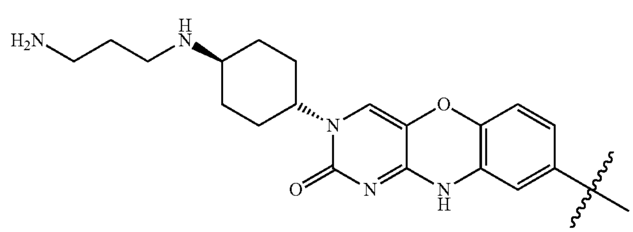 | 539.30 |

US 9,023,843 B2
TABLE 1-continued
| Comp. No. | Structure | LCMS |
|---|---|---|
| 954 | 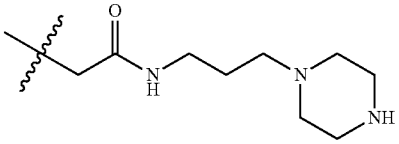 [SMILES: *CC(=O)NCCCN1CCNCC1] | 498.20 |
| 955 | 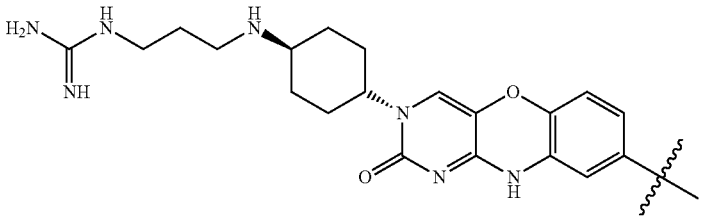 | 498.30 |
| 956 | 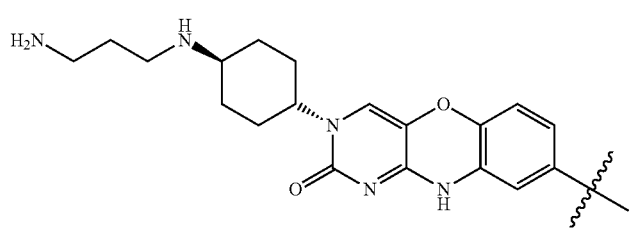 | 511.40 |
| 972 | 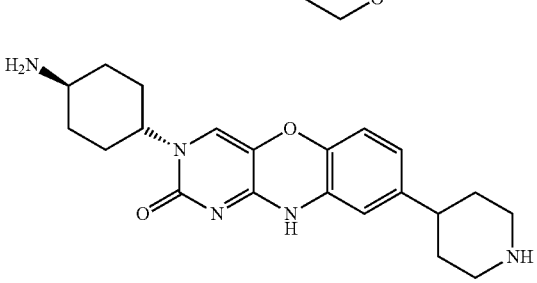 | 382.00 |

TABLE 1-continued

| Comp. No. | Structure | LCMS |
|---|---|---|
| 973 | 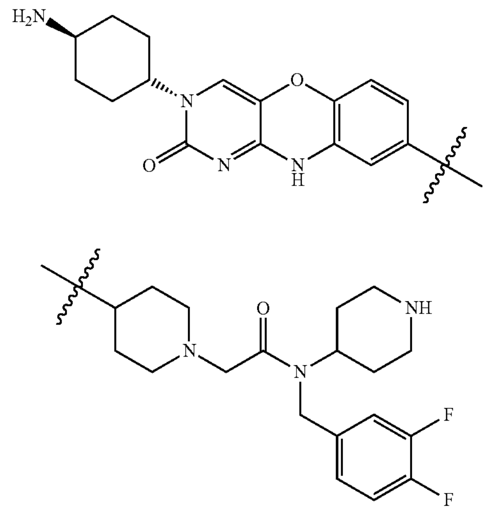 | 648.50 |
| | | |
| 976 | 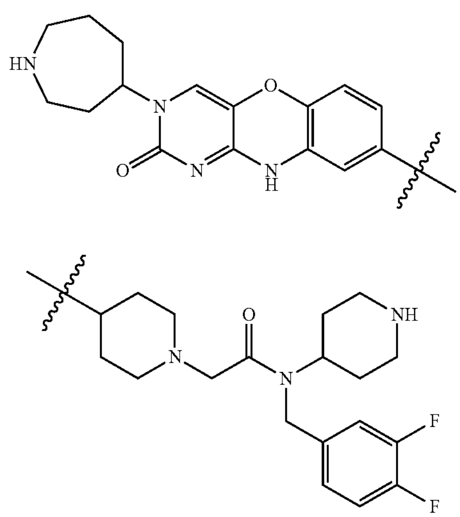 | 648.60 |
| | | |
| 993 | 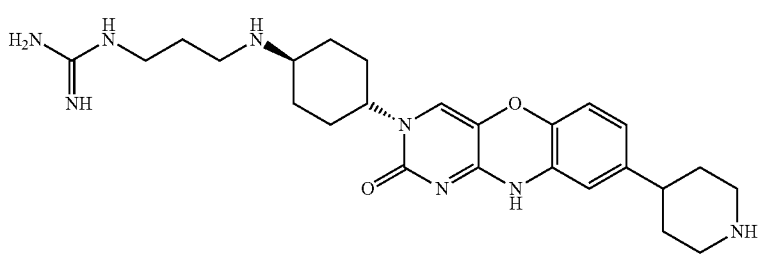 | 481.80 |
| 1006 | 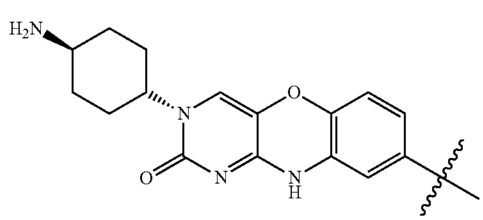 | 522.80 |

TABLE 1-continued
| Comp. No. | Structure | LCMS |
|---|---|---|
| | 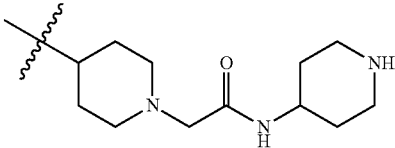 [SMILES: *C1CCN(CC(=O)NC2CCNCC2)CC1] | |
| 1007 | 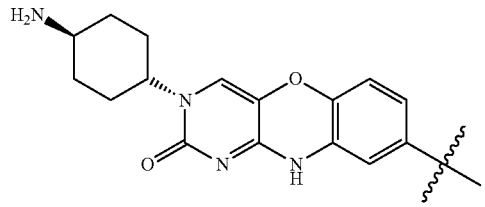 | 536.70 |
| | 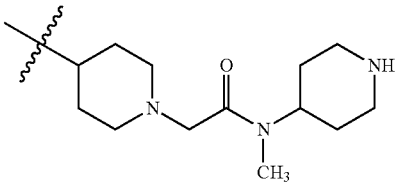 [SMILES: *C1CCN(CC(=O)N(C)C2CCNCC2)CC1] | |
| 1008 | 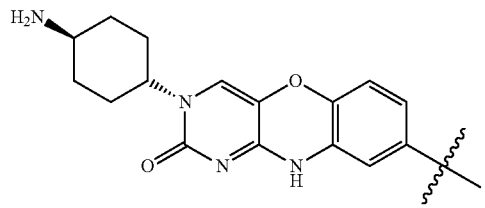 | 454.80 |
| | 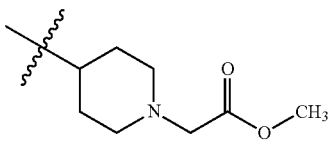 [SMILES: *C1CCN(CC(=O)OC)CC1] | |
| 1014 | 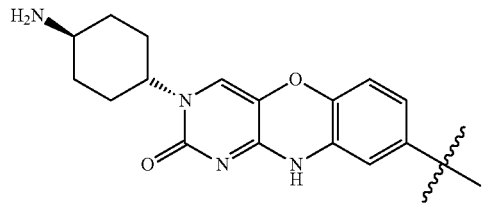 | 602.60 |
| | 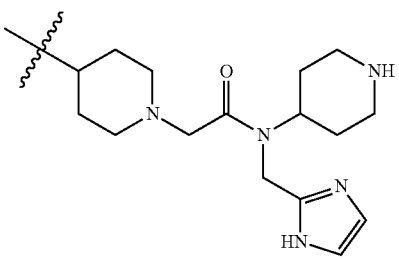 [SMILES: *C1CCN(CC(=O)N(Cc2ncc[nH]2)C2CCNCC2)CC1] | |

TABLE 1-continued
| Comp. No. | Structure | LCMS |
|---|---|---|
| 1016 | 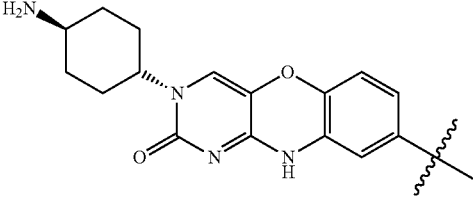 | 649.40 |
| 1025 | 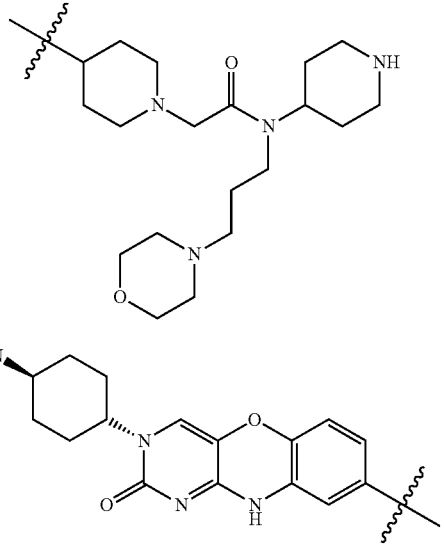 | 621.40 |
| 1026 | 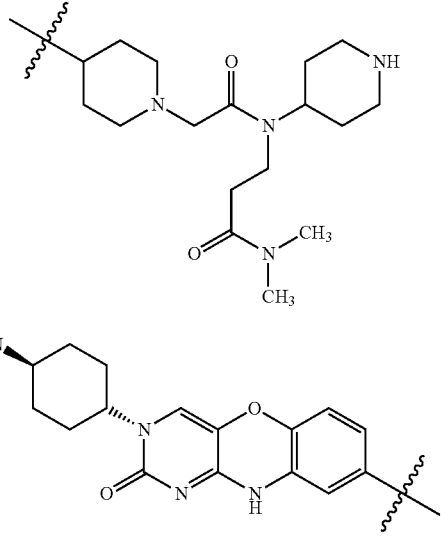 | 646.60 |

TABLE 1-continued

| Comp. No. | Structure | LCMS |
|---|---|---|
| 1030 | 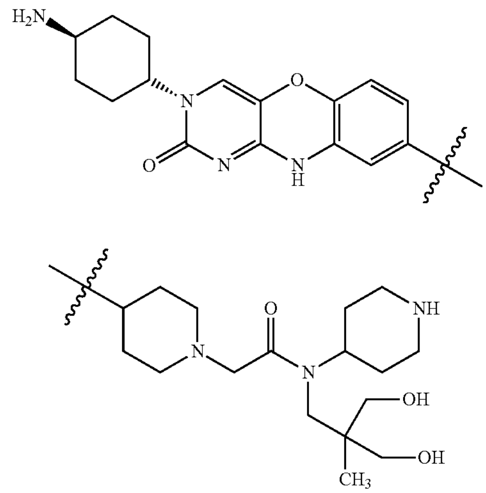 | 624.40 |
| 1031 | 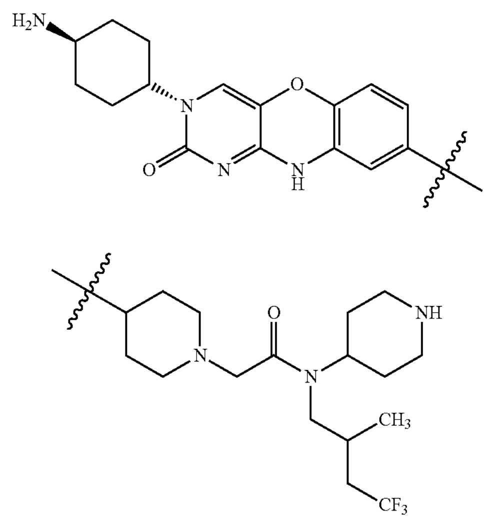 | 646.30 |
| 1032 | 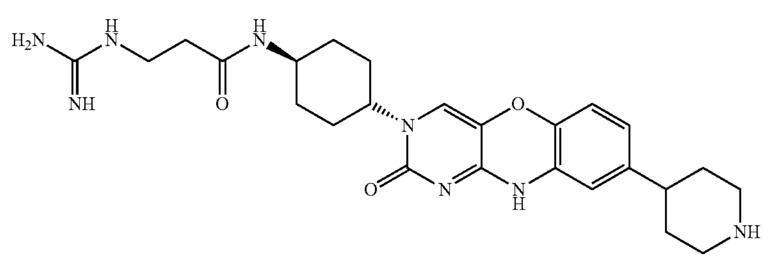 | 495.20 |
| 1033 | 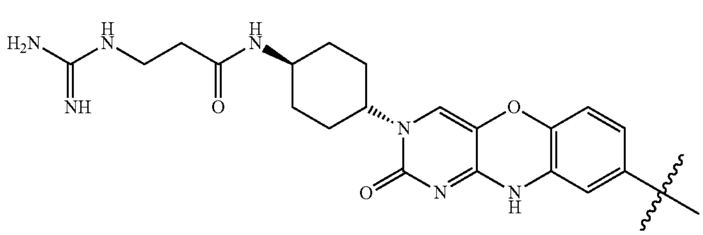 | 761.30 |

| Comp. No. | Structure | LCMS |
|---|---|---|
| 1041 | 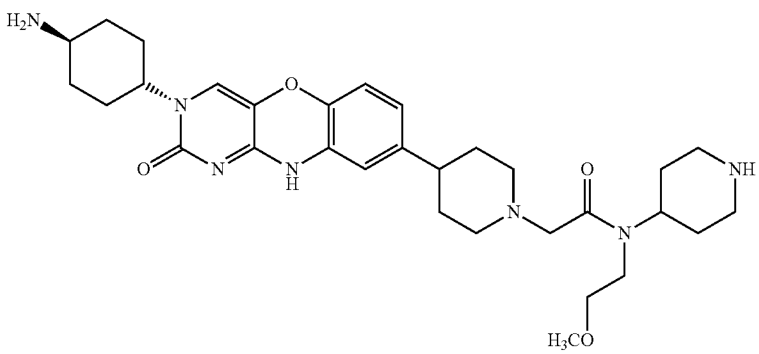 | 580.40 |
| 1042 | 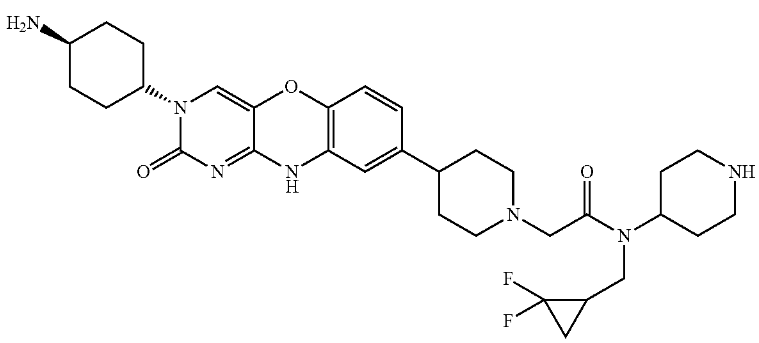 | 612.40 |
| 1055 | 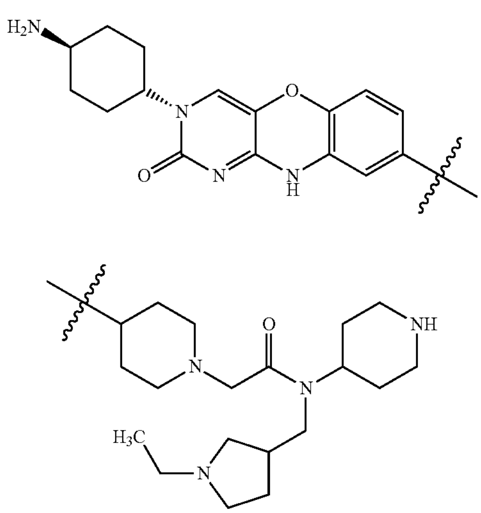 | 633.40 |

TABLE 1-continued
| Comp. No. | Structure | LCMS |
|---|---|---|
| 1056 | 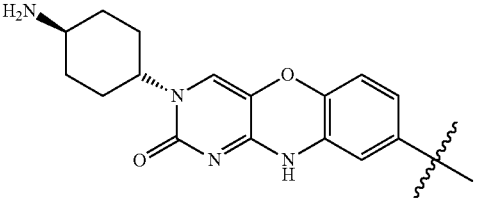 | 649.40 |
| 1058 | 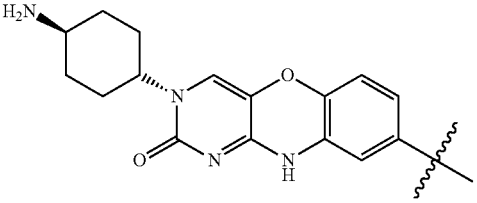 | 647.40 |
| 1070 | 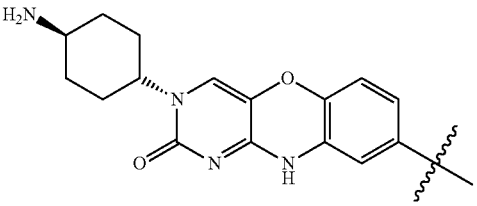 | 619.20 |

TABLE 1-continued
| Comp. No. | Structure | LCMS |
|---|---|---|
| 1071 | 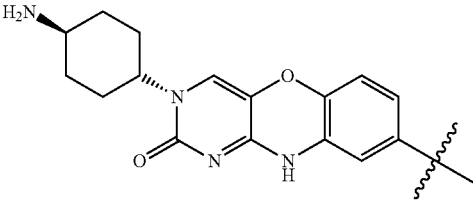 | 651.30 |
| 1072 | 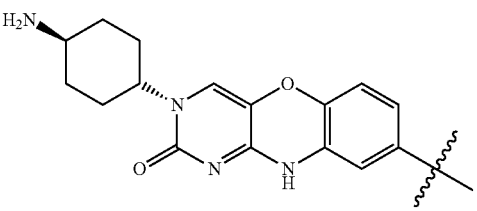 | 633.60 |
| 1073 | 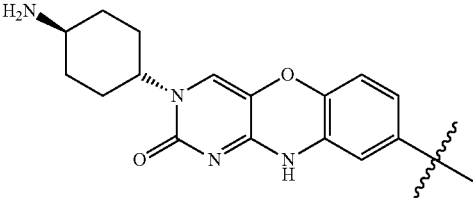 | 647.40 |

TABLE 1-continued
| Comp. No. | Structure | LCMS |
|---|---|---|
| | 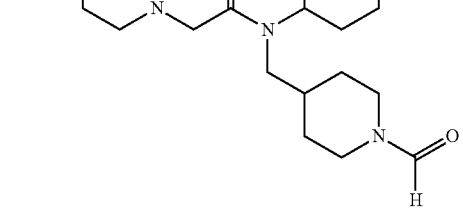 | |
| 1082 | 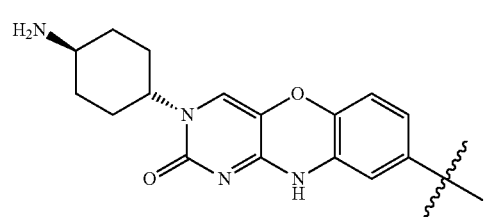 | 630.40 |
| | 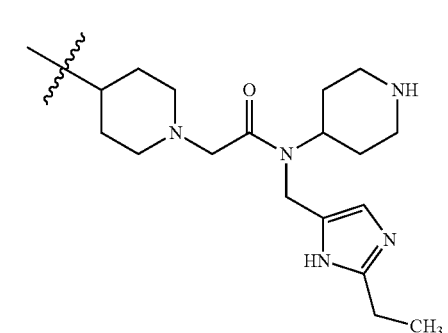 | |
| 1083 | 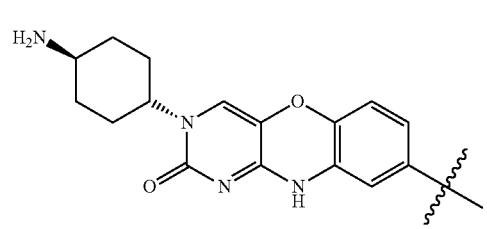 | 643.00 |
| | 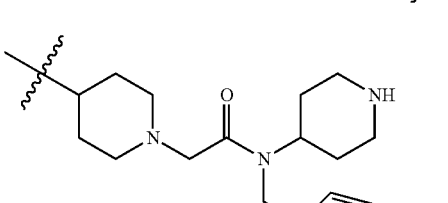 | |
| 1084 | 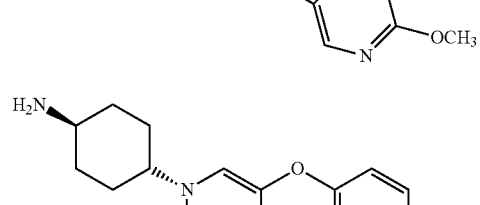 | 629.40 |

TABLE 1-continued

| Comp. No. | Structure | LCMS |
|---|---|---|
| | (structure continued from previous page) | |
| 1086 | 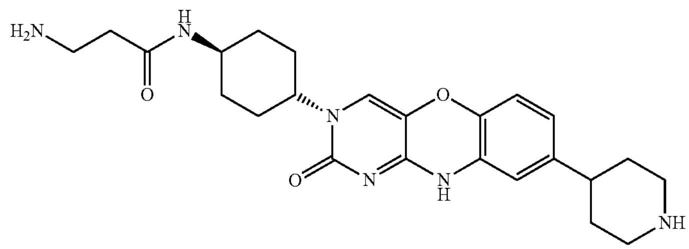 | 453.20 |
| 1096 | 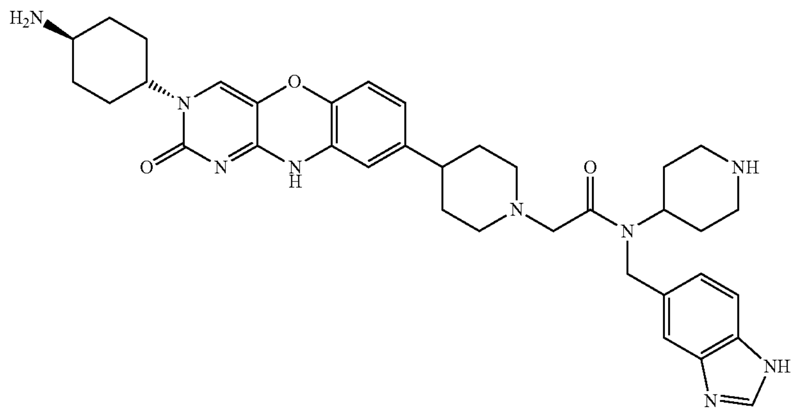 | 652.30 |
| 1133 | 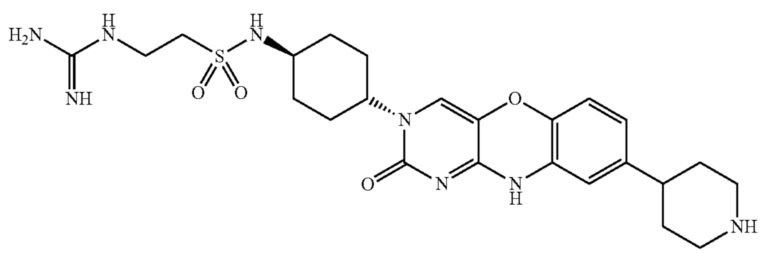 | 531.20 |
| 1134 | 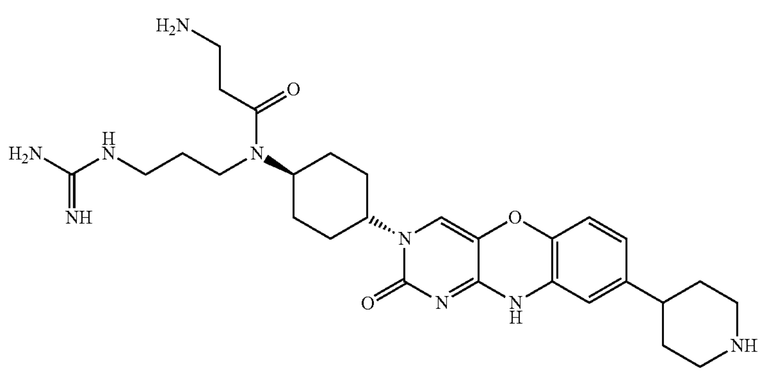 | 552.30 |

TABLE 1-continued
| Comp. No. | Structure | LCMS |
|---|---|---|
| 1135 | 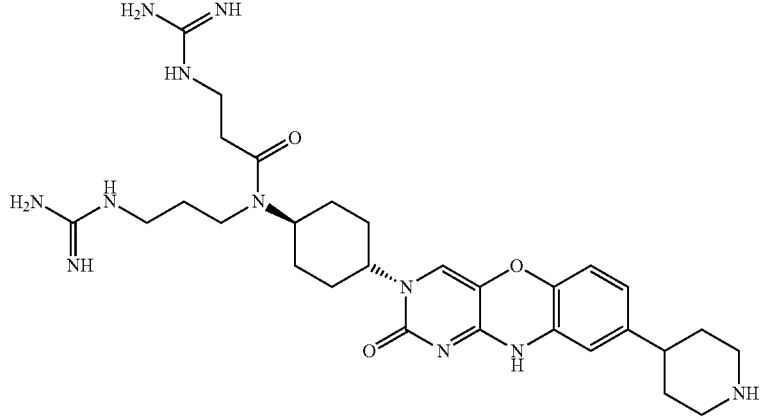 | 594.40 |
| 1145 | 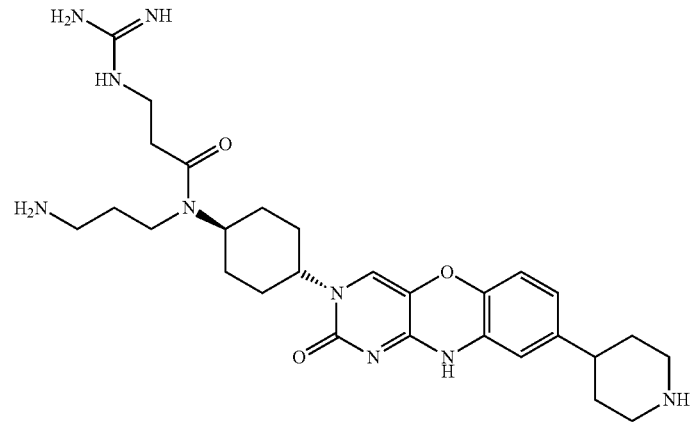 | 552.30 |
| 1146 | 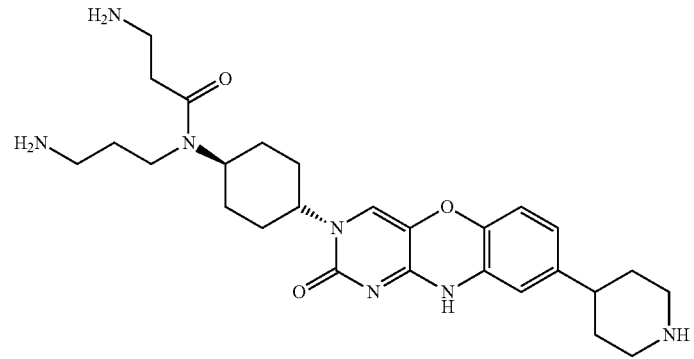 | 510.30 |
| 1147 | 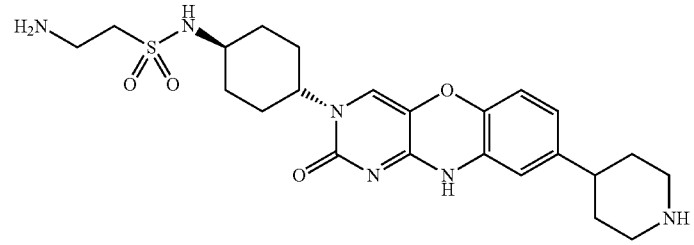 | 489.00 |

TABLE 1-continued

| Comp. No. | Structure | LCMS |
|---|---|---|
| 1192 | 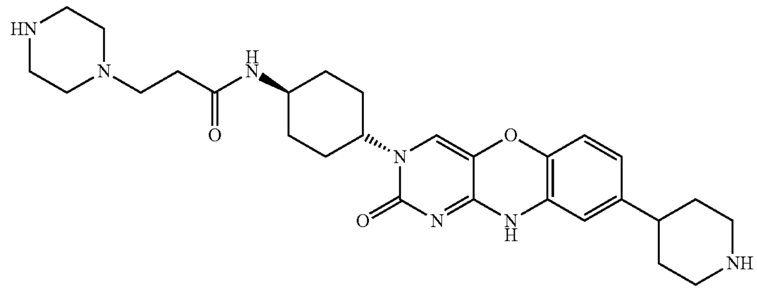 | 522.10 |
| 1193 | 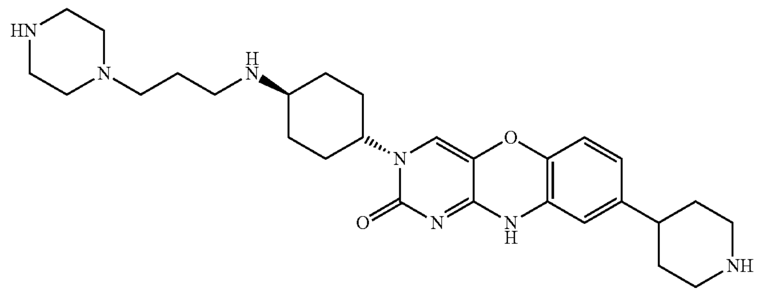 | 508.20 |
| 1197 | 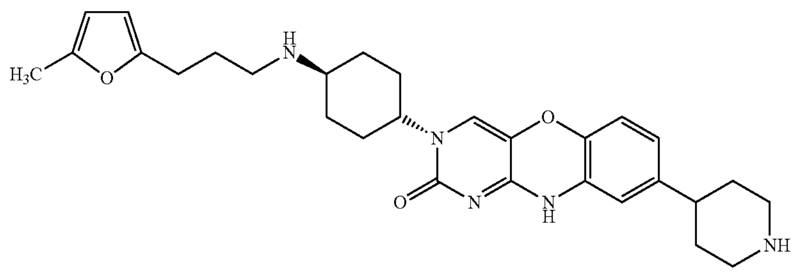 | 504.10 |
| 1198 | 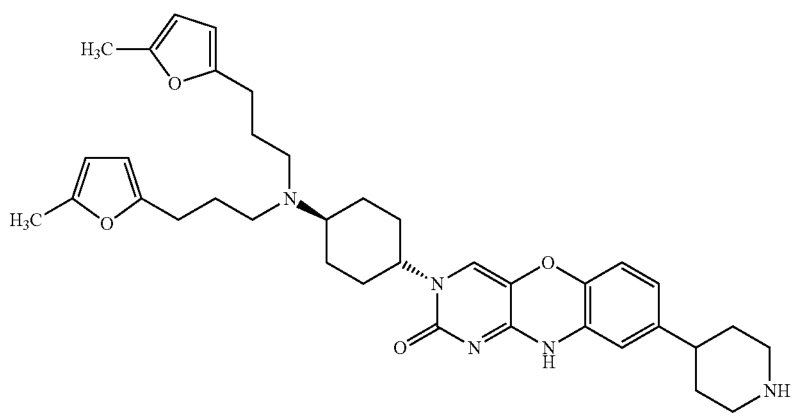 | 626.30 |
| 1212 | 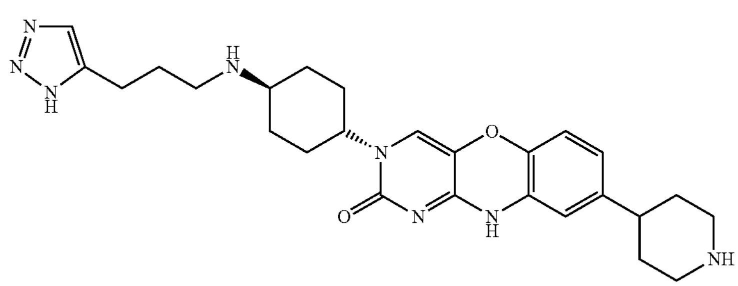 | 491.10 |

TABLE 1-continued

| Comp. No. | Structure | LCMS |
|---|---|---|
| 1213 | 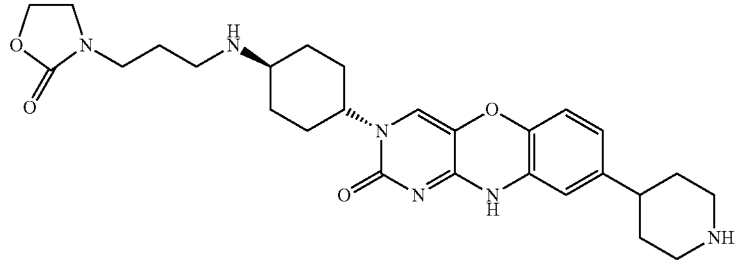 | 509.20 |
| 1234 | 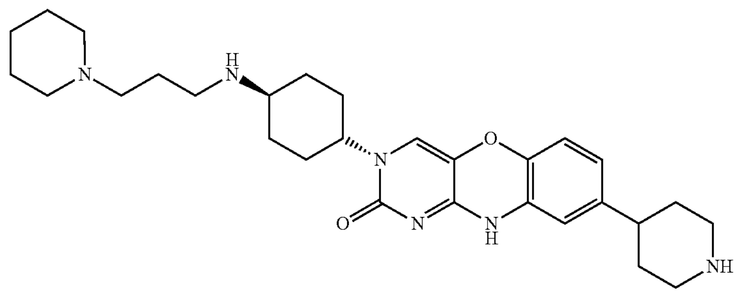 | 507.50 |
| 1235 | 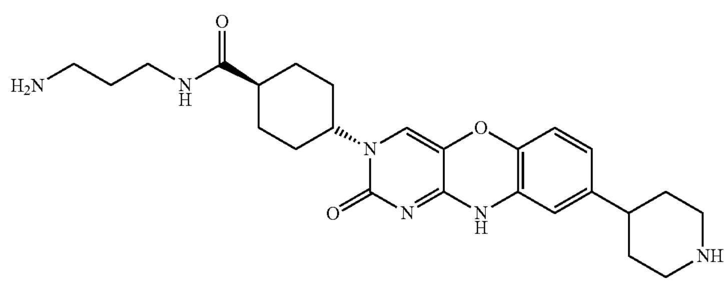 | 467.00 |
| 1236 | 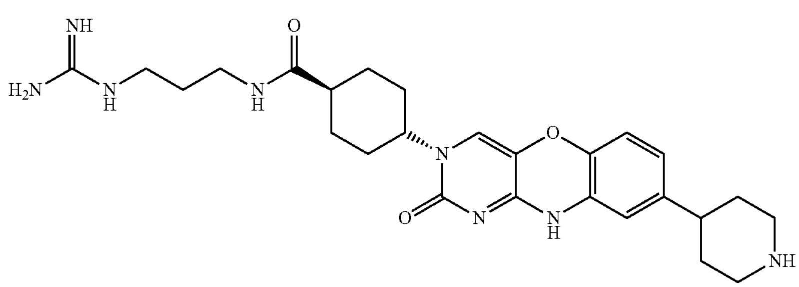 | 509.20 |
| 1237 | 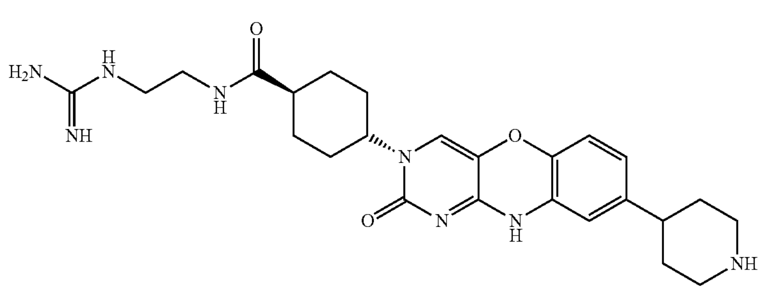 | 495.20 |

TABLE 1-continued
| Comp. No. | Structure | LCMS |
|---|---|---|
| 1238 | 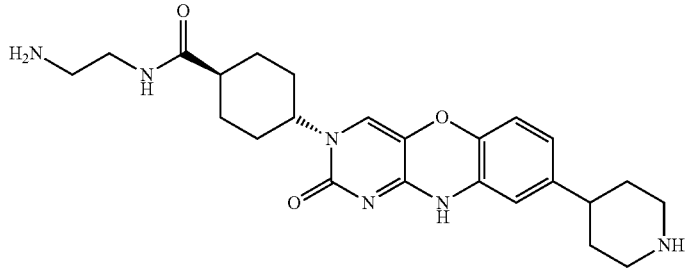 | 453.10 |
| 1244 | 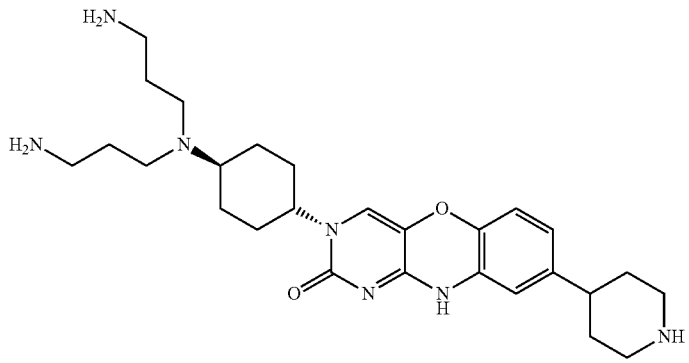 | 496.50 |
| 1269 | 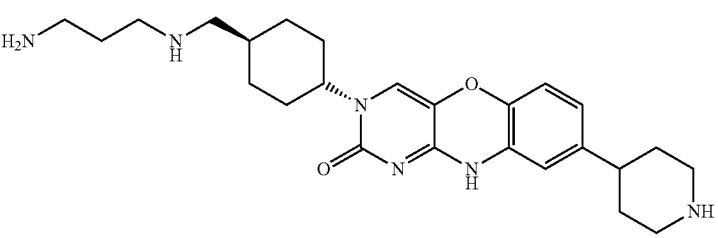 | 452.80 |
| 1270 | 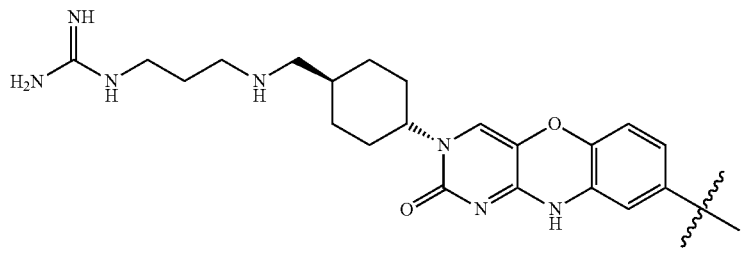 | 495.20 |
| 1271 | 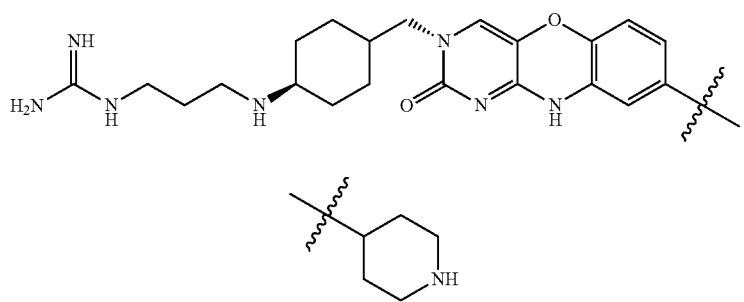 | 495.60 |

TABLE 1-continued

| Comp. No. | Structure | LCMS |
|---|---|---|
| 1368 | 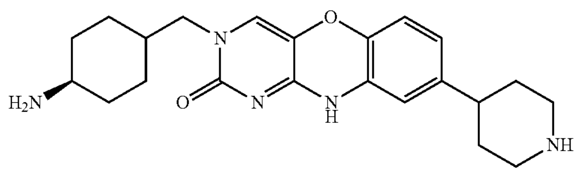 | 396.3 |
| 1369 | 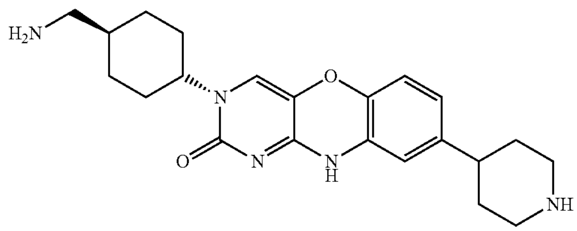 | 396.2 |
| 1370 | 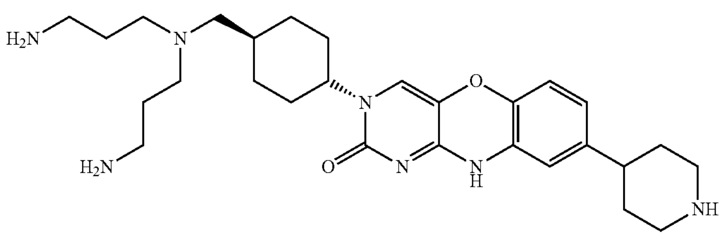 | 510.1 |
| 1421 | 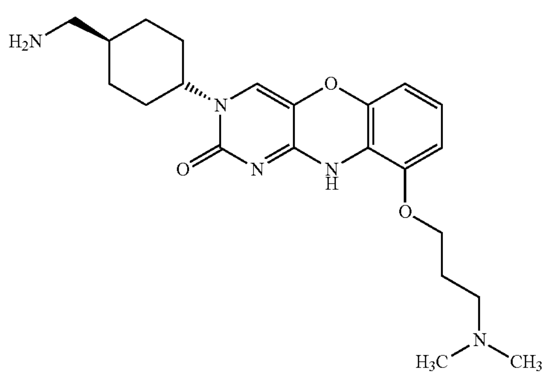 | 414.1 |
| 1426 | 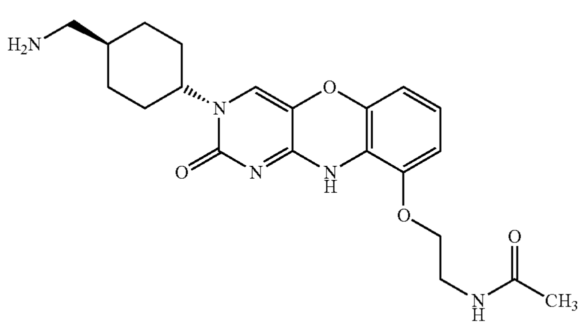 | 413.9 |

TABLE 1-continued

| Comp. No. | Structure | LCMS |
|---|---|---|
| 1427 | 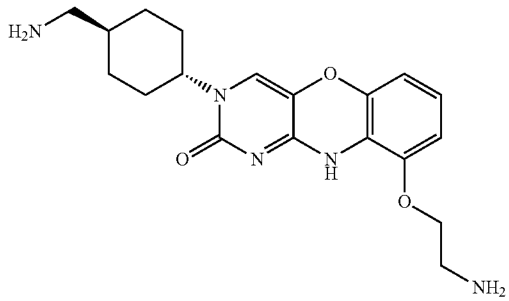 [SMILES: NCCOc1cccc2c1Nc1nc(=O)n([C@H]3CC[C@H](CN)CC3)cc1O2] | 371.9 |
| 1441 | 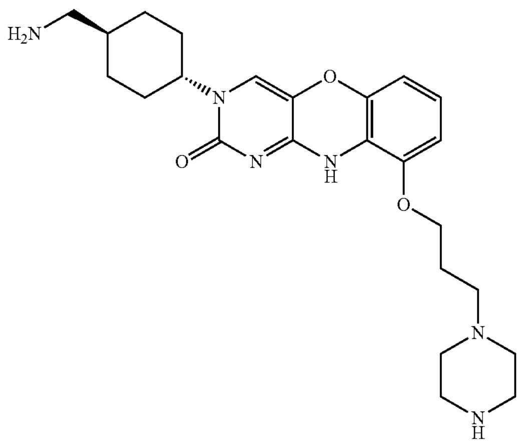 [SMILES: NC[C@H]1CC[C@H](n2cc3c(nc2=O)Nc2c(OCCCN4CCNCC4)cccc2O3)CC1] | 455.6 |
| 1449 | 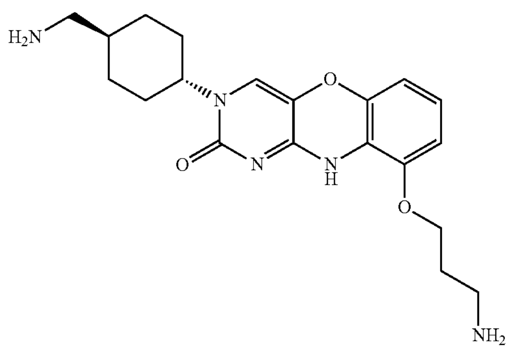 [SMILES: NCCCOc1cccc2c1Nc1nc(=O)n([C@H]3CC[C@H](CN)CC3)cc1O2] | 386.3 |
| 1450 | 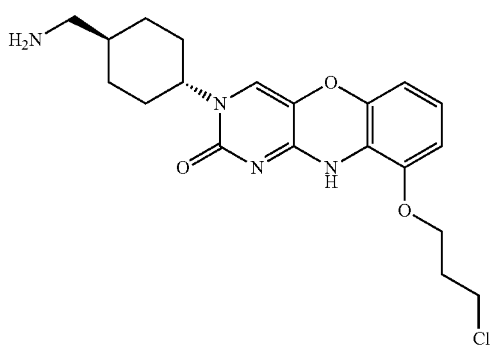 [SMILES: NC[C@H]1CC[C@H](n2cc3c(nc2=O)Nc2c(OCCCCl)cccc2O3)CC1] | 405.4 |
| 1464 | 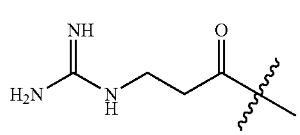 [SMILES: *C(=O)CCNC(=N)N] | 485.0 |

TABLE 1-continued
| Comp. No. | Structure | LCMS |
|---|---|---|
| | 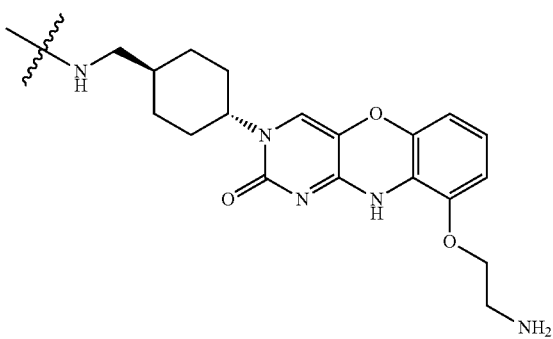 [SMILES: *NC[C@H]1CC[C@H](n2cc3c(nc2=O)Nc2c(OCCN)cccc2O3)CC1] | |
| 1465 | 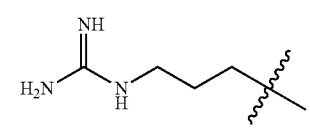 [SMILES: *CCCNC(=N)N] | 471.9 |
| | | |
| 1466 | 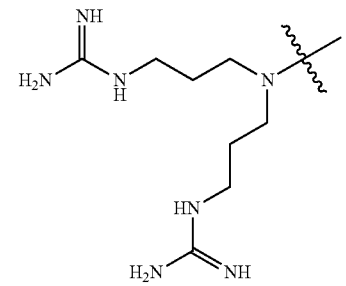 [SMILES: *N(CCCNC(=N)N)CCCNC(=N)N] | 570.4 |

TABLE 1-continued

| Comp. No. | Structure | LCMS |
|---|---|---|
| 1467 | 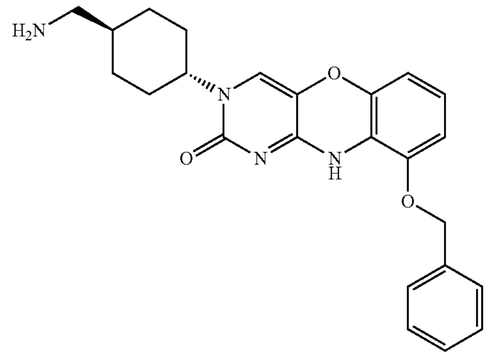 [SMILES: NC[C@H]1CC[C@H](n2cc3c(nc2=O)Nc2c(OCc4ccccc4)cccc2O3)CC1] | 419.0 |
| 360 | 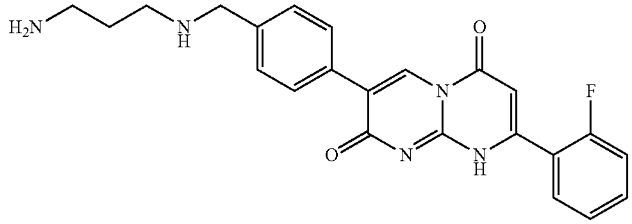 [SMILES: NCCCNCc1ccc(-c2cn3c(=O)cc(-c4ccccc4F)[nH]c3nc2=O)cc1] | 420.10 |
| 362 | 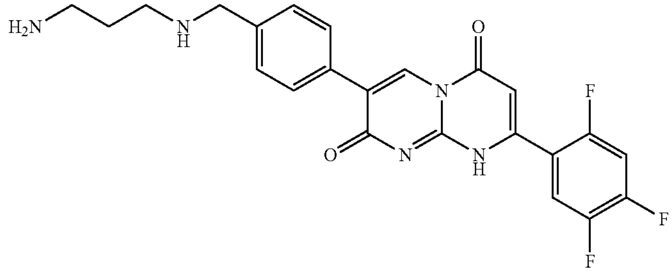 [SMILES: NCCCNCc1ccc(-c2cn3c(=O)cc(-c4cc(F)c(F)cc4F)[nH]c3nc2=O)cc1] | 456.10 |
| 367 | 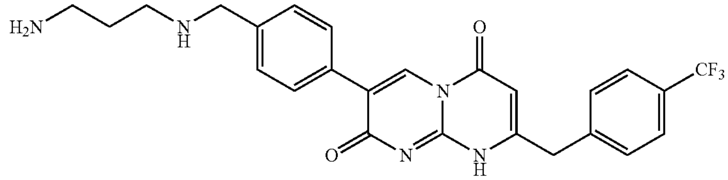 [SMILES: NCCCNCc1ccc(-c2cn3c(=O)cc(Cc4ccc(C(F)(F)F)cc4)[nH]c3nc2=O)cc1] | 484.10 |
| 371 | 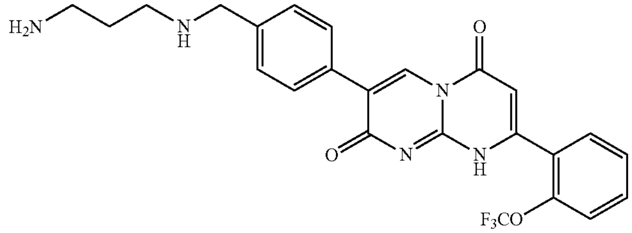 [SMILES: NCCCNCc1ccc(-c2cn3c(=O)cc(-c4ccccc4OC(F)(F)F)[nH]c3nc2=O)cc1] | 486.10 |
| 375 | 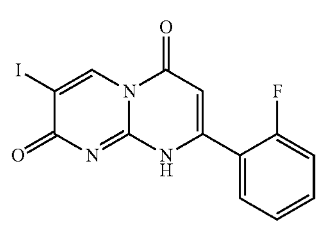 [SMILES: O=c1nc2[nH]c(-c3ccccc3F)cc(=O)n2cc1I] | 383.90 |

TABLE 1-continued
| Comp. No. | Structure | LCMS |
|---|---|---|
| 377 | 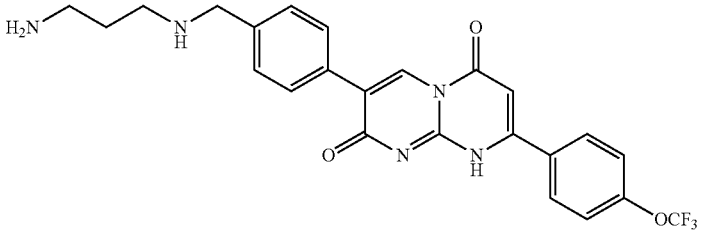 [SMILES: COc1ccc(-c2cc(=O)n3cc(-c4ccc(CNCCCN)cc4)c(=O)nc3[nH]2)cc1] | 486.10 |
| 378 | 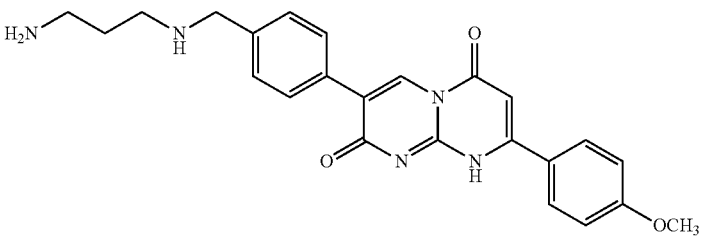 | 432.10 |
| 379 | 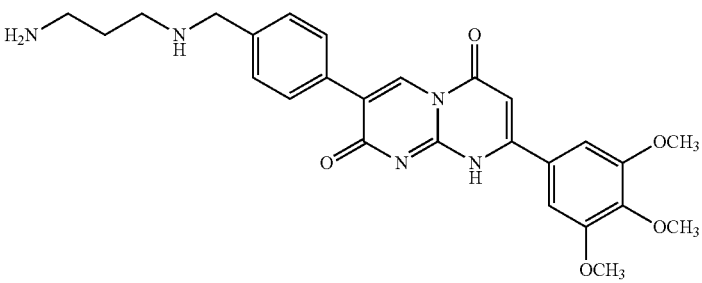 [SMILES: COc1cc(-c2cc(=O)n3cc(-c4ccc(CNCCCN)cc4)c(=O)nc3[nH]2)cc(OC)c1OC] | 492.10 |
| 380 | 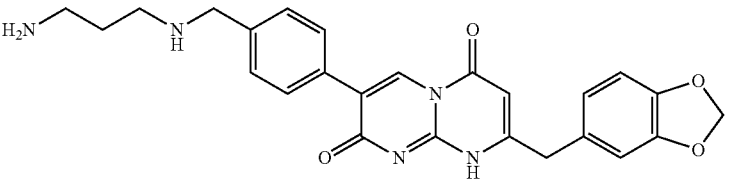 [SMILES: NCCCNCc1ccc(-c2cn3c(=O)cc(Cc4ccc5c(c4)OCO5)[nH]c3nc2=O)cc1] | 460.10 |
| 390 | 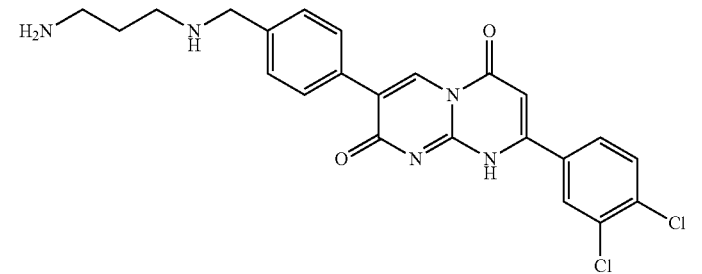 [SMILES: NCCCNCc1ccc(-c2cn3c(=O)cc(-c4ccc(Cl)c(Cl)c4)[nH]c3nc2=O)cc1] | 470.00 |
| 391 | 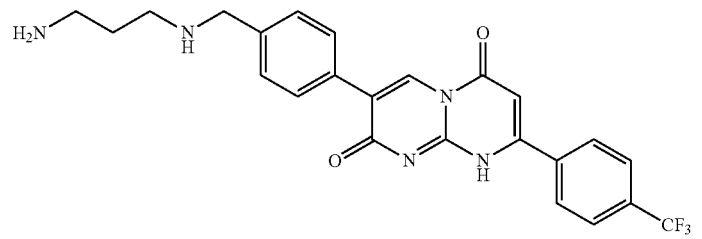 [SMILES: NCCCNCc1ccc(-c2cn3c(=O)cc(-c4ccc(C(F)(F)F)cc4)[nH]c3nc2=O)cc1] | 470.10 |

TABLE 1-continued
| Comp. No. | Structure | LCMS |
|---|---|---|
| 411 | 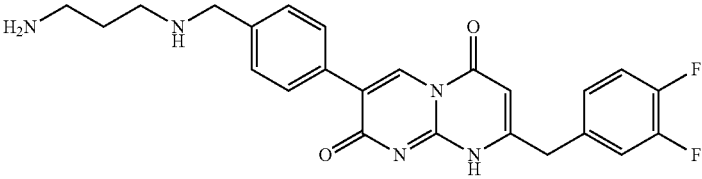 [SMILES: NCCCNCc1ccc(-c2cn3c(=O)cc(Cc4ccc(F)c(F)c4)[nH]c3nc2=O)cc1] | 452.10 |
| 426 | 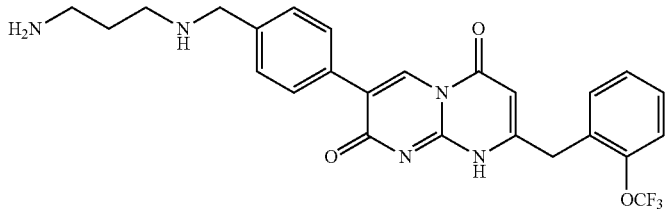 [SMILES: NCCCNCc1ccc(-c2cn3c(=O)cc(Cc4ccccc4OC(F)(F)F)[nH]c3nc2=O)cc1] | 500.10 |
| 430 | 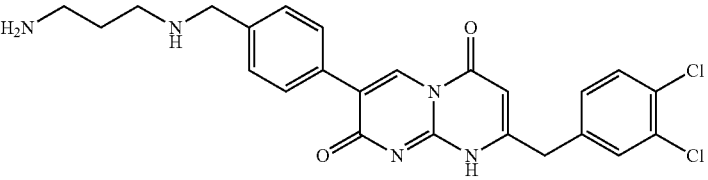 [SMILES: NCCCNCc1ccc(-c2cn3c(=O)cc(Cc4ccc(Cl)c(Cl)c4)[nH]c3nc2=O)cc1] | 484.00 |
| 447 | 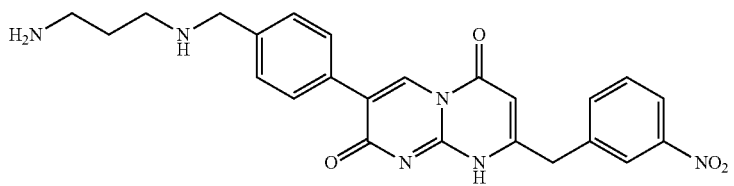 [SMILES: NCCCNCc1ccc(-c2cn3c(=O)cc(Cc4cccc([N+](=O)[O-])c4)[nH]c3nc2=O)cc1] | 461.10 |
| 469 | 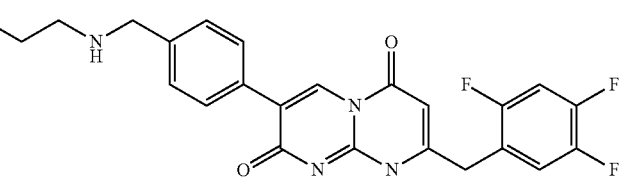 | 471.10 |
| 568 | 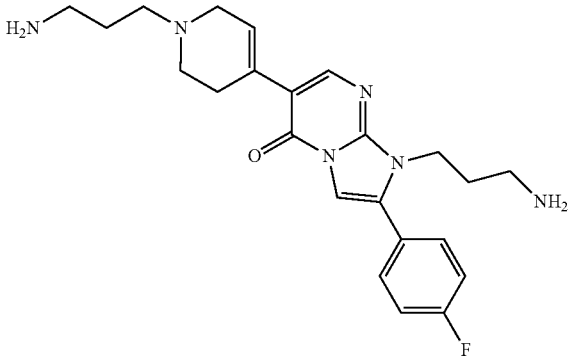 [SMILES: NCCCN1CC=C(c2cnc3n(CCCN)c(-c4ccc(F)cc4)cn3c2=O)CC1] | 425.00 |

TABLE 1-continued

| Comp. No. | Structure | LCMS |
|---|---|---|
| 569 | 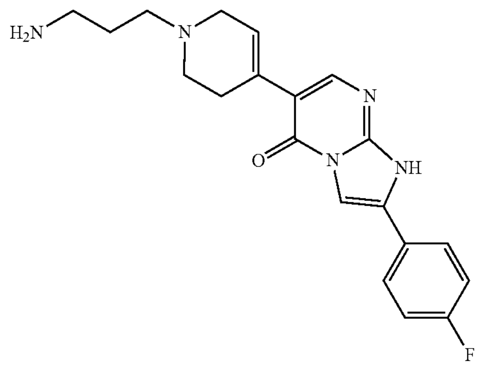 [SMILES: NCCCN1CC=C(c2cnc3[nH]c(-c4ccc(F)cc4)cn3c2=O)CC1] | 368.00 |
| 570 | 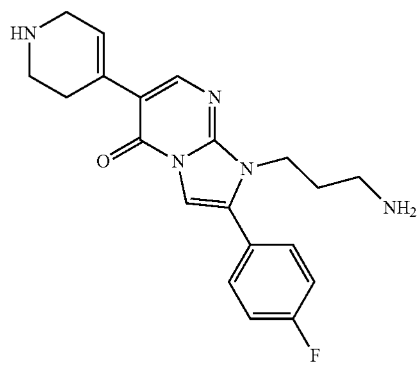 [SMILES: NCCCn1c(-c2ccc(F)cc2)cn2c(=O)c(C3=CCNCC3)cnc12] | 368.10 |
| 4000c | 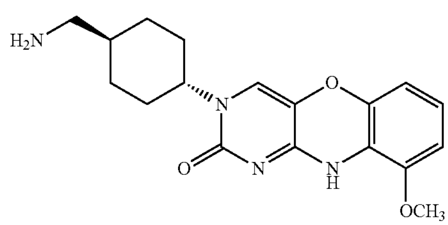 [SMILES: COc1cccc2c1Nc1nc(=O)n([C@H]3CC[C@H](CN)CC3)cc1O2] | 342.90 |
| 4001c | 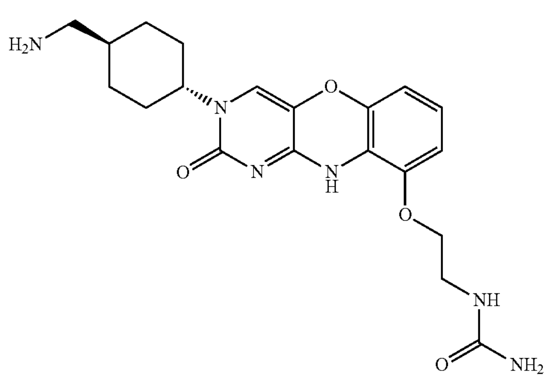 [SMILES: NC[C@H]1CC[C@H](n2cc3c(nc2=O)Nc2c(OCCNC(N)=O)cccc2O3)CC1] | 415.10 |

TABLE 1-continued
| Comp. No. | Structure | LCMS |
|---|---|---|
| 4002c | 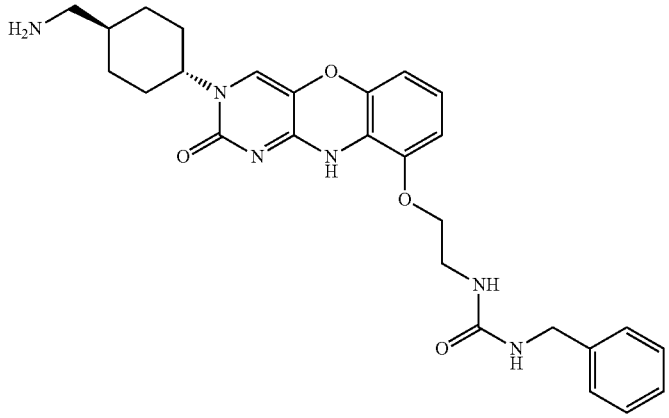 [SMILES: NC[C@H]1CC[C@H](n2cc3c(nc2=O)Nc2c(OCCNC(=O)NCc4ccccc4)cccc2O3)CC1] | 505.20 |
| 4003c | 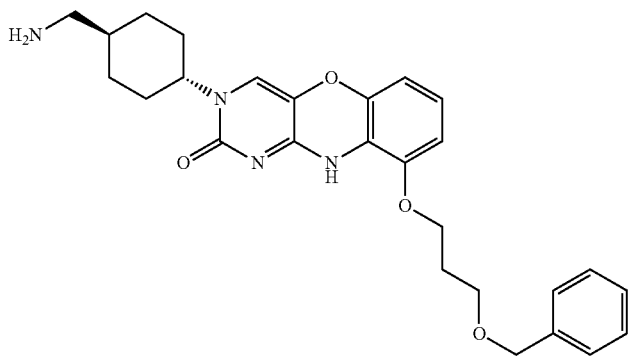 [SMILES: NC[C@H]1CC[C@H](n2cc3c(nc2=O)Nc2c(OCCCOCc4ccccc4)cccc2O3)CC1] | 477.30 |
| 4004c | 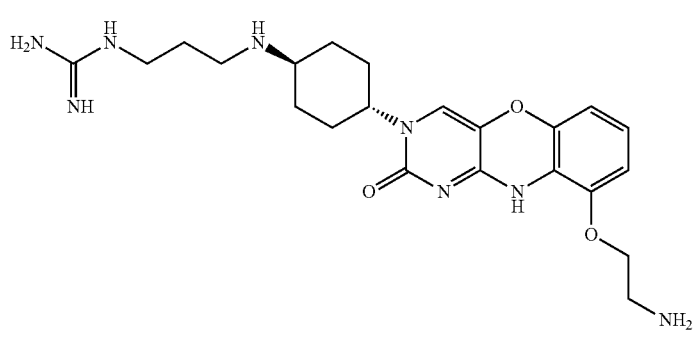 [SMILES: N=C(N)NCCCN[C@H]1CC[C@H](n2cc3c(nc2=O)Nc2c(OCCN)cccc2O3)CC1] | 457.90 |
| 4005c | 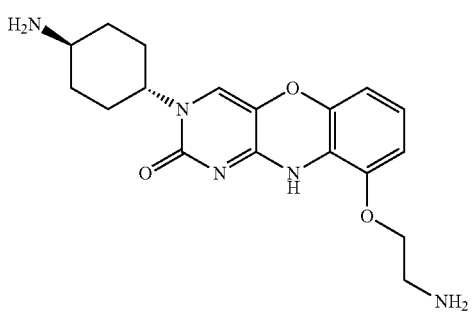 [SMILES: NCCOc1cccc2c1Nc1nc(=O)n([C@H]3CC[C@H](N)CC3)cc1O2] | 358.10 |

TABLE 1-continued

| Comp. No. | Structure | LCMS |
|---|---|---|
| 4006c | 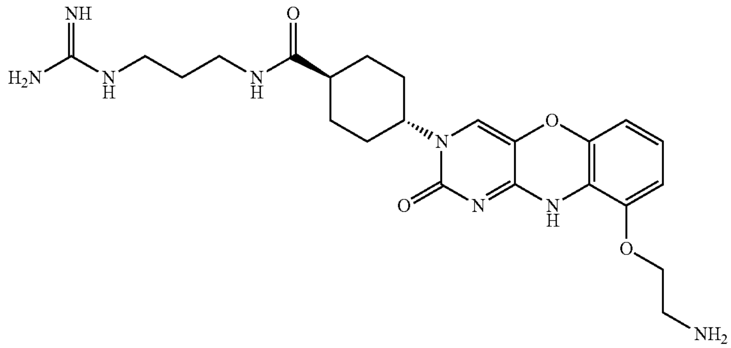 | 485.30 |
| 4007c | 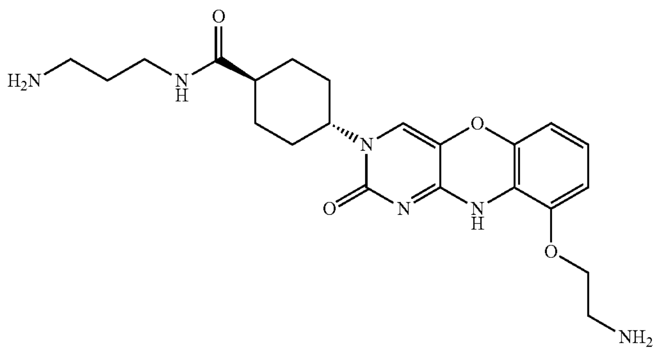 [SMILES: NCCCNC(=O)[C@H]1CC[C@H](n2cc3c(nc2=O)Nc2c(OCCN)cccc2O3)CC1] | 443.30 |
| 4008c | 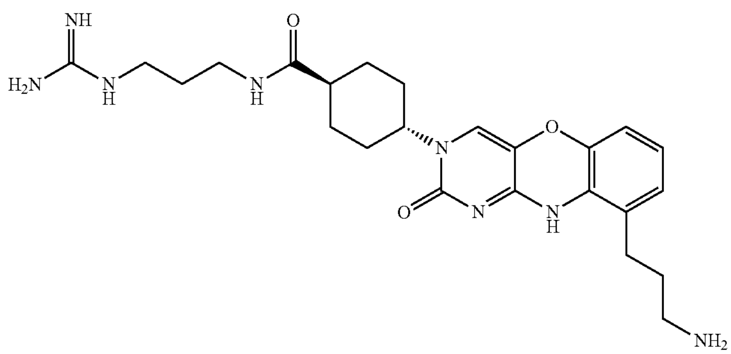 | 483.4 |

In further embodiments, the compounds of the present invention do not encompass a compound having the structure:

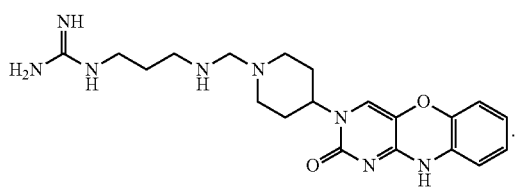 [SMILES: N=C(N)NCCCNCN1CCC(n2cc3c(nc2=O)Nc2ccccc2O3)CC1]

The compounds of the present invention can be made using synthetic chemical techniques well known to those of skill in the art.

Example 1

Synthesis of 592

The compounds of the present invention can be made using synthetic chemical techniques well known to those of skill in the art, including the schemes outlined herein. For illustrative purposes, the synthesis of compound 592 is described below.

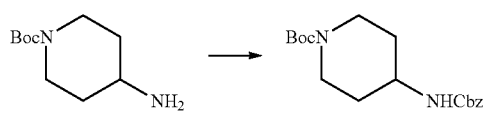

4-Benzyloxycarbonylamino-piperidine-1-carboxylic acid tert-butyl ester

To a solution of 4-amino-piperidine-1-carboxylic acid tert-butyl ester (11.98 g, 58.4 mmol, 1 equiv) in THF (80 mL) at 23° C. was added a saturated solution of sodium bicarbonate (200 mL) followed by benzyl chloroformate (9.19 mL, 64.2 mmol, 1.1 equiv). The reaction was stirred for 55 min then partitioned between ethyl acetate (200 mL) and water (100 mL). The organic layer was separated, washed with saturated brine solution (200 mL), dried (MgSO$_4$), filtered and concentrated to give 20.4 g of tan solid. This material was used in the next step without further purification.

Piperidin-4-yl-carbamic acid benzyl ester

To a solution of 4-benzyloxycarbonylamino-piperidine-1-carboxylic acid tert-butyl ester (20.4 g, crude from previous step) in dichloromethane (100 mL) at 23° C. was added trifluoroacetic acid (40 mL). After stirring for 45 min the reaction mixture was concentrated. The residue was dissolved in water (100 mL) then basified to pH 11 via addition of solid potassium carbonate. The resulting solution was extracted with dichloromethane (2×150 mL). The organic extracts were extremely cloudy; they were dried (Na$_2$SO$_4$), filtered and concentrated. The residue was dissolved/suspended in chloroform (70 mL) and the observed particulates were removed via filtration through a glass frit. The solution was concentrated to give 15 g of brown oil. This material was used without purification in the subsequent step.

(3-Bromo-propyl)-carbamic acid tert-butyl ester

To 3-bromopropylamine hydrobromide (12.8 g, 58.4 mmol, 1 equiv) in dichloromethane (200 mL) at 23° C. was added triethylamine (10.2 mmol, 73.6 mmol, 1.26 equiv) followed by di-tert-butyl dicarbonate (12.8 g, 58.4 mmol, 1 equiv). After stirring for 1 h the reaction mixture was washed successively with water (200 mL) then saturated brine solution (200 mL); then dried (MgSO$_4$), filtered and concentrated to give 13.9 g of the desired product as a clear oil. The material was used immediately in the next step.

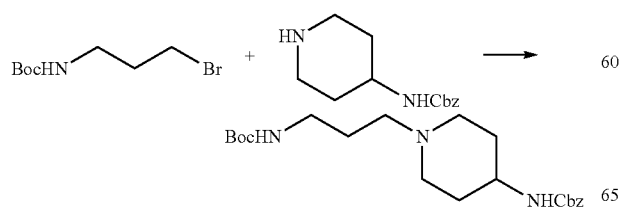

[1-(3-tert-Butoxycarbonylamino-propyl)-piperidin-4-yl]-carbamic acid benzyl ester To a solution of piperidin-4-yl-carbamic acid benzyl ester (15 g, 58.4 mmol, crude product from Boc-deprotection step) in dimethylformamide (60 mL) at 23° C. was added potassium carbonate (12.1 g, 87.6 mmol, 1.5 equiv), potassium iodide (4.85 g, 29.2 mmol, 0.5 equiv) and (3-bromo-propyl)-carbamic acid tert-butyl ester (13.9 g, 58.4 mmol, 1 equiv). The resulting mixture was warmed to 60° C. (oil bath). After 90 min at 60° C. the reaction mixture was cooled to 23° C. then partitioned between ethyl acetate and water (100 mL each). The organic layer was separated, washed with saturated brine solution (150 mL), dried (MgSO$_4$), filtered and concentrated. The product was purified using an Isco CombiFlash automated chromatography system. The residue was loaded onto a 330 g silica gel column as a solution in dichloromethane (25 mL) then eluted with 2 M ammonia in methanol in dichloromethane (0-12.5% 2 M ammonia in methanol linear gradient over 12 column volumes at a flow rate of 100 mL/min) to give 16.9 g (43.2 mmol, 74% over 3 steps) of the title compound as a clear

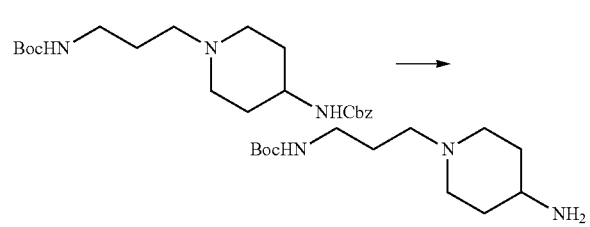

[3-(4-Amino-piperidin-1-yl)-propyl]carbamic acid tert-butyl ester

To a solution of [1-(3-tert-butoxycarbonylamino-propyl)-piperidin-4-yl]-carbamic acid benzyl ester (16.9 g, 43.2 mmol, 1 equiv) in ethanol (200 mL) at 23° C. was added palladium on carbon (2.25 g, 10 wt. %, wet, Degussa type). The reaction vessel was placed under an atmosphere of hydrogen (balloon) and stirred for 14 h. At this time tlc analysis indicated the reaction was incomplete, the mixture was filtered through a pad of Celite, washing with ethanol (100 mL). The resulting solution was treated with fresh palladium catalyst (2.25 g), then placed under an atmosphere of hydrogen (balloon) at 50° C. After 7 h tlc analysis indicates complete consumption of the starting material. The reaction mixture was cooled to 23° C., and then filtered through Celite, washing with ethanol (200 mL). The filtrate was concentrated to give 11.1 g (43.2 mmol, 100%) of the desired compound.

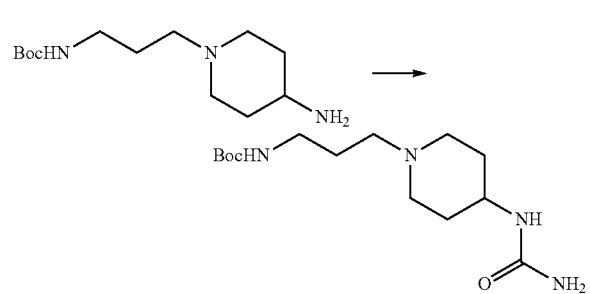

[3-(4-Ureido-piperidin-1-yl)-propyl]carbamic acid tert-butyl ester

To a solution of [3-(4-amino-piperidin-1-yl)-propyl]carbamic acid tert-butyl ester (7.34 g, 28.6 mmol, 1 equiv) in dichloromethane at 0° C. (ice-water bath) was added triethylamine (5.97 mL, 42.9 mmol, 1.5 equiv) followed by phenyl chloroformate (3.97 mL, 31.4 mmol, 1.1 equiv). The reaction mixture was stirred for 2.5 h at 0° C., then partitioned between dichloromethane (200 mL) and saturated aqueous sodium bicarbonate solution (250 mL). The organic layer was separated. The aqueous layer was re-extracted with dichloromethane (50 mL). The combined organic layers were dried (MgSO$_4$), filtered and concentrated to give 10.5 g of the phenyl carbamate as a white semi-solid. The crude residue was dissolved in methanol (60 mL) then treated with aqueous ammonium hydroxide solution (28% ammonia, 60 mL). After stirring for 15 h at 23° C. the reaction mixture was concentrated. The residue was treated with ethyl ether (300 mL) to give a precipitate. After standing at 23° C. for 2 h, the precipitate was collected via filtration through a medium porosity glass frit. The collect white solid was dried in vacuo to give 6.23 g (20.8 mmol, 73%) of the desired urea.

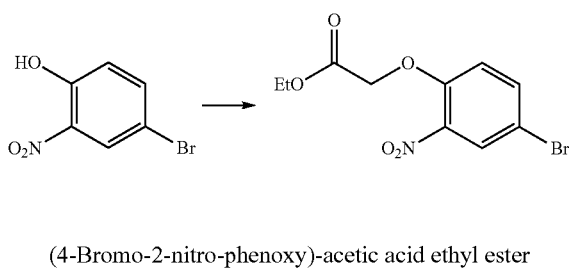

(4-Bromo-2-nitro-phenoxy)-acetic acid ethyl ester

To a solution of 4-bromo-2-nitro-phenol (3.28 g, 15.0 mmol, 1 equiv) in dimethylformamide (40 mL) at 23° C. was added potassium carbonate (4.14 g, 30 mmol, 2 equiv) followed by ethyl bromoacetate (1.84 mL, 16.6 mmol, 1.1 equiv). The resulting mixture was warmed to 60° C. (oil bath) for 90 min then cooled to 23° C. The reaction mixture was partitioned between ethyl acetate:heptane (1:1) and water (100 mL each). The organic layer was separated and washed successively with water, saturated brine solution (100 ml, each) then dried (MgSO$_4$), filtered and concentrated to give 4.50 g (11.5 mmol, 77%) of the product as a yellow oil.

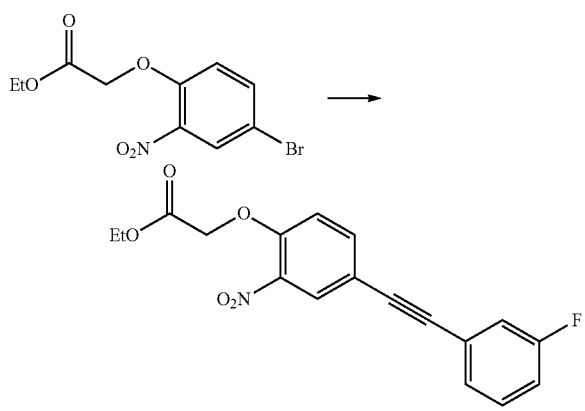

[4-(3-Fluoro-phenylethynyl)-2-nitro-phenoxy]-acetic acid ethyl ester

To a solution of (4-bromo-2-nitro-phenoxy)-acetic acid ethyl ester (2.95 g, 9.70 mmol, 1 equiv) and 1-ethynyl-3-fluorobenzene (1.34 mL, 11.6 mmol, 1.2 equiv) in dimethylformamide (15 mL) in a microwave reactor vessel was added triethylamine (4.05 mL, 29.1 mmol, 3 equiv), copper iodide (55 mg, 0.29 mmol, 0.03 equiv) and trans-dichlorobis(tri-o-tolylphosphine) palladium(II) (152 mg, 0.19 mmol, 0.02 equiv). The reaction was placed under an argon atmosphere then heated to 80° C. in a microwave reactor for 30 min. The reaction mixture was then partitioned between ethyl acetate: heptane (1:1) and 1.0 N aqueous hydrochloric acid (100 mL each). The organic layer was separated and washed successively with saturated aqueous sodium bicarbonate, 1:1 saturated aqueous sodium bicarbonate:saturated aqueous ammonium chloride, saturated brine solution (100 mL each) then dried (MgSO$_4$), filtered and concentrated. The product was purified using an Isco CombiFlash automated chromatography system. The residue was loaded onto a 120 g silica gel column as a solution in dichloromethane (5 mL) then eluted with ethyl acetate in heptane (0-40% ethyl acetate linear gradient over 16 column volumes at a flow rate of 85 mL/min) to give 1.72 g (5.01 mmol, 52%) of the title compound as a brown oil.

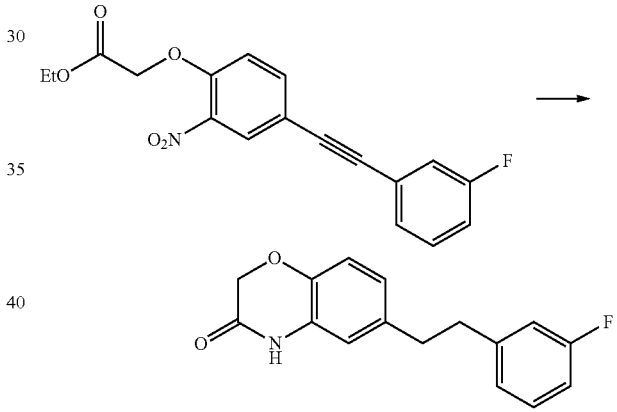

6-[2-(3-Fluoro-phenyl)-ethyl]-4H-benzo[1,4]oxazin-3-one

To a solution of [4-(3-fluoro-phenylethynyl)-2-nitro-phenoxy]-acetic acid ethyl ester (1.72 g, 5.01 mmol, 1 equiv) in ethyl acetate (50 mL) was added palladium on carbon (500 mg, 10 wt. %, wet, Degussa type). The reaction vessel was placed under an atmosphere of hydrogen (balloon) and stirred at 23° C. for 15 h. At this time LCMS analysis indicated the reaction contains a mixture of the desired benzoxazinone product (major) and uncyclized aniline (minor). The mixture was filtered through a pad of Celite, washing with ethyl acetate (100 mL). The solution was concentrated, then redissolved in ethyl acetate (100 mL) and refluxed for 2 h. LCMS analysis indicates no improvement in cyclized:uncyclized ratio. Para-toluenesulfonic acid hydrate (111 mg) was added and resulting solution was refluxed for a further 1 h. The solution was cooled to 23° C. then washed successively with water, 1.0 N aqueous hydrochloric acid, saturated aqueous brine (100 mL each), dried (MgSO$_4$), filtered and concentrated. The product was purified using an Isco Combi- Flash automated chromatography system. The residue was loaded onto a 80 g silica gel column as a solution in dichloromethane (5 mL) then eluted with methanol in dichloromethane (0-5% methanol linear gradient over 18 column volumes at a flow rate of 60 mL/min) to give 1.15 g (4.24 mmol, 85%) of the title compound as a tan solid.

biFlash automated chromatography system. The residue was loaded onto a 80 g silica gel column as a solution in dichloromethane (5 mL) then eluted with ethyl acetate in heptane (0-40% ethyl acetate linear gradient over 16 column volumes at a flow rate of 60 mL/min) to give 985 mg (2.86 mmol, 67%) of the title compound as an orange/brown oil.

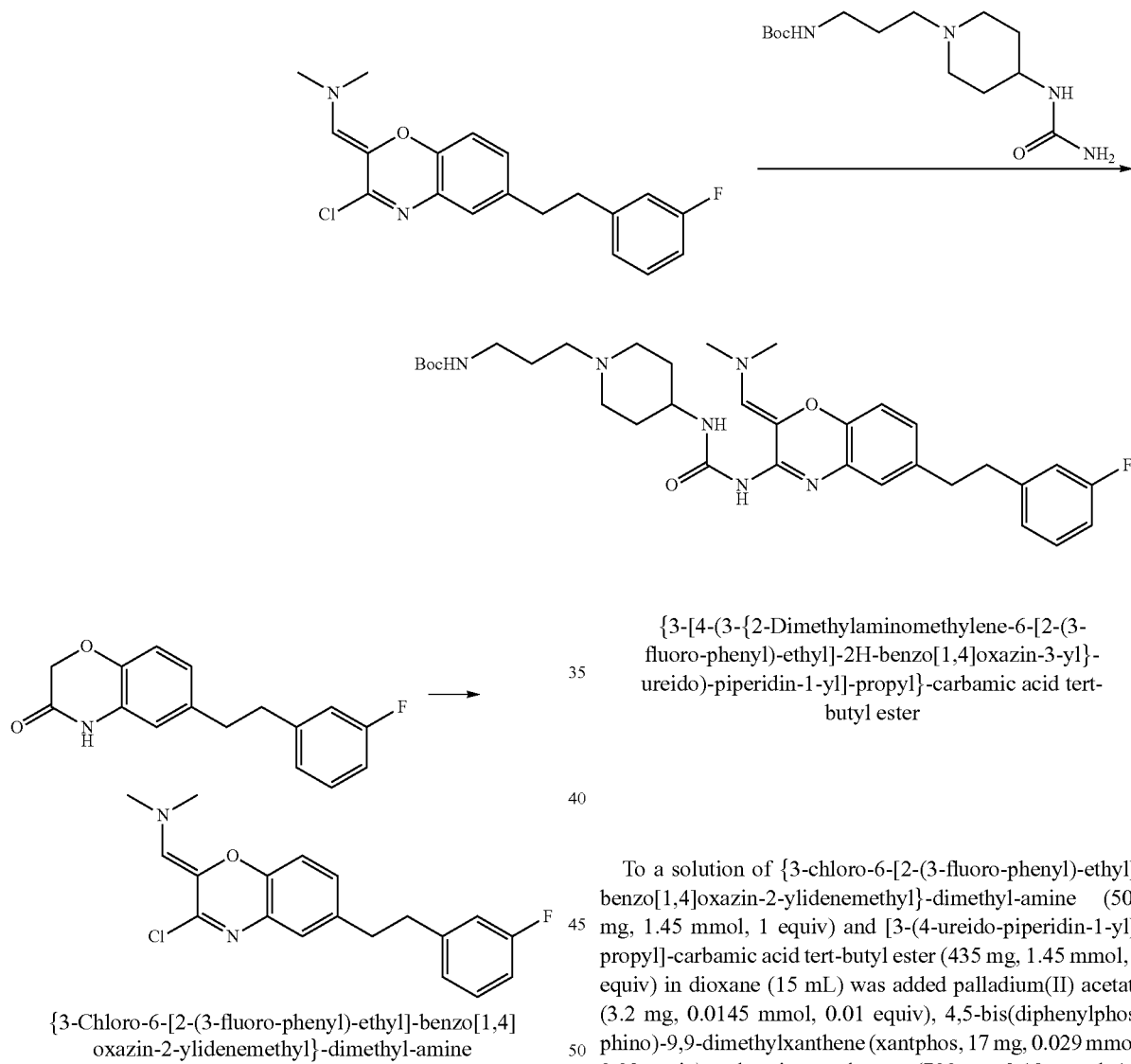

{3-[4-(3-{2-Dimethylaminomethylene-6-[2-(3-fluoro-phenyl)-ethyl]-2H-benzo[1,4]oxazin-3-yl}-ureido)-piperidin-1-yl]-propyl}-carbamic acid tert-butyl ester {3-Chloro-6-[2-(3-fluoro-phenyl)-ethyl]-benzo[1,4]oxazin-2-ylidenemethyl}-dimethyl-amine To a solution of dimethylformamide (0.82 mL, 10.6 mmol, 2.5 equiv) in chloroform (10 mL) at 0° C. was added phosphorus(V) oxychloride (0.78 mL, 8.49 mmol, 2 equiv). After stirring 10 min at 0° C., the reaction vessel was warmed to 23° C. for 10 min then re-cooled to 0° C. A solution of 6-[2-(3-fluoro-phenyl)-ethyl]-4H-benzo[1,4]oxazin-3-one in chloroform (7 mL) was added. After stirring a further 5 min at 0° C. the reaction was warmed to reflux (oil bath) for 4 h then cooled to 23° C. and partitioned between dichloromethane and water (100 mL each). The aqueous layer was adjusted to pH 12 with 5 N aqueous sodium hydroxide, and then the organic layer was separated. The organic layer was washed with brine (100 mL) and set aside. The original aqueous layer was re-extracted with dichloromethane (100 mL). The two organic extracts were combined, dried (MgSO$_4$), filtered and concentrated. The product was purified using an Isco Com- To a solution of {3-chloro-6-[2-(3-fluoro-phenyl)-ethyl]-benzo[1,4]oxazin-2-ylidenemethyl}-dimethyl-amine (500 mg, 1.45 mmol, 1 equiv) and [3-(4-ureido-piperidin-1-yl)-propyl]-carbamic acid tert-butyl ester (435 mg, 1.45 mmol, 1 equiv) in dioxane (15 mL) was added palladium(II) acetate (3.2 mg, 0.0145 mmol, 0.01 equiv), 4,5-bis(diphenylphosphino)-9,9-dimethylxanthene (xantphos, 17 mg, 0.029 mmol, 0.02 equiv) and cesium carbonate (709 mg, 2.18 mmol, 1.5 equiv). The reaction mixture was sparged with argon then the reaction vessel sealed (screw cap) and placed in 100° C. oil bath. After 14 h at 100° C. the reaction was cooled to 23° C., and then partitioned between ethyl acetate and water (100 mL each). The organic layer was separated and washed with saturated brine solution (100 mL) then dried (MgSO$_4$), filtered and concentrated. The product was purified using an Isco CombiFlash automated chromatography system. The residue was loaded onto an 80 g silica gel column as a solution in dichloromethane (5 mL) then eluted with 2 M ammonia in methanol in dichloromethane (0-8% 2 M ammonia in methanol linear gradient over 18 column volumes at a flow rate of 60 mL/min) to give 313 mg (0.515 mmol, 36%) of the title compound as a yellow/brown solid.

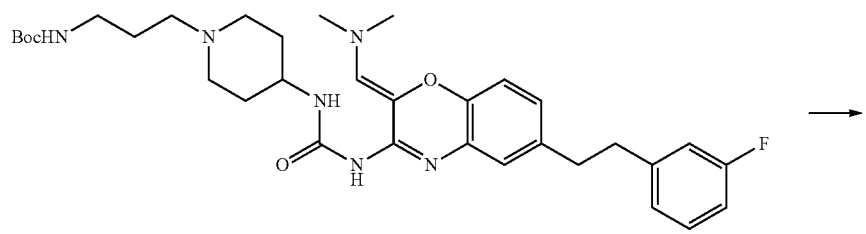

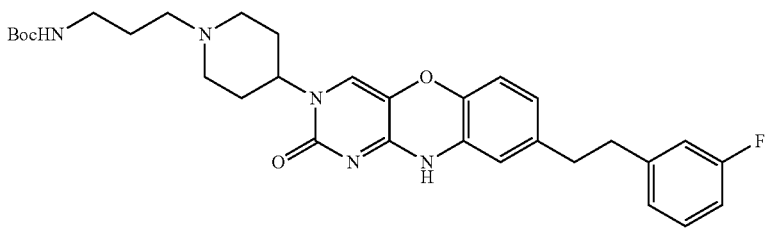

[3-(4-{7-[2-(3-Fluoro-phenyl)-ethyl]-2-oxo-2,9-dihydro-10-oxa-1,3,9-triaza-anthracen-3-yl}-piperidin-1-yl)-propyl]-carbamic acid tert-butyl ester A solution of {3-[4-(3-{2-dimethylaminomethylene-6-[2-(3-fluoro-phenyl)-ethyl]-2H-benzo[1,4]oxazin-3-yl}-ureido)-piperidin-1-yl]-propyl}-carbamic acid tert-butyl ester (310 mg, 0.510 mmol, 1 equiv) in acetic acid (15 mL) was placed in a microwave reactor vessel. The reaction was placed under an argon atmosphere then heated to 100° C. in a microwave reactor for 90 min. LCMS analysis indicated the desired product was obtained, but partial loss of Boc had occurred. The acetic acid solution was concentrated then the residue was dissolved in tetrahydrofuran (25 mL) and treated with potassium carbonate (600 mg, 4.34 mmol, 8.5 equiv) and di-tert-butyl dicarbonate (190 mg, 0.872 mmol, 1.7 equiv). After stirring for 30 min at 23° C. the reaction mixture was partitioned between ethyl acetate and water (60 mL each). The organic layer was separated and washed with saturated brine solution (50 mL) then dried (MgSO₄), filtered and concentrated. The residue was dissolved/suspended in 1:1 ethyl acetate:heptane (10 mL, hot). After cooling the solid was collected via filtration. The solid was adsorbed onto silica gel (5 g) then purified using an Isco CombiFlash automated chromatography system. The product was eluted through and 40 g silica gel cartridge with 2 M ammonia in methanol in dichloromethane (0-8% 2 M ammonia in methanol linear gradient over 24 column volumes at a flow rate of 40 mL/min) to give 94 mg (0.167 mmol, 33%) of the title compound as a pale yellow solid.

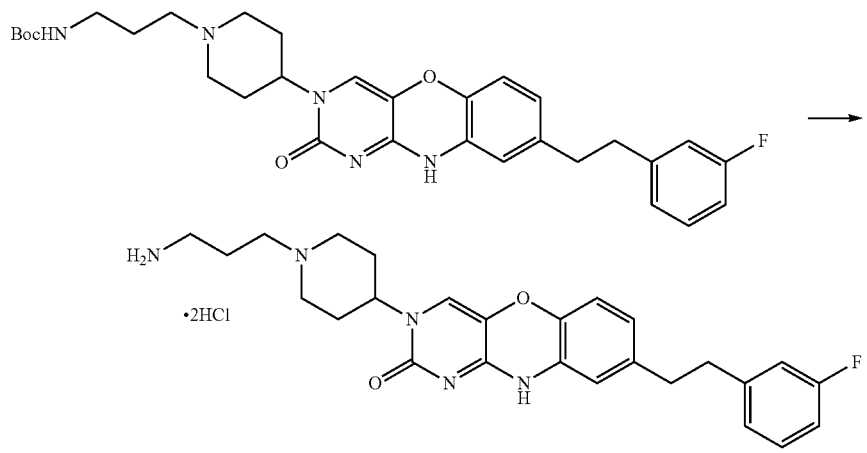

3-[1-(3-Amino-propyl)-piperidin-4-yl]-7-[2-(3-fluoro-phenyl)-ethyl]-3H,9H-10-oxa-1,3,9-triaza-anthracen-2-one To a solution of [3-(4-{7-[2-(3-fluoro-phenyl)-ethyl]-2-oxo-2,9-dihydro-10-oxa-1,3,9-triaza-anthracen-3-yl}-piperidin-1-yl)-propyl]-carbamic acid tert-butyl ester (94 mg, 0.167 mmol, 1 equiv) in dichloromethane (10 mL) at 23° C. was added trifluoroacetic acid (4.0 mL). The reaction was stirred for 30 min then concentrated. The residue was dissolved in water (10 mL) then treated with 1.0 N aqueous hydrochloric acid (2.0 mL). The resulting solution was concentrated, and then the residue was re-dissolved in water (10 mL), treated with hydrochloric acid (2.0 mL) and concentrated. The residue was dissolved in water (10 mL) and then the resulting solution was frozen and then lyophilized to give 88 mg (0.165 mmol, 99%) of the desired product (dihydrochloride salt) as a yellow solid. LCMS (EI): 464.1 (M+H)⁺.

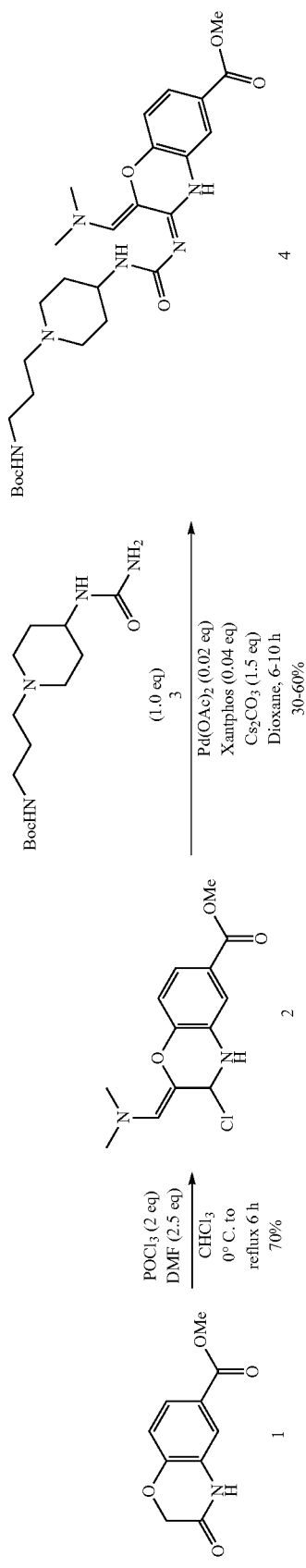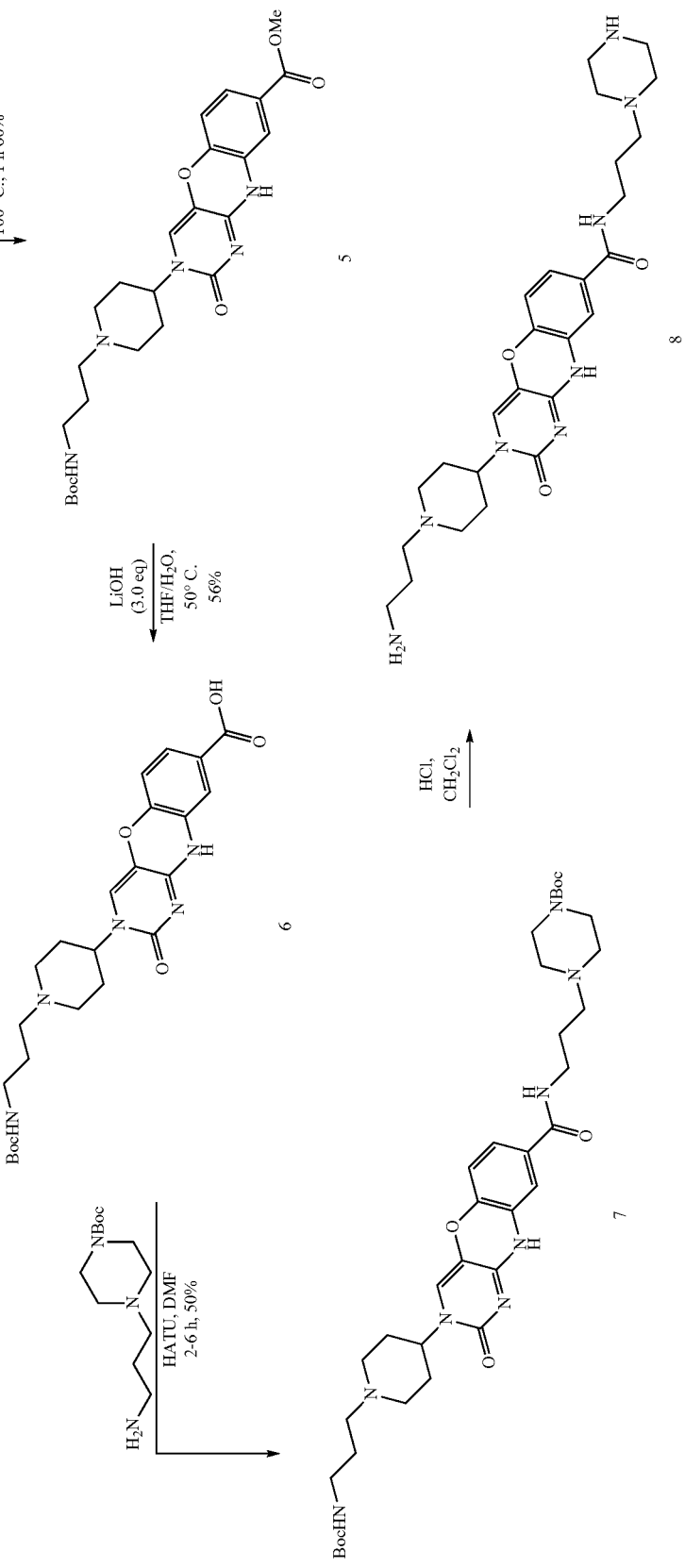

3-Chloro-2-dimethylaminomethylene-3,4-dihydro-2H-benzo[1,4]oxazine-6-carboxylic acid methyl ester (2) 4.05 mL of DMF (52.5 mmol, 2.5 equiv) was added to CHCl$_3$ (100 mL), the resulting solution was cooled to 0° C. before treated with trichlorophosphate (6.43 g, 42 mmol, 2.0 equiv). the reaction solution was warmed to RT and stirred for 20 minutes before cooled down to 0° C. again and added 3-Oxo-3,4-dihydro-2H-benzo[1,4]oxazine-6-carboxylic acid methyl ester (1) (4.36 g, 21 mmol, 1.0 equiv) at 0° C., and the resulting reaction mixture was heated up to reflux for 6 h. When TLC and LCMS showed the reaction was complete, the reaction mixture was cooled to RT and partitioned with dichloromethane and water, and aqueous layer was basified with 5N of NaOH to pH 12 and extracted with dichloromethane (3×100 mL). the combined organic layer was concentrated and purified by column chromatography (SiO$_2$, 20-50% EtOAc/Heptane gradient elution) to afford the desired 3-Chloro-2-dimethylaminomethylene-3,4-dihydro-2H-benzo[1,4]oxazine-6-carboxylic acid methyl ester (2) (4.13 g, 5.9 g, theoretical, 70%) as yellow solids.

3-{3-[1-(3-tert-Butoxycarbonylamino-propyl)-piperidin-4-yl]-ureido}-2-dimethylaminomethylene-3,4-dihydro-2H-benzo[1,4]oxazine-6-carboxylic acid methyl ester (4) and 3-[1-(3-tert-Butoxycarbonylamino-propyl)-piperidin-4-yl]-2-oxo-2,3,9,9a-tetrahydro-1H-10-oxa-1,3,9-triaza-anthracene-7-carboxylic acid methyl ester (5). A solution of 3-Chloro-2-dimethylaminomethylene-3,4-dihydro-2H-benzo[1,4]oxazine-6-carboxylic acid methyl ester (2) (1.28 g, 4.6 mmol, 1.0 equiv) and [3-(4-Ureido-piperidin-1-yl)-propyl]-carbamic acid tert-butyl ester (3) (1.37 g, 4.6 mmol, 1.0 equiv) in dioxane (20.0 mL) was treated with Pd(OAc)$_2$ (20.6 mg, 0.092 mmol, 0.02 equiv), Xantphos (10.6 mg, 0.18 mmol, 0.04 equiv) and Cs$_2$CO$_3$ (2.25 g, 6.9 mmol, 1.5 equiv), and the resulting reaction mixture was heated to 90° C. for 6 h. When TLC and MS showed the reaction was complete, the reaction mixture was directly added with Acetic acid (8 ml) stirred at 100° C. for 1 h without isolating 3-{3-[1-(3-tert-Butoxycarbonylamino-propyl)-piperidin-4-yl]-ureido}-2-dimethylaminomethylene-3,4-dihydro-2H-benzo[1,4]oxazine-6-carboxylic acid methyl ester (4) from the reaction mixture. The reaction solution was concentrated in vacuo, and the residue was directly purified by column chromatography (SiO$_2$, 0-5% MeOH/CH$_2$Cl$_2$ gradient elution) to afford the desired 3-[1-(3-tert-Butoxycarbonylamino-propyl)-piperidin-4-yl]-2-oxo-2,3,9,9a-tetrahydro-1H-10-oxa-1,3,9-triaza-anthracene-7-carboxylic acid methyl ester (5) (760 mg, 2295.4 mg theoretical, 33%) as a brown oily material. For 4: C$_{27}$H$_{40}$N$_6$O$_6$, LCMS (EI) m/e 545(M$^+$+H). For 5: C$_{25}$H$_{33}$N$_5$O$_6$, LCMS (EI) m/e 500(M$^+$+H).

3-[1-(3-tert-Butoxycarbonylamino-propyl)-piperidin-4-yl]-2-oxo-2,9-dihydro-3H-10-oxa-1,3,9-triaza-anthracene-7-carboxylic acid (6). 1M of LiOH aqueous solution (4.5 mL, 3 equiv) and 3-[1-(3-tert-Butoxycarbonylamino-propyl)-piperidin-4-yl]-2-oxo-2,3,9,9a-tetrahydro-1H-10-oxa-1,3,9-triaza-anthracene-7-carboxylic acid methyl ester (5, 760 mg, 1.52 mmol, 1.0 equiv) was added to THF (5 mL), warmed up to 50° C. and stirred until LCMS showed no starting material left. The reaction solution was cooled to RT and extracted with EtOAc. The aqueous layer was acidified to pH 2 and the desired product was precipitated and filtered to yield 3-[1-(3-tert-Butoxycarbonylamino-propyl)-piperidin-4-yl]-2-oxo-2,9-dihydro-3H-10-oxa-1,3,9-triaza-anthracene-7-carboxylic acid (412 mg, 738 mg theoretical, 56%) as a light brown solid. For 6: C$_{24}$H$_{31}$N$_5$O$_6$, LCMS (EI) m/e 486(M$^+$+H).

4-[3-({3-[1-(3-tert-Butoxycarbonylamino-propyl)-piperidin-4-yl]-2-oxo-2,9-dihydro-3H-10-oxa-1,3,9-triaza-anthracene-7-carbonyl}-amino)-propyl]-piperazine-1-carboxylic acid tert-butyl ester (7). A solution of 3-[1-(3-tert-Butoxycarbonylamino-propyl)-piperidin-4-yl]-2-oxo-2,9-dihydro-3H-10-oxa-1,3,9-triaza-anthracene-7-carboxylic acid (6) (150 mg, 0.31 mmol, 1 equiv) and 4-(3-Amino-propyl)-piperazine-1-carboxylic acid tert-butyl ester (150 mg, 0.62 mmol, 2.0 equiv) in DMF (5 mL) was treated with HATU(235 mg, 0.62 mmol, 2.0 equiv) and Hunig's base. The resulting solution was stirred at RT for 6 h. When TLC and LCMS showed the reaction was complete, the reaction solution was concentrated in vacuo, and the residue was directly purified by column chromatography (SiO$_2$, 0-10% MeOH/CH$_2$Cl$_2$ gradient elution) to afford the desired 4-[3-({3-[1-(3-tert-Butoxycarbonylamino-propyl)-piperidin-4-yl]-2-oxo-2,9-dihydro-3H-10-oxa-1,3,9-triaza-anthracene-7-carbonyl}-amino)-propyl]-piperazine-1-carboxylic acid tert-butyl ester (106 mg, 220 mg, theoretical, 48%), which was treated with 4M HCl in dioxane to afford the final product 3-[1-(3-Amino-propyl)-piperidin-4-yl]-2-oxo-2,9-dihydro-3H-10-oxa-1,3,9-triaza-anthracene-7-carboxylic acid (3-piperazin-1-yl-propyl)-amide (8). For 7: C$_{36}$H$_{54}$N$_8$O$_7$, LCMS (EI) m/e 711 (M$^+$+H). For 8: C$_{26}$H$_{38}$N$_8$O$_3$, LCMS (EI) m/e 511(M$^+$+H).

Example 2

Antimicrobial Activity

The compounds of the present invention were tested for antimicrobial activity. These data are presented in Table 2. The compounds were run against *Eschericia coli* strain ATCC25922 using a standard microdilution assay to determine minimum inhibitory concentrations (MICs). The data is presented whereby a "+" indicates that the compound has an MIC value of 16 micrograms/ml or less and a "−" indicates that the compound has an MIC value greater than 16 micrograms/ml. A "N/A" means that data is unavailable. It will be recognized by one skilled in the art that the compounds can be assessed against other bacterial organisms and that the presentation of data for activity against *Eschericia coli* is illustrative and in no way is intended to limit the scope of the present invention. The compounds of the present invention can be assayed against a range of other microorganisms depending upon the performance activity desired to be gathered. Furthermore, the "+", "−", and "N/A" representation and the selection of a cutoff value of 16 micrograms/ml is also illustrative and in no way is intended to limit the scope of the present invention. For example, a "−" is not meant to indicate that the compound necessarily lacks activity or utility, but rather that its MIC value against the indicated microorganism is greater than 16 micrograms/ml.

TABLE 2

| Compound Number | E. coli ATCC25922 MIC |
| --- | --- |
| 392 | − |
| 393 | − |
| 396 | − |
| 400 | − |
| 402 | − |
| 440 | − |
| 442 | − |
| 460 | − |
| 528 | − |
| 529 | − |
| 543 | − |
| 544 | − |
| 557 | − |
| 558 | − |

TABLE 2-continued

| Compound Number | E. coli ATCC25922 MIC |
|---|---|
| 575 | − |
| 576 | − |
| 578 | − |
| 579 | − |
| 592 | + |
| 595 | − |
| 598 | − |
| 603 | + |
| 604 | − |
| 606 | − |
| 614 | − |
| 615 | − |
| 627 | + |
| 638 | − |
| 639 | − |
| 641 | − |
| 642 | − |
| 643 | − |
| 651 | − |
| 656 | − |
| 657 | − |
| 658 | − |
| 659 | − |
| 660 | − |
| 664 | − |
| 667 | − |
| 669 | − |
| 671 | − |
| 672 | − |
| 674 | − |
| 675 | − |
| 676 | − |
| 681 | − |
| 685 | − |
| 686 | − |
| 689 | + |
| 690 | − |
| 691 | − |
| 694 | − |
| 695 | + |
| 696 | + |
| 707 | + |
| 708 | + |
| 714 | − |
| 715 | + |
| 718 | − |
| 729 | + |
| 730 | − |
| 731 | + |
| 732 | + |
| 733 | − |
| 738 | − |
| 740 | + |
| 741 | + |
| 748 | − |
| 749 | + |
| 750 | − |
| 751 | + |
| 752 | + |
| 753 | + |
| 754 | + |
| 763 | − |
| 765 | + |
| 774 | + |
| 776 | + |
| 777 | + |
| 781 | + |
| 782 | − |
| 783 | + |
| 792 | + |
| 793 | + |
| 794 | + |
| 795 | − |
| 798 | − |
| 811 | + |
| 812 | − |
| 818 | + |
| 832 | + |
| 833 | + |
| 858 | − |
| 859 | + |
| 868 | + |
| 869 | + |
| 870 | − |
| 888 | − |
| 889 | − |
| 890 | − |
| 891 | − |
| 903 | − |
| 904 | + |
| 908 | − |
| 909 | − |
| 916 | + |
| 917 | + |
| 919 | − |
| 920 | − |
| 921 | − |
| 929 | − |
| 938 | + |
| 941 | + |
| 942 | + |
| 950 | + |
| 953 | + |
| 954 | + |
| 955 | + |
| 956 | + |
| 972 | − |
| 973 | − |
| 976 | − |
| 993 | + |
| 1006 | − |
| 1007 | − |
| 1008 | − |
| 1014 | − |
| 1016 | − |
| 1025 | − |
| 1026 | − |
| 1030 | − |
| 1031 | − |
| 1032 | + |
| 1033 | + |
| 1041 | − |
| 1042 | − |
| 1055 | − |
| 1056 | − |
| 1058 | − |
| 1070 | − |
| 1071 | − |
| 1072 | − |
| 1073 | − |
| 1082 | − |
| 1083 | − |
| 1084 | − |
| 1086 | + |
| 1096 | − |
| 1133 | + |
| 1134 | + |
| 1135 | + |
| 1145 | + |
| 1146 | + |
| 1147 | − |
| 1192 | − |
| 1193 | − |
| 1197 | − |
| 1198 | − |
| 1212 | − |
| 1213 | − |
| 1234 | + |
| 1235 | + |
| 1236 | + |
| 1237 | + |
| 1238 | + |
| 1244 | + |
| 1269 | + |

TABLE 2-continued

| Compound Number | E. coli ATCC25922 MIC |
|---|---|
| 1270 | + |
| 1271 | + |
| 1368 | − |
| 1369 | − |
| 1370 | + |
| 1421 | − |
| 1426 | − |
| 1427 | − |
| 1441 | − |
| 1449 | − |
| 1450 | − |
| 1464 | − |
| 1465 | + |
| 1466 | + |
| 1467 | − |
| 360 | − |
| 362 | − |
| 367 | − |
| 371 | − |
| 375 | − |
| 377 | − |
| 378 | − |
| 379 | − |
| 380 | − |
| 390 | − |
| 391 | − |
| 411 | − |
| 426 | − |
| 430 | − |
| 447 | − |
| 469 | − |
| 568 | − |
| 569 | − |
| 570 | − |
| 4000c | − |
| 4001c | − |
| 4002c | − |
| 4003c | − |
| 4004c | + |
| 4005c | − |
| 4006c | + |
| 4007c | − |
| 4008c | − |

Incorporation by Reference

The entire disclosure of each of the patent documents and scientific articles referred to herein is incorporated by reference for all purposes.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed:

1. A compound having the formula:

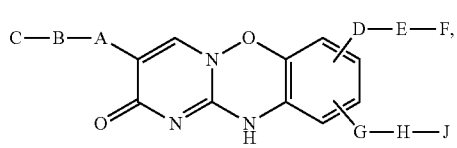

(VI)

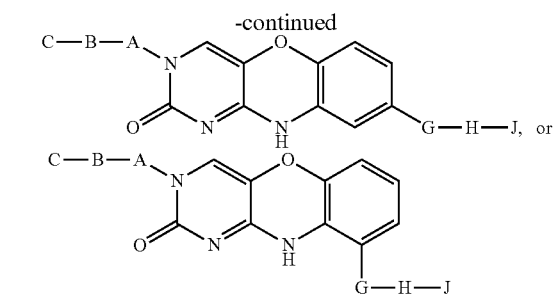

wherein -G-H-J is

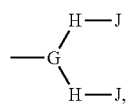

wherein each H and J is independently selected, or -G-H-J is

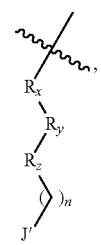

wherein $R_x$ is selected from $CH_2$, NH, $N(C_{1-8}$ alkyl), S, and O; $R_y$ and $R_z$ are C or CH each independently substituted with one or more F, $CH_3$, $CF_3$, OH, and $OCH_3$; or $R_x$, $R_y$, and $R_z$ are each independently selected from $CH_2$ and $CR^aR^b$ wherein $R^a$ and $R^b$ are taken together to form a $C_{1-5}$ carbocycle;

J' is selected from $NH_2$, $NH(C_{1-8}$ alkyl), $N(C_{1-8}$ alkyl$)_2$, $NHC(=O)CH_3$, $NHC(=O)NH_2$, $NHC(=NH)NH_2$, and $NHC(=NH)H$;

wherein n is 0, 1, or 2;

alternatively, -G-H-J is

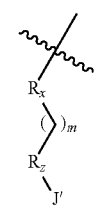

wherein $R_x$ is selected from $CH_2$, NH, $N(C_{1-8}$ alkyl), S, and O; $R_z$ is a C or CH, substituted with one or more $CH_3$ or $R_z$ is $CR^aR^b$ wherein $R^a$ and $R^b$ are taken together to form a $C_{1-5}$ carbocycle, wherein m is 1, 2, or 3;

J' is selected from $NH_2$, $NH(C_{1-8}$ alkyl), $N(C_{1-8}$ alkyl$)_2$, $NHC(=O)CH_3$, $NHC(=O)NH_2$, $NHC(=NH)NH_2$, and $NHC(=NH)H$;

C-B-A-, -D-E-F, and -G-H-J are chemical moieties, wherein

D and G are independently selected from the group consisting of:

(a) a single bond, (b) —(C$_{1-8}$ alkyl)-, (c) —(C$_{2-8}$ alkenyl)-, (d) —(C$_{2-8}$ alkynyl)-, wherein
  i) 0-4 carbon atoms in any of (b)-(d) immediately above optionally is replaced by a moiety selected from the group consisting of —O—, —S(O)$_p$—, —NR$^6$—, —(C=O)—, —S(O)$_p$NR$^6$—, —NR$^6$S(O)$_p$—, and —NR$^6$S(O)$_p$NR$^6$—,
  ii) any of (b)-(d) immediately above optionally is substituted with one or more R$^5$ groups, and
  iii) any of (b)-(d) immediately above optionally is substituted with —(C$_{1-8}$ alkyl) -R$^5$ groups;
(e) —O—, (f) —NR$^6$—, (g) —S(O)$_p$—, (h) —C(O)—, (i) —C(O)O—, (j) —OC(O)—, k) —OC(O)O—, (l) —C(O)NR$^6$—, (m) —NR$^6$CO—, (n) —NR$^6$C(O)NR$^6$—, (o) —C(=NR$^6$)—, (p) —C(=NR$^6$)O—, (q) —OC(=NR$^6$)—, (r) —C(=NR$^6$)NR$^6$—, (s) —NR$^6$C(=NR$^6$)—, (t) —C(=S)—, (u) —C(=S)NR$^6$—, (v) —NR$^6$C(=S)—, (w) —C(O)S—, (x) —SC(O)—, (y) —OC(=S)—, (z) —C(=S)O—, (aa) —NR$^6$(CNR$^6$)NR$^6$—, (bb) —CR$^6$R$^6$C(O)—, (cc) —C(O)NR$^6$(CR$^6$R$^6$)$_t$—, (dd) a 3-14 member saturated, unsaturated, or aromatic heterocycle containing one or more heteroatoms selected from the group consisting of nitrogen, oxygen, and sulfur, (ee) a 3-14 member saturated, unsaturated, or aromatic carbocycle, and (ff) —(CR$^6$R$^6$)$_t$—,
wherein (dd) or (ee) is optionally substituted with one or more R$^5$ groups;
E, and H are independently selected from the group consisting of:
  (a) a single bond,
  (b) a 3-14 member saturated, unsaturated, or aromatic heterocycle containing one or more heteroatoms selected from the group consisting of nitrogen, oxygen, and sulfur,
  (c) a 3-14 member saturated, unsaturated, or aromatic carbocycle,
wherein (b) or (c) is optionally substituted with one or more R$^5$ groups;
  (d) —(C$_{1-8}$ alkyl)-, (e) —(C$_{2-8}$ alkenyl)-, (f) —(C$_{2-8}$ alkynyl)-, wherein
  i) 0-4 carbon atoms in any of (d)-(f) immediately above optionally is replaced by a moiety selected from the group consisting of —O—, —S(O)$_p$—, —NR$^6$—, —(C=O)—, —C(=NR$^6$)—, —S(O)$_p$NR$^6$—, —NR$^6$S(O)$_p$—, and —NR$^6$S(O)$_p$NR$^6$—,
  ii) any of (d)-(f) immediately above optionally is substituted with one or more R$^5$ groups, and
  iii) any of (d)-(f) immediately above optionally is substituted with —(C$_{1-8}$ alkyl) -R$^5$ groups;
and (g) —(CR$^6$R$^6$)$_t$—,
F, and J are independently selected from the group consisting of:
  (a) hydrogen, (c) F, (d) Cl, (e) Br, (f) I, (g) —CF$_3$, (h) —CN, (i) —N$_3$ (j) —NO$_2$, (k) —NR$^6$(CR$^6$R$^6$)$_t$R$^8$, (l) —OR$^8$, (m) —S(O)$_p$(CR$^6$R$^6$)$_t$R$^8$, (n) —C(O)(CR$^6$R$^6$)$_t$R$^8$, (o) —OC(O)(CR$^6$R$^6$)$_t$R$^8$, (p) —SC(O)(CR$^6$R$^6$)$_t$R$^8$, (q) —C(O)O(CR$^6$R$^6$)$_t$R$^8$, (r) —NR$^6$C(O)(CR$^6$R$^6$)$_t$R$^8$, (s) —C(O)NR$^6$(CR$^6$R$^6$)$_t$R$^8$, (t) —C(=NR$^6$)(CR$^6$R$^6$)$_t$R$^8$, (u) —C(=NNR$^6$R$^6$)(CR$^6$R$^6$)$_t$R$^8$, (v) —C(=NNR$^6$C(O)R$^6$)(CR$^6$R$^6$)$_t$R$^8$, (w) —C(=NOR$^8$)(CR$^6$R$^6$)$_t$R$^8$, (x) —NR$^6$C(O)O(CR$^6$R$^6$)$_t$R$^8$, (y) —OC(O)NR$^6$(CR$^6$R$^6$)$_t$R$^8$, (z) —NR$^6$C(O)NR$^6$(CR$^6$R$^6$)$_t$R$^8$, (aa) —NR$^6$S(O)$_p$(CR$^6$R$^6$)$_t$R$^8$, (bb) —S(O)$_p$NR$^6$(CR$^6$R$^6$)$_t$R$^8$, (cc) —NR$^6$S(O)$_p$NR$^6$(CR$^6$R$^6$)$_t$R$^8$, (dd) —NR$^6$R$^8$, (ee) —NR$^6$(CR$^6$R$^6$)$_t$R$^8$, (ff) —OH, (gg) —NR$^8$R$^8$, (hh) —OCH$_3$, (ii) —S(O)$_p$R$^8$, (jj) —NC(O)R$^8$, (kk) —NR$^6$C(NR$^6$)NR$^6$R$^8$, (ll) a C$_{1-8}$ alkyl group, (mm) a C$_{2-8}$ alkenyl group, (nn) a C$_{2-8}$alkynyl group, (oo) a 3-14 member saturated, unsaturated, or aromatic heterocycle containing one or more heteroatoms selected from the group consisting of nitrogen, oxygen, and sulfur, (pp) a 3-14 member saturated, unsaturated, or aromatic carbocycle, (qq) —(CR$^6$R$^6$)$_t$NR$^6$(CR$^6$R$^6$)$_t$R$^8$, (rr) —N[(CR$^6$R$^6$)$_t$R$^8$][C=O(CR$^6$R$^6$)R$^8$], (ss) —(CR$^6$R$^6$)$_t$N[(CR$^6$R$^6$)$_t$R$^8$][(CR$^6$R$^6$)$_t$R$^8$], (tt) —(CR$^6$R$^6$)$_t$NR$^6$(C=O)(CR$^6$R$^6$)$_t$R$^8$, (uu) -haloalkyl, (vv) —C(O)(CR$^6$)[(CR$^6$R$^6$)$_t$R$^8$]R$^8$, (ww) —(CR$^6$R$^6$)$_t$ C(O)NR$^8$R$^8$, (xx) —(CR$^6$R$^6$)$_t$C(O)O(CR$^6$R$^6$)$_t$R$^8$, (yy) —NR$^6$C(O)CR$^8$R$^8$R$^8$, (zz) —N[(CR$^6$R$^6$)$_t$R$^8$]C(O)R$^8$, and (aaa) —S(O)$_p$NR$^8$R$^8$;
wherein (ll) through (pp) is optionally substituted with one or more R$^7$ groups;

C—B-A- is selected from the group consisting of:

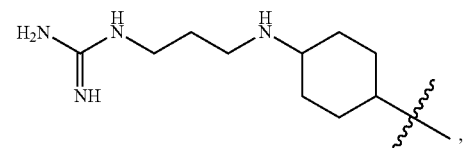

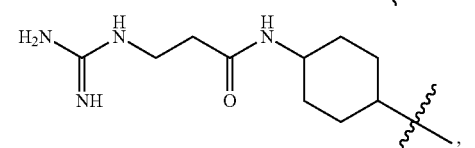

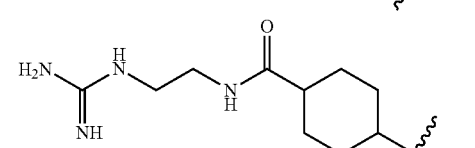

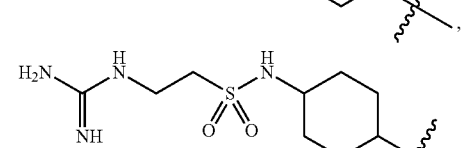

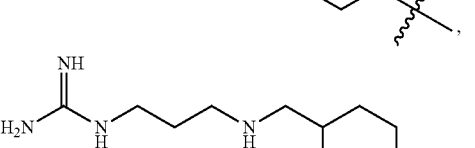

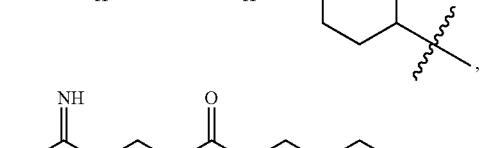

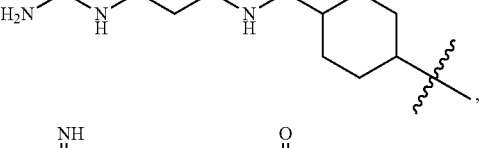

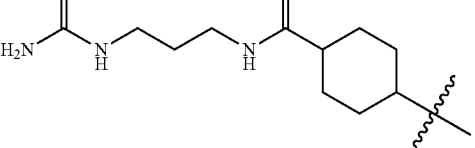

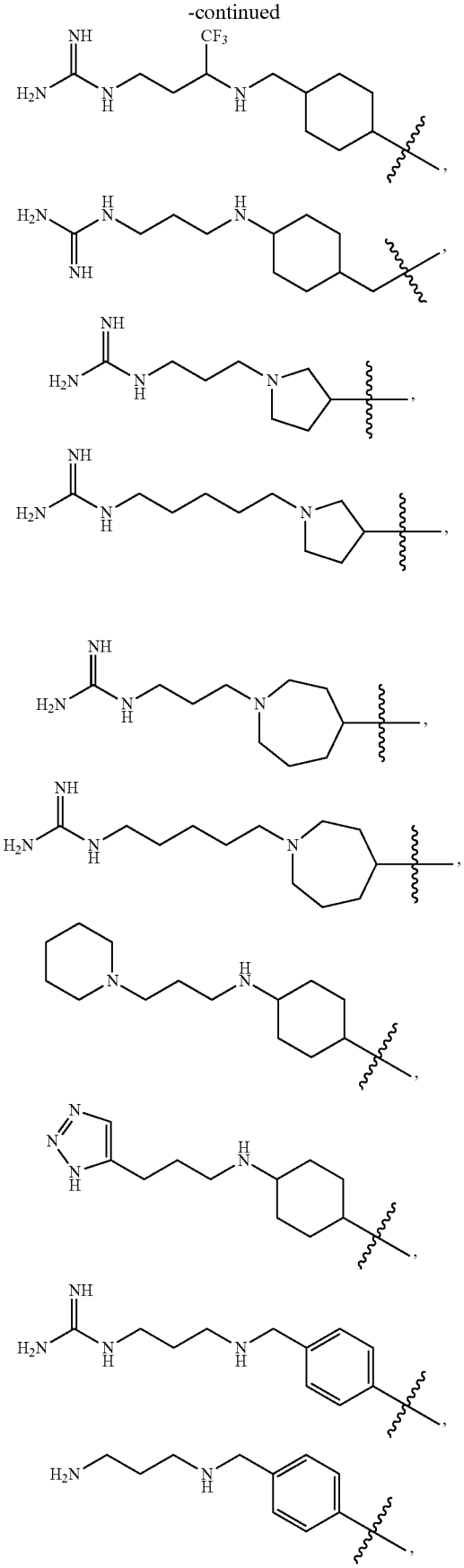
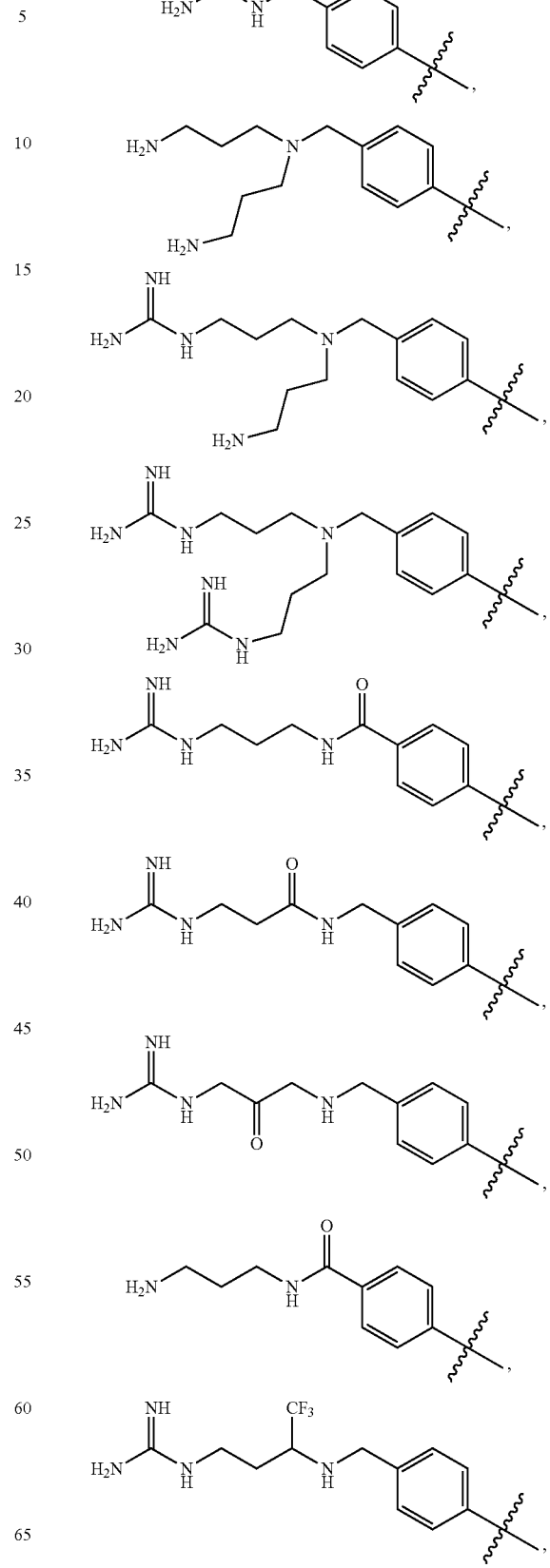

-continued

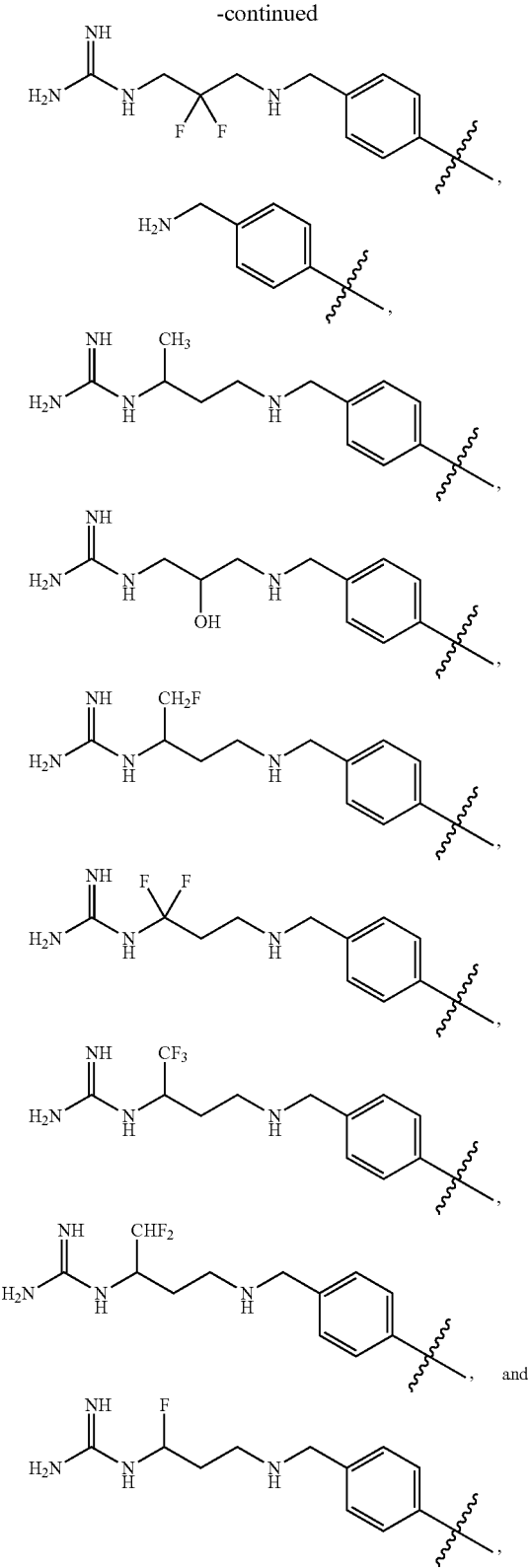

R[5] is selected from (a) hydrogen, (b) F, (c) Cl, (d) Br, (e) I, (f) —CF$_3$, (g) —CN, (h) —N$_3$ (i) —NO$_2$, (j) —NR$^6$R$^6$, (k) —OR$^8$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) —(C$_{1-8}$ alkyl)-(3-14 member saturated, unsaturated, or aromatic heterocycle containing one or more heteroatoms selected from the group consisting of nitrogen, oxygen, and sulfur), (q) —(C$_{1-8}$ alkyl)-(3-14 member saturated, unsaturated, or aromatic carbocycle), (r) -haloalkyl, (s) -SR$^6$, (t) -3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle; alternatively, two R$^5$ groups are taken together to form a carbocycle;

wherein (m) through (r) and (t) through (u) is optionally substituted with one or more R$^8$;

R$^6$ is selected from (a) hydrogen, (b) —C$_{1-8}$ alkyl or alternatively two R$^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle;

wherein (b) through (e) is optionally substituted with one or more R$^8$;

R$^7$ is selected from (a) hydrogen, (b) F, (c) Cl, (d) Br, (e) I, (f) -CF$_3$, (g) —CN, (h) —N$_3$ (i) —NO$_2$, (j) —NR$^6$R$^6$, (k) —OR$^6$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) —(C$_{1-8}$alkyl)-(3-14 member saturated, unsaturated, or aromatic heterocycle containing one or more heteroatoms selected from the group consisting of nitrogen, oxygen, and sulfur), (q) —(C$_{1-8}$ alkyl)-(3-14 member saturated, unsaturated, or aromatic carbocycle), (r) -haloalkyl, (s) —NR$^6$R$^8$, (t) —OR$_8$, (u) —(CR$^6$R$^6$)$_t$NR$^6$R$^8$, (v) -CR$^6$R$^8$R$^8$, (w) —SR$^6$, (x) -3-14 member saturated, unsaturated, or aromatic heterocycle containing one or more heteroatoms selected from the group consisting of nitrogen, oxygen, and sulfur, (y) -3-14 member saturated, unsaturated, or aromatic carbocycle, (z) —(CR$^6$R$^6$)$_t$C(O)NR$^8$R$^8$, (aa) —S(O)$_p$R$^8$, (bb) —NR$^6$C(O)NR$^6$R$^6$, (cc) —NR$^6$C(O)R$^6$, and (dd) —C(=NR$^6$)NR$^6$R$^6$;

wherein (m) through (q) and (x) through (y) are optionally substituted with one or more R$^9$;

R$^8$ is selected from (a) hydrogen, (b) F, (c) Cl, (d) Br, (e) I, (f) —CF$_3$, (g) -CN, (h) —N$_3$ (i) —NO$_2$, (j) —NR$^6$R$^9$, (k) —OR$^9$, (l) —NR$^6$(CNR$^6$)NR$^6$R$^6$, (m) —C$_{1-8}$ alkyl, (n) —C$_{1-8}$ alkenyl, (o) —C$_{1-8}$ alkynyl, (p) -(C$_{1-8}$alkyl)-(3-14 member saturated, unsaturated, or aromatic heterocycle containing one or more heteroatoms selected from the group consisting of nitrogen, oxygen, and sulfur), (q) ⁻(C$_{1-8}$ alkyl)-(3-14 member saturated, unsaturated, or aromatic carbocycle), (r) -3-14 member saturated, unsaturated, or aromatic heterocycle containing one or more heteroatoms selected from the group consisting of nitrogen, oxygen, and sulfur, (s) -3-14 member saturated, unsaturated, or aromatic carbocycle, (t) -haloalkyl, (u) —C(O)(CR$^6$R$^6$)$_t$R$^9$, (v) —SR$^6$, (w) —OC(O)(CR$^6$R$^6$)$_t$R$^9$, (x) —NR$^6$C(O)NR$^6$R$^9$, (y)—NR$^6$C(O)R$^9$, (z) —NR$^6$(CNR$^9$)(NR$^6$R$^6$), (aa) —ONR$^6$(CNR$^6$)NR$^6$R$^6$, (bb) —C(=NR$^9$)NR$^6$R$^6$, (cc) —S(O)$_p$R$^9$, (dd) —(CR$^6$R$^6$)$_t$C(O)NR$^6$R$^9$, (ee) —(CR$^6$R$^6$)$_t$OR$^9$, and (ff) (—CR$^6$R$^6$)$_t$NR$^6$R$^9$;

wherein (m) through (s) is optionally substituted with one or more R$^9$;

R$^9$ is selected from (a) hydrogen, (b) F, (c) Cl, (d) Br, (e) I, (f) —CF$_3$, (g) —CN, (h) —N$_3$ (i) —NO$_2$, (j) —NR$^6$R$^{10}$, (k) —OR$^6$, (l) —NR$^6$(CNR$^6$)NR$^6$R$^6$, (m) —C(O)(CR$^6$R$^6$)$_t$NR$^6$R$^6$, (n) —C$_{1-8}$ alkyl, (o) —C$_{1-8}$ alkenyl, (p) —C$_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —($CR^6R^6$)$_t$$OR^6$, (u) $O(CR^6R^6)_tNR^6R^{10}$, (v) —$C(O)R^6$, (w) —$SR^6$, (x) —$C(O)OR^{10}$, (y) —$S(O)_pR^6$, (z) (—$C_{1-8}$ alkyl)-(3-14 member saturated, unsaturated, or aromatic heterocycle containing one or more heteroatoms selected from the group consisting of nitrogen, oxygen, and sulfur), (aa) -($C_{1-8}$ alkyl) -(3-14 member saturated, unsaturated, or aromatic carbocycle), (bb) —$O(CR^6R^6)_t$$OR^6$, (cc) —$C(=NR^6)NR^6R^6$, (dd) —$ONR^6R^6$, (ee) —$NR^6C(O)NR^6R^6$, (ff) —$O(CR^6R^6)_tOR^6$, (gg) —$NR^6C(O)R^6$, and (hh) —$(CR^6R^6)_tNR^6R^{10}$;

wherein (n) through (r) and (z) through (aa) is optionally substituted with one or more $R^{10}$;

$R^{10}$ is selected from (a) hydrogen, (b) F, (c) Cl, (d) Br, (e) I, (f) -$CF_3$, (g) —CN, (h) —$N_3$ (i) —$NO_2$, (j) —$NR^6R^6$, (k) —$OR^6$, (l) —$NR^6(CNR^6)NR^6R^6$, (m) —$C(O)(CR^6R^6)_tNR^6R^6$, (n) —$C_{1-8}$ alkyl, (o) —$C_{1-8}$ alkenyl, (p) —$C_{1-8}$ alkynyl, (q) -3-14 member saturated, unsaturated, or aromatic heterocycle containing one or more heteroatoms selected from the group consisting of nitrogen, oxygen, and sulfur, (r) -3-14 member saturated, unsaturated, or aromatic carbocycle, (s) -haloalkyl, (t) —$(CR^6R^6)_tOR^6$, (u) —$O(CR^6R^6)_tNR^6R^6$, (v) —$C(O)R^6$, (w) —$SR^6$, (x) —$C(O)OR^6$, (y) —$S(O)_pR^6$, (z) —($C_{1-8}$alkyl )-(3-14 member saturated, unsaturated, or aromatic heterocycle containing one or more heteroatoms selected from the group consisting of nitrogen, oxygen, and sulfur), (aa) —($C_{1-8}$ alkyl) -(3-14 member saturated, unsaturated, or aromatic carbocycle), (bb) —$O(CR^6R^6)_tOR^6$, (cc) —$C(=NR^6)NR^6R^6$, (dd) —$ONR^6R^6$, (ee) —$NR^6C(0)NR^6R^6$, (ff) —$O(CR^6R^6)_tOR^6$, (gg) —$NR^6C(O)R^6$, and (hh) —$(CR^6R^6)_tNR^6R^6$;

wherein either the group -D-E-F or the group -G-H-J is absent, but both -D-E-F and -G-H-J are not simultaneously absent;

p is 0, 1, or 2, and t is 1, 2, or 3, or a pharmaceutically acceptable salt, ester, or tautomer thereof.

2. The compound according to claim 1 having the formula:

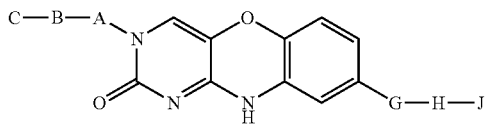

or a pharmaceutically acceptable salt, ester, or tautomer thereof.

3. The compound according to claim 1 having the formula:

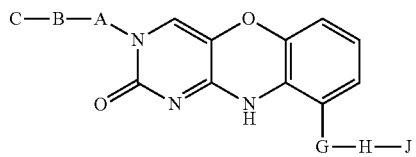

or a pharmaceutically acceptable salt, ester, or tautomer thereof.

4. The compound according to claim 1, wherein G is selected from (a) a single bond, (b) —($C_{1-8}$ alkyl)-, (c) —($C_{2-8}$ alkenyl)-, (d) —($C_{2-8}$ alkynyl)-, wherein i) 0-4 carbon atoms in any of (b)-(d) immediately above optionally is replaced by a moiety selected from the group consisting of —O—, —$S(O)_p$—, —$NR^6$—(C=O)—, —$C(=NR^6)$-, —$S(O)_pNR^6$-, —$NR^6S(O)_p$—, and —$NR^6S(O)_pNR^6$-, ii) any of (b)-(d) immediately above optionally is substituted with one or more $R^5$ groups, and iii) any of (b)-(d) immediately above optionally is substituted with —($C_{1-8}$ alkyl) - $R^5$ groups;

(e) a 3-14 member saturated, unsaturated, or aromatic heterocycle containing one or more heteroatoms selected from the group consisting of nitrogen, oxygen, and sulfur, and (f) a 3-14 member saturated, unsaturated, or aromatic carbocycle, wherein (e) or (f) is optionally substituted with one or more $R^5$ groups;

or a pharmaceutically acceptable salt, ester, or tautomer thereof.

5. The compound according to claim 1, wherein $R^5$ is selected from (a) hydrogen, (b) F, (c) Cl, (d) Br, (e) I, (f) —$CF_3$, (g) —CN, (h) —$N_3$ (i) —$NO_2$, (j) —$NH_2$, (k) $OR^6$, (l) —NHC(=NH)$NH_2$, (m) —$C_{1-8}$ alkyl, (n) —$C_{1-8}$ alkenyl, (o) —$C_{1-8}$ alkynyl, (p) —($C_{1-8}$ alkyl) -(3-14 member saturated, unsaturated, or aromatic heterocycle containing one or more heteroatoms slected from the group consisting of nitrogen, oxygen, and sulfur), (q) —($C_{1-8}$ -alkyl)(3-14 member saturated, unsaturated, or aromatic carbocycle), (r) -haloalkyl, (s) —$SR^6$, (t) -3-14 member saturated, unsaturated, or aromatic heterocycle containing one or more heteroatoms selected from the group consisting of nitrogen, oxygen, and sulfur, and (u) -3-14 member saturated, unsaturated, or aromatic carbocycle; alternatively, two $R^5$ groups are taken together to form a carbocycle; or a pharmaceutically acceptable salt, ester, or tautomer thereof.

6. The compound according to claim 1, wherein $R^6$ is selected from (a) hydrogen, (b) —$C_{1-8}$ alkyl or alternatively two $R^6$ groups are taken together to form a carbocycle, (c) -haloalkyl, (d) -3-14 member saturated, unsaturated, or aromatic heterocycle containing one or more heteroatoms selected from the group consisting of nitrogen, oxygen, and sulfur, and (e) -3-14 member saturated, unsaturated, or aromatic carbocycle; or a pharmaceutically acceptable salt, ester, or tautomer thereof.

7. The compound according to claim 1, wherein G is selected from (a) a single bond, (b) —($C_{1-8}$ alkyl)—, (c) —($C_{2-8}$ alkenyl)-, (d) —($C_{2-8}$ alkynyl)-, wherein i) 0-4 carbon atoms in any of (b)-(d) immediately above optionally is replaced by a moiety selected from the group consisting of —O—, —$S(O)_p$—,—$NR^6$, —(C=O)—, —$C(=NR^6)$-, —$S(O)_pNR^6$-, —$NR^6S(O)_p$—, and —$NR^6S(O)_pNR^6$-, ii) any of (b)-(d) immediately above optionally is substituted with one or more $R^5$ groups, and iii) any of (b)-(d) immediately above optionally is substituted with —($C_{1-8}$ alkyl) - $R^5$ groups;

wherein p is 0, 1, or 2, or a pharmaceutically acceptable salt, ester, or tautomer thereof.

8. The compound according to claim 5, wherein
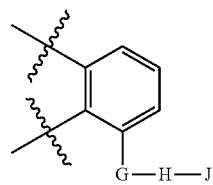
is selected from:
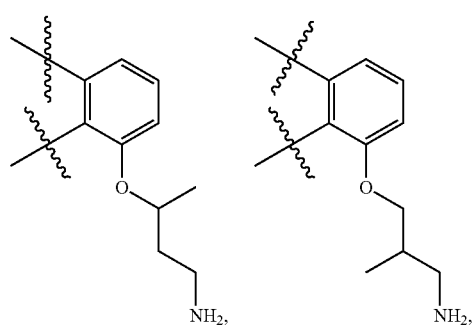
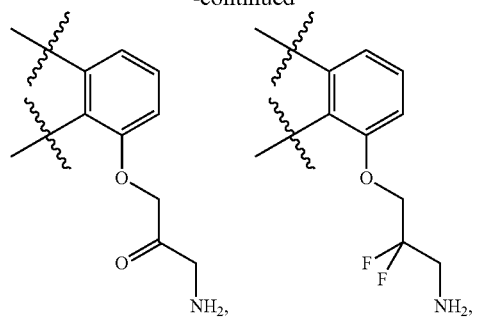

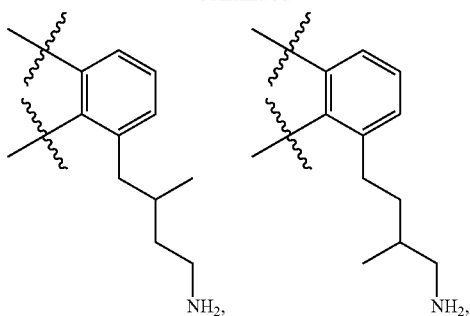
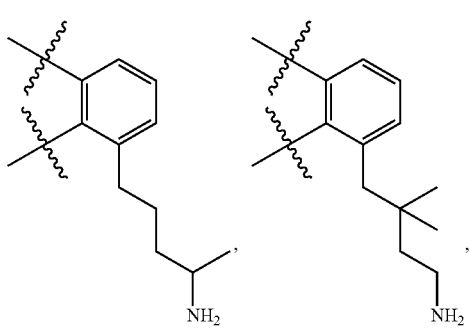
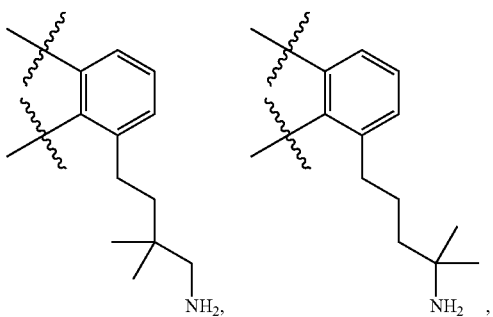
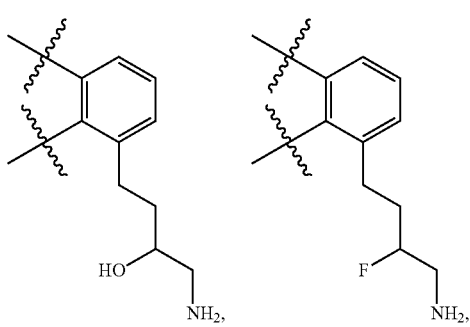
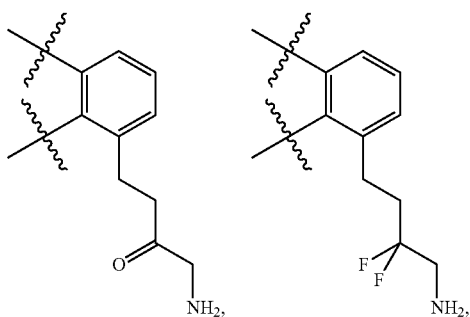

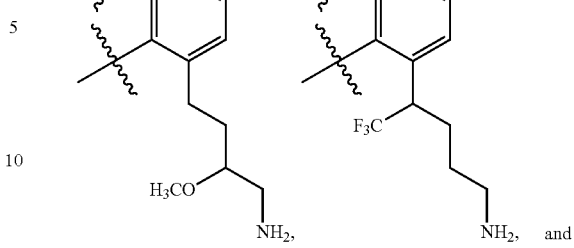

or -G-H-J is

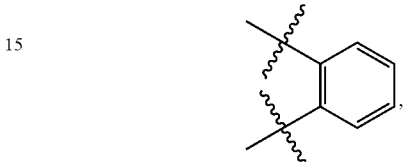

wherein $R_x$ is selected from $CH_2$, NH, N($C_{1-8}$ alkyl), S, and O; $R_y$ and $R_z$ are C or CH each independently substituted with one or more F, $CH_3$, $CF_3$, OH, and $OCH_3$; or $R_x$, $R_y$, and $R_z$ are each independently selected from $CH_2$ and $CR^aR^b$ wherein $R^a$ and $R^b$ are taken together to form a $C_{1-5}$ carbocycle;

J' is selected from $NH_2$, NH($C_{1-8}$ alkyl), N($C_{1-8}$ alkyl)$_2$, NHC(=O)$CH_3$, NHC(=O)$NH_2$, NHC(=NH)$NH_2$, and NHC(=NH)H;

wherein n is 0, 1, or 2;

alternatively, -G-H-J is

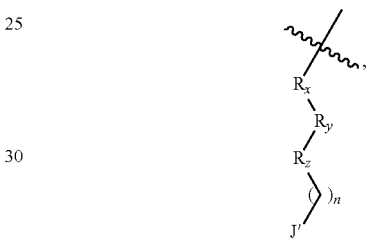

wherein $R_x$ is selected from $CH_2$, NH, N($C_{1-8}$ alkyl), S, and O; $R_z$ is a C or CH, substituted with one or more $CH_3$ or $R_z$ is $CR^aR^b$ wherein $R^a$ and $R^b$ are taken together to form a $C_{1-5}$ carbocycle, wherein m is 1, 2, or 3;

J' is selected from $NH_2$, NH($C_{1-8}$ alkyl), N($C_{1-8}$ alkyl)$_2$, NHC(=O)$CH_3$, NHC(=O)$NH_2$, NHC(=NH)$NH_2$, and NHC(=NH)H; or a pharmaceutically acceptable salt, ester, or tautomer thereof.

9. A compound selected from,
| Comp. No. | Structure |
|---|---|
| 392 | 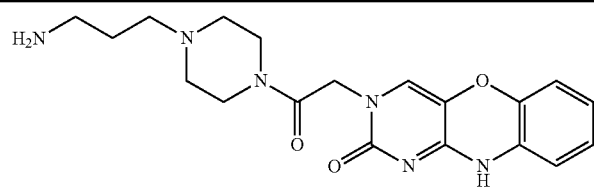 |
| 393 | 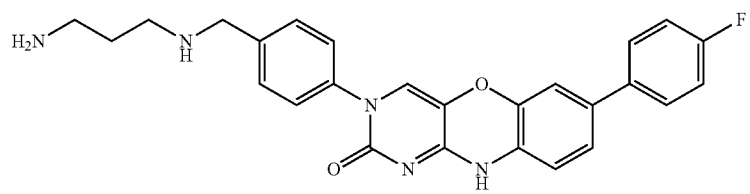 [SMILES: NCCCNCc1ccc(-n2cc3c(nc2=O)Nc2ccc(-c4ccc(F)cc4)cc2O3)cc1] |
| 396 | 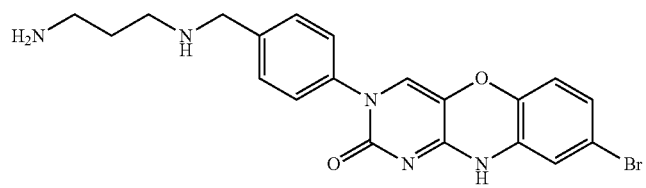 [SMILES: NCCCNCc1ccc(-n2cc3c(nc2=O)Nc2cc(Br)ccc2O3)cc1] |
| 400 | 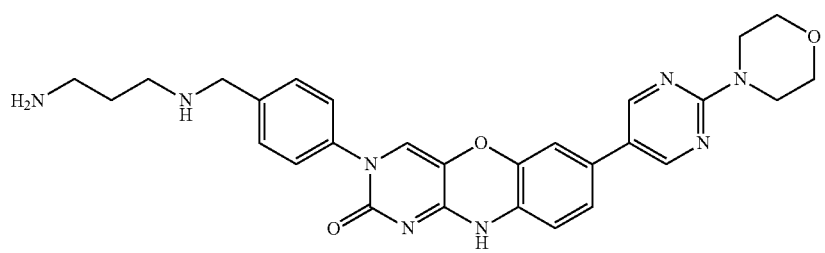 [SMILES: NCCCNCc1ccc(-n2cc3c(nc2=O)Nc2ccc(-c4cnc(N5CCOCC5)nc4)cc2O3)cc1] |
| 402 | 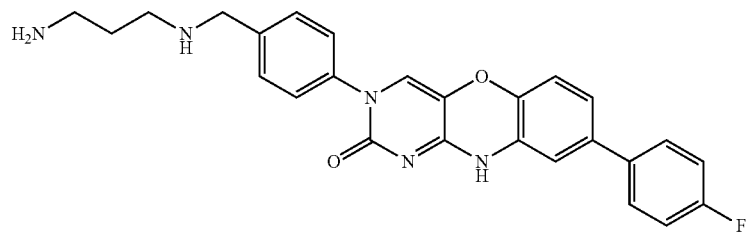 [SMILES: NCCCNCc1ccc(-n2cc3c(nc2=O)Nc2cc(-c4ccc(F)cc4)ccc2O3)cc1] |
| 440 | 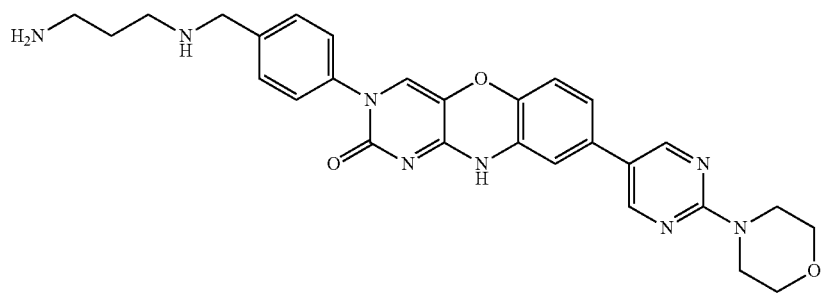 [SMILES: NCCCNCc1ccc(-n2cc3c(nc2=O)Nc2cc(-c4cnc(N5CCOCC5)nc4)ccc2O3)cc1] |
| 442 | 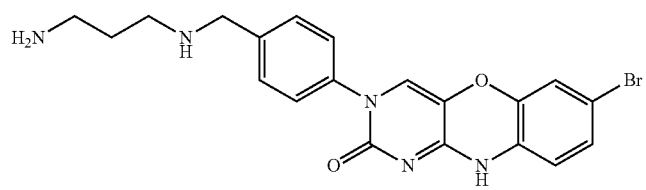 [SMILES: NCCCNCc1ccc(-n2cc3c(nc2=O)Nc2ccc(Br)cc2O3)cc1] |

-continued

| Comp. No. | Structure |
|---|---|
| 460 | 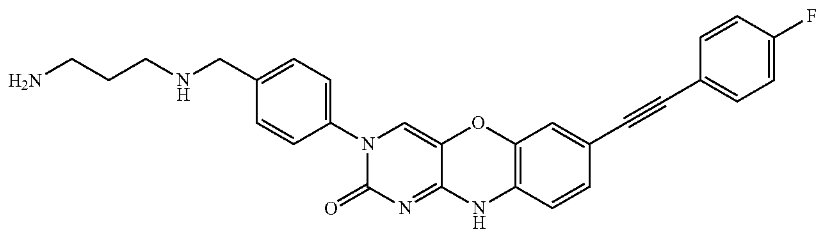 [SMILES: NCCCNCc1ccc(-n2cc3c(nc2=O)Nc2ccc(C#Cc4ccc(F)cc4)cc2O3)cc1] |
| 528 | 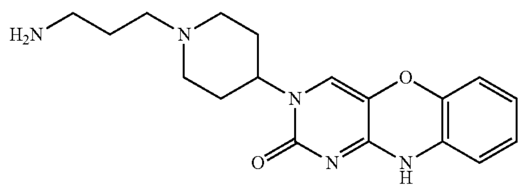 [SMILES: NCCCN1CCC(n2cc3c(nc2=O)Nc2ccccc2O3)CC1] |
| 529 | 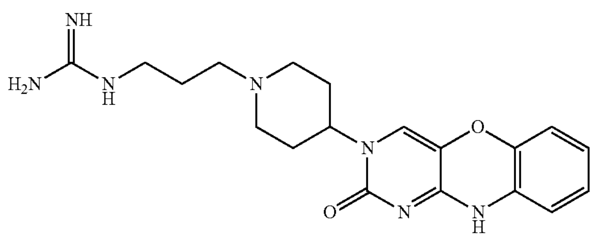 [SMILES: N=C(N)NCCCN1CCC(n2cc3c(nc2=O)Nc2ccccc2O3)CC1] |
| 543 | 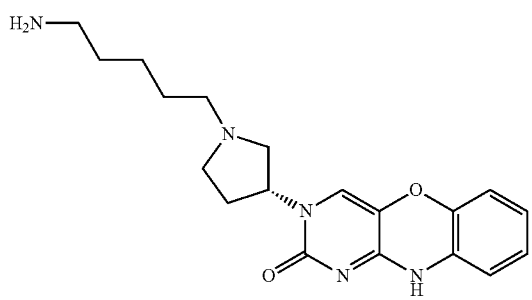 [SMILES: NCCCCCN1CC[C@@H](n2cc3c(nc2=O)Nc2ccccc2O3)C1] |
| 544 | 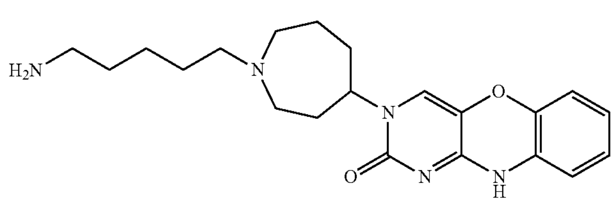 [SMILES: NCCCCCN1CCCC(n2cc3c(nc2=O)Nc2ccccc2O3)CC1] |
| 557 | 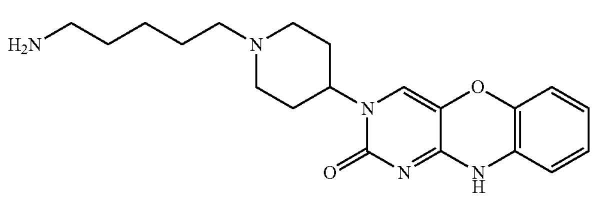 [SMILES: NCCCCCN1CCC(n2cc3c(nc2=O)Nc2ccccc2O3)CC1] |

-continued

| Comp. No. | Structure |
|---|---|
| 558 | 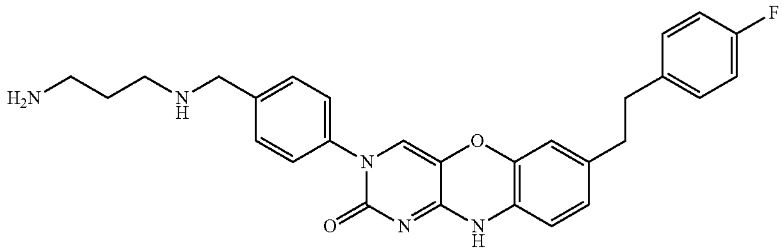 [SMILES: NCCCNCc1ccc(-n2cc3c(nc2=O)Nc2ccc(CCc4ccc(F)cc4)cc2O3)cc1] |
| 575 | 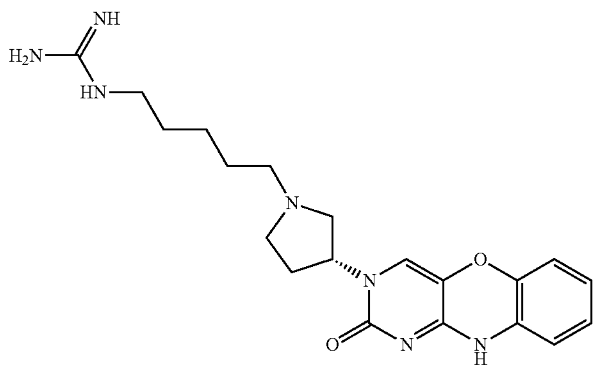 [SMILES: N=C(N)NCCCCCN1CC[C@@H](n2cc3c(nc2=O)Nc2ccccc2O3)C1] |
| 576 | 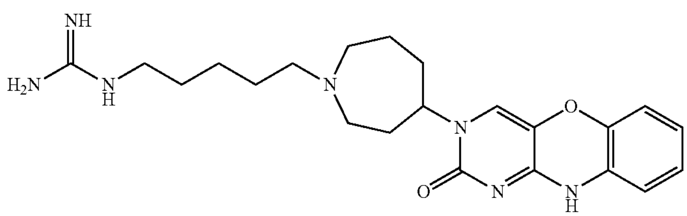 [SMILES: N=C(N)NCCCCCN1CCCC(n2cc3c(nc2=O)Nc2ccccc2O3)CC1] |
| 578 | 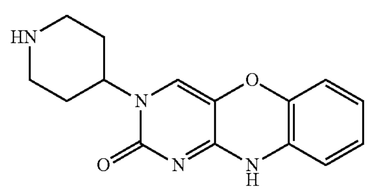 [SMILES: O=c1nc2c(cn1C1CCNCC1)Oc1ccccc1N2] |
| 579 | 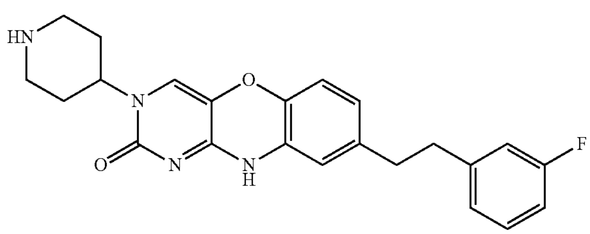 [SMILES: O=c1nc2c(cn1C1CCNCC1)Oc1ccc(CCc3cccc(F)c3)cc1N2] |
| 592 | 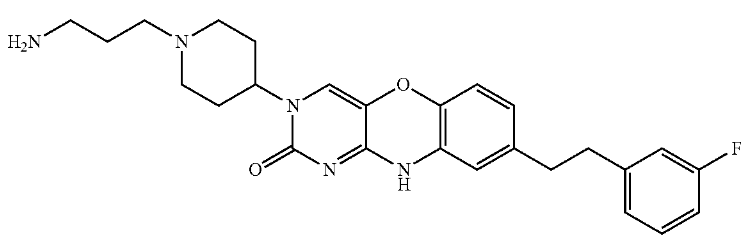 [SMILES: NCCCN1CCC(n2cc3c(nc2=O)Nc2cc(CCc4cccc(F)c4)ccc2O3)CC1] |

| Comp. No. | Structure |
|---|---|
| 595 | 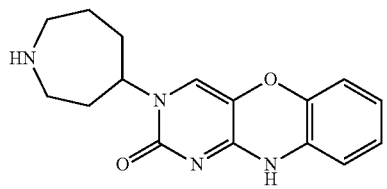 [SMILES: O=c1nc2c(cn1C1CCCNCC1)Oc1ccccc1N2] |
| 598 | 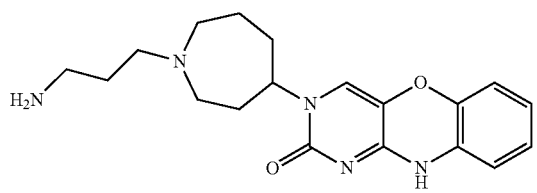 [SMILES: NCCCN1CCCC(n2cc3c(nc2=O)Nc2ccccc2O3)CC1] |
| 603 | 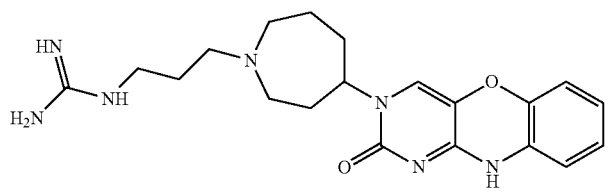 [SMILES: N=C(N)NCCCN1CCCC(n2cc3c(nc2=O)Nc2ccccc2O3)CC1] |
| 604 | 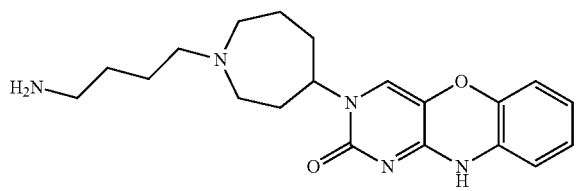 [SMILES: NCCCCN1CCCC(n2cc3c(nc2=O)Nc2ccccc2O3)CC1] |
| 606 | 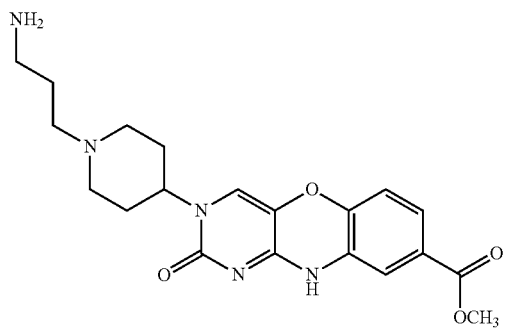 [SMILES: COC(=O)c1ccc2c(c1)Nc1nc(=O)n(C3CCN(CCCN)CC3)cc1O2] |
| 614 | 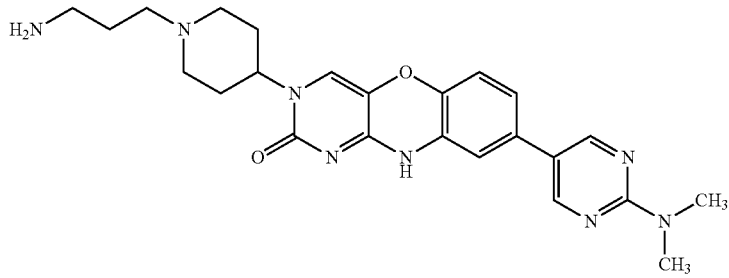 [SMILES: CN(C)c1ncc(-c2ccc3c(c2)Nc2nc(=O)n(C4CCN(CCCN)CC4)cc2O3)cn1] |

| Comp. No. | Structure |
|---|---|
| 615 | 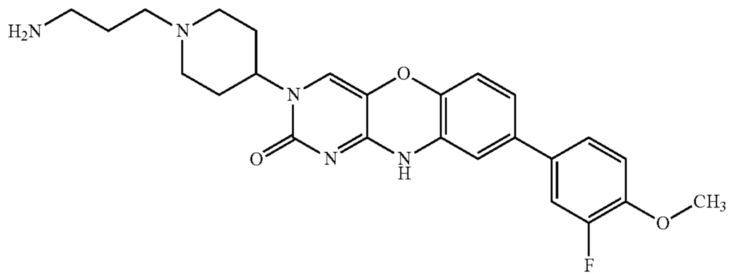 [SMILES: COc1ccc(-c2ccc3c(c2)Nc2nc(=O)n(C4CCN(CCCN)CC4)cc2O3)cc1F] |
| 627 | 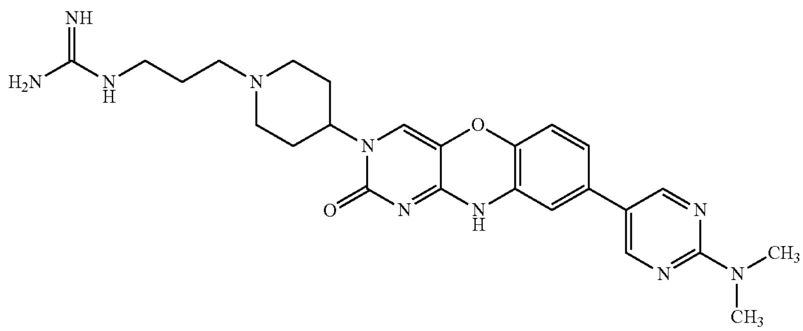 [SMILES: CN(C)c1ncc(-c2ccc3c(c2)Nc2nc(=O)n(C4CCN(CCCNC(=N)N)CC4)cc2O3)cn1] |
| 638 | 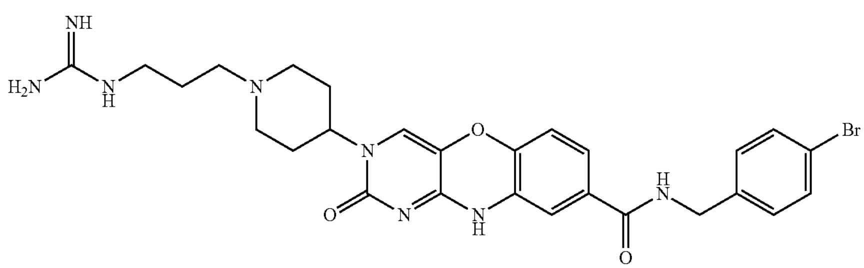 [SMILES: N=C(N)NCCCN1CCC(n2cc3c(nc2=O)Nc2cc(C(=O)NCc4ccc(Br)cc4)ccc2O3)CC1] |
| 639 | 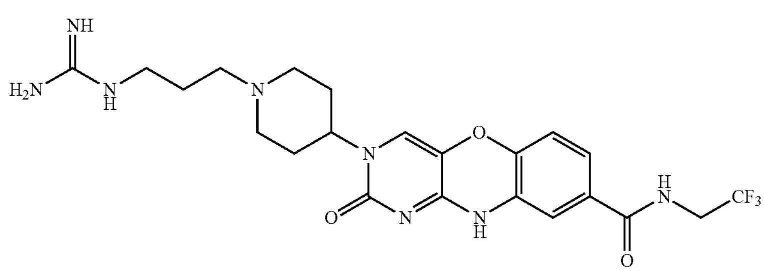 [SMILES: N=C(N)NCCCN1CCC(n2cc3c(nc2=O)Nc2cc(C(=O)NCC(F)(F)F)ccc2O3)CC1] |
| 641 | 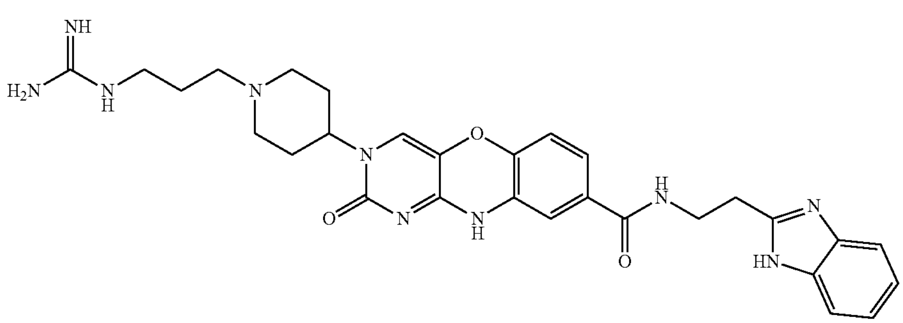 [SMILES: N=C(N)NCCCN1CCC(n2cc3c(nc2=O)Nc2cc(C(=O)NCCc4nc5ccccc5[nH]4)ccc2O3)CC1] |

US 9,023,843 B2
201                                                                  202
-continued
| Comp. No. | Structure |
|---|---|
| 642 | 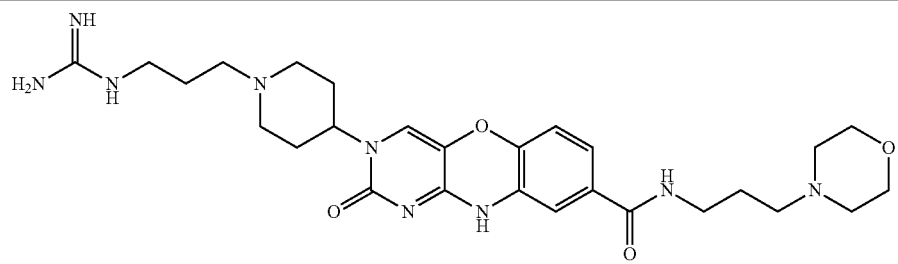 [SMILES: N=C(N)NCCCN1CCC(n2cc3c(nc2=O)Nc2cc(C(=O)NCCCN4CCOCC4)ccc2O3)CC1] |
| 643 | 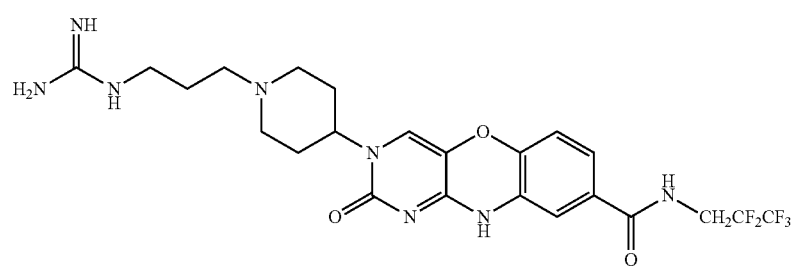 |
| 651 | 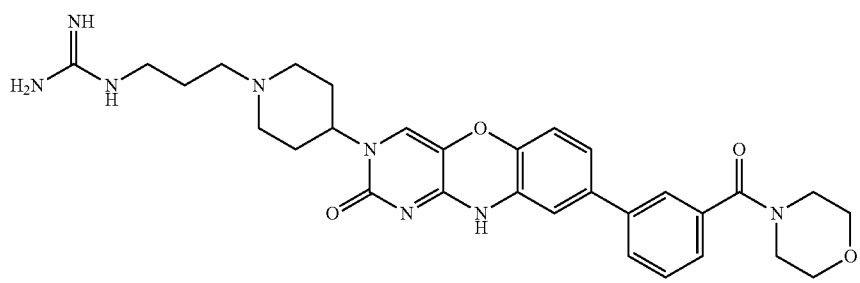 [SMILES: N=C(N)NCCCN1CCC(n2cc3c(nc2=O)Nc2cc(-c4cccc(C(=O)N5CCOCC5)c4)ccc2O3)CC1] |
| 656 | 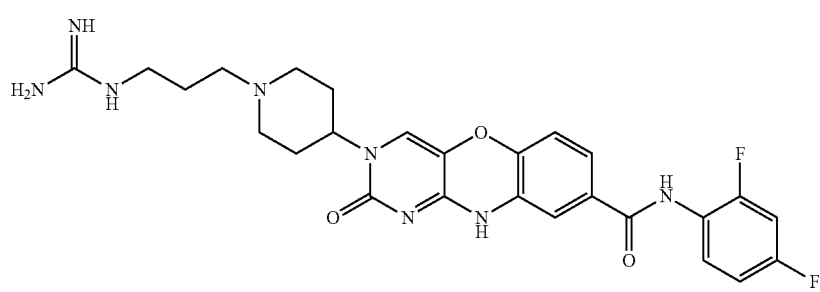 [SMILES: N=C(N)NCCCN1CCC(n2cc3c(nc2=O)Nc2cc(C(=O)Nc4ccc(F)cc4F)ccc2O3)CC1] |
| 657 | 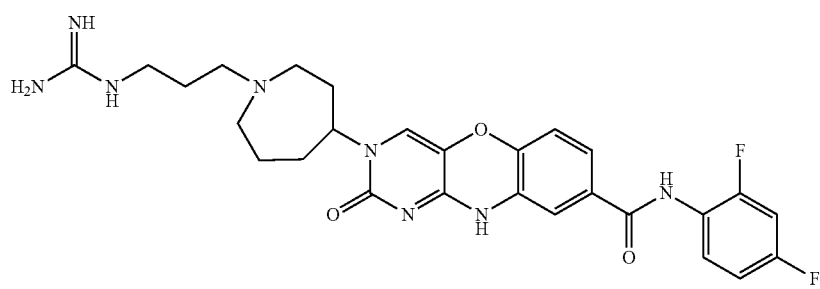 [SMILES: N=C(N)NCCCN1CCCC(n2cc3c(nc2=O)Nc2cc(C(=O)Nc4ccc(F)cc4F)ccc2O3)CC1] |

203 -continued
| Comp. No. | Structure |
|---|---|
| 658 | 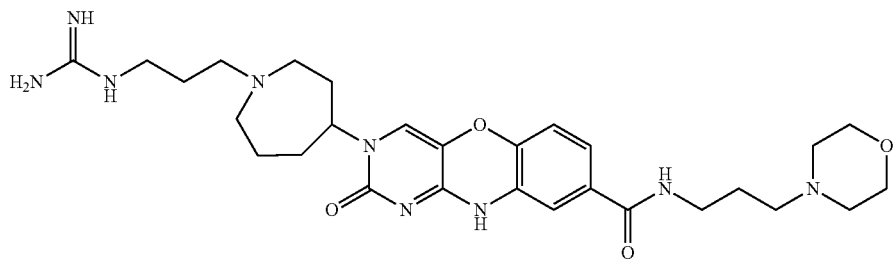 [SMILES: N=C(N)NCCCN1CCCC(n2cc3c(nc2=O)Nc2cc(C(=O)NCCCN4CCOCC4)ccc2O3)CC1] |
| 659 | 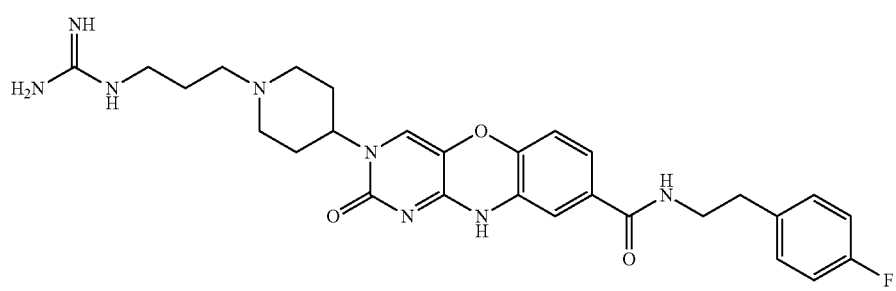 [SMILES: N=C(N)NCCCN1CCC(n2cc3c(nc2=O)Nc2cc(C(=O)NCCc4ccc(F)cc4)ccc2O3)CC1] |
| 660 | 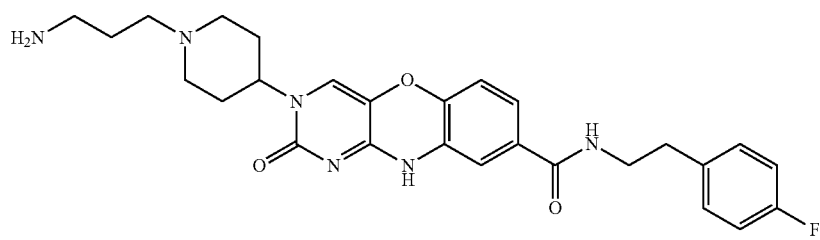 [SMILES: NCCCN1CCC(n2cc3c(nc2=O)Nc2cc(C(=O)NCCc4ccc(F)cc4)ccc2O3)CC1] |
| 664 | 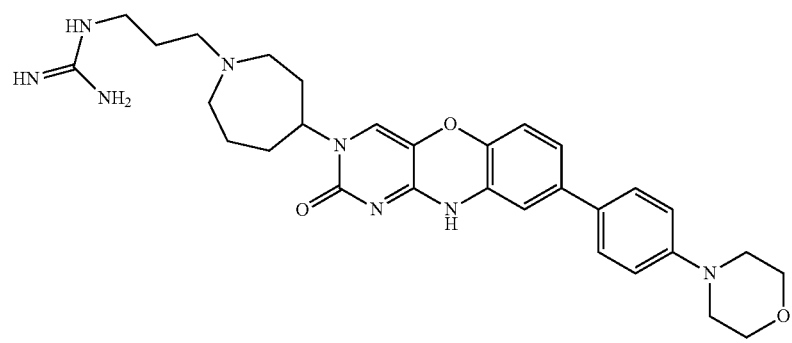 [SMILES: N=C(N)NCCCN1CCCC(n2cc3c(nc2=O)Nc2cc(-c4ccc(N5CCOCC5)cc4)ccc2O3)CC1] |
| 667 | 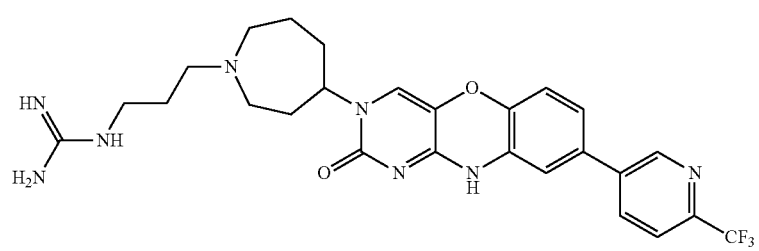 [SMILES: N=C(N)NCCCN1CCCC(n2cc3c(nc2=O)Nc2cc(-c4ccc(C(F)(F)F)nc4)ccc2O3)CC1] |

-continued
| Comp. No. | Structure |
|---|---|
| 669 | 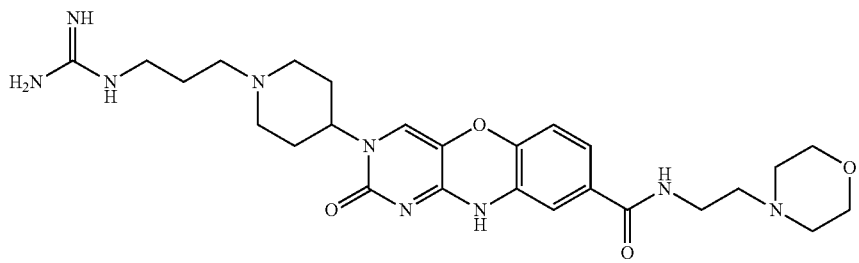 [SMILES: N=C(N)NCCCN1CCC(n2cc3c(nc2=O)Nc2cc(C(=O)NCCN4CCOCC4)ccc2O3)CC1] |
| 671 | 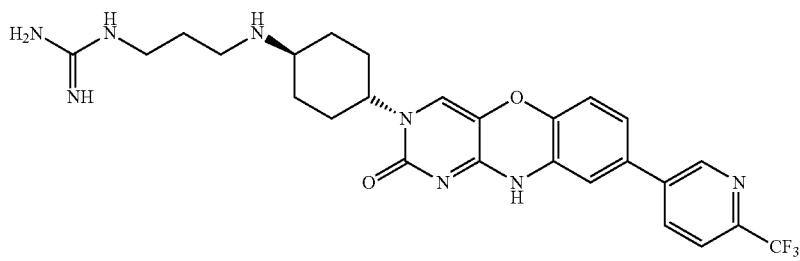 |
| 672 | 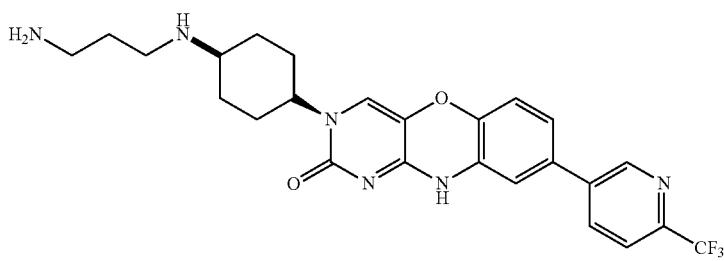 |
| 674 | 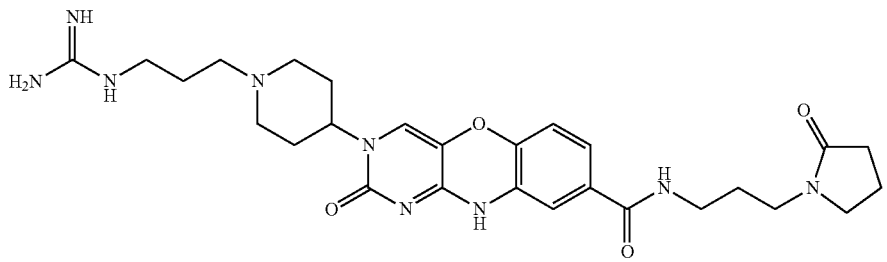 [SMILES: N=C(N)NCCCN1CCC(n2cc3c(nc2=O)Nc2cc(C(=O)NCCCN4CCCC4=O)ccc2O3)CC1] |
| 675 | 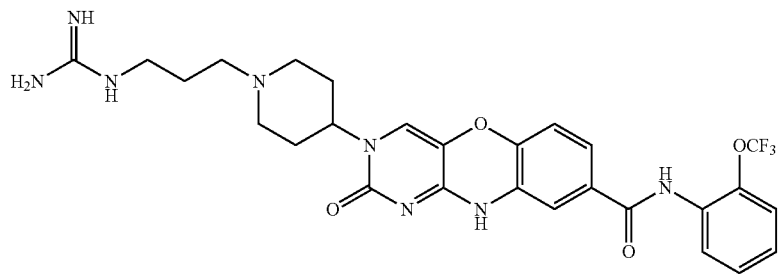 [SMILES: N=C(N)NCCCN1CCC(n2cc3c(nc2=O)Nc2cc(C(=O)Nc4ccccc4OC(F)(F)F)ccc2O3)CC1] |
| 676 | 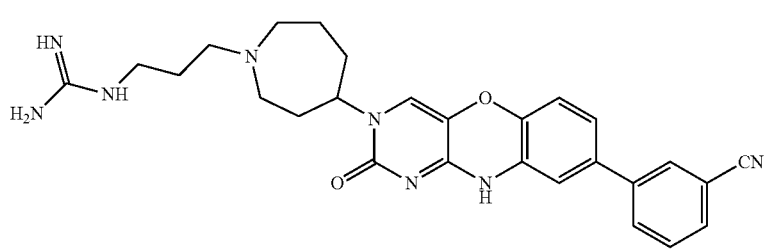 [SMILES: N#Cc1cccc(-c2ccc3c(c2)Nc2nc(=O)n(C4CCCN(CCCNC(=N)N)CC4)cc2O3)c1] |

| Comp. No. | Structure |
|---|---|
| 681 | 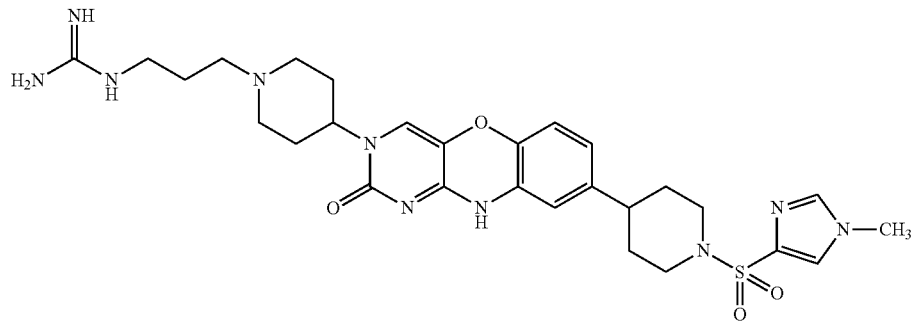 [SMILES: Cn1cnc(S(=O)(=O)N2CCC(c3ccc4c(c3)Nc3nc(=O)n(C5CCN(CCCNC(=N)N)CC5)cc3O4)CC2)c1] |
| 685 | 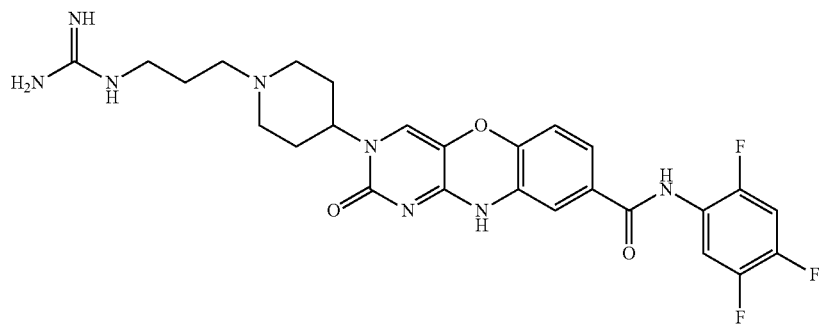 [SMILES: N=C(N)NCCCN1CCC(n2cc3c(nc2=O)Nc2cc(C(=O)Nc4cc(F)c(F)cc4F)ccc2O3)CC1] |
| 686 | 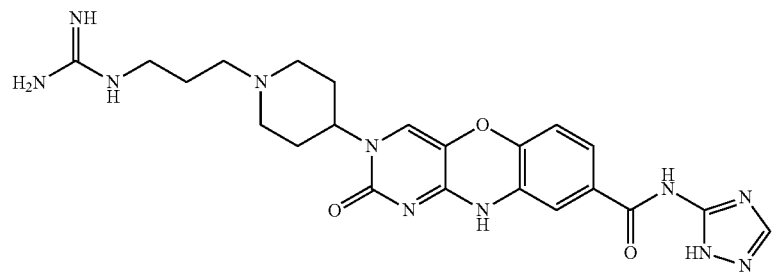 [SMILES: N=C(N)NCCCN1CCC(n2cc3c(nc2=O)Nc2cc(C(=O)Nc4ncn[nH]4)ccc2O3)CC1] |
| 689 | 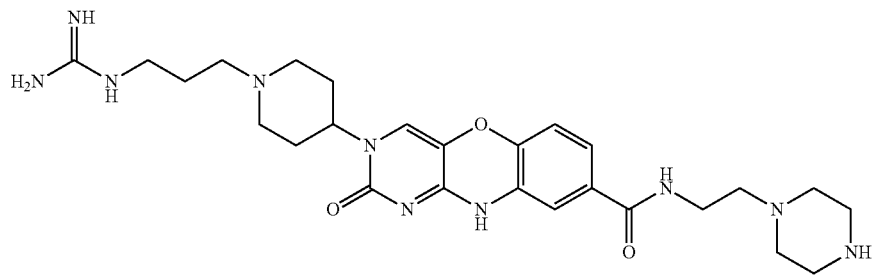 [SMILES: N=C(N)NCCCN1CCC(n2cc3c(nc2=O)Nc2cc(C(=O)NCCN4CCNCC4)ccc2O3)CC1] |
| 690 | 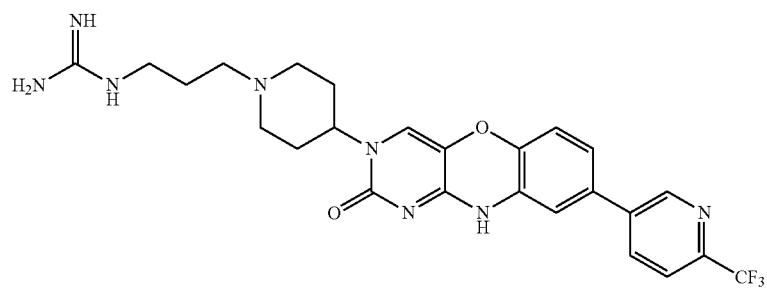 [SMILES: N=C(N)NCCCN1CCC(n2cc3c(nc2=O)Nc2cc(-c4ccc(C(F)(F)F)nc4)ccc2O3)CC1] |

| Comp. No. | Structure |
|---|---|
| 691 | 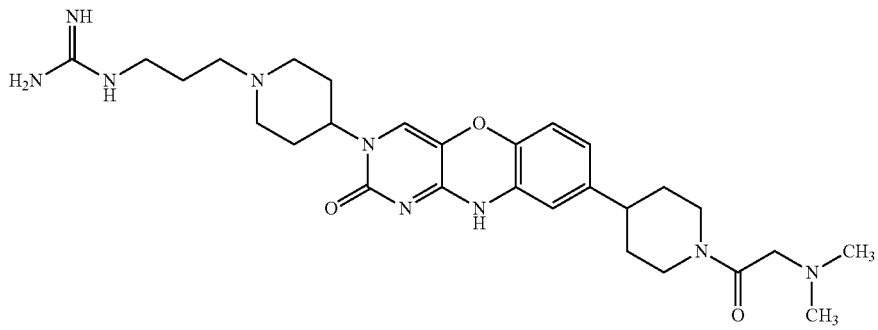 [SMILES: CN(C)CC(=O)N1CCC(c2ccc3c(c2)Nc2nc(=O)n(C4CCN(CCCNC(=N)N)CC4)cc2O3)CC1] |
| 694 | 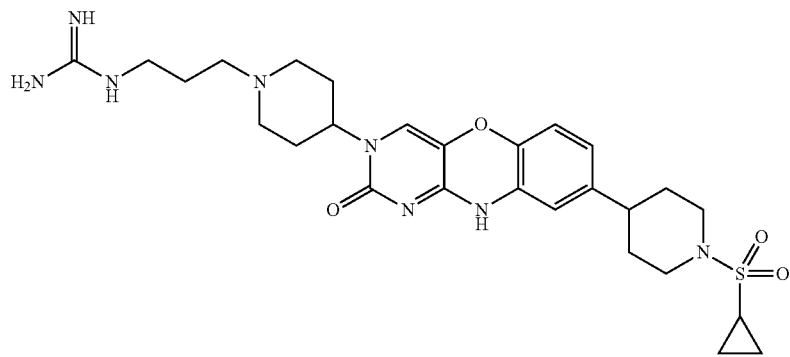 [SMILES: N=C(N)NCCCN1CCC(n2cc3c(nc2=O)Nc2cc(C4CCN(S(=O)(=O)C5CC5)CC4)ccc2O3)CC1] |
| 695 | 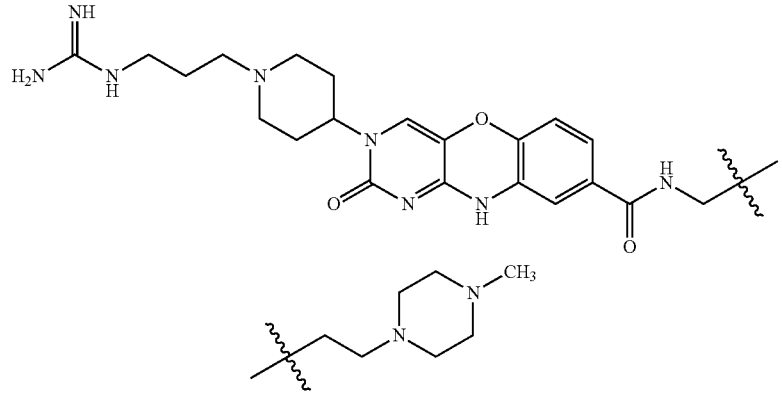 |
| 696 | 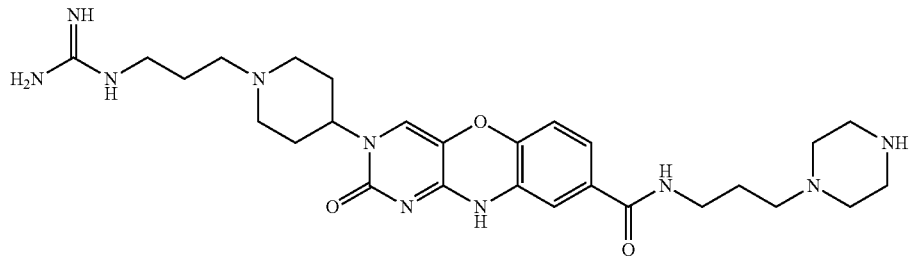 [SMILES: N=C(N)NCCCN1CCC(n2cc3c(nc2=O)Nc2cc(C(=O)NCCCN4CCNCC4)ccc2O3)CC1] |

-continued
| Comp. No. | Structure |
|---|---|
| 707 | 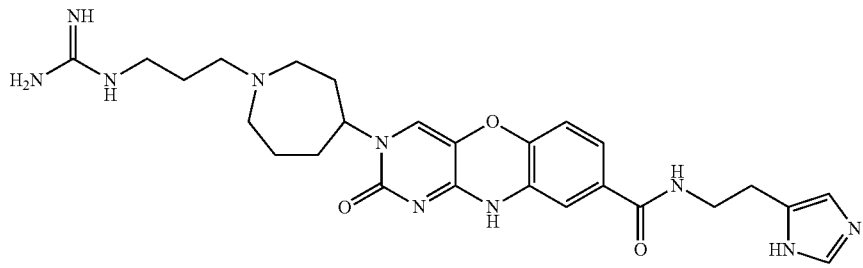 [SMILES: N=C(N)NCCCN1CCCC(n2cc3c(nc2=O)Nc2cc(C(=O)NCCc4cnc[nH]4)ccc2O3)CC1] |
| 708 | 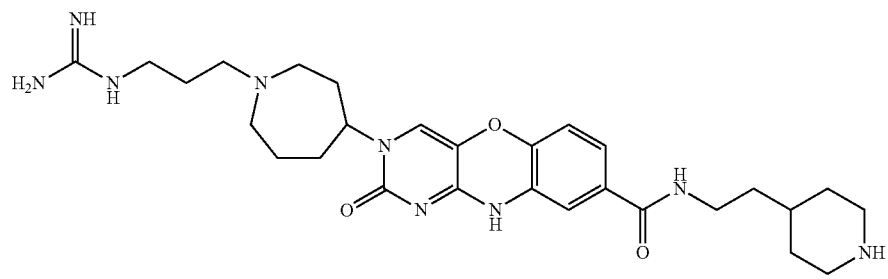 [SMILES: N=C(N)NCCCN1CCCC(n2cc3c(nc2=O)Nc2cc(C(=O)NCCC4CCNCC4)ccc2O3)CC1] |
| 714 | 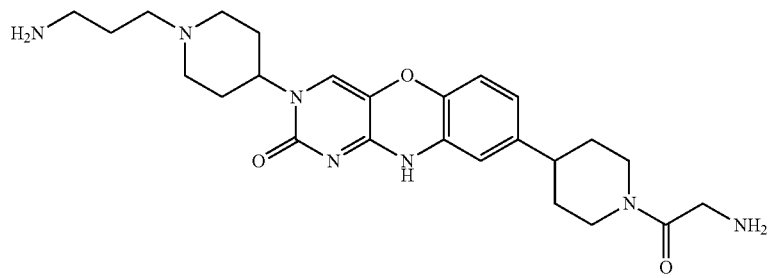 [SMILES: NCCCN1CCC(n2cc3c(nc2=O)Nc2cc(C4CCN(C(=O)CN)CC4)ccc2O3)CC1] |
| 715 | 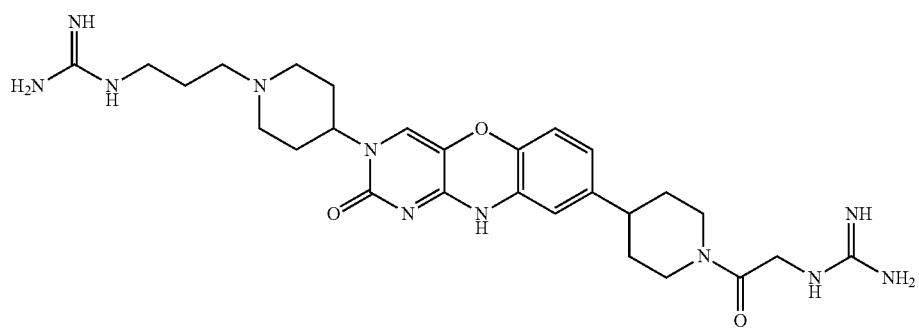 [SMILES: N=C(N)NCCCN1CCC(n2cc3c(nc2=O)Nc2cc(C4CCN(C(=O)CNC(=N)N)CC4)ccc2O3)CC1] |
| 718 | 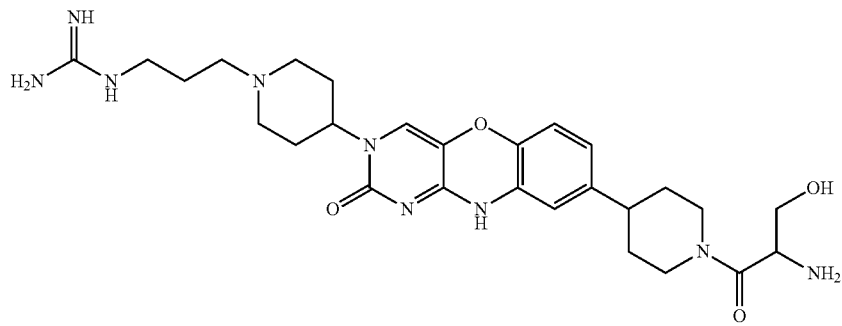 [SMILES: N=C(N)NCCCN1CCC(n2cc3c(nc2=O)Nc2cc(C4CCN(C(=O)C(N)CO)CC4)ccc2O3)CC1] |

-continued
| Comp. No. | Structure |
|---|---|
| 729 | 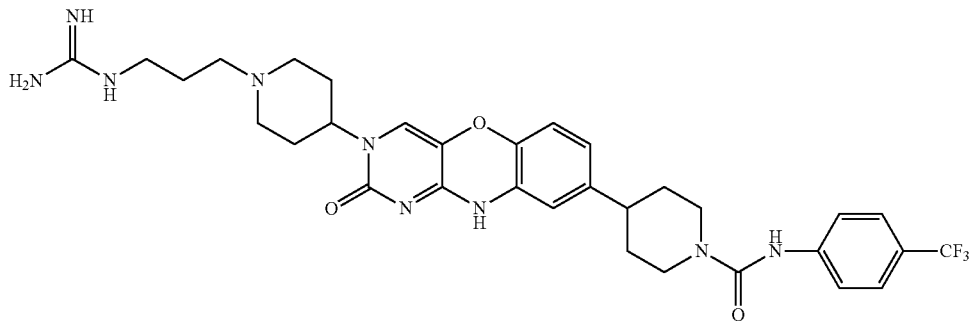 [SMILES: N=C(N)NCCCN1CCC(n2cc3c(nc2=O)Nc2cc(C4CCN(C(=O)Nc5ccc(C(F)(F)F)cc5)CC4)ccc2O3)CC1] |
| 730 | 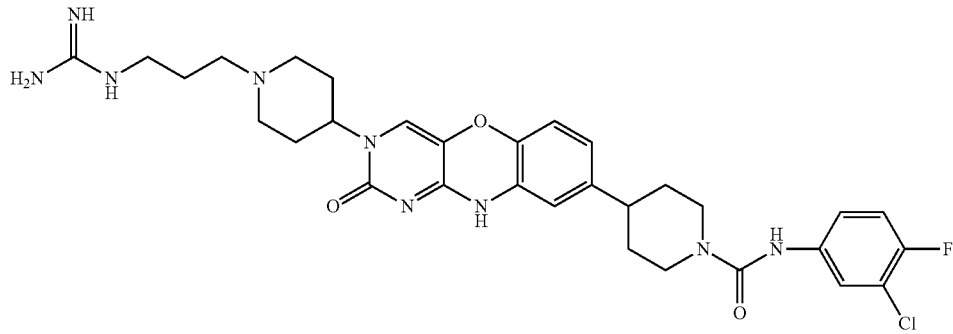 [SMILES: N=C(N)NCCCN1CCC(n2cc3c(nc2=O)Nc2cc(C4CCN(C(=O)Nc5ccc(F)c(Cl)c5)CC4)ccc2O3)CC1] |
| 731 | 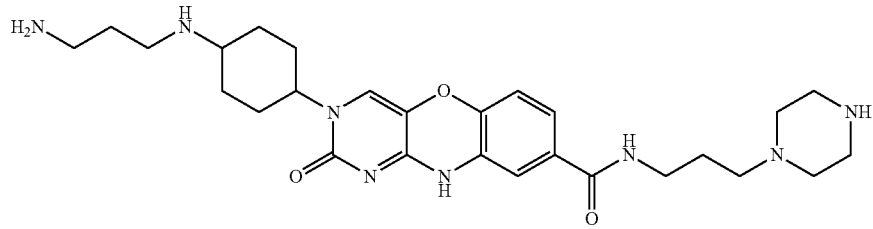 [SMILES: NCCCNC1CCC(n2cc3c(nc2=O)Nc2cc(C(=O)NCCCN4CCNCC4)ccc2O3)CC1] |
| 732 | 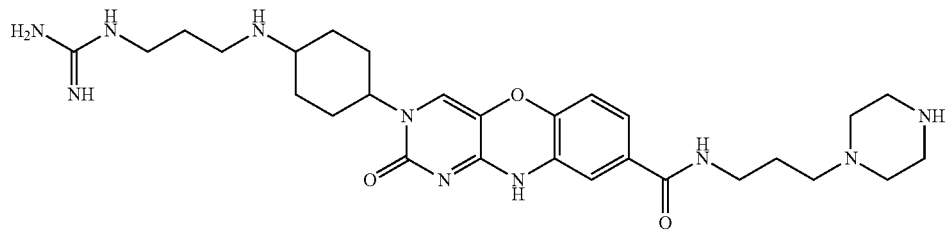 [SMILES: N=C(N)NCCCNC1CCC(n2cc3c(nc2=O)Nc2cc(C(=O)NCCCN4CCNCC4)ccc2O3)CC1] |
| 733 | 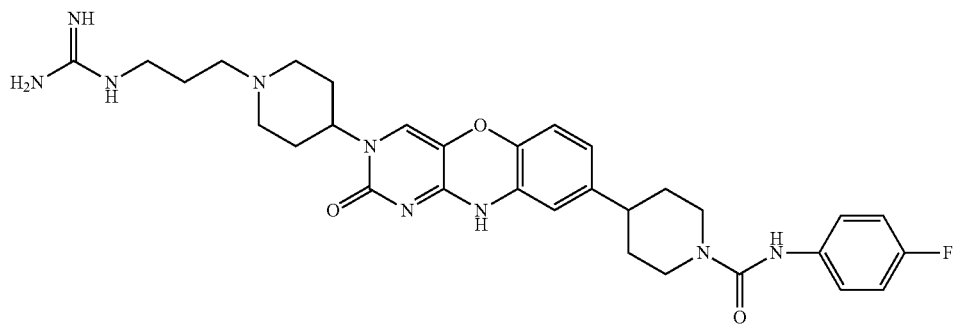 [SMILES: N=C(N)NCCCN1CCC(n2cc3c(nc2=O)Nc2cc(C4CCN(C(=O)Nc5ccc(F)cc5)CC4)ccc2O3)CC1] |

| Comp. No. | Structure |
|---|---|
| 738 | 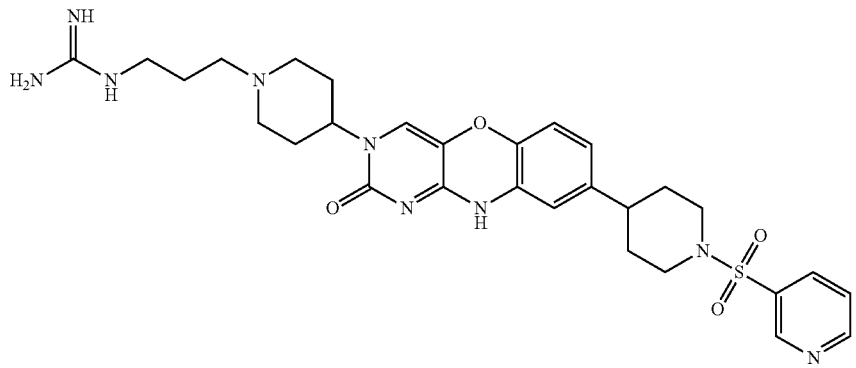 [SMILES: N=C(N)NCCCN1CCC(n2cc3c(nc2=O)Nc2cc(C4CCN(S(=O)(=O)c5cccnc5)CC4)ccc2O3)CC1] |
| 740 | 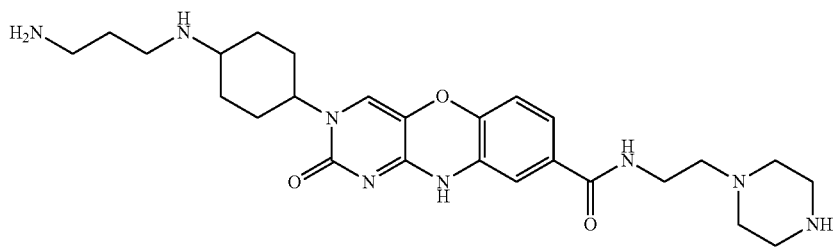 [SMILES: NCCCNC1CCC(n2cc3c(nc2=O)Nc2cc(C(=O)NCCN4CCNCC4)ccc2O3)CC1] |
| 741 | 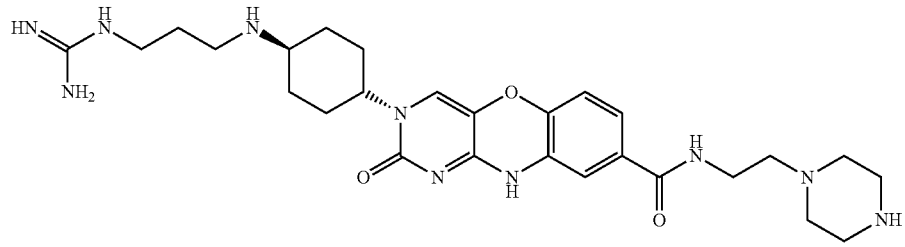 |
| 748 | 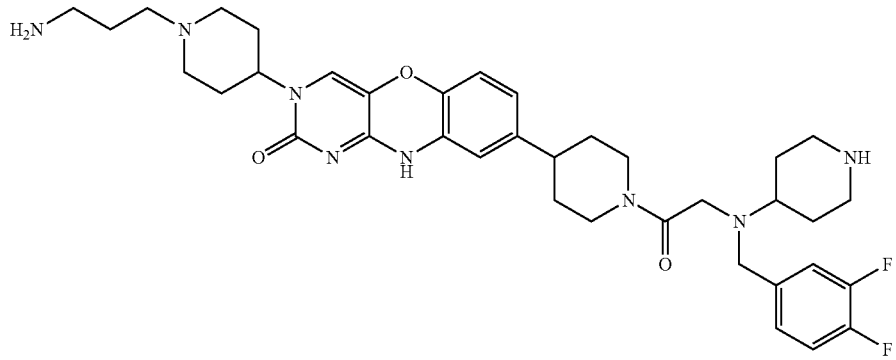 [SMILES: NCCCN1CCC(n2cc3c(nc2=O)Nc2cc(C4CCN(C(=O)CN(Cc5ccc(F)c(F)c5)C5CCNCC5)CC4)ccc2O3)CC1] |

-continued
| Comp. No. | Structure |
|---|---|
| 749 | 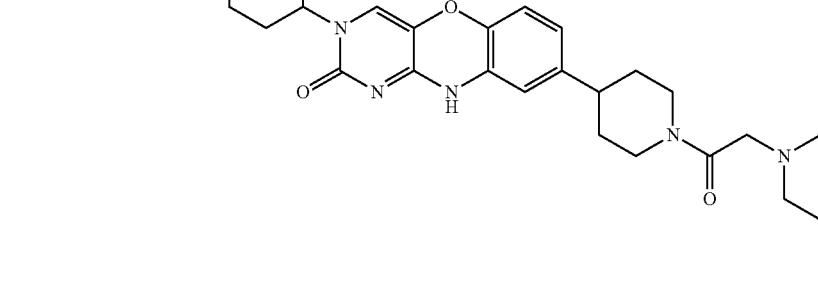 |
| 750 | 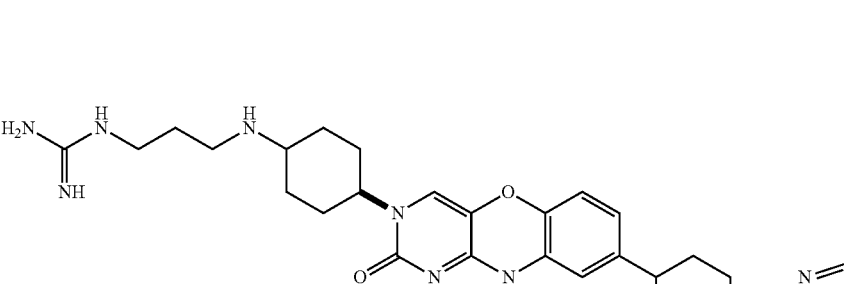 |
| 751 | 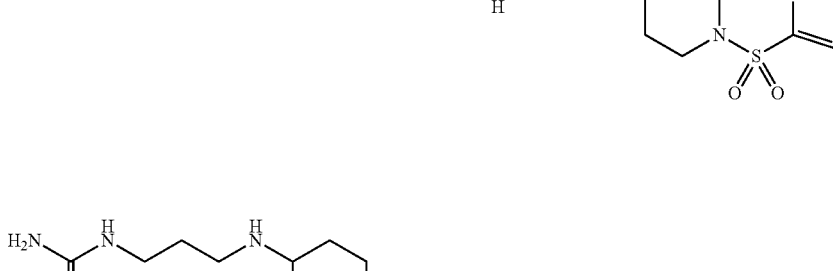 |
| 752 | 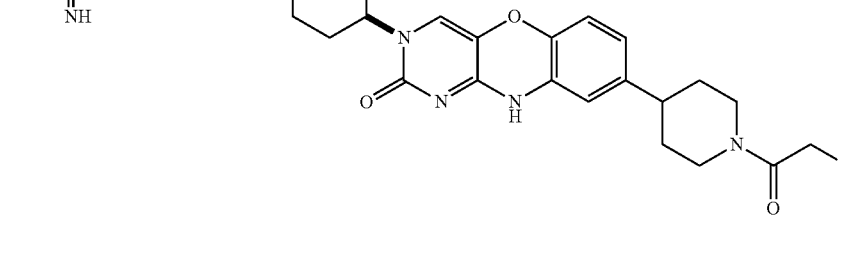 |

-continued
| Comp. No. | Structure |
|---|---|
| 753 | 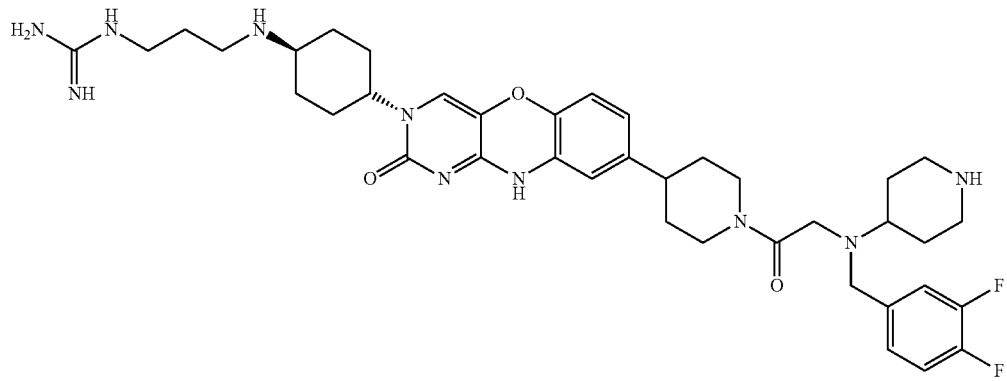 |
| 754 | 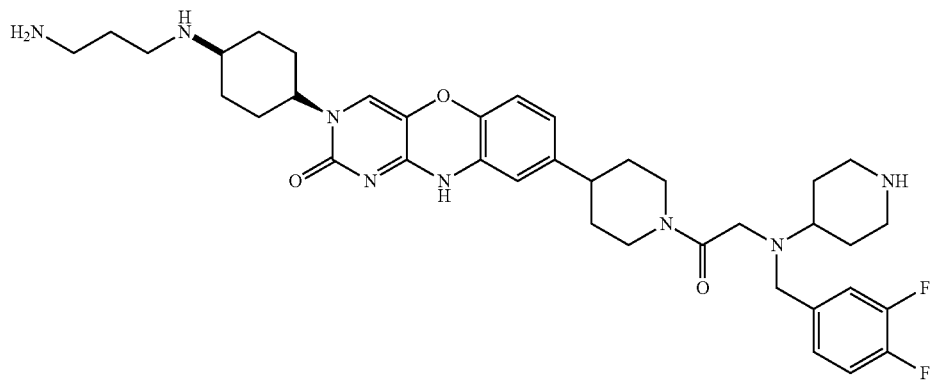 |
| 763 | 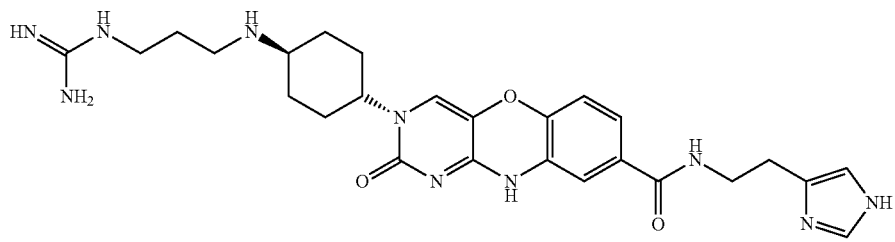 |
| 765 | 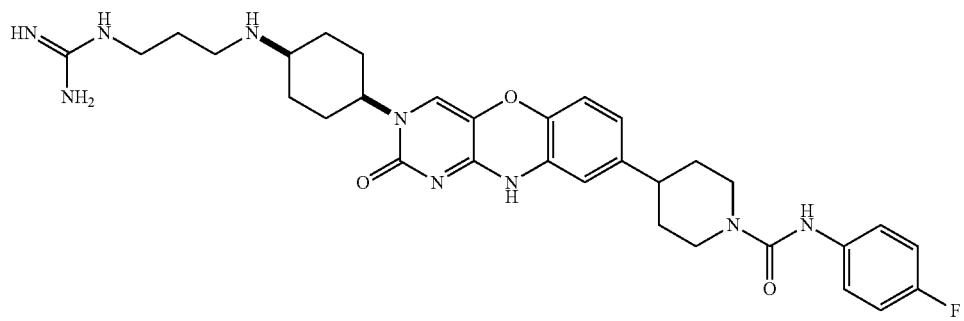 |
| 774 | 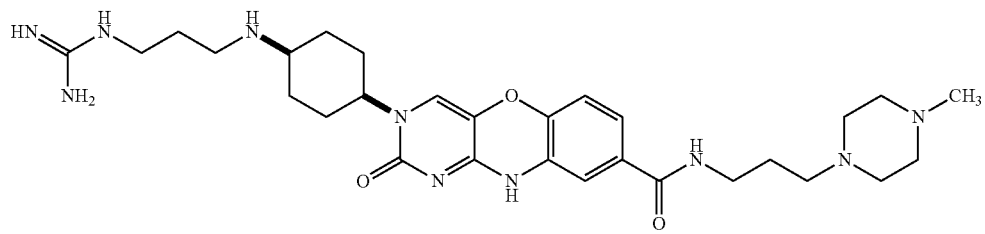 |

| Comp. No. | Structure |
|---|---|
| 776 | 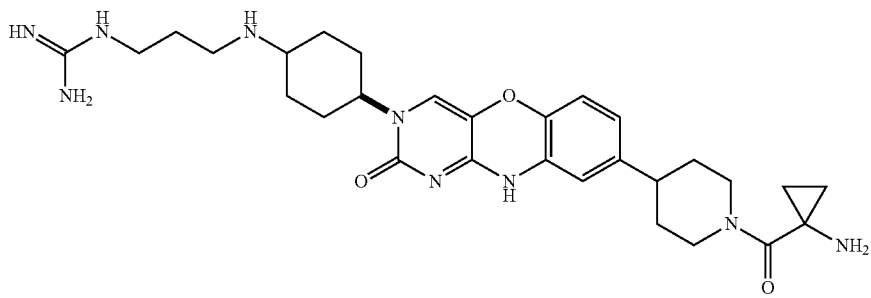 |
| 777 | 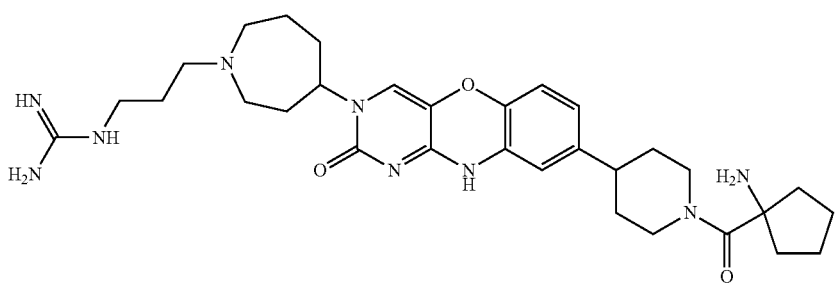 [SMILES: N=C(N)NCCCN1CCCC(n2cc3c(nc2=O)Nc2cc(C4CCN(C(=O)C5(N)CCCC5)CC4)ccc2O3)CC1] |
| 781 | 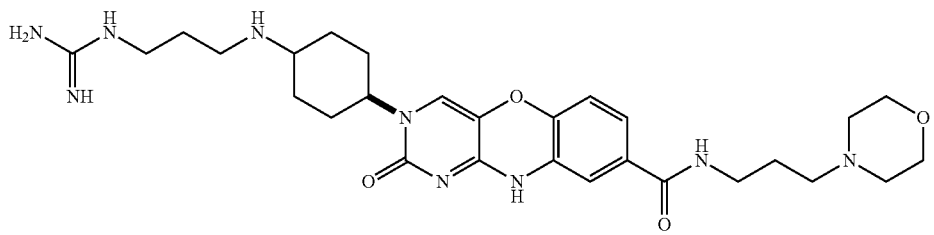 |
| 782 | 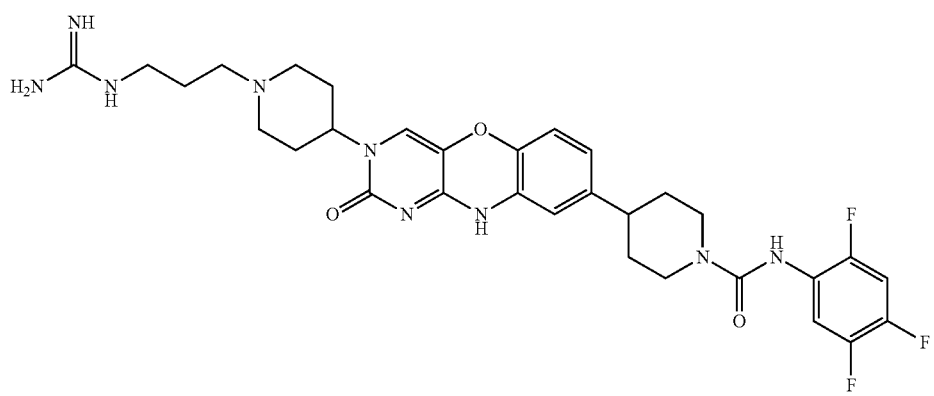 [SMILES: N=C(N)NCCCN1CCC(n2cc3c(nc2=O)Nc2cc(C4CCN(C(=O)Nc5cc(F)c(F)cc5F)CC4)ccc2O3)CC1] |
| 783 | 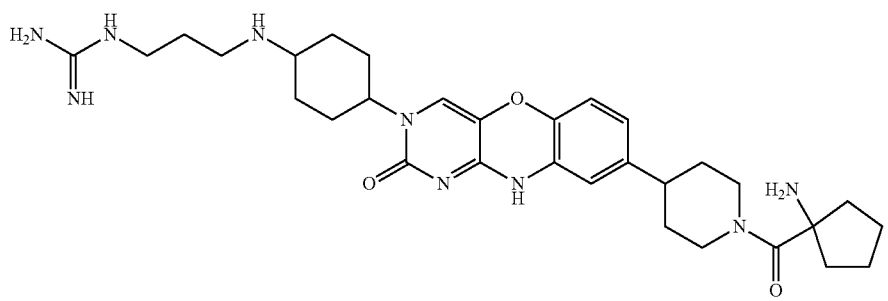 [SMILES: N=C(N)NCCCNC1CCC(n2cc3c(nc2=O)Nc2cc(C4CCN(C(=O)C5(N)CCCC5)CC4)ccc2O3)CC1] |

| Comp. No. | Structure |
|---|---|
| 792 | 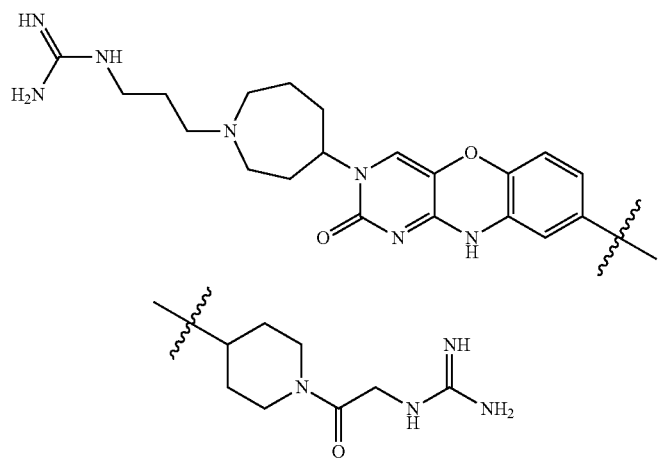 |
| 793 | 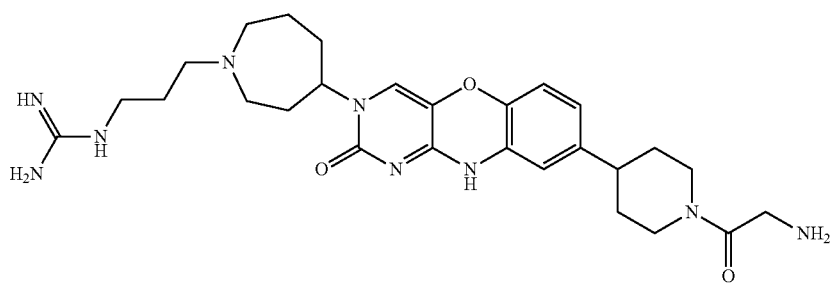 [SMILES: N=C(N)NCCCN1CCCC(n2cc3c(nc2=O)Nc2cc(C4CCN(C(=O)CN)CC4)ccc2O3)CC1] |
| 794 | 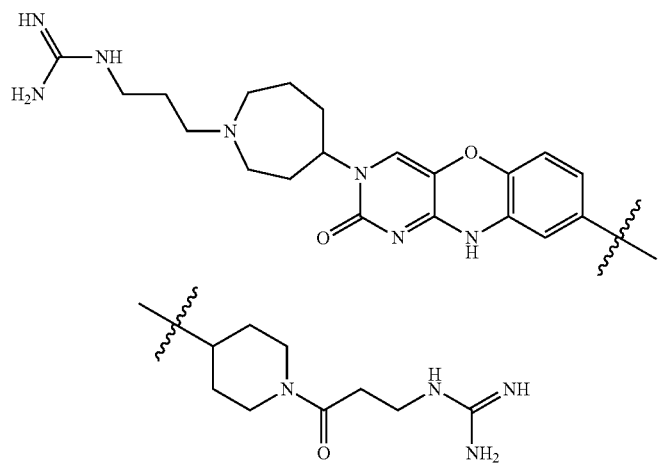 |
| 795 | 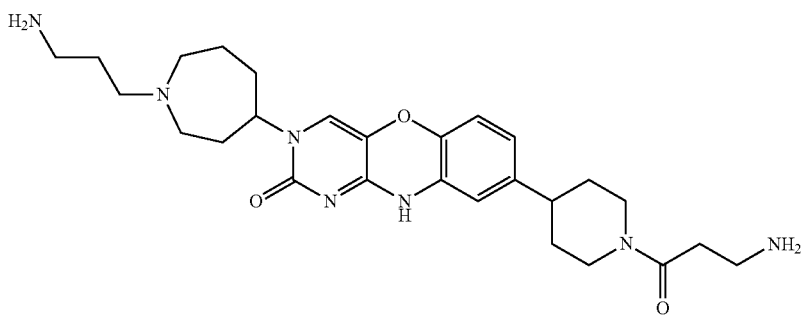 [SMILES: NCCCN1CCCC(n2cc3c(nc2=O)Nc2cc(C4CCN(C(=O)CCN)CC4)ccc2O3)CC1] |

-continued
| Comp. No. | Structure |
|---|---|
| 798 | 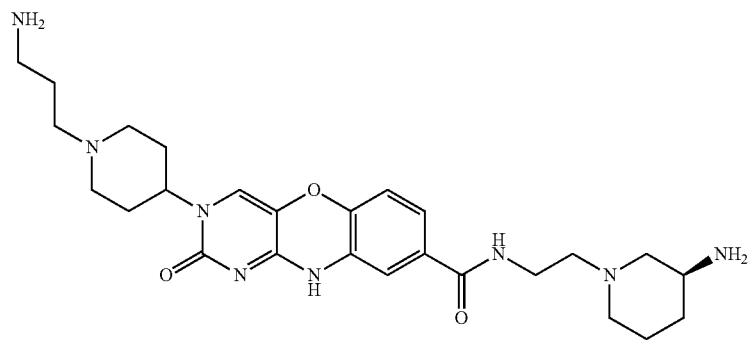 [SMILES: NCCCN1CCC(n2cc3c(nc2=O)Nc2cc(C(=O)NCCN4CCC[C@H](N)C4)ccc2O3)CC1] |
| 811 | 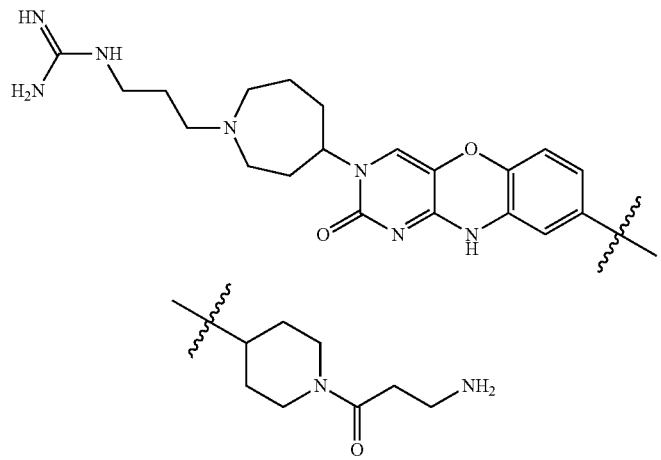 |
| 812 | 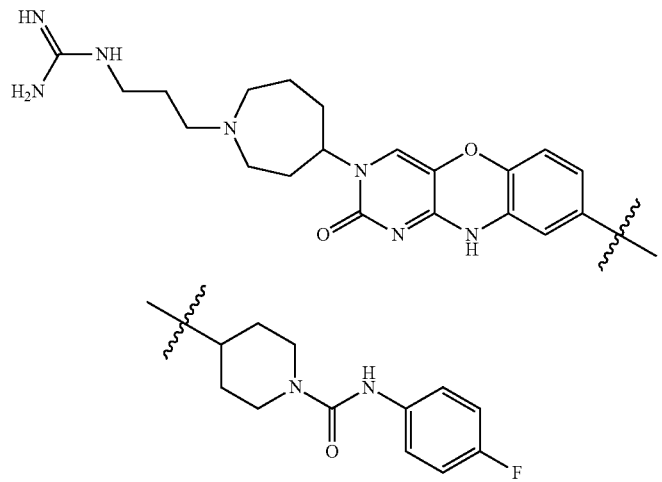 |

-continued
| Comp. No. | Structure |
|---|---|
| 818 | 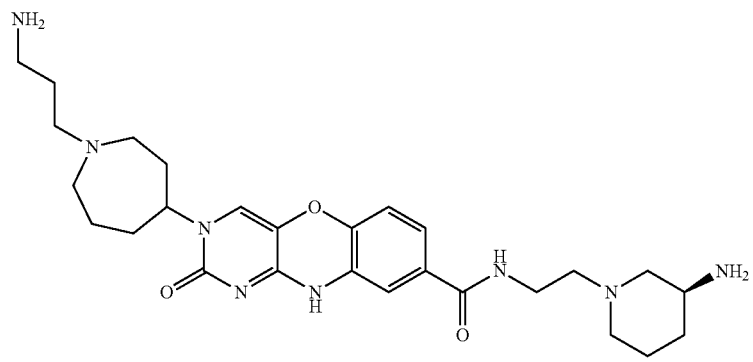 [SMILES: NCCCN1CCCC(n2cc3c(nc2=O)Nc2cc(C(=O)NCCN4CCC[C@H](N)C4)ccc2O3)CC1] |
| 832 | 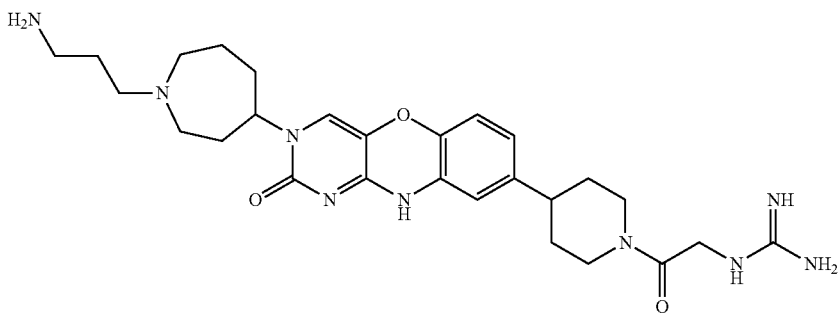 [SMILES: N=C(N)NCC(=O)N1CCC(c2ccc3c(c2)Nc2nc(=O)n(C4CCCN(CCCN)CC4)cc2O3)CC1] |
| 833 | 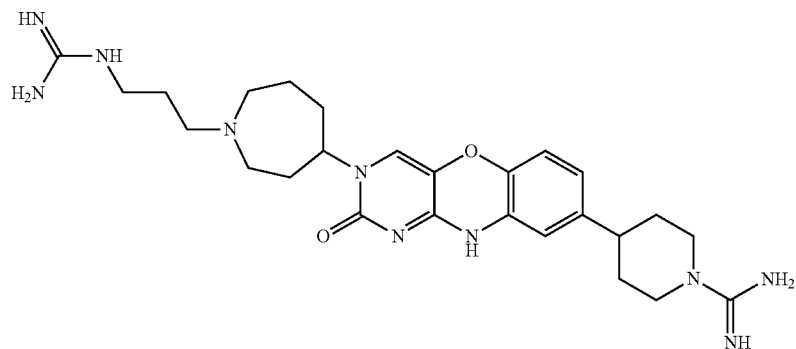 [SMILES: N=C(N)NCCCN1CCCC(n2cc3c(nc2=O)Nc2cc(C4CCN(C(=N)N)CC4)ccc2O3)CC1] |
| 858 | 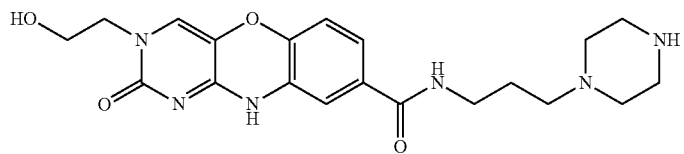 [SMILES: O=C(NCCCN1CCNCC1)c1ccc2c(c1)Nc1nc(=O)n(CCO)cc1O2] |

|Comp. No.|Structure|
|---|---|
|859|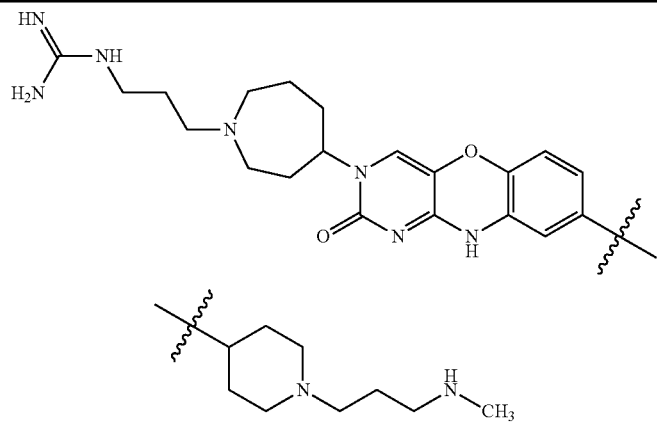|
|868|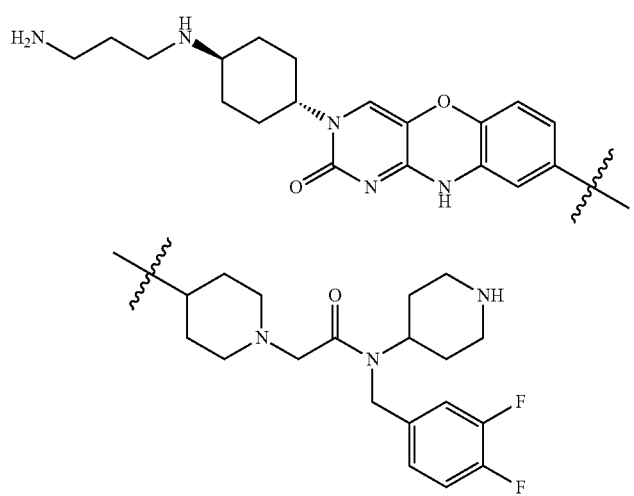|
|869|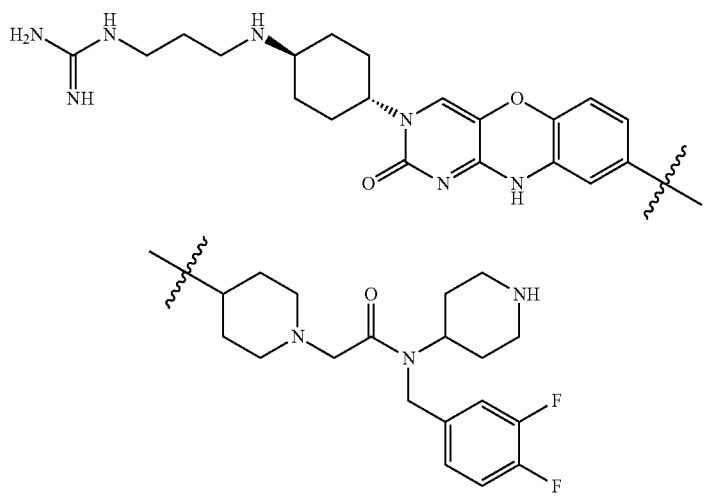|

-continued
| Comp. No. | Structure |
|---|---|
| 870 | 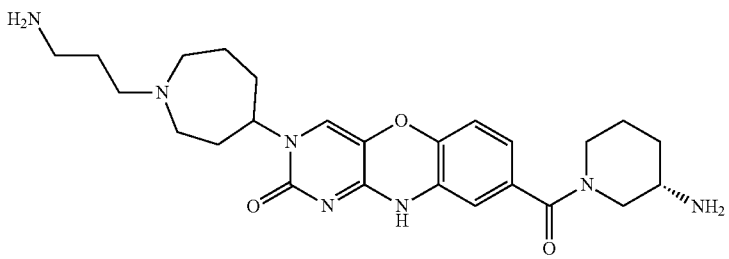 [SMILES: NCCCN1CCCC(n2cc3c(nc2=O)Nc2cc(C(=O)N4CCC[C@H](N)C4)ccc2O3)CC1] |
| 888 | 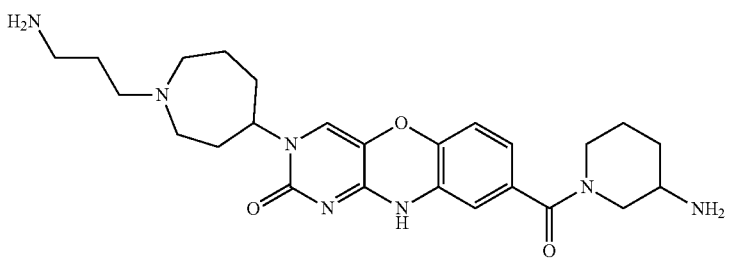 [SMILES: NCCCN1CCCC(n2cc3c(nc2=O)Nc2cc(C(=O)N4CCCC(N)C4)ccc2O3)CC1] |
| 889 | 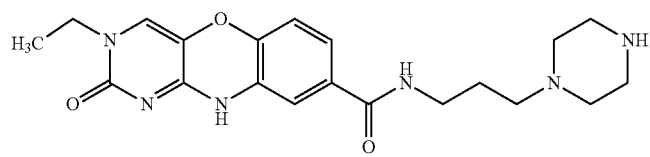 [SMILES: CCn1cc2c(nc1=O)Nc1cc(C(=O)NCCCN3CCNCC3)ccc1O2] |
| 890 | 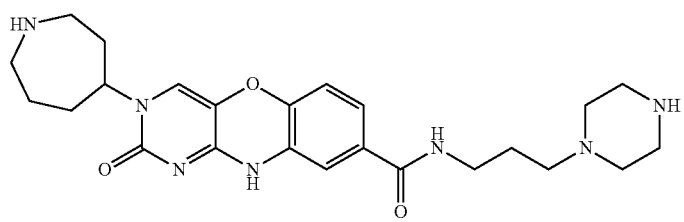 [SMILES: O=C(NCCCN1CCNCC1)c1ccc2c(c1)Nc1nc(=O)n(C3CCCNCC3)cc1O2] |
| 891 | 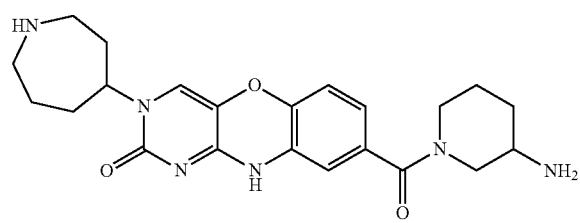 [SMILES: NC1CCCN(C(=O)c2ccc3c(c2)Nc2nc(=O)n(C4CCCNCC4)cc2O3)C1] |
| 903 | 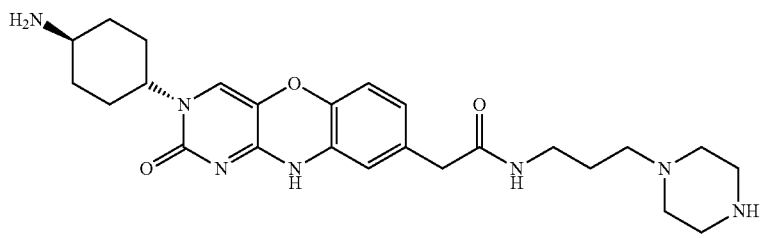 |

| Comp. No. | Structure |
|---|---|
| 904 | 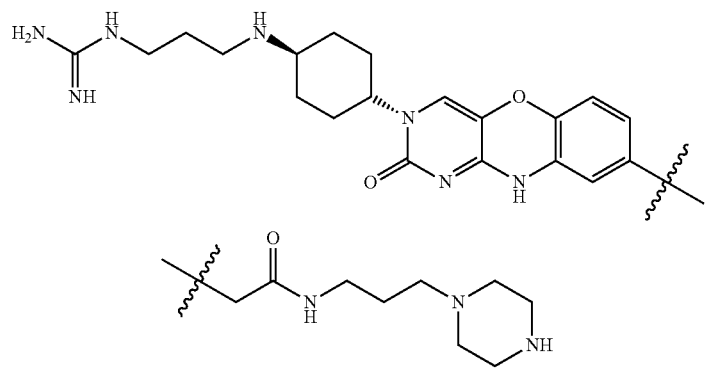 |
| 908 | 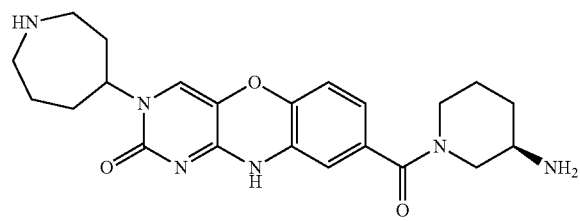 [SMILES: N[C@@H]1CCCN(C(=O)c2ccc3c(c2)Nc2nc(=O)n(C4CCCNCC4)cc2O3)C1] |
| 909 | 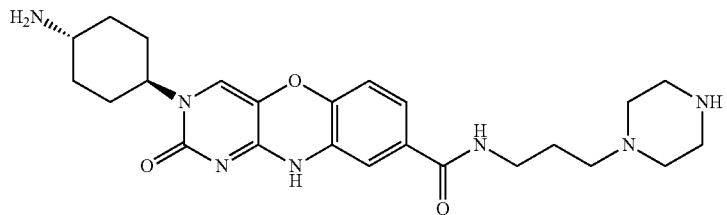 [SMILES: N[C@H]1CC[C@H](n2cc3c(nc2=O)Nc2cc(C(=O)NCCCN4CCNCC4)ccc2O3)CC1] |
| 916 | 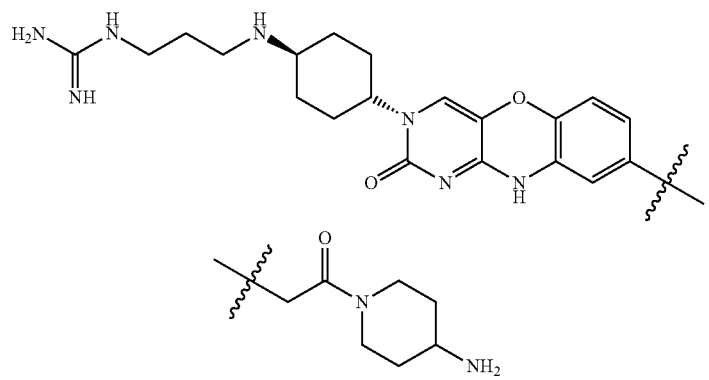 |
| 917 | 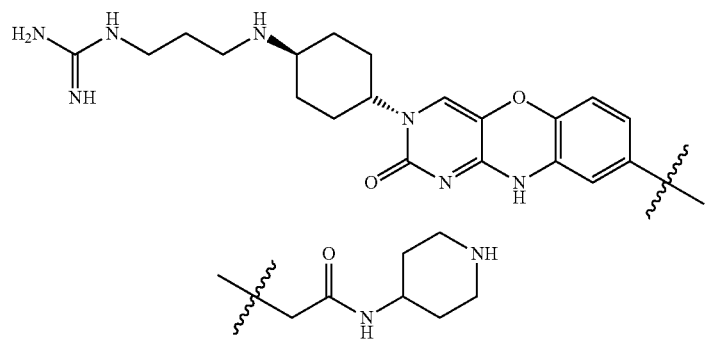 |

| Comp. No. | Structure |
|---|---|
| 919 | 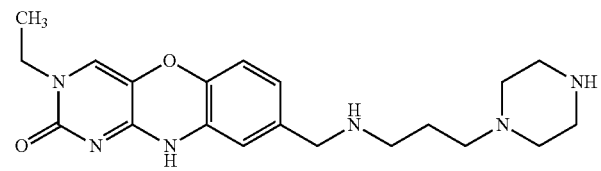 [SMILES: CCn1cc2c(nc1=O)Nc1cc(CNCCCN3CCNCC3)ccc1O2] |
| 920 | 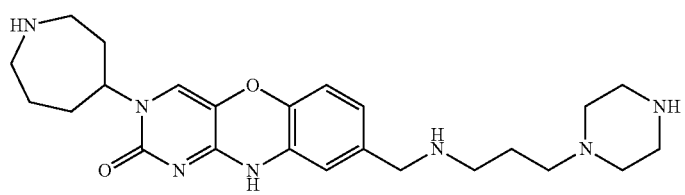 [SMILES: O=c1nc2c(cn1C1CCCNCC1)Oc1ccc(CNCCCN3CCNCC3)cc1N2] |
| 921 | 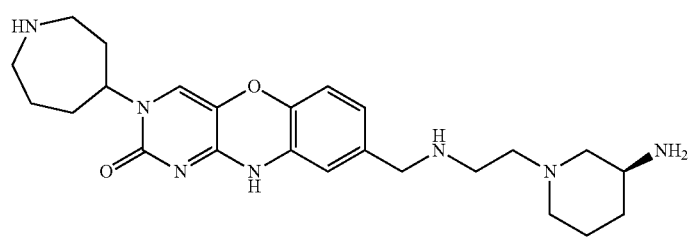 [SMILES: N[C@H]1CCCN(CCNCc2ccc3c(c2)Nc2nc(=O)n(C4CCCNCC4)cc2O3)C1] |
| 938 | 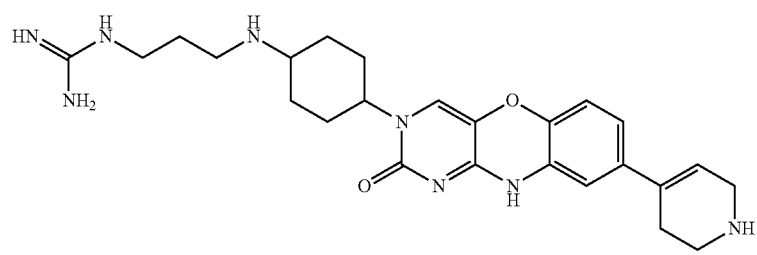 [SMILES: N=C(N)NCCCNC1CCC(n2cc3c(nc2=O)Nc2cc(C4=CCNCC4)ccc2O3)CC1] |
| 941 | 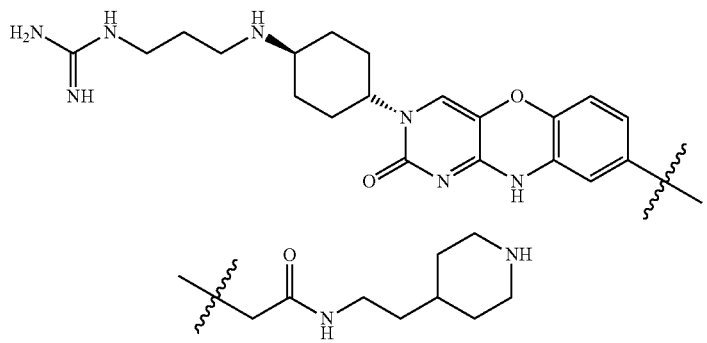 |
| 942 | 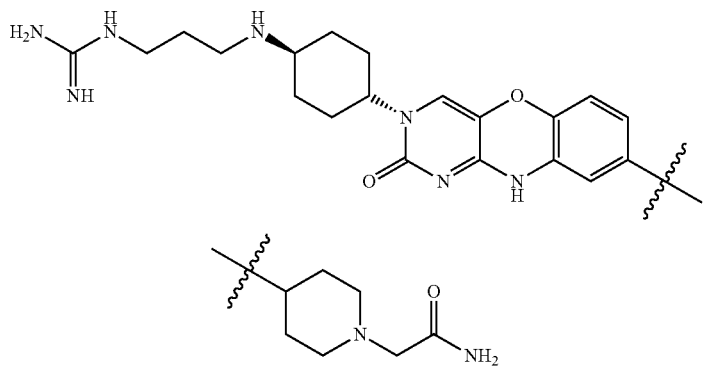 |

| Comp. No. | Structure |
|---|---|
| 950 | 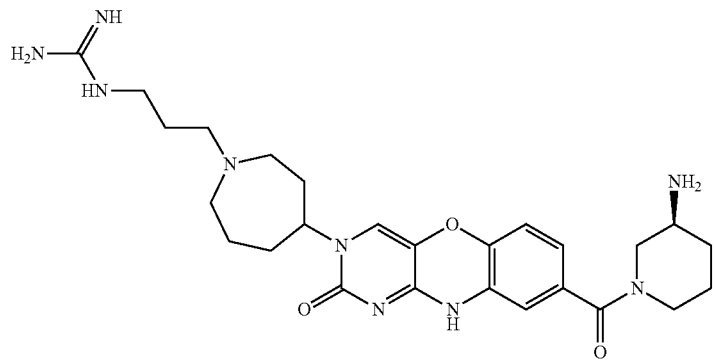 [SMILES: N=C(N)NCCCN1CCCC(n2cc3c(nc2=O)Nc2cc(C(=O)N4CCC[C@H](N)C4)ccc2O3)CC1] |
| 953 | 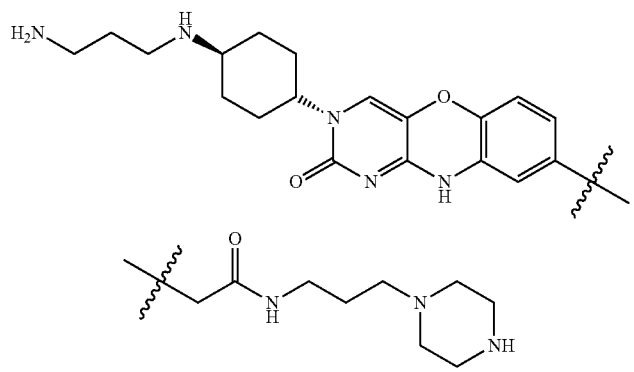 |
| 954 | 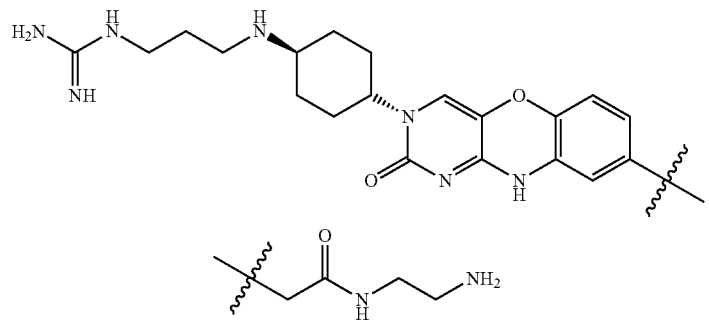 |
| 955 | 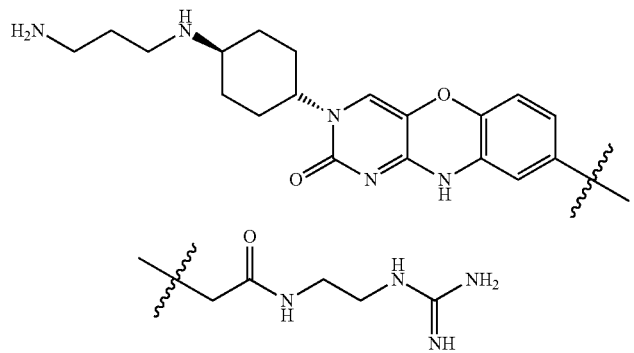 |

| Comp. No. | Structure |
|---|---|
| 956 | 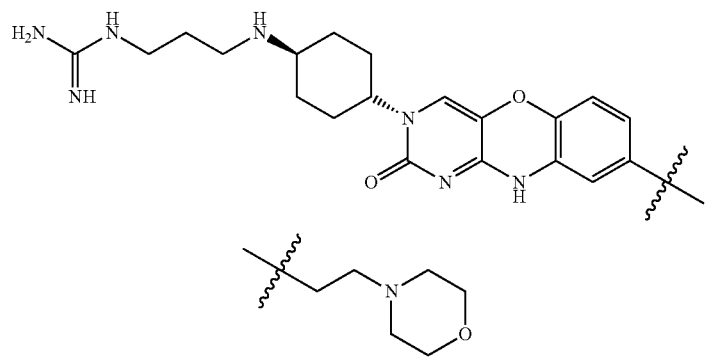 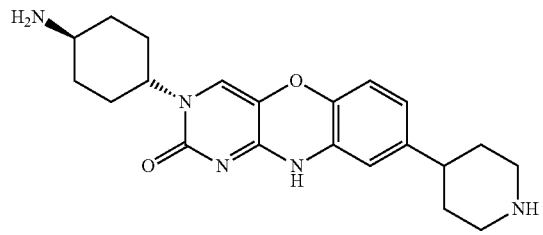 |
| 972 | 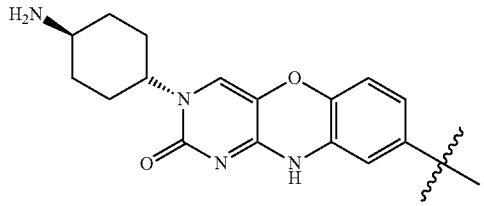 |
| 973 | 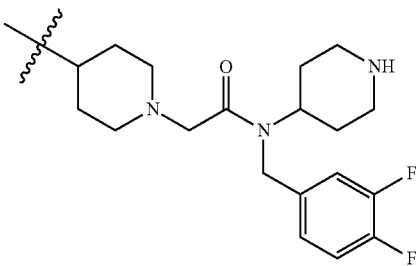 [SMILES: *C1CCN(CC(=O)N(Cc2ccc(F)c(F)c2)C2CCNCC2)CC1] 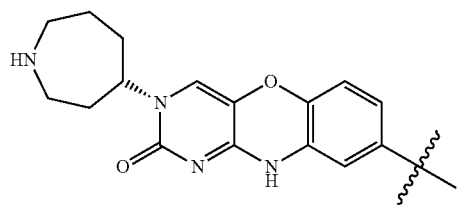 |
| 976 | 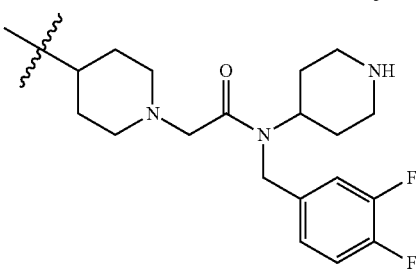 |

| Comp. No. | Structure |
|---|---|
| 993 | 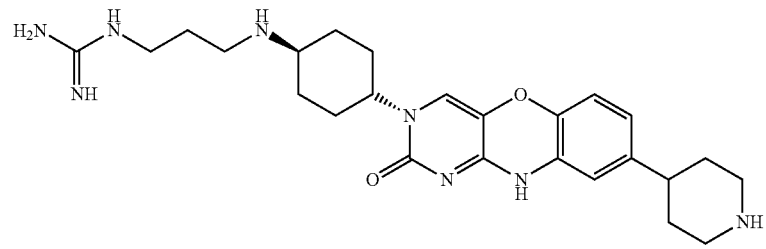 |
| 1006 | 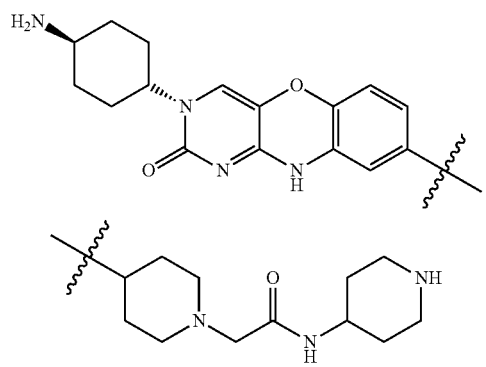 |
| 1007 | 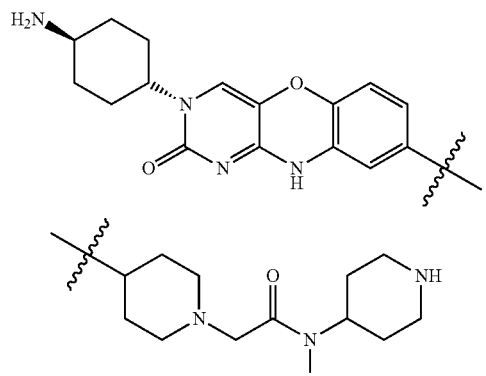 |
| 1008 | 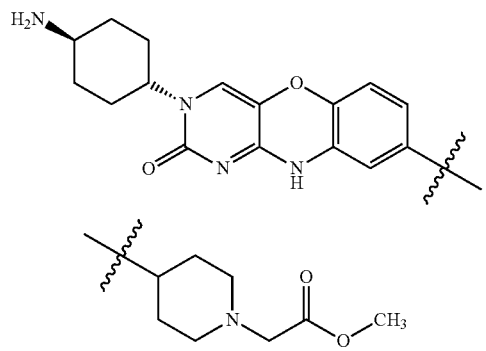 |

| Comp. No. | Structure |
|---|---|
| 1014 | 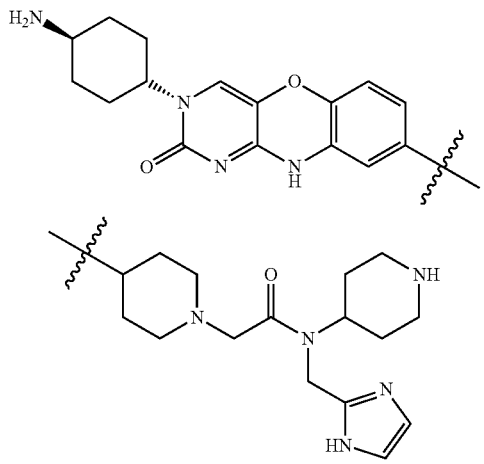 |
| 1016 | 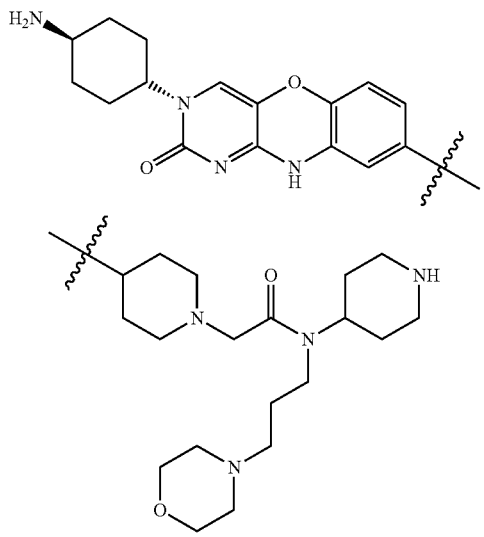 |
| 1025 | 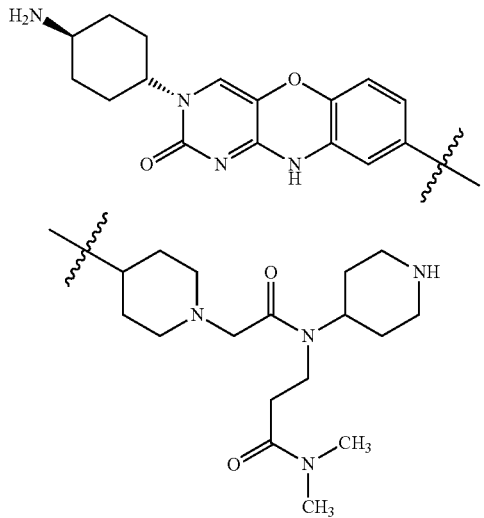 |

| Comp. No. | Structure |
|---|---|
| 1026 | 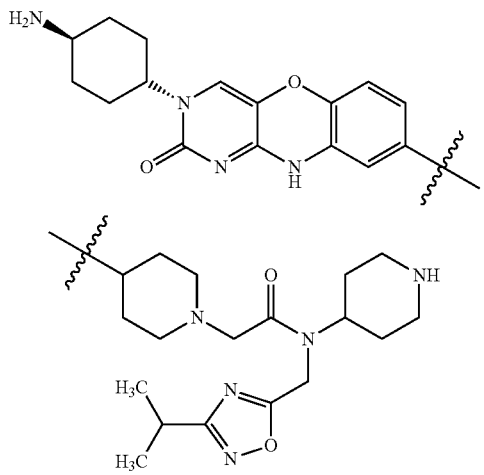 |
| 1030 | 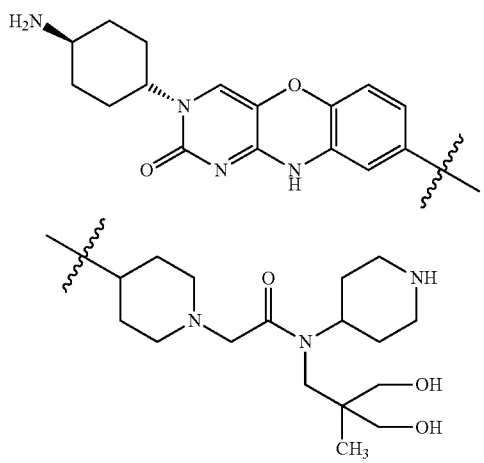 |
| 1031 | 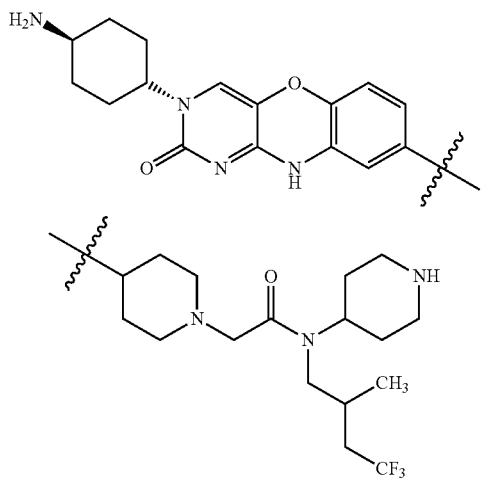 |

| Comp. No. | Structure |
|---|---|
| 1032 | 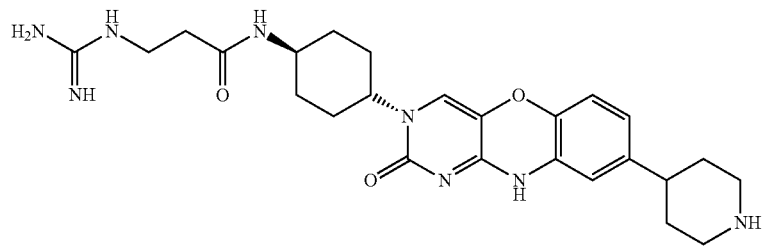 |
| 1033 | 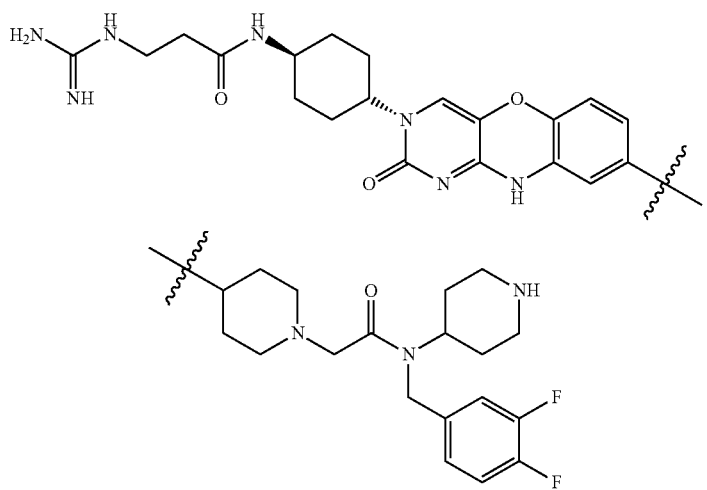 |
| 1041 | 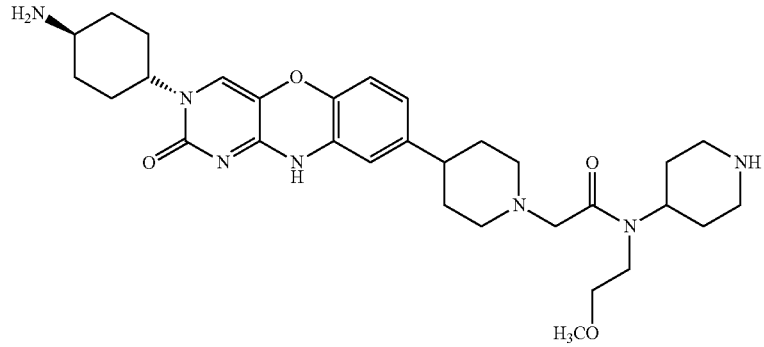 |
| 1042 | 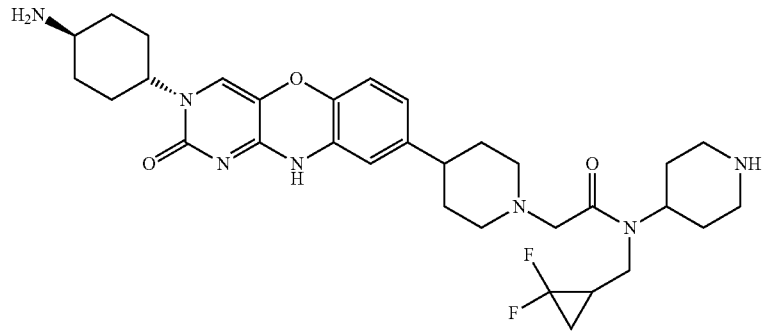 |

| Comp. No. | Structure |
|---|---|
| 1055 | 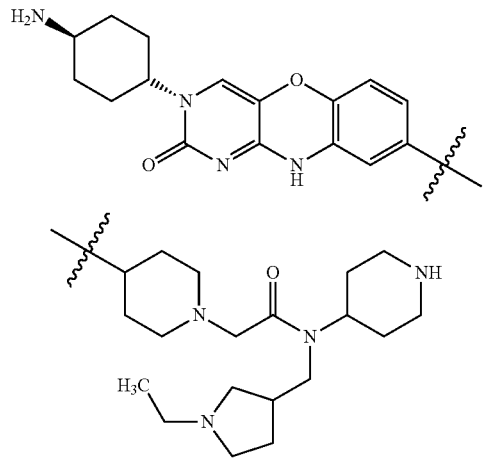 |
| 1056 | 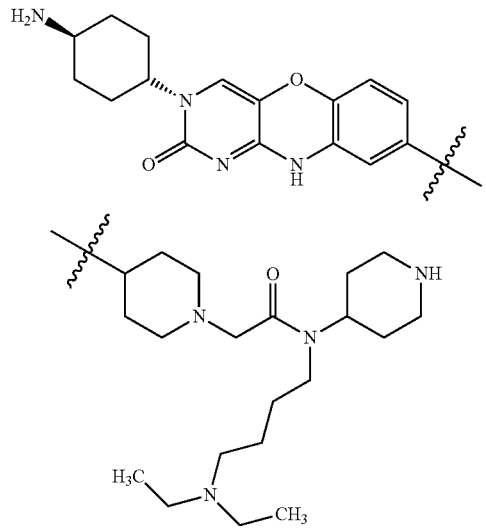 |
| 1058 | 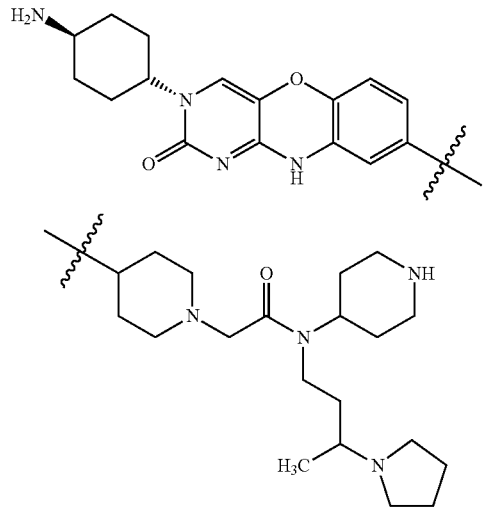 |

-continued
| Comp. No. | Structure |
|---|---|
| 1070 | 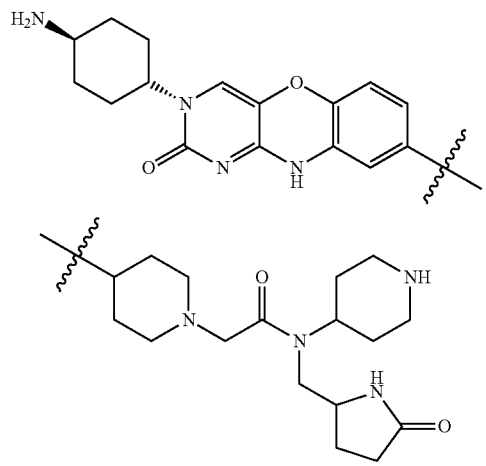 |
| 1071 | 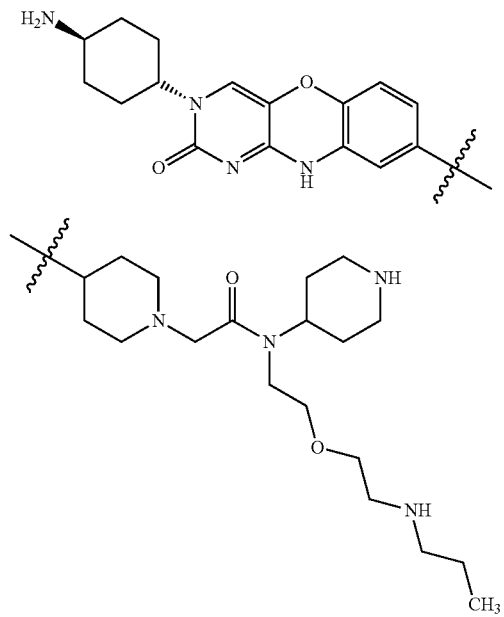 |
| 1072 | 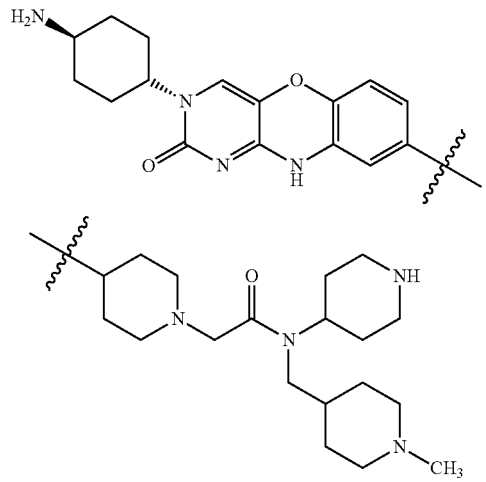 |

| Comp. No. | Structure |
|---|---|
| 1073 | 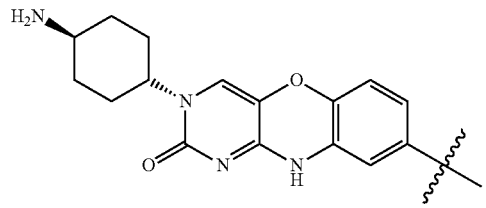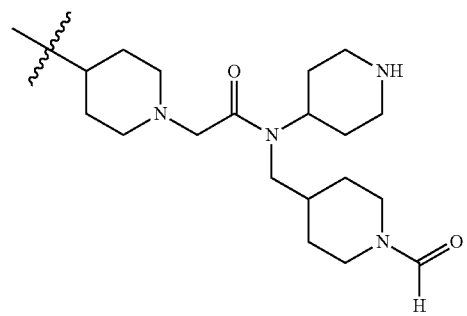 [SMILES: *C1CCN(CC(=O)N(CC2CCN(C=O)CC2)C2CCNCC2)CC1] |
| 1082 | 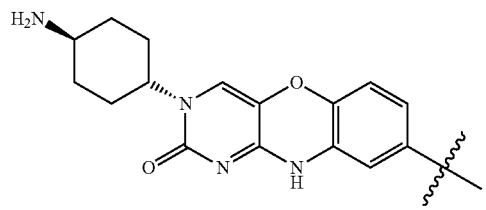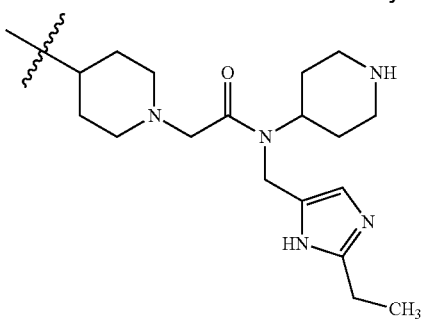 |
| 1083 | 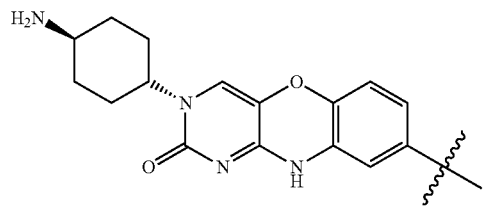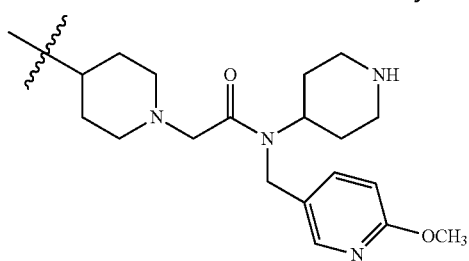 |

| Comp. No. | Structure |
|---|---|
| 1084 | 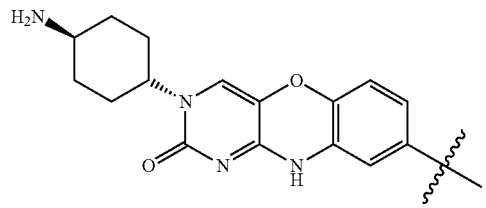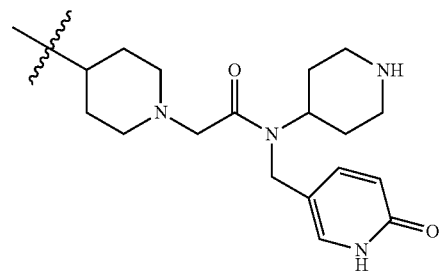 [SMILES: *C1CCN(CC(=O)N(Cc2ccc(=O)[nH]c2)C2CCNCC2)CC1] |
| 1086 | 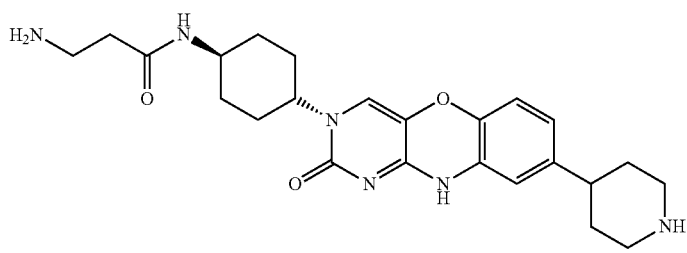 |
| 1096 | 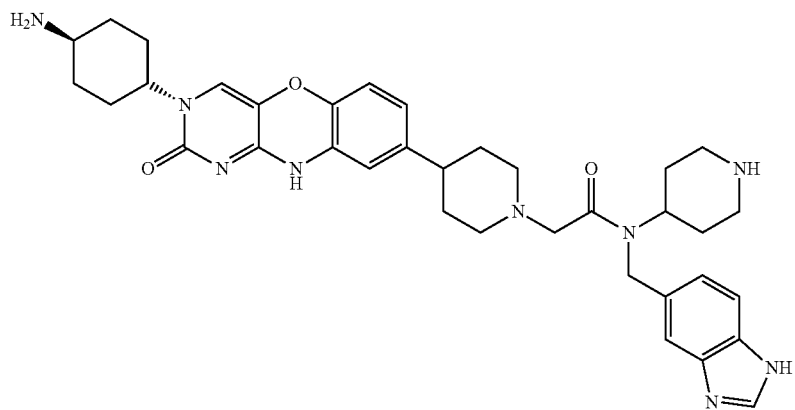 |
| 1133 | 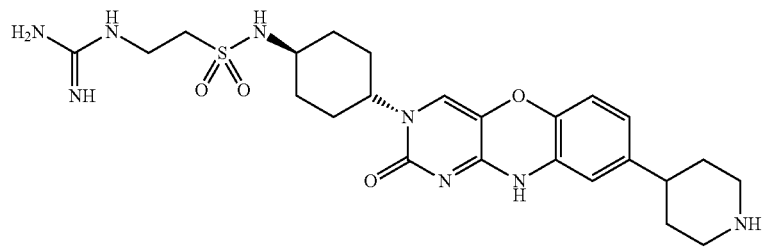 |

| Comp. No. | Structure |
|---|---|
| 1134 | 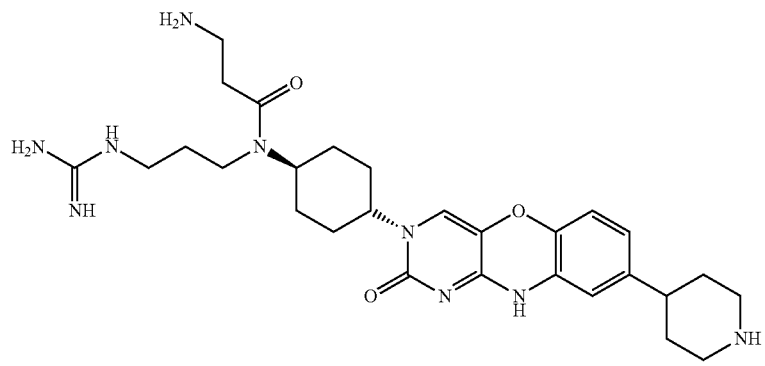 |
| 1135 | 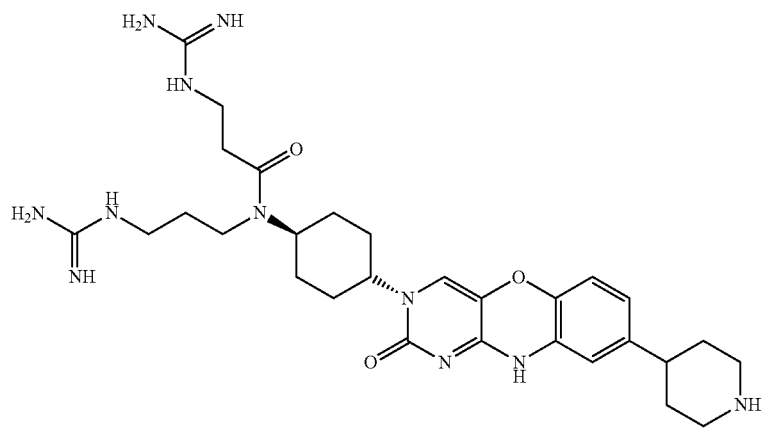 |
| 1145 | 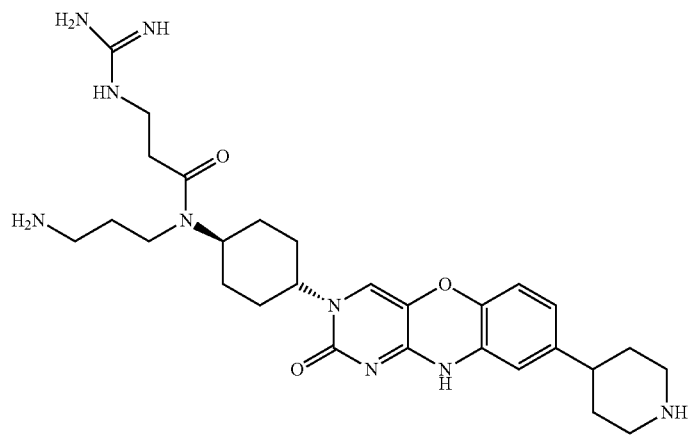 |
| 1146 | 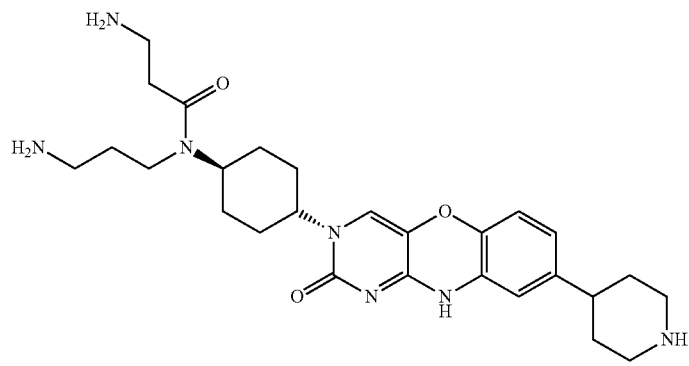 |

-continued
| Comp. No. | Structure |
|---|---|
| 1147 | 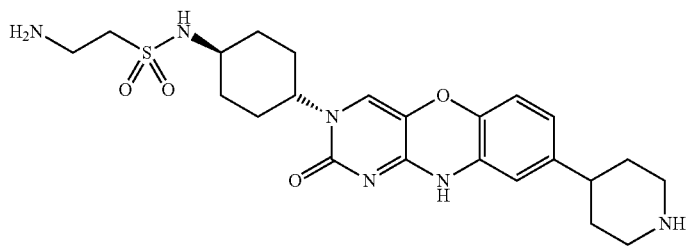 |
| 1192 | 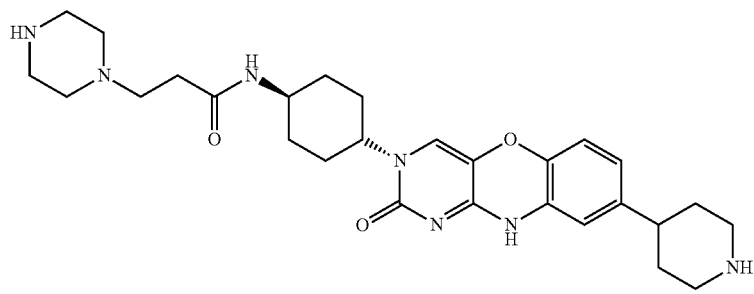 |
| 1193 | 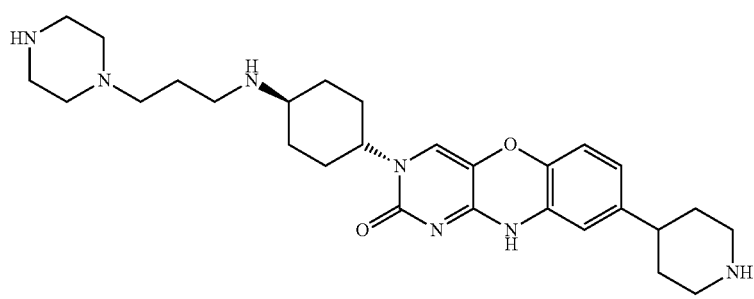 |
| 1197 | 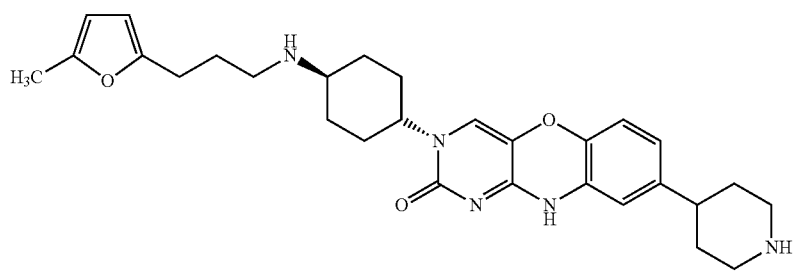 |
| 1198 | 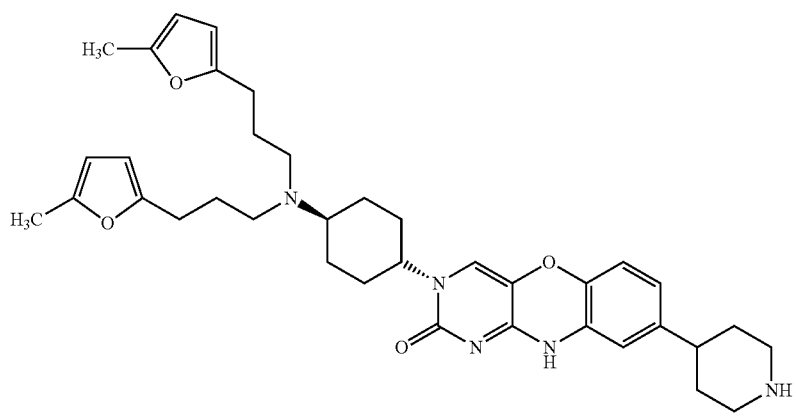 |

-continued
| Comp. No. | Structure |
|---|---|
| 1212 | 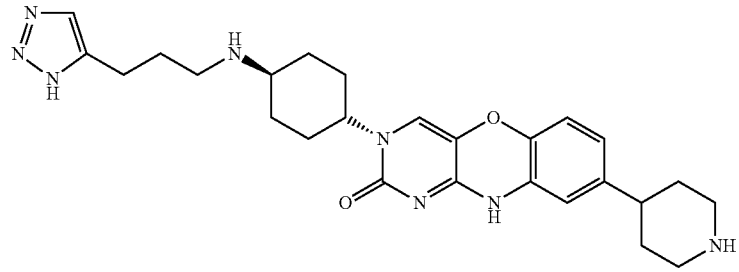 |
| 1213 | 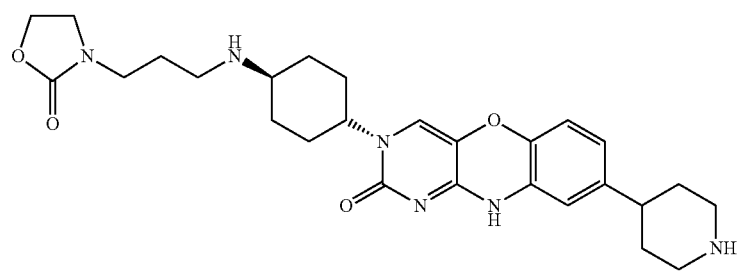 |
| 1234 | 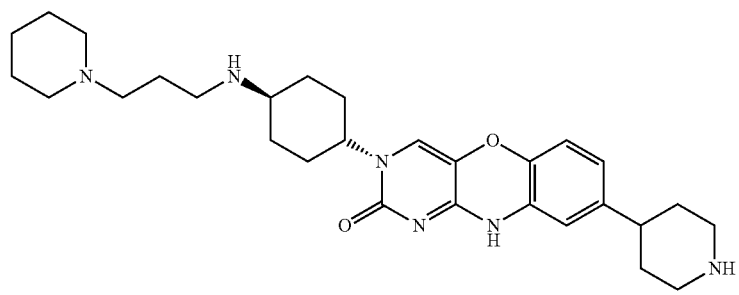 |
| 1235 | 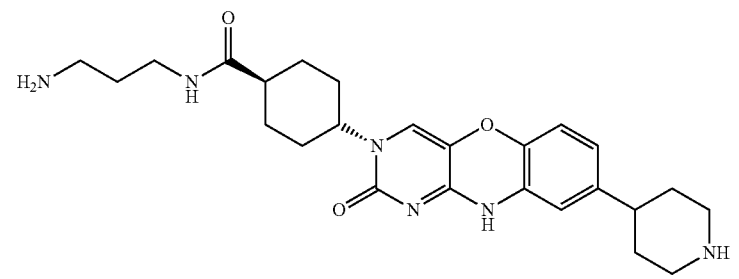 |
| 1236 | 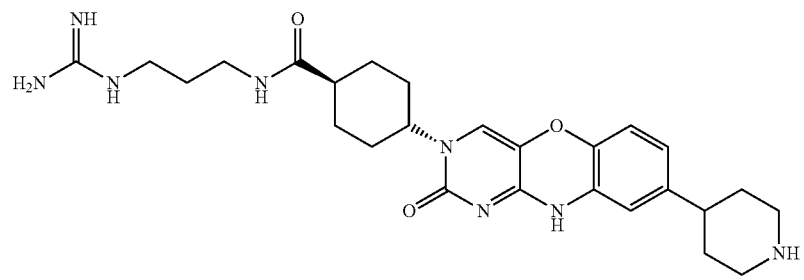 |

| Comp. No. | Structure |
|---|---|
| 1237 | 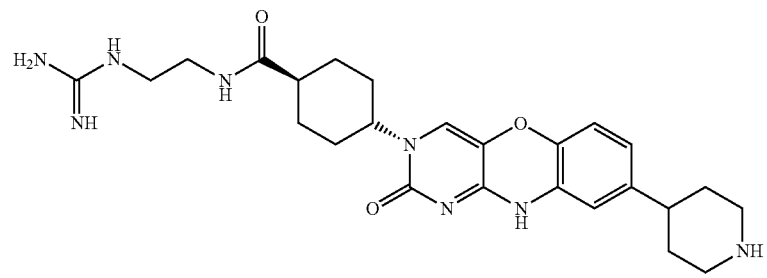 |
| 1238 | 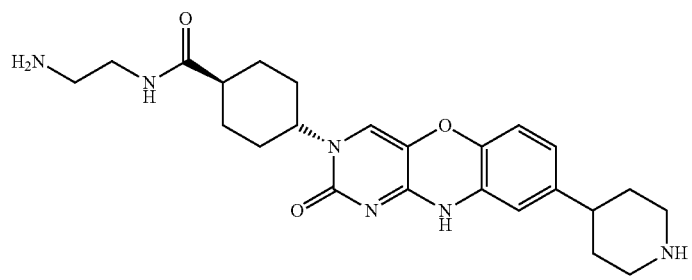 |
| 1244 | 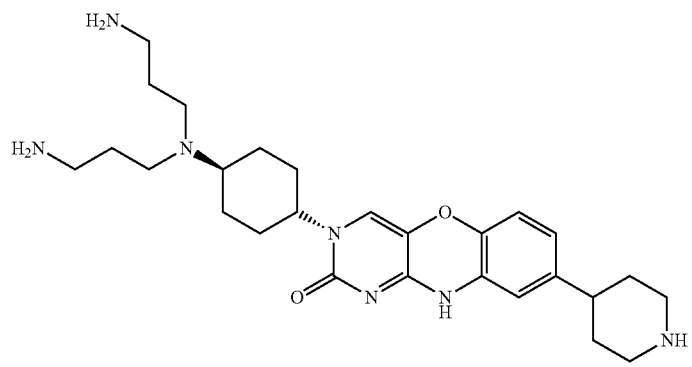 |
| 1269 | 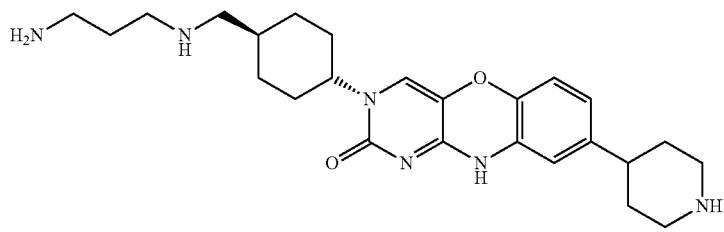 |
| 1270 | 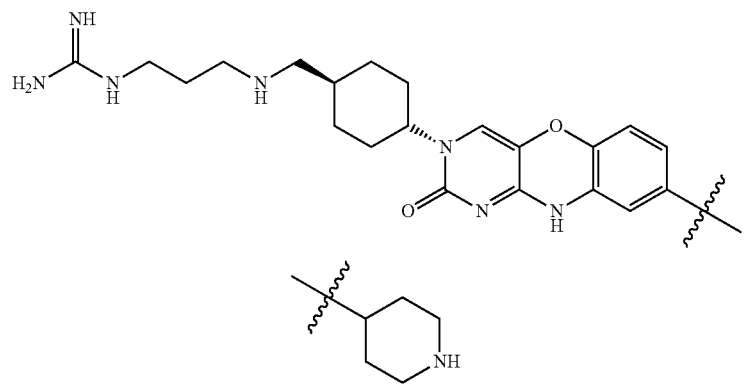 |

| Comp. No. | Structure |
|---|---|
| 1271 | 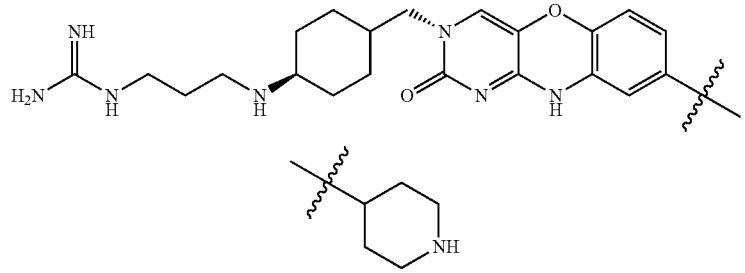 |
| 1368 | 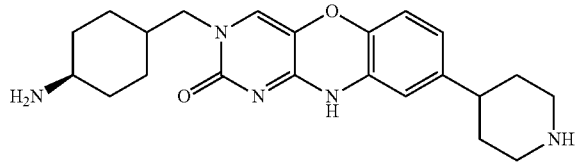 |
| 1369 | 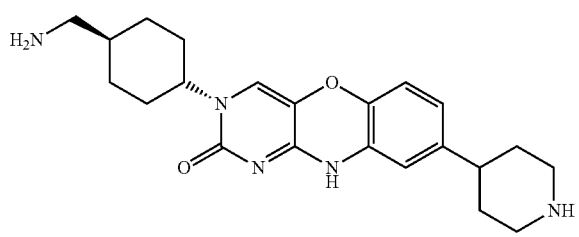 |
| 1370 | 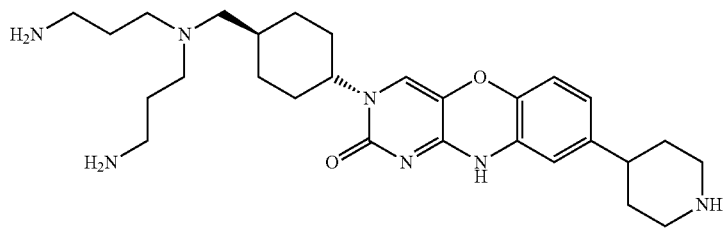 |
| 1421 | 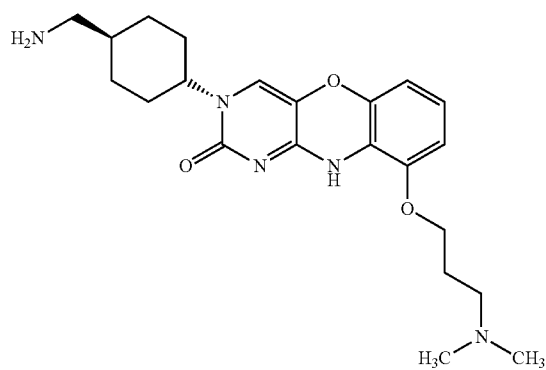 |

-continued
| Comp. No. | Structure |
|---|---|
| 1426 | 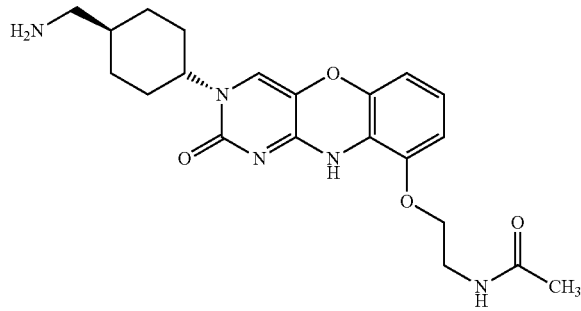 |
| 1427 | 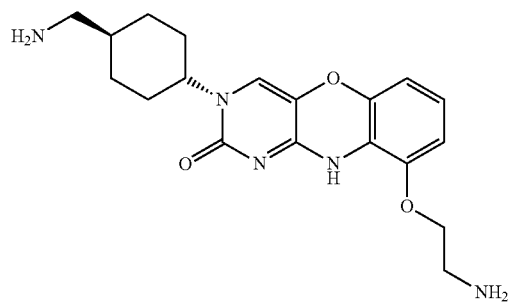 |
| 1441 | 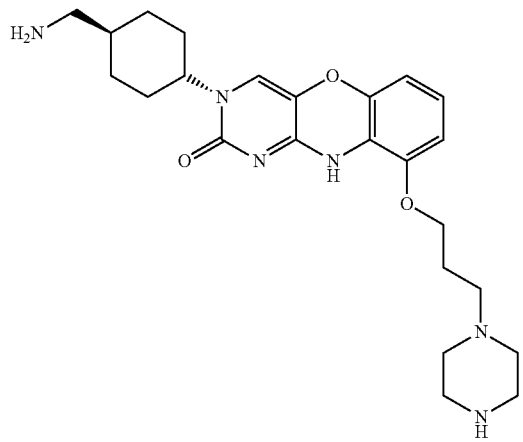 |
| 1449 | 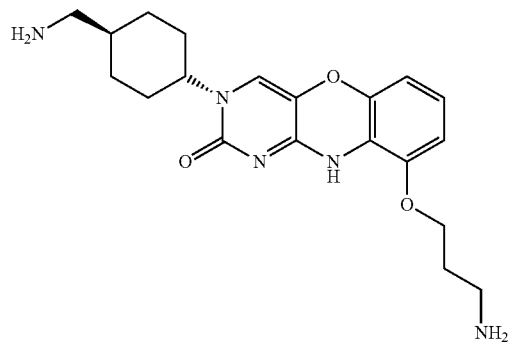 |

| Comp. No. | Structure |
|---|---|
| 1450 | 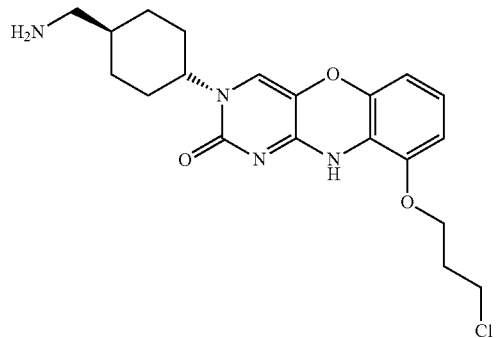 |
| 1464 | 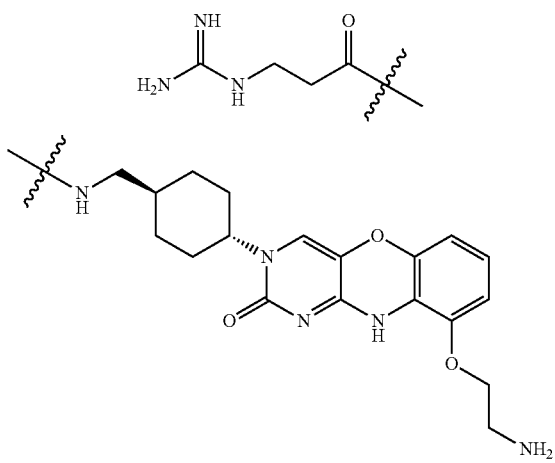 |
| 1465 | 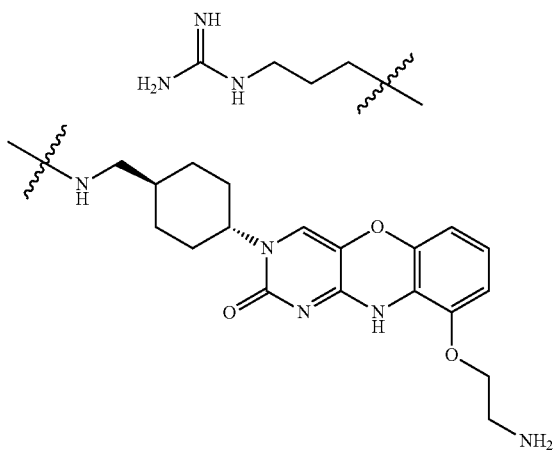 |

| Comp. No. | Structure |
|---|---|
| 1466 | 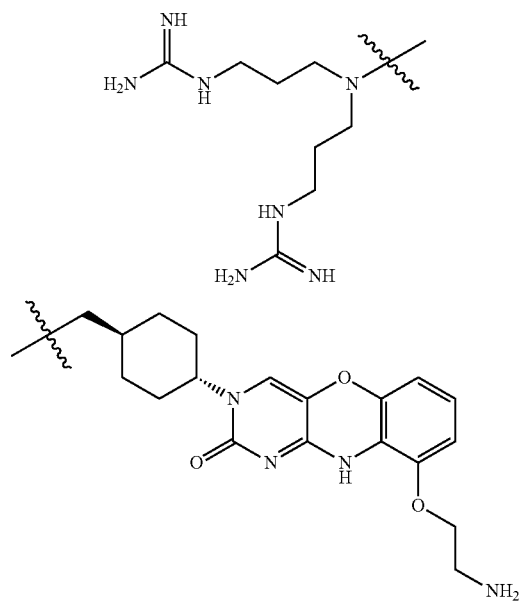 |
| 1467 | 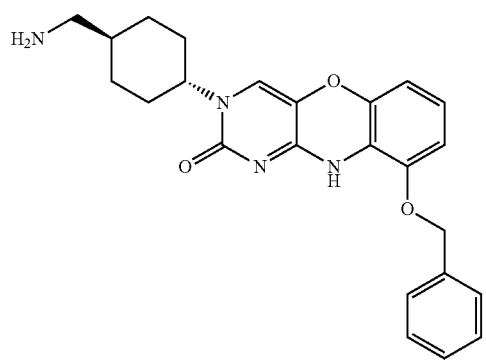 [SMILES: NC[C@H]1CC[C@H](n2cc3c(nc2=O)Nc2c(OCc4ccccc4)cccc2O3)CC1] |
| 4000c | 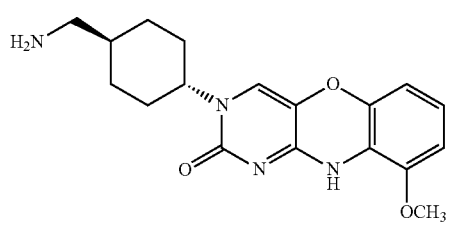 [SMILES: COc1cccc2c1Nc1nc(=O)n([C@H]3CC[C@H](CN)CC3)cc1O2] |
| 4001c | 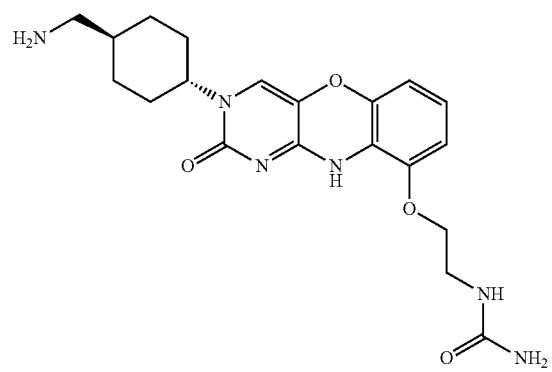 [SMILES: NC[C@H]1CC[C@H](n2cc3c(nc2=O)Nc2c(OCCNC(N)=O)cccc2O3)CC1] |

-continued
| Comp. No. | Structure |
|---|---|
| 4002c | 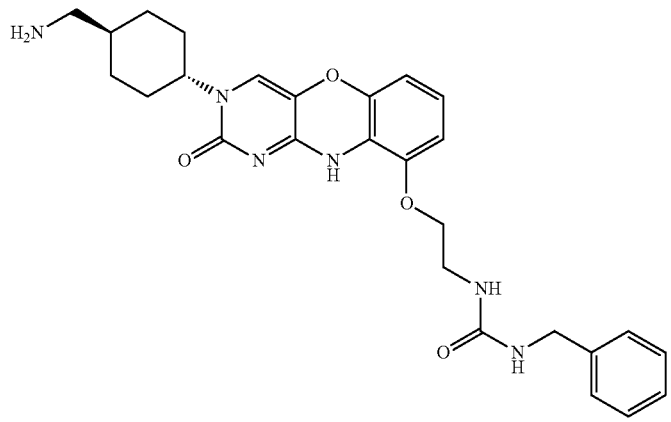 [SMILES: NC[C@H]1CC[C@H](n2cc3c(nc2=O)Nc2c(OCCNC(=O)NCc4ccccc4)cccc2O3)CC1] |
| 4003c | 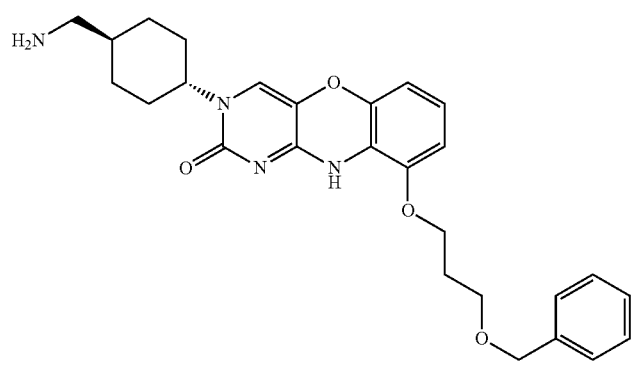 [SMILES: NC[C@H]1CC[C@H](n2cc3c(nc2=O)Nc2c(OCCCOCc4ccccc4)cccc2O3)CC1] |
| 4004c | 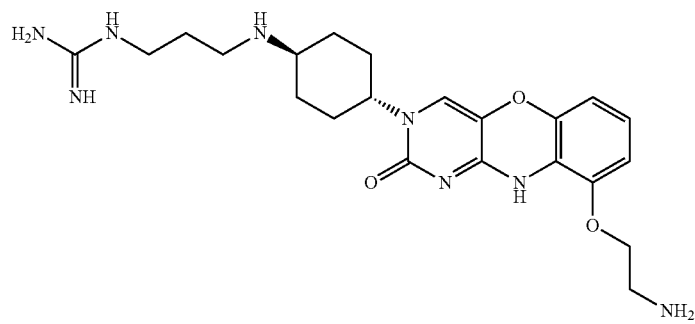 [SMILES: N=C(N)NCCCN[C@H]1CC[C@H](n2cc3c(nc2=O)Nc2c(OCCN)cccc2O3)CC1] |
| 4005c | 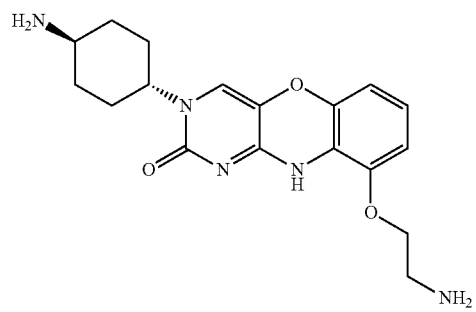 [SMILES: NCCOc1cccc2c1Nc1nc(=O)n([C@H]3CC[C@H](N)CC3)cc1O2] |

| Comp. No. | Structure |
|---|---|
| 4006c | 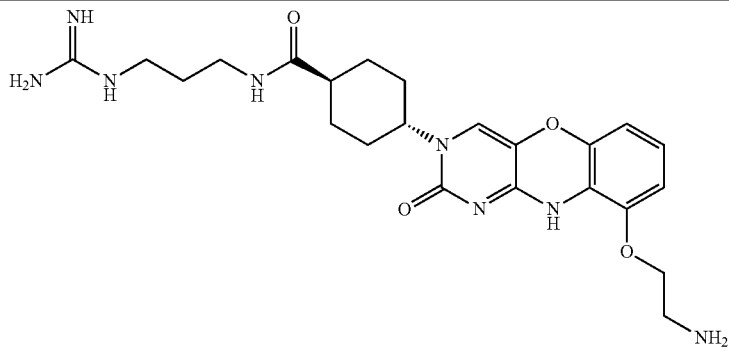 |
| 4007c | 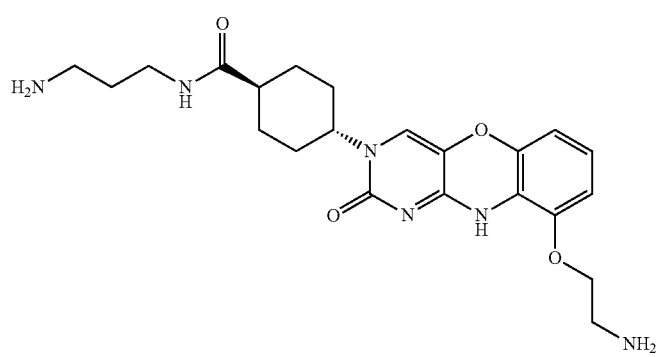 |
| 4008c | 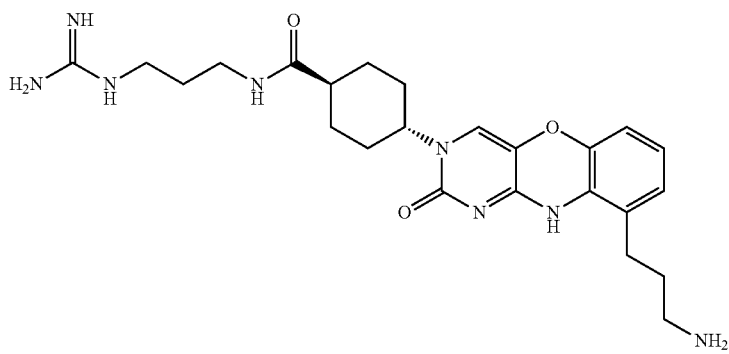 [SMILES: N=C(N)NCCCNC(=O)[C@H]1CC[C@H](n2cc3c(nc2=O)Nc2c(OCCN)cccc2O3)CC1] | or a pharmaceutically acceptable salt, ester, or tautomer thereof.

10. A pharmaceutical composition comprising a compound according to claim 1, or a pharmaceutically acceptable salt, ester, or tautomer thereof, and a pharmaceutically acceptable carrier.

11. A method of treating a microbial infection in a human or animal comprising administering to the human or animal an effective amount of a compound according to claim 1, or a pharmaceutically acceptable salt, ester, or tautomer thereof.

12. A method of treating or reducing the risk of a microbial infection in a human or animal comprising administering to the human or animal an effective amount of a compound according to claim 1, or a pharmaceutically acceptable salt, ester, or tautomer thereof, wherein the microbial infection is selected from the group consisting of:

a skin infection, a Gram positive infection, a Gram negative infection, nosocomial pneumonia, community acquired pneumonia, post-viral pneumonia, hospital acquired pneumonia/ventilator associated pneumonia, a respiratory tract infection, acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, a *Bacillus anthracis* infection, a *Francisella tularensis* infection, a *Yersinia pestis* infection, and tuberculosis.

13. The method according to claim 12, wherein the compound, or a pharmaceutically acceptable salt, ester, or tautomer thereof, is administered otically, ophthalmically, nasally, orally, parenterally, intravenously, or topically.

* * * * *

UNITED STATES PATENT AND TRADEMARK OFFICE
CERTIFICATE OF CORRECTION

PATENT NO. : 9,023,843 B2
APPLICATION NO. : 13/501836
DATED : May 5, 2015
INVENTOR(S) : Duffy et al.

It is certified that error appears in the above-identified patent and that said Letters Patent is hereby corrected as shown below:

In the claims

Claim 1, Column 176, line 37:

Replace "one or more F, $CH_3$, $CF_3$, OH, and $OCH_3$" with

--one or more F, $CH_3$, $CF_3$, OH, or $OCH_3$--

Claim 1, Column 176, line 40:

Replace "$C_{1-5}$ carbocycle" with --$C_{3-7}$ carbocycle--

Claim 1, Column 176, line 60:

Replace "$C_{1-5}$ carbocycle" with --$C_{3-7}$ carbocycle--

Claim 1, Column 177, line 29:

Replace "E, and H are independently selected from" with

--E and H are independently selected from--

Claim 1, Column 177, line 52:

Replace "F, and J are independently selected from" with

--F and J are independently selected from--

Claim 1, Column 177, line 61:

Replace "(v) $-C(=NNR^6C(O\ )R^6)(CR^6R^6)_tR^8$" with

--(v) $-C(=NNR^6C(O)R^6)(CR^6R^6)_tR^8$--

Claim 1, Column 178, line 13:

Replace "(ww) $-(CR^6R^6)_tC(O)NR^8R^8$" with --(ww) $-(CR^6R^6)_tC(O)NR^8R^8$--

Claim 1, Column 183, line 66:

Replace "(n) $-C_{1-8}$ alkenyl, (o) $-C_{1-8}$ alkynyl" with

--(n) $-C_{2-8}$ alkenyl, (o) $-C_{2-8}$ alkynyl--

Signed and Sealed this
Fifth Day of April, 2016

Michelle K. Lee
*Director of the United States Patent and Trademark Office*

Claim 1, Column 184, line 25:

Replace "(n) –$C_{1-8}$ alkenyl, (o) –$C_{1-8}$ alkynyl, (p) –($C_{1-8}$alkyl)–(3–14 member saturated, unsaturated, or aromatic heterocycle containing one or more heteroatoms selected from the group consisting of nitrogen, oxygen, and sulfur)" with --(n) –$C_{2-8}$ alkenyl, (o) –$C_{2-8}$ alkynyl, (p) –($C_{1-8}$ alkyl)–(3–14 member saturated, unsaturated, or aromatic heterocycle containing one or more heteroatoms selected from the group consisting of nitrogen, oxygen, and sulfur)--

Claim 1, Column 184, line 44:

Replace "(n) –$C_{1-8}$ alkenyl, (o) –$C_{1-8}$ alkynyl, (p) –($C_{1-8}$alkyl)–(3–14 member saturated, unsaturated, or aromatic heterocycle containing one or more heteroatoms selected from the group consisting of nitrogen, oxygen, and sulfur)" with --(n) –$C_{2-8}$ alkenyl, (o) –$C_{2-8}$ alkynyl, (p) –($C_{1-8}$ alkyl)–(3–14 member saturated, unsaturated, or aromatic heterocycle containing one or more heteroatoms selected from the group consisting of nitrogen, oxygen, and sulfur)--

Claim 1, Column 184, line 48:

Replace "(q) ⁻($C_{1-8}^-$ alkyl)–(3–14 member saturated, unsaturated, or aromatic carbocycle)" with --(q) –($C_{1-8}$ alkyl)–(3–14 member saturated, unsaturated, or aromatic carbocycle)--

Claim 1, Column 184, line 59:

Replace "(ff) (–$CR^6R^6)_tNR^6R^9$" with --(ff) –$(CR^6R^6)_tNR^6R^9$--

Claim 1, Column 184, lines 65-66:

Replace "(o) –$C_{1-8}$ alkenyl, (p) –$C_{1-8}$ alkynyl" with --(o) –$C_{2-8}$ alkenyl, (p) –$C_{2-8}$ alkynyl--

Claim 1, Column 185, line 4:

Replace "(t) (–$CR^6R^6)_tOR^6$" with --(t) –$(CR^6R^6)_tOR^6$--

Claim 1, Column 185, lines 19-20:

Replace "(o) –$C_{1-8}$ alkenyl, (p) –$C_{1-8}$ alkynyl" with --(o) –$C_{2-8}$ alkenyl, (p) –$C_{2-8}$ alkynyl--

Claim 1, Column 185, line 27:

Replace "(z) –($C_{1-8}$alkyl)–(3–14 member saturated, unsaturated, or aromatic heterocycle containing one or more heteroatoms selected from the group consisting of nitrogen, oxygen, and sulfur)" with --(z) –($C_{1-8}$ alkyl)–(3–14 member saturated, unsaturated, or aromatic heterocycle containing one or more heteroatoms selected from the group consisting of nitrogen, oxygen, and sulfur)--

Claim 1, Column 185, line 33:

Replace "(ee) –$NR^6C(0)NR^6R^6$," with --(ee) –$NR^6C(O)NR^6R^6$--

CERTIFICATE OF CORRECTION (continued)

Claim 5, Column 186, lines 28-29:

Replace "(n) –$C_{1-8}$ alkenyl, (o) –$C_{1-8}$ alkynyl," with --(n) –$C_{2-8}$ alkenyl, (o) –$C_{2-8}$ alkynyl--

Claim 5, Column 186, line 31:

Replace "slected" with --selected--

Claim 5, Column 186, line 32:

Replace "(q) –($C_{1-8}$ -alkyl)–(3–14 member saturated, unsaturated, or aromatic carbocycle)" with --(q) –($C_{1-8}$ alkyl)–(3–14 member saturated, unsaturated, or aromatic carbocycle)--

Claim 8, Column 187, line 1:

Replace "according to claim 5" with --according to claim 3--

Claim 8, Column 190, line 38:

Replace "one or more F, $CH_3$, $CF_3$, OH, and $OCH_3$" with --one or more F, $CH_3$, $CF_3$, OH, or $OCH_3$--

Claim 8, Column 190, line 41:

Replace "$C_{1-5}$ carbocycle" with --$C_{3-7}$ carbocycle--

Claim 8, Column 190, line 62:

Replace "$C_{1-5}$ carbocycle" with --$C_{3-7}$ carbocycle--

Claim 9, Columns 217-218, Comp. No. 750:

Replace

"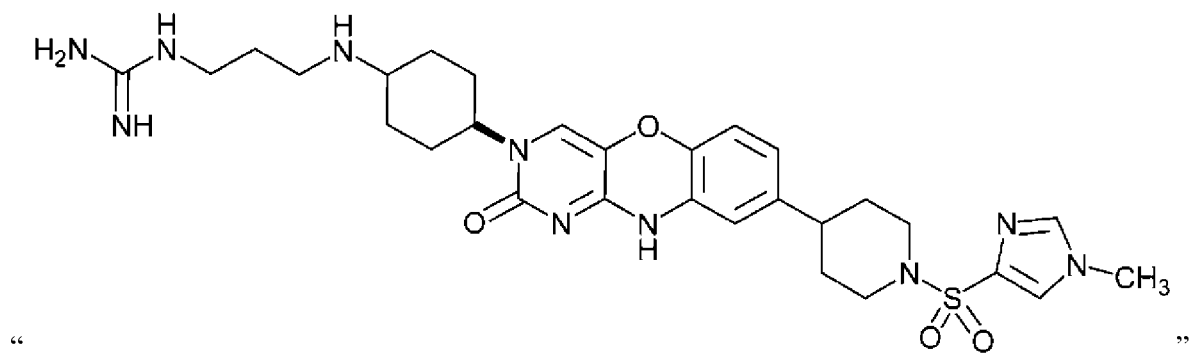"

with

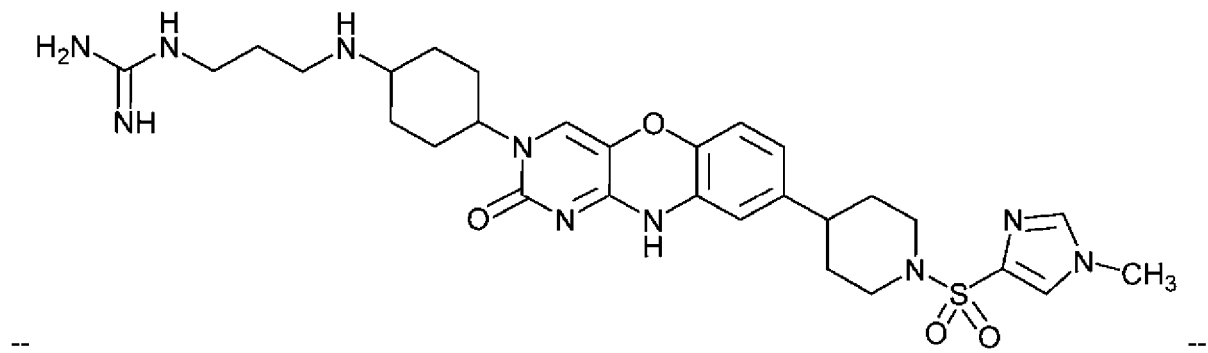

--

Claim 9, Columns 219-220, Comp. No. 765:
Replace
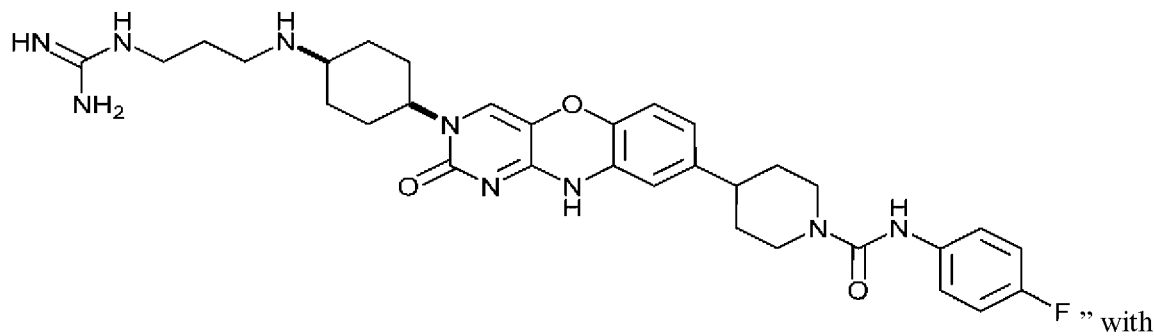
" with
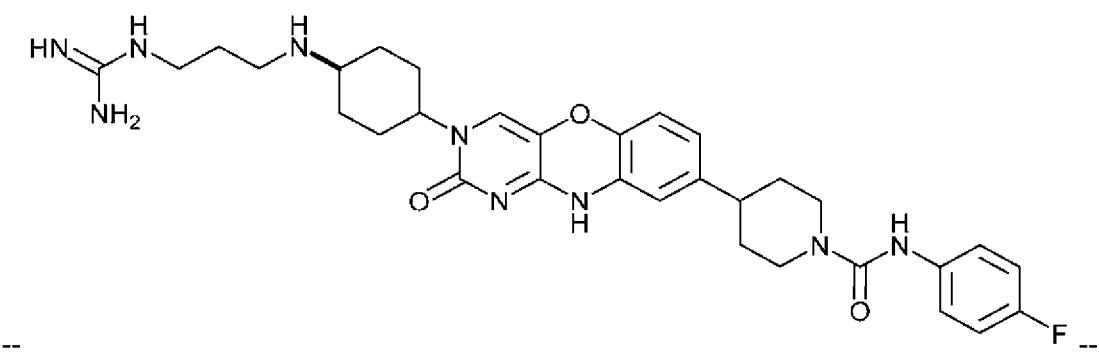
--
Claim 9, Columns 219-220, Comp. No. 774:
Replace
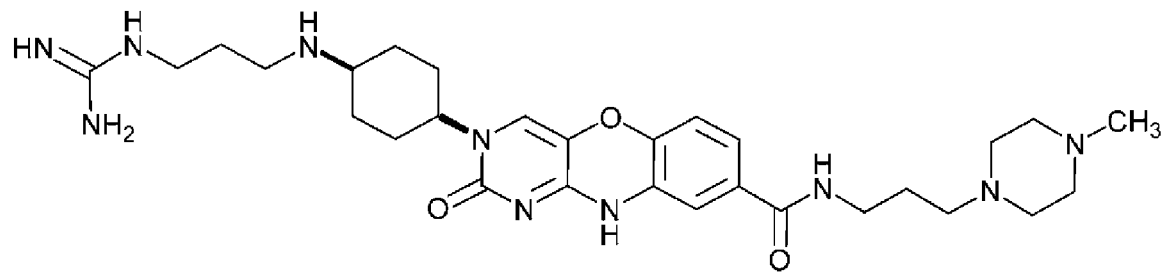
" "
with
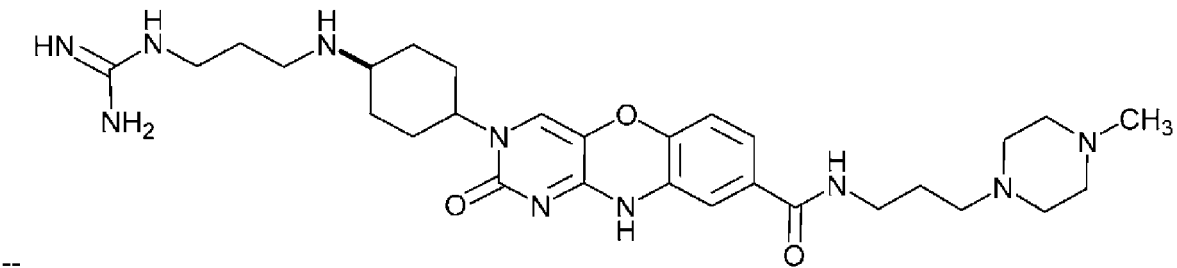
-- --

Claim 9, Columns 221-222, Comp. No. 776:
Replace
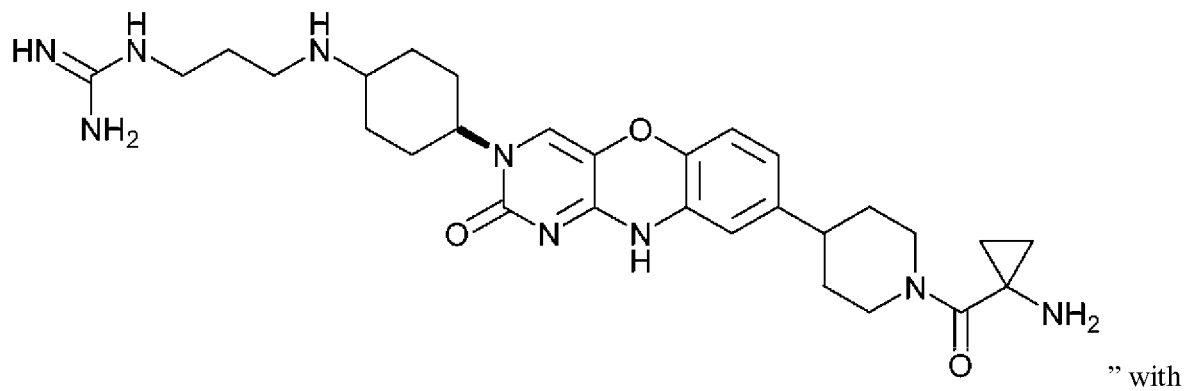
" with
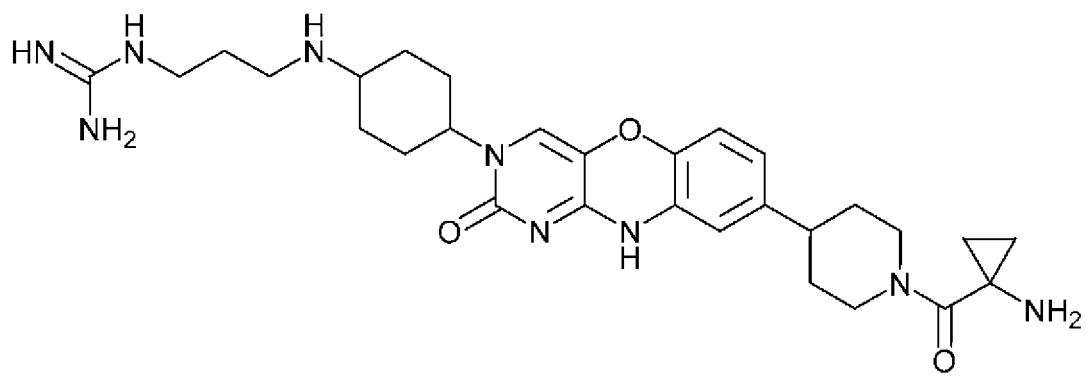
--
Claim 9, Columns 221-222, Comp. No. 781:
Replace
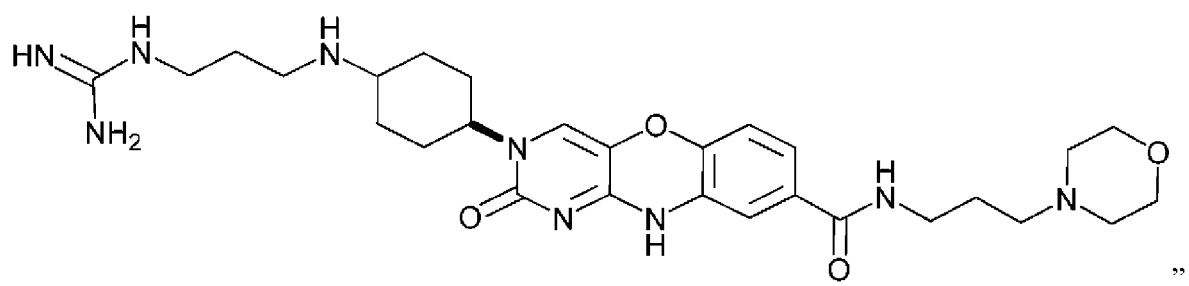
"
with
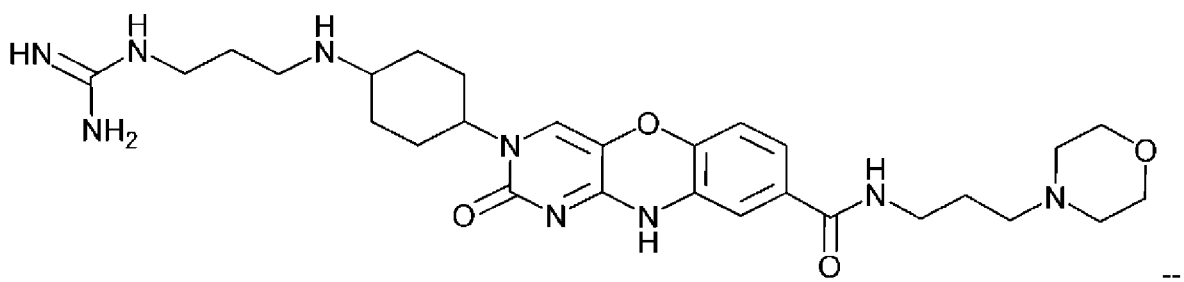
--

Claim 9, Column 239-240, Comp. No. 976:

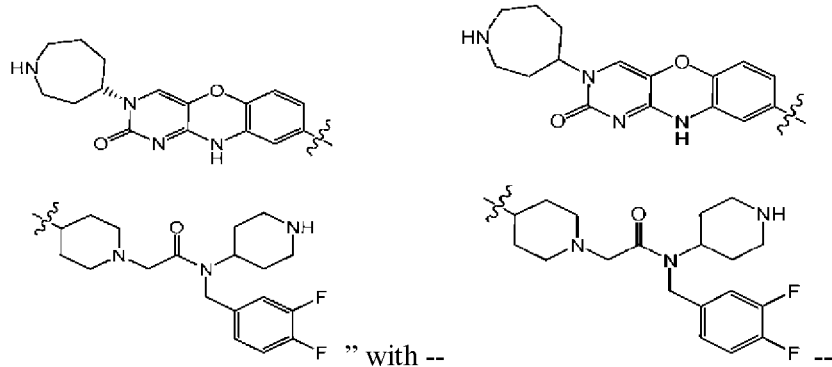

Replace " [structure] " with -- [structure] --

Claim 12, Column 276, line 63:

Replace "a methicillin–resistant *Staphylococcus aureus*infection" with --a methicillin–resistant *Staphylococcus aureus* infection--

Claim 12, Column 276, line 64:

Replace "a vancomycin–resistant Enterococci infection" with --a vancomycin–resistant *Enterococci* infection--

Claim 12, Column 276, line 66:

Replace "a *Yersinia pestis*infection" with --a *Yersinia pestis* infection--